(12) United States Patent
Piens et al.

(10) Patent No.: US 9,347,050 B2
(45) Date of Patent: May 24, 2016

(54) MANNOSIDASES CAPABLE OF UNCAPPING MANNOSE-1-PHOSPHO-6-MANNOSE LINKAGES AND DEMANNOSYLATING PHOSPHORYLATED N-GLYCANS AND METHODS OF FACILITATING MAMMALIAN CELLULAR UPTAKE OF GLYCOPROTEINS

(75) Inventors: Kathleen Camilla Telesphore Alida Maria Piens, Gent (BE); Wouter Vervecken, Landskouter (BE); Albena Vergilieva Valevska, Astene (BE); Gwenda Noëlla Pynaert, Aalter (BE)

(73) Assignee: Oxyrane UK Limited, Manchester (GB)

(*) Notice: Subject to any disclaimer, the term of this patent is extended or adjusted under 35 U.S.C. 154(b) by 0 days.

(21) Appl. No.: 13/876,769

(22) PCT Filed: Sep. 29, 2011

(86) PCT No.: PCT/IB2011/002770
§ 371 (c)(1),
(2), (4) Date: Jun. 19, 2013

(87) PCT Pub. No.: WO2012/042386
PCT Pub. Date: Apr. 5, 2012

(65) Prior Publication Data
US 2013/0267473 A1    Oct. 10, 2013

Related U.S. Application Data

(60) Provisional application No. 61/477,014, filed on Apr. 19, 2011, provisional application No. 61/387,940, filed on Sep. 29, 2010.

(51) Int. Cl.

| | | |
|---|---|---|
| *C12P 19/26* | (2006.01) | |
| *C12P 21/00* | (2006.01) | |
| *A61K 38/43* | (2006.01) | |
| *C12N 15/81* | (2006.01) | |
| *C12N 9/10* | (2006.01) | |
| *C12N 9/24* | (2006.01) | |
| *A61K 38/17* | (2006.01) | |
| *A61K 38/16* | (2006.01) | |
| *A61K 38/00* | (2006.01) | |

(52) U.S. Cl.
CPC .............. *C12N 9/2488* (2013.01); *A61K 38/16* (2013.01); *A61K 38/1709* (2013.01); *C12N 9/2402* (2013.01); *C12P 21/005* (2013.01); *C12Y 302/01024* (2013.01); *A61K 38/00* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,307,717 A | 12/1981 | Hymes et al. |
| 4,352,883 A | 10/1982 | Lim |
| 4,353,888 A | 10/1982 | Sefton |
| 4,407,957 A | 10/1983 | Lim |
| 4,704,362 A | 11/1987 | Itakura et al. |
| 4,837,148 A | 6/1989 | Cregg |
| 4,879,231 A | 11/1989 | Stroman et al. |
| 4,882,279 A | 11/1989 | Cregg |
| 4,883,666 A | 11/1989 | Sabel et al. |
| 4,929,555 A | 5/1990 | Cregg et al. |
| 4,968,733 A | 11/1990 | Muller et al. |
| 4,976,859 A | 12/1990 | Wechs |
| 5,084,350 A | 1/1992 | Chang et al. |
| 5,158,881 A | 10/1992 | Aebischer et al. |
| 5,272,070 A | 12/1993 | Lehrman et al. |
| 5,284,761 A | 2/1994 | Aebischer et al. |
| 5,585,089 A | 12/1996 | Queen et al. |
| 5,798,113 A | 8/1998 | Dionne et al. |
| 5,800,828 A | 9/1998 | Dionne et al. |
| 6,110,703 A | 8/2000 | Egel-Mitani et al. |
| 6,265,185 B1 | 7/2001 | Muller et al. |
| 6,699,658 B1 | 3/2004 | Wittrup et al. |
| 6,803,225 B2 | 10/2004 | Contreras et al. |
| 6,872,392 B2 | 3/2005 | Nakamura et al. |
| 7,029,872 B2 | 4/2006 | Gerngross |
| 7,259,007 B2 | 8/2007 | Bobrowicz et al. |
| 7,262,287 B2 | 8/2007 | Kang et al. |
| 7,326,681 B2 | 2/2008 | Gerngross |
| 7,390,884 B2 | 6/2008 | Segal et al. |
| 7,422,742 B2 | 9/2008 | Greenfeder et al. |
| 7,422,890 B2 | 9/2008 | Gopalakrishnakone et al. |
| 7,431,927 B2 | 10/2008 | Couto et al. |

(Continued)

FOREIGN PATENT DOCUMENTS

| | | |
|---|---|---|
| AU | 2012 206 984 | 8/2012 |
| EP | 1408117 | 4/2004 |

(Continued)

OTHER PUBLICATIONS

Cardone et al., "Abnormal mannose-6-phosphate receptor trafficking impairs recombinant alpha-glucosidase uptake in Pompe disease fibroblasts," PathoGenetics 1:1-22 (2008).*

(Continued)

*Primary Examiner* — Julie Ha
*Assistant Examiner* — Kristina M Hellman
(74) *Attorney, Agent, or Firm* — Fish & Richardson P.C.

(57) ABSTRACT

The invention provides mannosidases capable of uncapping mannose-1-phospho-6-mannose moieties and demannosylating phosphorylated N-glycans, methods of using such mannosidases, glycoproteins produced using the methods, as well as methods of facilitating mammalian cellular uptake of glycoproteins.

7 Claims, 36 Drawing Sheets

(56) References Cited

U.S. PATENT DOCUMENTS

| | | | |
|---|---|---|---|
| 7,442,772 | B2 | 10/2008 | Goddard et al. |
| 7,449,308 | B2 | 11/2008 | Gerngross et al. |
| 7,488,591 | B2 | 2/2009 | Miura et al. |
| 7,785,856 | B2 | 8/2010 | LeBowitz |
| 8,026,083 | B2 | 9/2011 | Callewaert et al. |
| 8,597,906 | B2 | 12/2013 | Callewaert |
| 2002/0127219 | A1 | 9/2002 | Okkels et al. |
| 2002/0137125 | A1 | 9/2002 | Zhu |
| 2003/0147868 | A1 | 8/2003 | Treco et al. |
| 2003/0186374 | A1 | 10/2003 | Hufton et al. |
| 2004/0018588 | A1 | 1/2004 | Contreras et al. |
| 2004/0018590 | A1 | 1/2004 | Gerngross et al. |
| 2005/0014270 | A1 | 1/2005 | Picataggio et al. |
| 2005/0064539 | A1* | 3/2005 | Chiba et al. .......... 435/68.1 |
| 2005/0170452 | A1 | 8/2005 | Wildt et al. |
| 2005/0265988 | A1 | 12/2005 | Choi et al. |
| 2006/0014264 | A1 | 1/2006 | Sauer et al. |
| 2006/0030521 | A1 | 2/2006 | Defrees et al. |
| 2006/0040353 | A1 | 2/2006 | Davidson et al. |
| 2006/0148039 | A1 | 7/2006 | Kobayashi et al. |
| 2006/0286637 | A1 | 12/2006 | Hamilton |
| 2007/0037248 | A1 | 2/2007 | Bobrowicz et al. |
| 2008/0171359 | A1 | 7/2008 | Botes et al. |
| 2009/0186011 | A1 | 7/2009 | Vellard et al. |
| 2010/0291059 | A1 | 11/2010 | Sakuraba et al. |
| 2011/0201540 | A1 | 8/2011 | Callewaert et al. |
| 2011/0207676 | A1 | 8/2011 | Callewaert et al. |
| 2012/0135461 | A1 | 5/2012 | Cook et al. |
| 2013/0053550 | A1 | 2/2013 | Geysens et al. |
| 2013/0096281 | A1 | 4/2013 | Ryckaert et al. |
| 2013/0158239 | A1 | 6/2013 | Callewaert et al. |
| 2013/0190253 | A1 | 7/2013 | Callewaert et al. |
| 2013/0195835 | A1 | 8/2013 | Callewaert et al. |
| 2013/0243746 | A1 | 9/2013 | Vervecken |
| 2013/0295603 | A1 | 11/2013 | Piens |
| 2015/0031081 | A1 | 1/2015 | Vervecken et al. |

FOREIGN PATENT DOCUMENTS

| | | |
|---|---|---|
| FR | 2954349 | 6/2011 |
| JP | 57-054588 | 4/1982 |
| JP | 2002-369679 | 12/2002 |
| JP | 2004-313074 | 11/2004 |
| KR | 20040062304 | 7/2004 |
| WO | WO 92/19195 | 11/1992 |
| WO | WO 95/05452 | 2/1995 |
| WO | WO 96/04378 | 2/1996 |
| WO | WO 96/21038 | 7/1996 |
| WO | WO 98/01473 | 1/1998 |
| WO | WO 98/01535 | 1/1998 |
| WO | WO 98/48025 | 10/1998 |
| WO | WO 99/36569 | 7/1999 |
| WO | WO 99/37758 | 7/1999 |
| WO | WO 01/49830 | 7/2001 |
| WO | WO 01/88143 | 11/2001 |
| WO | WO 02/18570 | 3/2002 |
| WO | WO 03/029456 | 4/2003 |
| WO | WO 03/056914 | 7/2003 |
| WO | WO 2004/003194 | 1/2004 |
| WO | WO 2004/074458 | 9/2004 |
| WO | WO 2004/074461 | 9/2004 |
| WO | WO 2004/074498 | 9/2004 |
| WO | WO 2004/074499 | 9/2004 |
| WO | WO 2005/100584 | 10/2005 |
| WO | WO2005106010 A3 | 8/2007 |
| WO | WO 2008/100816 | 8/2008 |
| WO | WO 2008/120107 | 10/2008 |
| WO | WO 2009/033507 | 3/2009 |
| WO | WO 2009/105357 | 8/2009 |
| WO | WO 2010/099195 | 9/2010 |
| WO | WO 2011/039634 | 4/2011 |
| WO | WO 2011/061629 | 5/2011 |
| WO | WO 2012/042387 | 4/2012 |
| WO | WO2012042386 A2 | 4/2012 |
| WO | WO 2013/098651 | 7/2013 |

OTHER PUBLICATIONS

De Pourcq et al., "Engineering of glycosylation in yeast and other fungi: current state and perspectives," Appl Microbiol Biotechnol., 87(5)1617-1631. Epub Jun. 29, 2010.

De Pourcq et al., "Engineering the yeast Yarrowia lipoytica for the production of therapeutic proteins homogeneously glycosylated with Man8GlcNAc2 and MansGlcNAc2," Microbial Cell Factories, 11:53, 1-12, May 1, 2012.

Inoue et al., "Molecular cloning and nucleotide sequence of the 1,2-alpha-D-mannosidase gene, msdS, from Aspergillus saitoi and expression of the gene in yeast cells," Biochim Biophys Acta. 1253(2):141-145, Dec. 6, 1995.

Jacobs et al. "Engineering complex-type N-glycosylation in Pichia pastoris using GlycoSwitch technology," Nat Protoc., 2009;4(1):58-70., Epub Dec. 18, 2008.

Liu et al., "Disruption of the OCH1 and MNN1 genes decrease N-glycosylation on glycoprotein expressed in Kluyveromyces lactis," J Biotechnol., 143(2):95-102, Epub Jun. 24, 2009.

Mille et al., "Identification of a new family of genes involved in beta-1,2-mannosylation of glycans in Pichia pastoris and Candida albicans," J Biol Chem., 283(15):9724-9736. Epub Jan. 30, 2008.

Seffernick et al., "Melamine deaminase and atrazine chlorohydrolase: 98 percent identical but functionally different," J Bacteriol., 183(8):2405-2410, Apr. 2001.

Swennen et al., "Folding proteome of Yarrowia lipolytica targeting with uracil permease mutants," J Proteome Res., 9 (12):6169-6179, Epub Nov. 12, 2010.

Vervecken et al., "Modification of the N-glycosylation pathway to produce homogeneous, human-like glycans using GlycoSwitch plasmids," Methods Mol Biol., 389:119-138, 2007.

Witkowski et al. "Conversion of a beta-ketoacyl synthase to a malonyl decarboxylase by replacement of the active-site cysteine with glutamine," Biochemistry, 38(36):11643-11650, Sep. 7, 1999.

"Arxula adeninivorans," Wikipedia [online] Jan. 13, 2010 [retrieved on Jan. 31, 2010]. Retrieved from the Internet: <URL: http://en.wikipedia.org/wiki/Arxula_adeninivorans>, 2 pages.

"Eukaryotes Genomes—Yarrowia Lipolytica," The European Bioinformatics Institute [online] [retrieved on Jun. 26, 2012]. Retrieved from the Internet: <URL: http://www.ebi.ac.uk/2can/genomes/eukaryotes/Yarrowia_lipolytica.html>, 1 page.

Aebi et al., "Cloning and characterization of the ALG3 gene of Saccharomyces cerevisiae," Glycobiology, vol. 6, No. 4, (1996), pp. 439-444.

Akcapinar et al., "Effect of codon optimization on the expression of Trichoderma reesei endoglucanase 1 in Pichia pastoris." Biotechnol Prog,. Sep.-Oct. 2011; 27(5):1257-1263. doi: 10.1002/btpr.663. Epub Jul. 2011.

Akeboshi et al., "Production of Recombinant Beta-Hexosaminidase A, a Potential Enzyme for Replacement Therapy for Tay-Sachs and Sandhoff Diseases, in the Methylotrophic Yeast Ogataea minuta", Appl. Environ. Microbiol., 73(15):4805-4812 (2007).

Alessandrini et al., "Alterations of Glucosylceramide-b-Glucosidase Levels in the Skin of Patients with Psoriasis Vulgaris," J. Invest. Dermatol, 23(6):1030-1036, 2004.

Bagiyan et al., "The Action of α-Mannosidase from Oerskova sp. on the Mannose-Rich O-Linked Sugar Chains of Glycoproteins," Eur. J. Biochem., 249(1):286-292, 1997.

Baharaeen and Vishniac, "A fixation method for visualization of yeast ultrastructure in the electron microscope ," Mycopathologia, 77(1):19-22, 1982.

Ballou, "Isolation, characterization, and properties of Saccharomyces cerecisiae mnn mutants with nonconditional protein glycosylation defects," Methods in Enzymology, vol. 185, (1990) pp. 440-470.

Barnay-Verdier et al., "Identification and characterization of two alpha-1,6-mannosyltransferases, Anl1p and Och1p, in the yeast yarrowia lipolytica", Microbiology, 150:2185-2195 (2004).

(56) References Cited

OTHER PUBLICATIONS

Barth and Gaillardin, "Physiology and genetics of the dimorphic fungus Yarrowia lipolytica," *FEMS Microbiology Reviews*, 19(4):219-237, Apr. 1997 [print], Jan. 2006 [online].
Bennetzen and Hall, "Codon Selection in Yeast," *J. Biol. Chem.*, 257(6):3026-3031, 1982.
Bentley et al., "Complete genome sequence of the model actinomycete Streptomyces coelicolor A3(2)," *Nature*, 417:141-147, (May 2002).
Bobrowicz et al., "Engineering of an artificial glycosylation pathway blocked in core oligosaccharide assembly in the yeast Pichia pastoris: production of complex humanized glycoproteins with terminal galactose," *Glycobiology*, 14(9):757-766 (2004).
Boisrame et al. "Sls1p, an endoplasmic retculum component, is involved in the protein translocation process in the yeast Yarrowia lipolytica," *J. Biol. Chem.* 271(20):11668-75, 1996.
Bretthauer, "Genetic engineering of Pichia pastoris to humanize N-glycosylation of proteins," *TRENDS in Biotechnology*, 21(11): 459-462 (Nov. 2003).
Burda et al., "Ordered assembly of the asymmetrically branced lipid-linked oligosaccharide in the endoplasmic reticulum is ensured by the substrate specificity of the individual glycosyltransferases", *Glycobiology*, 9(6):617-625 (1999).
Burton and Harding, "Hydrophobic charge induction chromatography: salt independent protein adsorption and facile elution with aqueous buffers.," *J. Chromatogr. A* 814(1-2):71-81, Jul. 1998.
Callewaert et al, "Use of HDEL-tagged Trichoderma reesei mannosyl oligosaccharide 1,2-alpha-D-mannosidase for N-glycan engineering in Pichia pastoris.," *FEBS Lett.*, 503(2-3):173-178, (Aug. 2001).
Callewaert et al., "Ultrasensitive profiling and sequencing of N-linked oligosaccharides using standard DNA-sequencing equipment," *Glycobiology* 11(4):275-281, Apr. 2001.
Carter et al., "Humanization of an anti-p185HER2 antibody for human cancer therapy," *Proc Natl Acad Sci USA*, 89(10): 4285-4289, (May 1992).
Chiba et al., "Production in yeast of alpha-galactosidase A, a lysosomal enzyme applicable to enzyme replacement therapy for Fabry disease," *Glycobiology*, 12(12):821-828 (2002).
Choe-Min-Hui: "Structural analysis of N-linked oligosaccharides assembled on recombinant proteins secreted from Yarrowia lipolytica Yloch1 and Yloch1 Ylmnn4 mutants," Thesis, Chungnam National University: Department of Microbiology, Republic of Korea, pp. 1-39, XP008160421, Retrieved from the Internet: URL: http://www.riss.kr/search/detail/DetailView.do?p_mat_type=75f99de66db18cf6&control_no=4cbf0006e9061fb5ffe0bdc3ef48d419 (2006).
Choi et al. "Use of combinatorial genetic libraries to humanize N-linked glycosylation in the yeast Pichia pastoris," *Proc. Natl. Acad. Sci. USA*, 100(9):5022-5027, Apr. 2003.
Cipollo and Trimble, "The accumulation of Man(6)GlcNAc(2)-PP-dolichol in the *Saccharomyces cerevisiae* Deltaalg9 mutant reveals a regulatory role for the Alg3p alpha1,3-Man middle-arm addition in downstream oligosaccharide-lipid and glycoprotein glycan processing," *J Biol Chem.*, 275(6):4267-4277, (Feb. 2000).
Cobucci-Ponzano et al., "The molecular characterization of a novel GH38 alpha-mannosidase from the crenarchaeon Sulfolobus solfataricus revealed its ability in de-mannosylating glycoproteins," *Biochimie.*, 92(12):1895-1907, (Aug. 2010).
Codon usage table: Yarrowia lipolytica CLIB122 [gbpln]: 5967 CDS'S (2945919 codons), *Codon Usage Database* [online], [retrieved on Jul. 10, 2012]. Retrieved from the Internet:< URL: http://www.kazusa.or.jp/codon/cgi-bin/showcodon.cgi?species=284591>, 1 page.
Connock et al., "A systematic review of the clinical effectiveness and cost-effectiveness of enzyme replacement therapies for Fabry's disease and mucopolysaccharidosis type 1," *Health Technol Assess.*, 10(20):iii-iv, ix-113, 2006.

Database Accession No. P41546, UniProt (online), "RecName: Full Transcriptionmanal Activator HAC1"; XP002509286, Nojima et al., Nov. 1, 1995, 3 pages.
Database UniProt[Online] Aug. 1, 1998, "SubName: Full= Putative secreted protein;" XP002628929 retrieved from EBI accession No. UNIPROT:O69822 Database accession No. O69822, 3 pages.
Database UniProt[Online] Jul. 11, 2006, "SubName: Full= Alpha-1, 2-mannosidase, putative; Flags: Precursor;" XP002628931 retrieved from EBI accession No. UNIPROT:Q1ASW5 Database accession No. Q1ASW5, 2 pages.
Database UniProt[Online] Apr. 29, 2008, "SubName: Full= Putative uncharacterized protein;" XP002628930 retrieved from EBI accession No. UNIPROT:B1BZG6 Database accession No. B1BZG6, 2 pages.
Davies et al, "Nomenclature for sugar-binding subsites in glycosyl hydrolases," *Biochem. J.*, 321:557-559 (1997).
Fickers et al. "New disruption cassettes for rapid gene disruption and marker rescue in the yeast Yarrowia lipolytica," 2003 *J. Microbiol. Methods.* 55(3):727-737, Dec. 2003.
Fickers et al., "Carbon and nitrogen sources modulate lipase production in the yeast Yarrowia lipolytica," *J. of Applied Microbiology*, vol. 96, No. 4 (2004), pp. 742-749.
Fickers, P. et al. "Hydrophobic substrate utilization by the yeast Yarrowia lipolytica and its potential applications," *FEMS Yeast Research*, Apr. 2005, vol. 5, No. 6-7, pp. 527-543.
Freire et al. "Efficient monitoring of enzymatic conjugation reaction by surface-enhanced laser desorption/ionization time of flight mass spectrometry for process optimization," *Bioconjug. Chem.* 17(2):559-564, 2006.
Fujita and Takegawa, "Chemoenzymatic Synthesis of Neoglycoproteins Using Transglycosylation with Endo-Beta-N-acetylglucosaminidase A," *Biochem. Biophs. Res. Commun.*, 282(3):678-682, (Apr. 2001).
Gao et al. "UpGene: Application of a web-based DNA codon optimization algorithm," *Biotechnol. Prog.*, 20(2): 443-448, 2004.
Gellissen, et al., "New yeast expression platforms based on methylotrophic Hansenula polymorpha and Pichia pastoris and on dimorphic Arxula adeninivorans and Yarrowia lipolytica—A comparison," *FEMS Yeast Res.*, 5(11): 1079-1096, 2005.
Genbank Acccession No. XM_502922 GI:50550898, "Yarrowia lipolytica YALI0D17028p (YALI0D17028g) mRNA, complete cds," Oct. 29, 2008, 2 pages.
Genbank Acccession No. XM_503217 GI:50551486, "Yarrowia lipolytica YALI0D24101p (YALI0D24101g) mRNA, complete cds," Oct. 29, 2008, 2 pages.
Genbank Accession No. AAF34579 GI:6979644, "1,2-a-D-mannosidase [Trichoderma reesei]" Feb. 16, 2000, 1 page.
Genbank Accession No. AAO78636.1 GI:29340846, putative alpha-1,2-mannosidase [Bacteroides thetaiotaomicron VPI-5482] Feb. 8, 2011, 2 pages.
Genbank Accession No. AAO79070.1 GI:29341282, "putative alpha-1,2-mannosidase [Bacteroides thetaiotaomicron VPI-5482]," Feb. 8, 2011, 2 pages.
Genbank Accession No. AAO79099.1, "putative alpha-1,2-mannosidase [Bacteroides thetaiotaomicron VPI-5482]," Feb. 8, 2011, 2 pages.
Genbank Accession No. AF212153 GI:6979643, "Hypocrea jecorina 1,2-a-D-mannosidase (MDS1) mRNA, complete cds," Feb. 16, 2000, 2 pages.
GenBank Accession No. AF441127 GI:16974782, "Yarrowia lipolytica Mnn9p (mnn9) gene, complete cds," Apr. 11, 2003, 2 pages.
GenBank Accession No. AJ563920 GI:38488499, "Yarrowia lipolytica och1 gene for alpha 1,6 mannosyltransferase," Nov. 20, 2003, 2 pages.
GenBank Accession No. AJ865333 GI:56266607, "Trypanosoma brucei brucei glcasella gene for glucosidase II alpha subunit precursor," Oct. 25, 2005, 2 pages.
GenBank Accession No. BAA08634 GI:1171477, "alpha-mannosidase [Aspergillus saitoi]" Feb. 10, 1999, 1 page.
GenBank Accession No. NP_630514 GI:21224735, "hypothetical protein SCO6428 [Streptomyces coelicolor A3(2)]," Jan. 19, 2012, 3 pages.

(56) References Cited

OTHER PUBLICATIONS

GenBank Accession No. NP_812442 GI:29348939, "alpha-1,2-mannosidase [Bacteroides thetaiotaomicron VPI-5482]" Jan. 20, 2012, 2 pages.

Genbank Accession No. XM_499811 GI:50543289, "Yarrowia lipolytica YALI0A06589p (YALI0A06589g) mRNA, complete cds," Oct. 29, 2008, 2 pages.

GenBank Accession No. XM_500574 GI:50546093, "Yarrowia lipolytica YALI0B06600p (YALI0B06600g) mRNA, complete cds," Oct. 29, 2008, 2 pages.

Genbank Accession No. XM_500811 GI:50546682, "Yarrowia lipolytica YALI0B12716p (YALI0B12716g) mRNA, complete cds," Oct. 29, 2008, 2 pages.

GenBank Accession No. XM_503488 GI:50552026, "Yarrowia lipolytica YALI0E03190p (YALI0E03190g) mRNA, complete cds," Oct. 29, 2008, 2 pages.

GenBank Accession No. YP_003013376 YP_003013376, "alpha-1,2-mannosidase [*Paenibacillus* sp. JDR-2]" Jun. 15, 2012, 3 pages.

GenBank Accession No. YP_003120664 GI:256420011, "alpha-1,2-mannosidase [Chitinophaga pinensis DSM 2588]," Jun. 18, 2012, 2 pages.

GenBank Accession No. YP_003584502 GI:295133826, "alpha-1,2-mannosidase [Zunongwangia profunda SM-A87]," Nov. 21, 2011, 2 pages.

GenBank Accession No. Z49631 GI:1015863, "S.cerevisiae chromosome X reading frame ORF YJR131w," Aug. 11, 1997, 2 pages.

GenBank Accession No. ZP_01061975 GI:86143590, "putative alpha-1,2-mannosidas [Leeuwenhoekiella blandensis MED217]," Nov. 9, 2010, 1 page.

GenBank Accession No. ZP_01885202 GI:149279069, "putative alpha-1,2-mannosidase [*Pedobacter* sp. BAL39]," Nov. 9, 2010, 1 page.

GenBank Accession No. ZP_02866543 GI:169349605, "hypothetical protein CLOSPI_00343 [Clostridium spiroforme DSM 1552]," Nov. 9, 2010, 2 pages.

GenBank Accession No. ZP_03677957 GI: 224537418, "hypothetical protein BACCELL 02296 [Bacteroides cellulosilyticus DSM 14838]," Nov. 10, 2010, 1 page.

GenBank Accession No. ZP_04848482 GI:253571075, "conserved hypothetical protein [*Bacteroides* sp. 1_1_6]" Jun. 9, 2010, 2 pages.

GenBank Accession No. ZP_05522540 GI:256784109, "secreted protein [Streptomyces lividans TK24]," Dec. 9, 2010, 2 pages.

GenBank Accession No. ZP_06527366 GI:289767988, "secreted protein [Streptomyces lividans TK24]" Oct. 26, 2010, 3 pages.

GenBank Accession No. ZP_07083984 GI:300774115, "probable alpha-1,2-mannosidase [Sphingobacterium spiritivorum ATCC 33861]," Dec. 1, 2010, 1 page.

Gentzsch and Tanner, "The PMT gene family: protein O-glycosylation in *Saccharomyces cerevisiae* is vital," *Embo J*, 15(21):5752-5759, (1996).

Gerngross, "Advances in the production of human therapeutic proteins in yeasts and filamentous fungi," *Nature Biotech.*, 22(11):1409-1414, (2004).

Ghaemmaghami et al., "Global analysis of protein expression in yeast." *Nature*. vol. 425, No. 6959 (Oct. 2003) pp. 737-741.

Gonzalez and Jordan, "The alpha-mannosidases: Phylogeny and adaptive diversification," *Mol Biol Evol.*, 17(2):292-300, (Feb. 2000).

Gossen and Bujard, "Studying gene function in eukaryotes by conditional gene inactivation," *Ann. Rev. Genetics* 36:153-173, (2002).

Grinna and Robbins, "Substrate specificities of rat liver microsomal glucosidases which process glycoproteins," *J. Biol. Chem.*, 255(6):2255-2258, (1980).

Guarente et al., "A GAL10-CYC1 hybrid yeast promoter identifies the GAL4 regulatory region as an upstream site," *Proc. Natl. Acad. Sci. USA* 79(23):7410-7414, (1982).

Hamilton and Gerngross, "Glycosylation engineering in yeast: the advent of fully humanized yeast," *Curr Opin Biotechnol.*, 18(5):387-392, (Oct. 2007).

Hamilton et al, "Production of complex human glycoproteins in yeast.," *Science*, 301(5637):1244-1246, Aug. 2003.

Henderson and Finn, "Human tumor antigens are ready to fly," *Advances in Immunology*, 62:217-256 (1996).

Hermans et al., "Human lysosomal alpha-glucosidase: functional characterization of the glycosylation sites," *Biochem J.*, 289 ( Pt 3):681-686, (Feb. 1993).

Hinnen et al. "Transformation of yeast," *Proc. Nat. Acad. Sci. USA* 75(4):1929-1933, (1978).

Howard et al., "Identification of the Active Site Nucleophile in Jack Bean alpha-Mannosidase Using 5-Fluoro-beta-L-Gulosyl Fluoride," *J. Biol. Chem.*, 273(4):2067-2072, 1998.

Hudson and Kortt, "High avidity scFv multimers; diabodies and triabodies," *J. Immunol. Methods*, 231(1-2):177-189, (1999).

Huston et al. "Engineered antibodies takes center stage," *Hum. Antibodies*, 10(3-4):127-142, (2001).

Ichishima et al., "Molecular and enzymic properties of recombinant 1,2-alpha-mannosidase from Aspergillus saitoi overexpressed in Aspergillus oryzae cells," *Biochem. J.*, 339: 589-597, (1999).

Ito et al., "Transformation of intact yeast cells treated with alkali cations," *J. Bacteriol.*, 153(1):163-168, (1983).

Kornfeld and Kornfeld, "Assembly of asparagine-linked oligosaccharides," *Annu Rev Biochem.*, 54:631-664, (1985).

Kotula and Curtis, "Evaluation of foreign gene condon optimization in yeast: expression of a mouse IG kappa chain," *Biotechnology (N Y).*, 9(12):1386-1389, (1991).

Kuroda et al., "Production of Man5GlcNAc2-type sugar chain by the methylotrophic yeast Ogataea minuta," *FEMS Yeast Res.*, 6:1052-1062 (2006).

Laroy et al., "Glycome mapping on DNA sequencing equipment," *Naure Protocols*, 1: 397-405 (2006).

Lee and Park, "Enzymatic in vitro glycosylation using peptide-N-glycosidase F," *Enzyme and Microbial Technology*, 30(6):716-720, (2002).

Liao et al., "Cloning, expression, purification, and characterization of the human broad specificity lysosomal acid alpha-mannosidase," *J. Biol Chem.*, 271(45):28348-28358, (Nov. 1996).

Lobsanov et al., "Modulation of activity by Arg407: structure of a fungal alpha-1,2-mannosidase in complex with a substrate analogue," *Acta Crystallogr D Biol Crystallogr.*, 64(Pt 3):227-236, (2008).

Luer and Hatton, "Vancomycin administration into the cerebrospinal fluid: a review ," *Annals of Pharmacotherapy*, 27:912-921, 1993.

Madzak et al., "Strong hybrid promoters and integrative expression/secretion vectors for quasi-constitutive expression of heterologous proteins in the yeast Yarrowia lipolytica," *J Mol Microbiol Biotechnol.*, 2(2):207-216, (Apr. 2000).

Madzak et al., "Heterologous Protein Expression and Secretion in the Non-conventional Yeast Yarrowia lipolytica: A Review," *J. Biotechnol.*, 109:63-81 (2004).

Maras et al., "Molecular cloning and enzymatic characterization of a Trichoderma reesei 1, 2-alpha-D-mannosidase," *J. Biotechnol*, 77: 255-263 (2000).

Martinet et al., "Protection of mice against a lethal influenza challenge by immunization with yeast-derived recombinant influenza neuraminidase," *Eur J Biochem.*, 247(1):332-338, (Jul. 1997).

Merkle et al., Cloning, expression, purification, and characterization of the murine lysosomal acid alpha-mannosidase, *Biochim Biophys Acta.*, 1336(2):132-146, (Aug. 1997).

Moreau et al. "Cell-free transfer of membrane lipids. Evidence for lipid processing," *J. Biol. Chem*. 266(7):4329-4333, (1991).

Moreau et al. "Trafficking of lipids from the endoplasmic reticulum to the Golgi apparatus in a cell-free system from rat liver," *J. Biol. Chem.*, 266(7):4322-4328 (1991).

Mori et al., "Signalling from endoplasmic reticulum to nucleus: transcription factor with a basic-leucine zipper motif is required for the unfolded protein-response pathway," *Genes Cells*, vol. 1, No. 9 (Sep. 1996), pp. 803-817.

Newman and Ferro-Novick, "Characterization of new mutants in the early part of the yeast secretory pathway isolated by a [3H]mannose suicide selection," *J. Cell Biol.*, 105(4):1587-1594, (1987).

Orlean et al., "Cloning and sequencing of the yeast gene for dolichol phosphate mannose synthase, an essential protein," *J. Biol. Chem.*, vol. 263, (Nov. 1988), pp. 17499-17507.

(56) References Cited

OTHER PUBLICATIONS

Paulik et al., "Cell-free transfer of the vesicular stomatitis virus G protein from an endoplasmic reticulum compartment of baby hamster kidney cells to a rat liver Golgi apparatus compartment for Man8-9 to Man5 processing," *Arch. Biochem. Biophys.*, 367(2):265-273, (1999).
Platt and Lachmann, "Treating lysosomal storage disorders: Current practice and future prospects," *Biochim Biophys Acta*, 1793(4):737-745, 2009.
Poljak, "Production and structure of diabodies," *Structure*, 2(12):1121-1123, (1994).
Protein Data Bank, "Structure of the GH92 Family Glycosylhydrolase CCMAN5" Deposition: Sep. 29, 2010 [retrieved on Jul. 17, 2012]. Retrieved from the Internet: < URL: http://www.pdb.org/pdb/explore/explore.do?structureId=2XSG>, 2 pages.
Rexach and Schekman, "Distinct biochemical requirements for the budding, targeting, and fusion of ER-derived transport vesicles," *J. Cell Biol.*, 114(2):219-229, (1991).
Richard et al., "Tagging morphogenetic genes by insertional mutagenesis in the yeast Yarrowia lipolytica," *J Bacteriol.*, 183(10):3098-3107, (May 2001).
Smith and Waterman, "Comparison of biosequences," *Adv. Appl. Math.*, 2(4):482-489, (Dec. 1981).
Song et al., "Characterization of Genes Involved in N-glycosylation in Yarrowia lipolytica," *Yeast*, 20:S147 (2003).
Song et al., "Engineering of the Yeast Yarrowia lipolytica for the Production of Glycoproteins Lacking the Outer-Chain Mannose Residues of N-Glycans," *Appl Environ Microbiol.*, vol. 73, No. 14 (Jul. 2007), pp. 4446-4454.
Sreekrishna et al., "Invertase gene (SUC2) of *Saccharomyces cerevisiae* as a dominant marker for transformation of Pichia pastoris," *Gene*, 59(1):115-125 (1987).
Stocks, "Intrabodies: production and promise," *Drug Discov. Today* 9(22):960-966, (Nov. 2004).
Tremblay and Herscovics, "Cloning and expression of a specific human alpha 1,2-mannosidase that trims Man9GlcNAc2 to Man8GlcNAc2 isomer B during N-glycan biosynthesis," *Glycobiology.*, 9(10):1073-1078, (Oct. 1999).
UniProtKB/Swiss-Prot: P06280.1 GI:113499, "RecName: Full=Alpha-galactosidase A; AltName: Full=Alpha-D-galactosidase A; AltName: Full=Alpha-D-galactoside galactohydrolase; AltName: Full=Melibiase; AltName: INN=Agalsidase; Flags: Precursor," Jun. 13, 2012, 26 pages.
UniProtKB/Swiss-Prot: P15291.5 GI:116241264, "RecName: Full=Beta-1,4-galactosyltransferase 1; Short=Beta-1,4-GalTase 1; Short=Beta4Gal-T1; Short=b4Gal-T1; AltName: Full=UDP-Gal:beta-GlcNAc beta-1,4-galactosyltransferase 1; AltName: Full=UDP-galactose:beta-N-acetylglucosamine beta-1,4-galactosyltransferase . . . " Jun. 13, 2012, 10 pages.
UniProtKB/Swiss-Prot: P26572.2 GI:311033399, "RecName: Full=Alpha-1,3-mannosyl-glycoprotein 2-beta-N-acetylglucosaminyltransferase; AltName: Full=N-glycosyl-oligosaccharide-glycoprotein N-acetylglucosaminyltransferase I; Short=GNT-I; Short=GlcNAc-T I," Apr. 18, 2012, 6 pages.
UniProtKB/Swiss-Prot: P27809.1 GI:127214, "RecName: Full=Glycolipid 2-alpha-mannosyltransferase; AltName: Full=Alpha-1,2-mannosyltransferase," Jun. 13, 2012, 8 pages.
UniProtKB/Swiss-Prot: P38069.1 GI:586137, "RecName: Full=Alpha-1,2-mannosyltransferase MNN2; AltName: Full=Calcium resistance and vanadate sensitivity protein 4; AltName: Full=Mannan synthesis protein MNN2," Jun. 13, 2012, 5 pages.
UniProtKB/Swiss-Prot: Q09326.1 GI:1169978, "RecName: Full=Alpha-1,6- mannosyl-glycoprotein 2-beta-N-acetylglucosaminyltransferase; AltName: Full=Beta-1,2-N-acetylglucosaminyltransferase II; AltName: Full=GlcNAc-T II; Short=GNT-II; AltName: Full=Mannoside acetylglucosaminyltransferase 2; AltName: Full=N-g . . . ," Jun. 13, 2012, 3 pages.
UniProtKB/Swiss-Prot: Q24451.2 GI:32130434, "RecName: Full=Alpha-mannosidase 2; AltName: Full=Golgi alpha-mannosidase II; Short=AMan II; Short=Man II; AltName: Full=Mannosyl-oligosaccharide 1,3-1,6-alpha-mannosidase," Apr. 18, 2012, 13 pages.
UniProtKB/Swiss-Prot: Q9Y7X5.1 GI:74698597, "RecName: Full=Uncharacterized protein C365.14c," May 16, 2012, 2 pages.
Vandersall-Nairn et al., "Cloning, expressopm. purification, and characterization of the acid α-mannosidase from Trypanosoma cruzi," *Glycobiology*, 8(12):1183-1194, (1998).
Verostek et al., "Glycoprotein biosynthesis in the alg3 *Saccharomyces cerevisiae* mutant. I. Role of glucose in the initial glycosylation of invertase in the endoplasmic reticulum," *The Journal of Biological Chemistry*, vol. 268, (Jun. 5, 1993), pp. 12095-12103.
Verostek et al., "Glycoprotein biosynthesis in the alg3 *Saccharomyces cerevosoae* mutant. II. Structure of novel Man6-10GlcNAc2 processing intermediates on secreted invertase," *The Journal of Biological Chemistry*, vol. 268, pp. 12104-12115, (Jun. 5, 1993).
Vervecken et al. "In Vivo Synthesis of Mammalian-Like, Hybrid-Type N-Glycans in Pichia pastoris," *Appl. Environ. Microb.*, 70(5):2639-2646, (May 2004).
Vocadlo et al., "Mechanistic insights into glycosidase chemistry," *Curr. Opin. Chem Biol.*, 12:539-555 (2008).
Ward et al., "Characterization of Humanized Antibodies Secreted by *Aspergillus niger*," *Appl. Environ. Microbiol.*, 70(5):2567-2576, (May 2004).
Wheeler et al. "Intrabody and Intrakine Strategies for Molecular Therapy," *Mol. Ther.*, 8(3):355-366, (Sep. 2003).
Yang et al., "Cell-surface display of the active mannanase in Yarrowia lipolytica with a novel surface-display system," *Biotechnol Appl Biochem*, vol. 54, No. 3 (Oct. 2009), pp. 171-176.
Yue et al., "Construction of a new plasmid for surface display on cells of Yarrowia lipolytica," *J Microbiol Methods*, vol. 72, No. 2 (Feb. 2008), pp. 116-123.
Zhu and Zhang, "SCPD: a promotor database of the yeast *Saccharomyces cerevisiae*," *Bioinformatics*, 15(7-8):607-611, (1999).
Zhu et al., "Mechanistic insights into a Ca2+-dependent family of alpha-mannosidases in a human gut symbiont," *Nat. Chem. Biol.*, 6(2):125-132. Epub Dec. 27, 2009 (2010).
Zimm et al., "Cerebrospinal fluid pharmacokinetics of intraventricular and intravenous aziridinylbenzoquinone," *Cancer Research*, 44(4):1698-1701, Apr. 1984.
International Search Report and Written Opinion for PCT/IB2011/002770, mailed Mar. 20, 2012, 20 pages.
International Preliminary Report on Patentability for PCT/IB2011/002770, mailed Jan. 22, 2013, 16 pages.
Aravind and Koonin, "The fukutin family—predicted enzymes modifying cell-surface molecules," *Curr Biol.*, 9(22):R836-R837, Nov. 18, 1999.
Bijvoet et al., "Recombinant human acid alpha-glucosidase: high level production in mouse milk, biochemical characteristics, correction of enzyme deficiency in GSDII KO mice," *Hum Mol Genet.*, 7(11):1815-1824, Oct. 1998.
Cardone et al., "Abnormal mannose-6-phosphate receptor trafficking impairs recombinant alpha-glucosidase uptake in Pompe disease fibroblasts," *Pathogenetics*, 1(1):6, Dec. 1, 2008.
Ettinger et al., "Intrathecal methotrexate overdose without neurotoxicity: case report and literature review," *Cancer*, 41 (4):1270-1273, Apr. 1978.
Le Dall et al., "Multiple-copy integration in the yeast Yarrowia lipolytica," *Curr Genet.*, 26(1):38-44, Jul. 1994.
Moreland et al., "Lysosomal acid alpha-glucosidase consists of four different peptides processed from a single chain precursor," *J Biol Chem.*, 280(8):6780-6791, Epub Nov. 1, 2004.
Nakadai et al., "Purification and Properties of Alkaline Proteinase from Aspergillus oryzae," *Agr. Biol. Chem.*, 37(12): 2685-2694, 1973.
Tiels et al., "A bacterial glycosidase enables mannose-6-phosphate modification and improved cellular uptake of yeast-produced recombinant human lysosomal enzymes," *Nat Biotechnol.*, 30(12):1225-1231, Epub Nov. 18, 2012.

(56) References Cited

OTHER PUBLICATIONS

Van Hove et al., "High-level production of recombinant human lysosomal acid alpha-glucosidase in Chinese hamster ovary cells which targets to heart muscle and corrects glycogen accumulation in fibroblasts from patients with Pompe disease," Proc Natl Acad Sci U S A., 93(1):65-70, Jan. 9, 1996.
Zhu et al., "Glycoengineered acid alpha-glucosidase with improved efficacy at correcting the metabolic aberrations and motor function deficits in a mouse model of Pompe disease," Mol Ther., 17(6):954-963, Epub Mar. 10, 2009.
Choi, et al., "Structural analysis of N-linked oligosaccharides assembled on recombinant proteins secreted from Yarrowia lipolytica Yloch1 and Yloch1 Ylmnn4 mutants.," XXIIth International Conference on Yeast Genetics and Molecular Biology, 09—Protein biosynthesis, maturation, modification and degradation, Yeast, 22:S131, 9-35, 2005.
Peberdy et al., "Protein secretion by fungi," Applied Micology and Biotechnology, Agriculture and Food Production, 1:73-114, 2001.
Wu et al., Asparagine-linked glycosylational modifications in yeast, Cell Engineering, 3:215-232, 2002.
De Pourcq et al, "Engineering Yarrowia lipolytica to produce glycoproteins homogeneously modified with the universal Man3GlcNAc2 N-glycan core," PLoS One, 7(6):e39976, 12 pages, Epub Jun. 29, 2012.
Park et al, "Essential role of YlMPO1, a novel Yarrowia lipolytica homologue of Saccharomyces cerevisiae MNN4, in mannosylphosphorylation of N- and O-linked glycans," Appl Environ Microbiol., 77(4):1187-1195, Epub Dec. 23, 2010.
GenBank Accession No. AAO78636, "putative alpha-1,2-mannosidase [Bacteroides thetaiotaomicron VPI-5482]," 1 page, Oct. 24, 2007.
GenBank Accession No. NP_630514, "secreted protein [Streptomyces coelicolor A3(2)]," 2 pages, Sep. 26, 2008.
Jaafar et al., "Isolation of the MNN9 gene of Yarrowia lipolytica (YlMNN9) and phenotype analysis of a mutant ylmnn9 Delta strain," Yeast, 20(7):633-644, May 2003.
"Glycoside Hydrolase Family 38," cazy.org [online] captured Sep. 11, 2010. Retrieved from the Internet: <URL: http://www.cazy.org/GH38.html>, 1 page.
"Glycoside Hydrolase Family 47," cazy.org [online] captured Sep. 12, 2010. Retrieved from the Internet: <URL: http://www.cazy.org/GH47.html>, 1 page.
"Glycoside Hydrolase Family 92," cazy.org [online] captured Sep. 12, 2010. Retrieved from the Internet: <URL: http://www.cazy.org/GH92.html>, 1 page.
Bourbonnais et al., "Production of full-length human pre-elafin, an elastase specific inhibitor, from yeast requires the absence of a functional yapsin 1 (Yps1p) endoprotease," Protein Expr Purif., 20(3):485-491, Dec. 2000.
Cantarel et al., "The Carbohydrate-Active EnZymes database (CAZy): an expert resource for Glycogenomics," Nucleic Acids Res., 37(Database issue):D233-D238, Epub Oct. 5, 2008.
Devos and Valencia, "Practical limits of function prediction," Proteins., 41(1):98-107, Oct. 1, 2000.
Gagnon-Arsenault et al., "Activation mechanism, functional role and shedding glycosylphosphatidylinositol-anchored Yps1p at the Saccharomyces cerevisiae cell surface," Mol Microbiol., 69(4):982-993, Epub Jun. 28, 2008.
Gagnon-Arsenault et al., "Fungal yapsins and cell wall: a unique family of aspartic peptidases for a distinctive cellular function," FEMS Yeast Res., 6(7):966-978, Nov. 2006.
Gatlin et al., "Automated identification of amino acid sequence variations in proteins by HPLC/microspray tandem mass spectrometry," Anal Chem., 72(4):757-763, Feb. 15, 2000.
GenBank Accession No. XP_503768, GI: 50552716, "YALI0E10175p [Yarrowia lipolytica CLIB122]," Oct. 29, 2008, 2 pages.
GenBank, "Yarrowia lipolytica CLIB122 [gbpln]: 5967 CDS's (2945919 codons)," Codon Usage Database, [online], Jun. 15, 2007 [retrieved on Aug. 15, 2014]. Retrieved from the Internet: <URL: http://www.kazusa.or.jp/codon/cgi-bin/showcodon.cgi?species=284591>, 1 page.
Gilbert, "Glycoside Hydrolase Family 92," CAZypedia [online], Mar. 4, 2010. Retrieved from the Internet: <URL: http://www.cazypedia.org/index.php/Glycoside_Hydrolase_Family_92>, 3 pages.
Henrissat, "A classification of glycosyl hydrolases based on amino acid sequence similarities," Biochem J., 280 ( Pt 2):309-316, Dec. 1, 1991.
Komeda et al., "Construction of protease-deficient Candida boidinii strains useful for recombinant protein production: cloning and disruption of proteinase A gene (PEP4) and proteinase B gene (PRBI)," Biosci Biotechnol Biochem., 66(3):628-631, Mar. 2002.
Kuroda et al., "Antibody expression in protease-deficient strains of the methylotrophic yeast Ogataea minuta," FEMS Yeast Res., 7(8):1307-1316. Epub Aug. 22, 2007.
Li et al., "Optimization of humanized IgGs in glycoengineered Pichia pastoris," Nat Biotechnol., 24(2):210-215, Epub Jan. 22, 2006.
Mast and Moremen, "Family 47 alpha-mannosidases in N-glycan processing," Methods Enzymol., 415:31-46, 2006.
Penttilä et al., "Expression of two Trichoderma reesei endoglucanases in the yeast Saccharomyces cerevisiae," Yeast., 3(3):175-185, Sep. 1987.
Potgieter et al., "Production of monoclonal antibodies by glycoengineered Pichia pastoris," J Biotechnol., Feb. 23, 2009;139(4):318-325, Epub Dec. 27, 2008.
Rose, "Glycoside Hydrolase Family 38," CAZypedia [online], Feb. 2, 2010. Retrieved from the Internet: <URL: http://www.cazypedia.org/index.php/Glycoside_Hydrolase_Family_38>, 3 pages.
Swiss Protein Accession No. P15291, Nov. 30, 2010, 9 pages.
Swiss Protein Accession No. P26572, Nov. 30, 2010, 4 pages.
Swiss Protein Accession No. P38069, Nov. 30, 2010, 3 pages.
Swiss Protein Accession No. Q09326, Nov. 30, 2010, 3 pages.
Swiss Protein Accession No. Q24451, Nov. 30, 2010, 12 pages.
van den Elsen et al., "Structure of Golgi alpha-mannosidase II: a target for inhibition of growth and metastasis of cancer cells," EMBO J., 20(12):3008-3017, Jun. 15, 2001.
Whisstock and Lesk, "Prediction of protein function from protein sequence and structure," Q Rev Biophys., 36(3):307-340, Aug. 2003.
YALI0A16819g YALI0A16819p[Yarrowia lipolytica CLIB122] Gene ID: 2906333, created on Jul. 24, 2004, 2 pages.
YALI0C10135g YALI0C10135p[Yarrowia lipolytica CLIB122] Gene ID: 7009445, created on Oct. 29, 2008, 2 pages.
YALI0D10835g YALI0D10835p[Yarrowia lipolytica CLIB122] Gene ID: 2910442, created on Jul. 24, 2004, 2 pages.
YALI0E10175g YALI0E10175p[Yarrowia lipolytica CLIB122] Gene ID: 2912589, created on Jul. 28, 2004, 2 pages.
YALI0E20823g YALI0E20823p[Yarrowia lipolytica CLIB122] Gene ID: 2911836, created on Jul. 28, 2004, 2 pages.
YALI0E22374g YALI0E22374p[Yarrowia lipolytica CLIB122] Gene ID: 2912981, created on Jul. 28, 2004, 2 pages.
YALI0E24981g YALI0E24981p[Yarrowia lipolytica CLIB122 Gene ID: 2912672, created on Jul. 28, 2004, 2 pages.
YALI0E34331g YALI0E34331p[Yarrowia lipolytica CLIB122] Gene ID: 2912367, created on Jul. 28, 2004, 2 pages.
Yao et al., "Degradation of HSA-AX15(R13K) when expressed in Pichia pastoris can be reduced via the disruption of YPS1 gene in this yeast," J Biotechnol., Jan. 15, 2009;139(2):131-136. Epub Oct. 8, 2008.
Abe et al., "In vitro oligosaccharide synthesis using intact yeast cells that display glycosyltransferases at the cell surface through cell wall-anchored protein Pir.," Glycobiology, 13(2):87-95, print Feb. 2003, ePub Nov. 2002.
Ackerman et al., "Highly avid magnetic bead capture: an efficient selection method for de novo protein engineering utilizing yeast surface display," Biotechnol Prog., 25(3):774-783, May-Jun. 2009.
Almeciga et al., "Production of an active recombinant human N-acetylgalactosamine-6-sulfate sulfatase enzyme in Pichia pastoris," Molecular Genetics and Metabolism, 111(2):S19, Abstract 11, Jan. 27, 2014.

(56) References Cited

OTHER PUBLICATIONS

Andrés et al., "Use of the cell wall protein Pir4 as a fusion partner for the expression of Bacillus sp. BP-7 xylanase A in Saccharomyces cerevisiae," Biotechnol Bioeng, 89(6): 690-697, Mar. 2005.
Boder and Wittrup, "Yeast surface display for screening combinatorial polypeptide libraries," Nat. Biotechnol., 15, 553-557, Jun. 1997.
Boder et al. "Directed evolution of antibody fragments with monovalent femtomolar antigen-binding affinity," Proc Natl Acad Sci U S A., 97(20):10701-5, Sep. 2000.
Brady, "Enzyme replacement for lysosmal diseases," Annu. Rev. Med., 57:283-296, 2006.
Brady, "The lipid storage diseases: new concepts and control," Ann Intern Med., 82(2):257-61, Feb. 1975.
Carlson et al., "Function and structure of a prokaryotic formylglycine-generating enzyme," J Biol Chem., 283(29):20117-20125, Epub Apr. 4, 2008.
Chao et al., "Isolating and engineering human antibodies using yeast surface display," Nat. Protoc., 1(2):755-768, 2006.
Chiba et al., "Production of human compatible high mannose-type (Man5GlcNAc2) sugar chains in Saccharomyces cerevisiae," J Biol Chem., 273(41):26298-26304, Oct. 9, 1998.
Cho et al., "Structure of the extracellular region of HER2 alone and in complex with the Herceptin," Nature, 421(6924):756-760, Feb. 2003.
Davidow et al., "Cloning and sequencing of the alkaline extracellular protease gene of Yarrowia lipolytica," J. Bacteriol., 169(10):4621-4629, Oct. 1987.
Dragosits et al., "The effect of temperature on the proteome of recombinant Pichia pastoris," J. Proteome Res., 8(3):1380-1392, Mar. 2009.
Fournier et al., "Scarcity of ars sequences isolated in a morphogenesis mutant of the yeast Yarrowia lipolytica," Yeast, 7(1):25-36, Jan. 1991.
Fujii, "Antibody Affinity Maturation by Random Mutagenesis," Antibody Engineering, vol. 248, pp. 345-359, 2004.
Gasser et al., "Engineering of Pichia pastoris for improved production of antibody fragments," Biotechnol. Bioeng., 94(2):353-361, Jun. 2006.
Grubb et al., "New strategies for enzyme replacement therapy for lysosomal storage diseases," Rejuvenation Res., 13(2-3):229-236, Apr.-Jun. 2010.
Klis et al., "Cell wall construction in Saccharomyces cerevisiae," Yeast, 23(3):185-202, 2006.
Landgrebe et al., "The human SUMF1 gene, required for post-translational sulfatase modification, defines a new gene family which is conserved from pro- to eukaryotes," Gene., 316:47-56, Oct. 16, 2003.
Lin et al., "Display of a functional hetero-oligomeric catalytic antibody on the yeast cell surface," App. Microbiol Biotechol., 62(2-3): 226-232, print Aug. 2003, Epub Mar. 2003.
Matsuoka et al., "Analysis of regions essential for the function of chromosomal replicator sequences from Yarrowia lipolytica," Mol. Gen. Genet., 237(3):327-333, Mar. 1993.
Nicaud et al., "Protein expression and secretion in the yeast Yarrowia lipolytica," FEMS Yeast Res., 2(3):371-379, Aug. 2002.
Pignéde et al., "Characterization of an extracellular lipase encoded by LIP2 in Yarrowia lipolytica," J. Bacteriol., 182(10):2802-10, May 2000.
Rakestraw and Wittrup, "Contrasting secretory processing of simultaneously expressed heterologous proteins in Saccharomyces cerevisiae," Biotechnol. Bioeng., 93(5):896-905, Apr. 2006.
Rodriguez et al., "Production of recombinant human N-acetylgalactosamine-6-sulfate sulfatase enzyme in Pichia pastoris," Molecular Genetics and Metabolism, 108(2):S79-S80, Abstract 197, Feb. 1, 2013.
Ruiz-Herrera and Sentandreu, "Different effectors of dimorphism in Yarrowia lipolytica," Arch. Microbiol., 178(6): 477-483, print Dec. 2002, Epub Oct. 2002.
Ryckaert et al., "Isolation of antigen-binding camelid heavy chain antibody fragments (nanobodies) from an immune library displayed on the surface of Pichia pastoris," J Biotechnol.145(2):93-98 Epub Oct. 2009, print Jan. 2010.
Shusta et al., "Increasing the secretory capacity of Saccharomyces cerevisiae for production of single-chain antibody fragments," Nat. Biotechnol., 16(8): 773-777, Aug. 1998.
Shusta et al., "Yeast polypeptide fusion surface display levels predict thermal stability and soluble secretion efficiency," J. Mol. Biol., 292(5):949-956, Oct. 1999.
Swennen et al., "Secretion of active anti-Ras single-chain Fv antibody by the yeasts Yarrowia lipolytica and Kluyveromyces lactis," Microbiology, 148(Pt 1):41-50, Jan. 2002.
Tajima et al., "Use of a modified alpha-N-acetylgalactosaminidase in the development of enzyme replacement therapy for Fabry disease," Am J Hum Genet., 85(5):569-580 Epub Oct. 22, 2009.
Tanino et al., "Construction of a Pichia pastoris cell-surface display system using Flo1p anchor system," Biotechnol. Prog., 22(4): 989-993, Jul.-Aug. 2006.
Ueda et al., "Cell surface engineering of yeast: construction of arming yeast with biocatalyst," J. Biosci. Bioeng., 90(2): 125-136, 2000.
VanAntwerp and Wittrup, "Fine affinity discrimination by yeast surface display and flow cytometry," Biotechnol. Prog., 16(1): 31-7, Jan.-Feb. 2000.
Vega et al., "Partial characterization of α-mannosidase from Yarrowia lipolytica," J Basic Microbiol., 28(6):371-379, ePub Jan. 10, 2007.
Vernis et al., "An origin of replication and a centromere are both needed to establish a replicative plasmid in the yeast Yarrowia lipolytica," Mol. Cell Biol., 17(4): 1995-2004, Apr. 1997.
Wang and Shusta, "The use of scFv-displaying yeast in mammalian cell surface selections," J. Immunol. Methods, 304(1-2):30-42, Sep. 2005.
Wang et al., "A new yeast display vector permitting free scFv amino termini can augment ligand binding affinities," Protein Eng. Des. Sel., 18(7): 337-343, print Jul. 2005, Epub Jun. 2005.
Wang et al., "Construction of a novel Pichia pastoris cell-surface display system based on the cell wall protein Pir1," Curr. Microbiol., 56(4): 352-357, Apr. 2008.
Yeung and Wittrup, "Quantitative screening of yeast surface-displayed polypeptide libraries by magnetic bead capture," Biotechnol. Prog., 18(2):212-220, Mar.-Apr. 2002.
Ying et al., "Soluble monomeric IgG1 Fc," J Biol Chem., 287(23):19399-19408, Epub Apr. 19, 2012.
Lobsanov et al., "Structure of Penicillium citrinum alpha 1,2-mannosidase reveals the basis for differences in specificity of the endoplasmic reticulum and Golgi class I enzymes," J Biol Chem., 277(7):5620-5630, Epub Nov. 19, 2001.
NCBI Reference Sequence: XP_502492.1, "YALI0D06589p [Yarrowia lipolytica CLIB122]," 2 pages, Oct. 29, 2008.
NCBI Reference Sequence: XP_502939.1, "YALI0D17424p [Yarrowia lipolytica CLIB122]," 2 pages, Oct. 29, 2008.
Nett et al., "A combinatorial genetic library approach to target heterologous glycosylation enzymes to the endoplasmic reticulum or the Golgi apparatus of Pichia pastoris," Yeast., 28(3):237-252, Epub Jan. 6, 2011.
Zhu et al., "Mechanistic insights into a Ca2+-dependent family of alpha-mannosidases in a human gut symbiont," Nat. Chem. Biol., 6(2):125-132. Supplementary Information, 25 pages. Epub 2009 Dec. 27, 2010.

* cited by examiner

FIGURE 1A

ATGAAGCTTTCCACCATCCTCTTCACAGCCTGCGCTACCCTGGCTGCCGCCCAGCAGGGAGCCT
CTCGACCCGGACCCCGAGATGCCCAGGCTCACCCCGGACGACCTCGAGCTGTGCCCACCCAGTGTG
ACGTGCCCCCCAACTCTCGATTCGACTGTGCCCCCGACAAGGCCATCACCCAGGAGCAGTGCGAGG
CCCGAGGCTGTTGTTACATCCCCGCTAAGCAGGGCCTGCAGGGCGCTCAGATGGGCCAGCCCTGGT
GTTTCTTCCCCCCCTCTTACCCCTCCTACAAGCTGGAGAACCTGTCCTCTTCGGAGATGGGCTACAC
CGCCACCCTGACCCGAACCACCCCCACCTTTTTCCCCAAGGACATCCTGACCCTGCGACTGGACGTG
ATGATGGAGACCGAGAACCGACTGCACTTCACCATCAAGGACCCCGCCAACCGACGATACGAGGT
GCCCCTGGAGACCCCCCACGTGCACTCTCGAGCCCCTTCCCCCCTGTACTCTGTGGAGTTCTCTGAG
GAGCCCTTCGGCGTGATCGTGCGACGACAGCTGGACGGCCGAGTGCTGCTGAACACCACCGTGGCC
CCCCTGTTCTTCGCCGACCAGTTCCTGCAGCTGTCTACCTCTCTGCCCTCTCAGTACATCACCGGCCT
GGCCGAGCACCTGTCCCCCCTGATGCTGTCCACCTCTTGGACTCGAATCACCCTGTGGAACCGACA
CCTGGCCCCCACCCCCGGTGCCAACCTGTACGGCTCTCACCCCTTCTACCTGGCCCTGGAGGACGGC
GGCTCTGCCCACGGCGTGTTTCTGCTGAACTCTAACGCCATGGACGTGGTGCTGCAGCCCTCTCCCG
CCCTGTCTTGGCGATCTACCGGCGGCATCCTGGACGTGTACATCTTCCTGGGCCCTGAGCCCAAGTC
TGTGGTCCAGCAGTACCTGGACGTGGTCGGATACCCCTTCATGCCCCCCTACTGGGGCCTGGGCTTC
CACCTGTGTCGATGGGGCTACTCTTCTACCGCCATCACCCGACAGGTGGTGGAGAACATGACCCGA
GCCCACTTCCCCCTGGACGTGCAATGGAACGACCTGGACTACATGGACTCTCGACGAGACTTCACC
TTCAACAAGGACGGCTTCCGAGACTTCCCCGCCATGGTCCAGGAGCTGCACCAGGGAGGACGACG
ATACATGATGATCGTGGACCCCGCCATCTCTTCTTCCGGACCCGCCGGATCTTACCGACCCTACGAC
GAGGGCCTGCGACGAGGCGTGTTCATCACCAACGAGACCGGCCAGCCCCTGATCGGCAAGGTGTG
GCCCGGCTCTACCGCCTTCCCCGACTTCACCAACCCCACCGCCCTGGCTTGGTGGGAGGACATGGT
GGCCGAGTTCCACGACCAGGTGCCCTTCGACGGCATGTGGATCGACATGAACGAGCCCTCTAACTT
CATCCGAGGCTCTGAGGACGGCTGTCCCAACAACGAGCTGGAGAACCCCCCCTACGTGCCCGGCGT
GGTGGGCGGAACCCTGCAGGCCGCCACCATCTGTGCCTCTTCGCACCAGTTTCTGTCTACCCACTAC
AACCTGCACAACCTGTACGGACTGACCGAGGCCATTGCCTCTCACCGAGCCCTGGTGAAGGCCCGA
GGCACCCGACCCTTCGTGATCTCTCGATCTACCTTCGCCGGCCACGGCCGATACGCCGGACACTGG
ACCGGCGATGTGTGGTCCTCTTGGGAGCAGCTGGCCTCTTCTGTGCCCGAGATCCTGCAGTTCAACC
TGCTGGGCGTGCCCCTGGTGGGCGCCGACGTGTGTGGCTTCCTGGGCAACACCTCTGAGGAGCTGT
GTGTTCGATGGACCCAGCTCGGCGCCTTCTACCCTTTCATGCGAAACCACAACTCCCTGCTGTCTCT
GCCCCAGGAGCCCTACTCGTTCTCTGAGCCCGCTCAGCAGGCCATGCGAAAGGCTCTGACCCTGCG
ATACGCCCTGCTGCCCCACCTGTACACCCTGTTCCACCAGGCCCACGTGGCTGGAGAGACCGTGGC
CCGACCCCTGTTCCTGGAGTTCCCTAAGGACTCTTCTACCTGGACCGTGGACCATCAGCTGCTGTGG
GGCGAGGCCCTCCTGATCACCCCCGTGCTGCAGGCCGGCAAGGCTGAGGTGACCGGCTACTTCCCT
CTGGGCACCTGGTACGACCTGCAGACCGTGCCTGTGGAGGCCCTGGGATCTCTGCCCCCTCCTCCCG
CCGCTCCCCGAGAGCCCGCCATCCACTCTGAGGGCCAGTGGGTGACCCTGCCCGCTCCCCTGGACA
CCATCAACGTGCACCTGCGAGCCGGCTACATCATCCCTCTGCAGGGACCCGGCCTGACCACCACCG
AGTCTCGACAGCAGCCCATGGCCCTGGCCGTGGCTCTGACCAAGGGCGGAGAGGCCCGAGGCGAG
CTGTTCTGGGACGATGGCGAGTCTCTGGAGGTGCTGGAGCGAGGCGCCTACACCCAGGTGATCTTT
CTGGCCCGAAACAACACCATCGTGAACGAGCTGGTGCGAGTGACCTCTGAGGGCGCTGGTCTGCAG
CTCCAGAAGGTGACCGTCCTGGGCGTGGCCACCGCTCCCCAGCAGGTCCTGTCTAACGGCGTGCCC
GTGTCTAACTTCACCTACTCTCCCGACACCAAGGTGCTGGACATCTGTGTGTCTCTGCTGATGGGCG
AGCAGTTCCTGGTGTCTTGGTGTTAAC

FIGURE 1B

MKLSTILFTACATLAAAQQGASRPGPRDAQAHPGRPRAVPTQCDVPPNSRFDCAPDK
AITQEQCEARGCCYIPAKQGLQGAQMGQPWCFFPPSYPSYKLENLSSSEMGYTATLTRT
TPTFFPKDILTLRLDVMMETENRLHFTIKDPANRRYEVPLETPHVHSRAPSPLYSVEFSE
EPFGVIVRRQLDGRVLLNTTVAPLFFADQFLQLSTSLPSQYITGLAEHLSPLMLSTSWTR
ITLWNRDLAPTPGANLYGSHPFYLALEDGGSAHGVFLLNSNAMDVVLQPSPALSWRST
GGILDVYIFLGPEPKSVVQQYLDVVGYPFMPPYWGLGFHLCRWGYSSTAITRQVVENM
TRAHFPLDVQWNDLDYMDSRRDFTFNKDGFRDFPAMVQELHQGGRRYMMIVDPAISS
SGPAGSYRPYDEGLRRGVFITNETGQPLIGKVWPGSTAFPDFTNPTALAWWEDMVAEF
HDQVPFDGMWIDMNEPSNFIRGSEDGCPNNELENPPYVPGVVGGTLQAATICASSHQF
LSTHYNLHNLYGLTEAIASHRALVKARGTRPFVISRSTFAGHGRYAGHWTGDVWSSWE
QLASSVPEILQFNLLGVPLVGADVCGFLGNTSEELCVRWTQLGAFYPFMRNHNSLLSLP
QEPYSFSEPAQQAMRKALTLRYALLPHLYTLFHQAHVAGETVARPLFLEFPKDSSTWT
VDHQLLWGEALLITPVLQAGKAEVTGYFPLGTWYDLQTVPVEALGSLPPPPAAPREPAI
HSEGQWVTLPAPLDTINVHLRAGYIIPLQGPGLTTTESRQQPMALAVALTKGGEARGEL
FWDDGESLEVLERGAYTQVIFLARNNTIVNELVRVTSEGAGLQLQKVTVLGVATAPQQ
VLSNGVPVSNFTYSPDTKVLDICVSLLMGEQFLVSWC*

FIGURE 3A atgtattcgcacttcaacaacgagcctgtggcgaagcgggtgaacaacctgtttaccgaccgacttcgccagttcaccagcgac
ggcgaataccggtctctcaacctgccagcttctacgagcgagaacgactggatggcaagaaccatgtggcgattgaaacgtat
gccgtttcagatctacgacggccactgttcaaagacgccctcaaagaggcagatggccactggaaaccagcaaagaagggct
ccgagtacggaccttcctgggccactcactggttcaagatccaggtctgtgtgccccagagtggaagaagaactactacaaaa
agggcgacctggtggtgttcaattggaatctcaactgtgagggtctcgtgttcagcgagtctggagaagctcttattggtttatccg
gcgaggaacgacgagaatggcccattcccgacaactggttcgacggaaagtgccataccttttacattgaggccagttgcaatg
gcatgttcggcaacgcaacgggatcttccatccagcccccagcgacaacagatatttcagactggactctgcagacctcgttgt
catcaactccgaggcccgacatctctttgtggattttggattatcggagatgcggcccgggagttcccaggggattcgtggcaac
gtggaaaggcactagatgtcgctaacaagatcatggatgcctttgatcctgaaaacccagatgagagtatcgccgagggccgaa
aacttgccaaggaatacctcggagatactacaaaggcctacaagcaacagctaccattcgctgatggcctagtttacgcactcgg
taactgccacatcgataccgcgtggctatgccctttgctgagactcgtcgaaaggcaggtcgatcttgggcttctcaacttgagc
tcatcgacaagtaccccgagtacgtgtttgtggcttccaggcccagcagttcaagtggctcaaggaagactaccccgacttgttt
gccaagattcaaaagcaggctaagaagggccgcttccttcctgtcggaggcgcctggaccgagtgtgacactaacctgccctct
ggagagtctctcctgcgccagttcctgcttggtcagcgattcttcctcgaacactttggctcccttctgacacttctggctgcctga
cactttcggatactctgctcaggttcctcagctgtgtcgattggctggcatggaccgtttcttgacccagaagttgtcctggaataac
atcaactcgttccccaattcaacatttaattgggtggctctggatggctcgcaggtgctctgtcacatgccacccaacaacacctac
acttctatggccaactttggtgacgtctcacgaactcagaaacagaacaagaatcttgacaccactcgaaactccctcatgctctat
ggccacggagacggaggaggaggcccccactgctgagatgctggagaagctgcgtcgatgccgaggtgtgtccaacaccgtc
ggggaacttcctcctgtaatccagggacaatctgtgaccgacttctacaatgagcttcttgatcagactaacaacggcaaggatct
cgtaacctgggtcggggagctgtactttgagttccaccgtggtacctacaccagtcaagcccagactaaaaagggtaaccgagt
gtcggagaacctgctacacgatgtcgagttgttggccactctggccagtattcgagactcatcttacaagtaccccttgcacagct
tgagtctctctgggaggatgtgtgtctttgccagttccatgatgttcttcctggatcatgcattgagatggtctacaaggatgttaaaa
agatccatggacgggttattgatactgcttcccacctcattgataaagccgcttctgccttgggtcttctggtcaccctccaagga
ctccttcgactgcactcctgttgctctcaacaccatgccttggtcgcgaaccgaggtcgtcgctgttccccagccacattgggatg
ccaccgtggagcttgctgagggtgtcgagatccaagaagactcgggcaatgccctcgtcatgatgtctgaatctggacctgttgt
caccactcaatctgtagacttgttcaagtctgaagacgcctacatccttgagaatagccaggtcaaggtgacgatttgcaaggatg
atggtaccctcaccagcatttacgacaaagagaatgaccgtcgggtcctgtctggaacaggtaaccgactggtattgttcgacga
ccagccgttgtcgtggcaggcttgggacactgaggtgttttctcttggtaagaagcagtacattggtgccgagaatgtgactcgtc
attccatcgtctcttctgccctctgcgatcaactgtcgccttcacttacgaattcaacaaatctgttgtcacaaccgagatttctctcg
acgctaactcgcctctggtaacttttaacaccgtgccgactggcatgaaacttgcaagtttctaaaggtggaatttcctgtggacg
tccacagtgagtctgcttcgtacgagtctcagtttggtgttgttaagcgcccactcattacaacacctcttgggacgtggccaagtt
tgaggtatgctgccacaagtttgcggatctgtccgaactcgactacgcgtgtccatcttgaatgactgcaagtatggattcgcca
cccatggtaatctcatgcgactgtcgctgctgcgggcccctaaggctcccgacgctcatgctgatatgggtcatcatgagttcaag
tacggagtccttgctcacaagggaccccttggtgctacaactgttcgggccgcttacaacttcaacaaccctcttcgggtcaagta
tgtgggtctctctgaagtttccaccaagcaggcctttctctcaaaggccctgcgaatctggtgctcagccaggttaagagggccg
aagttgaccgatctaagaagtccaccaatgtcatcttgcgagtttacgaggctctcggaggccgaactcgaggcaaactcgttat
cgacttgcccaacgtggtgtctgtgaccaagacctgtgctctggagtacccaaggagaaacaggttgttgccaagagcgaggg
tgtcacttctgtagacatttctctacgtgcttttgaggttgccacctacaaggttgagttggctcatcatcaccatcaccactag

FIGURE 3B atgcatcatcaccatcaccactattcgcacttcaacaacgagcctgtggcgaagcgggtgaacaacctgtttaccgaccgactte
gccagttcaccagcgacggcgaataccggtctctcaacctgccagctttctacgagcgagaacgactggatggcaagaaccat
gtggcgattgaaacgtatgccgtttcagatctacgacggccactgttcaaagacgccctcaaagaggcagatggccactggaaa
ccagcaaagaagggctccgagtacggaccttcctgggccactcactggttcaagatccaggtctgtgtgcccccagagtggaa
gaagaactactacaaaaagggcgacctggtggtgttcaattggaatctcaactgtgagggtctcgtgttcagcgagtctggagaa
gctcttattggtttatccggcgaggaacgacgagaatggccattcccgacaactggttcgacggaaagtgccatacctttacatt
gaggccagttgcaatggcatgttcggcaacgcaacgggatcttccatccagccccccagcgacaacagatatttcagactggac
tctgcagacctcgttgtcatcaactccgaggcccgacatctctttgtggattttggattatcggagatgcggcccgggagttccca
ggggattcgtggcaacgtggaaaggcactagatgtcgctaacaagatcatggatgcctttgatcctgaaaacccagatgagagt
atcgccgagggccgaaaacttgccaaggaatacctcggagatactacaaaggcctacaagcaacagctaccattcgctgatgg
cctagtttacgcactcggtaactgccacatcgataccgcgtggctatggcccttttgctgagactcgtcgaaaggcaggtcgatctt
gggcttctcaacttgagctcatcgacaagtaccccgagtacgtgtttgtggcttcccaggcccagcagttcaagtggctcaagga
agactaccccgacttgtttgccaagattcaaaagcaggctaagaagggccgcttccttcctgtcggaggcgcctggaccgagtg
tgacactaacctgccctctggagagtctctcctgcgccagttcctgcttggtcagcgattcttcctgaacactttggctcccttctg
acacttctggctgcctgacacttcggatactctgctcaggttcctcagctgtgtcgattggctggcatggaccgtttcttgaccca
gaagttgtcctggaataacatcaactcgttccccaattcaacatttaattgggtggctctgatggctcgcaggtgctctgtcacatg
ccacccaacaacacctacacttctatggccaactttggtgacgtctcacgaactcagaaacagaacaagaatcttgacaccactc
gaaactccctcatgctctatgccacggagacggaggaggaggcccccactgctgagatgctggagaagctgcgtcgatgccg
aggtgtgtccaacaccgtcggggaacttcctcctgtaatccaggggacaatctgtgaccgacttctacaatgagcttcttgatcaga
ctaacaacggcaaggatctcgtaacctgggtcggggagctgtactttgagttccaccgtggtacctacaccagtcaagcccaga
ctaaaagggtaaccgagtgtcggagaacctgctacacgatgtcgagttgttggccactctggccagtattcgagactcatcttac
aagtacccccttgcacagcttgagtctctctgggaggatgtgtgtctttgccagttccatgatgttcttcctggatcatgcattgagat
ggtctacaaggatgttaaaaagatccatggacgggttattgatactgcttcccacctcattgataaagccgcttctgccttgggtcttt
ctggtcacccttccaaggactccttcgactgcactcctgttgctctcaacaccatgccttggtcgcgaaccgaggtcgtcgctgttc
cccagccacattgggatgccaccgtggagcttgctgagggtgtcgagatccaagaagactcgggcaatgccctcgtcatgatgt
ctgaatctggacctgttgtcaccactcaatctgtagacttgttcaagtctgaagacgcctacatccttgagaatagccaggtcaagg
tgacgatttgcaaggatgatggtaccctcaccagcatttacgacaaagagaatgaccgtcgggtcctgtctgtggaacaggtaacc
gactggtattgttcgacgaccagccgttgtcgtggcaggcttgggacactgaggtgttttctcttggtaagaagcagtacattggtg
ccgagaatgtgactcgtcattccatcgtctcttctggccctctgcgatcaactgtcgccttcacttacgaattcaacaaatctgttgtc
acaaccgagatttctctcgacgctaactcgcctctggtaactttttaacacccgtgccgactggcatgaaactgcaagtttctaaag
gtggaatttcctgtggacgtccacagtgagtctgcttcgtacgagtctcagttggtgttgttaagcgcccccactcattacaacacct
cttgggacgtggccaagtttgaggtatgctgccacaagtttgcggatctgtccgaactcgactacggcgtgtccatcttgaatgac
tgcaagtatggattcgccacccatggtaatctcatgcgactgtcgctgctgcgggccccctaaggctcccgacgctcatgctgatat
gggtcatcatgagttcaagtacggagtccttgctcacaagggacccctggtgctacaactgttcggggccgcttacaacttcaaca
acccctcttcggggtcaagtatgtgggtctctctgaagtttccaccaagcaggcctttctctcaaaggccctgcgaatctggtgctca
gccaggttaagagggccgaagttgaccgatctaagaagtccaccaatgtcatcttgcgagtttacgaggctctcggaggccgaa
ctcgaggcaaactcgttatcgacttgcccaacgtggtgtctgtgaccaagacctgtgctctggagtactccaaggagaaacaggt
tgttgccaagagcgagggtgtcacttctgtagacattctctacgtgcttttgaggttgccacctacaaggttgagttggcttag

FIGURE 3C

```
MYSHFNNEPVAKRVNNLFTDRLRQFTSDGEYRSLNLPAFYERERLDGKNHVAIETYAVSD
LRRPLFKDALKEADGHWKPAKKGSEYGPSWATHWFKIQVCVPPEWKKNYYKKGDLVVFNW
NLNCEGLVFSESGEALIGLSGEERREWPIPDNWFDGKCHTFYIEASCNGMFGNATGSSIQ
PPSDNRYFRLDSADLVVINSEARHLFVDFWIIGDAAREFPGDSWQRGKALDVANKIMDAF
DPENPDESIAEGRKLAKEYLGDTTKAYKQQLPFADGLVYALGNCHIDTAWLWPFAETRRK
AGRSWASQLELIDKYPEYVFVASQAQQFKWLKEDYPDLFAKIQKQAKKGRFLPVGGAWTE
CDTNLPSGESLLRQFLLGQRFFLEHFGSLSDTFWLPDTFGYSAQVPQLCRLAGMDRFLTQ
KLSWNNINSFPNSTFNWVALDGSQVLCHMPPNNTYTSMANFGDVSRTQKQNKNLDTTRNS
LMLYGHGDGGGGPTAEMLEKLRRCRGVSNTVGELPPVIQGQSVTDFYNELLDQTNNGKDL
VTWVGELYFEFHRGTYTSQAQTKKGNRVSENLLHDVELLATLASIRDSSYKYPFAQLESL
WEDVCLCQFHDVLPGSCIEMVYKDVKKIHGRVIDTASHLIDKAASALGLSGHPSKDSFDC
TPVALNTMPWSRTEVVAVPQPHWDATVELAEGVEIQEDSGNALVMMSESGPVVTTQSVDL
FKSEDAYILENSQVKVTICKDDGTLTSIYDKENDRRVLSGTGNRLVLFDDQPLSWQAWDT
EVFSLGKKQYIGAENVTRHSIVSSGPLRSTVAFTYEFNKSVVTTEISLDANSPLVTFNTR
ADWHETCKFLKVEFPVDVHSESASYESQFGVVKRPTHYNTSWDVAKFEVCCHKFADLSEL
DYGVSILNDCKYGFATHGNLMRLSLLRAPKAPDAHADMGHHEFKYGVLAHKGPLGATTVR
AAYNFNNPLRVKYVGLSEVSTKQAFSLKGPANLVLSQVKRAEVDRSKKSTNVILRVYEAL
GGRTRGKLVIDLPNVVSVTKTCALEYSKEKQVVAKSEGVTSVDISLRAFEVATYKVELA
```

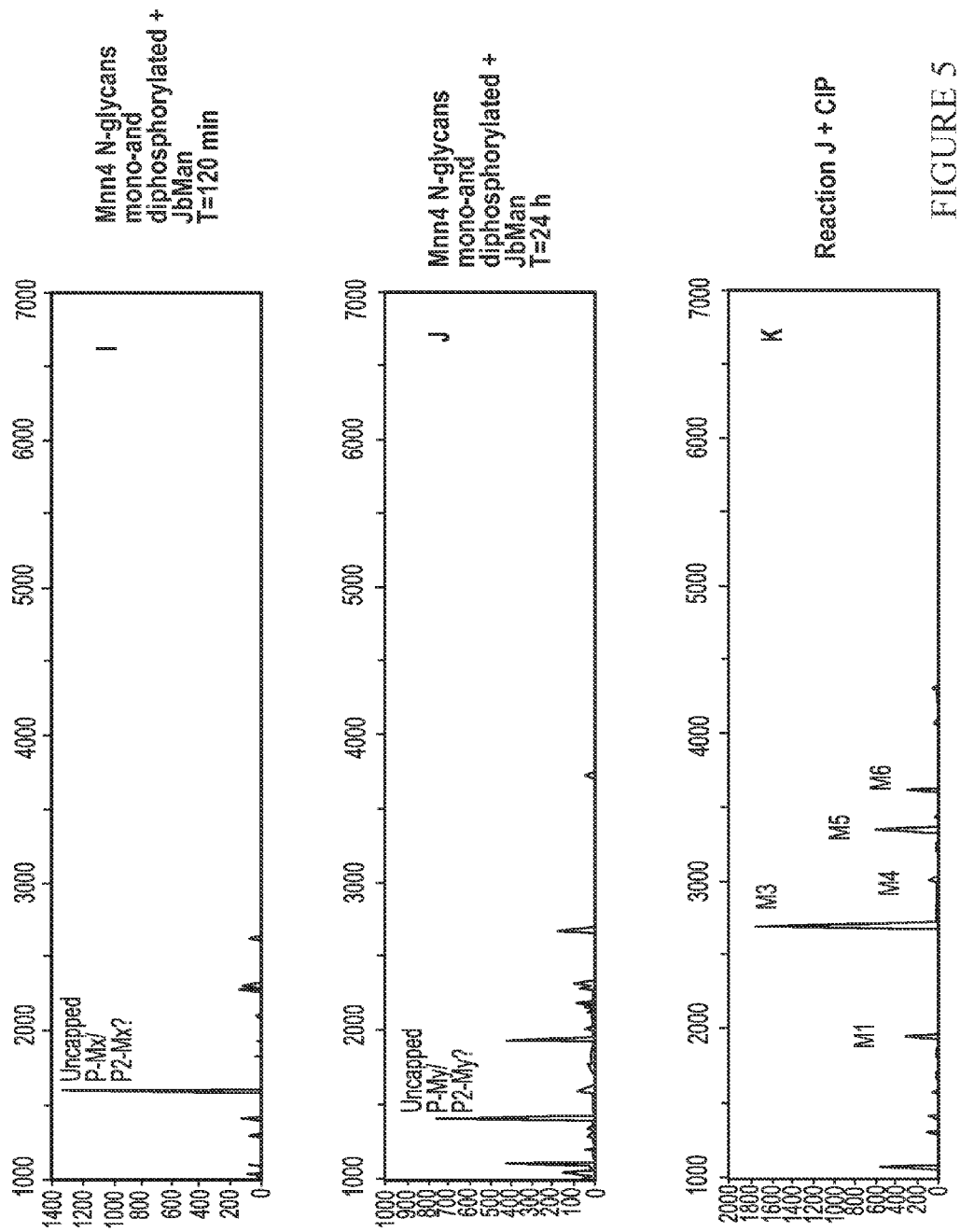

FIGURE 8A

>DsbA-6xHis-CcMan5 (107bp - 5167bp, direct) 5061bp From pLSAHCcMan5
ATGAAAAAGATTTGGCTGGCGCTGGCTGGTTTAGTTTTAGCGTTTAGCGCATCGGCCGG
CCATCACCATCATCACCACGTGGGGCCCGGCTCGGACGAAGTGGATGCACCGGAACCTC
CGAGCGCAGATTATGCAAGCCTGGTTGATGTTTTTGTTGGCACCGAAGGTGATTTTGGT
AATGATATGCCTGCAGCACAGGCACCGAATGGTCTGGCAAAAGTTAATCCGCGTACCAC
ACCGGGTCGTAATAATACCGGTTATGATTATGCCCAGAGCAAAATTAGCGGTTTTACCC
ATACCAATCTGGATGGTGTTGGTGGTAGCGGTGGTGGTGGTGATCTGCTGGTTGTTCCG
ACCAGCGGTAGCTATACCGCACGTCCGGGTACAGGCACCTATGCACATCCGTTTAGCCA
TGATGATGAAGATGCAGGTCCGGGTTTTTATAGCGTTGGTCTGGGTAATGTTGCAGGCA
CCGATGGTGCAATTACCGGTGCTCCGGGTACAATTGAAGCAGAAGTTGCAGCAGCAACC
CGTAGCGGTGTTCATCGTTATGCATTTCCGGCAGGTAGCACCCCGAGCCTGGTTGTTGA
TCTGGAAACCAATAATACCAGCCGTCGTAGCAGCAGCGTTCAGGTTGAAACCCGTGCAG
ATGGCACCGTTGAACTGAGCGGTCAGGTTACCGGCTATTTTTATAATGCAGCCTATACC
CTGTATTATACCGCACGCACCCTGCAGCCTGCAACCGTTCAGACCTGGGGTGATGATGA
TCGTCTGGTTGATGCAACCGCACAGGATGGTGTTGATACCGGTGCAATTCTGACCTTTG
ATCCGGCAGATGCCGGTGAAATTGGTCTGCAGGTTACCCTGTCTCCGGTTAGCGTTGAA
CAGGCACGTATTGATCAGCAGGTTGAACTGGGTGATCTGAGCTTTGATGCAATTCGTGA
TCGTACCCGTGCAGAATGGAATGCAACCCTGGGTCGTGTTGCAATTGATGCAAGCACCG
CAACCGATCCGACCGGTGAACTGCAGCGTCTGTTTTATACCCATCTGTATCGCATGTTT
GCAATGCCGATGAATGCAACCAGCACCAGCGGCACCTATCGTGGTGTTGATGGTGCAGT
TCATGCAGCACAGGGCTTTACCTATTATGATAGCTGGGCAACCTGGGATGATTTTCGCA
AATTTAGCGTGATTGCCTATATTGATCCGGCACTGTATCGTGATATGGTTCAGAGCCTG
GTTTACCTGTTTGCAGATGCAGAAGCAACCGGTACAGGCGGTGGTCTGGGTGGTTTTGT
TCATAGCGTTCCGACCGTTCGTTGGGAACGTAGCAGCGTTGTTGTTGCAGATGCAATTG
CCAAAGGCTTTGATGGTTTTGATCGTCTGGATGAAGCATATCCGGCACTGCAGCGCCTG
GTTGGTCAGTATAGCGCAGATGAACTGCGTCGTGGTTATGTTGCAGGTAATCCGGGTGC
AAGCGTTCAGCGTGGTTATGATCAGTATGGTCTGAGCGTTATTGCCGATGAACTGGGTC
TGACCGAAGAAGCAGAAACCCTGCGCGAACAGGCAAGCTGGCCGATTGAAAAACTGACC
AAACCGGGTGCATGGACCGCAGCAGATGGTACACAGGTTGGTCTGCTGACACCGCGTGC
AGCCGATGGTAGCTGGCAGAGCGCAGATCATGCCAAATTTGAAGCAGCAGGTCTGTATC
AGGGCACCCTGTGGCAGTATCATTGGTATGATGCCTATGATATGGATGCACTGGTTGAA
GCAATGGGTGGTCATGAAGCAGCCCGTCTGGGTATGCGTCATATGTTTGGTGAACATGC
ACCGGATGATGGTAAAGCAATGCTGCATAGCAATGCCAATGAAATTGATCTGCAGGCAC
CGTACCTGTTTAATTATACCGGTGAACCGAGCCTGACCCAGAAATGGGCACGTGCAATT
TATACCAAAGAAACCTGGAATCGCTATATTGCAACCGGTAGCAGCTCTGCAGTTCCGTC
AGGTGGTGGTGAATTTACACCTCCGCTGAAAACCAAAGTTTATCGTCTGGACCCTCGTG
GTATGCTGCCGACCATGGATAATGATGCAGGTACAATGAGCACCATGTTTGTTGCAGCA
GCCGTTGGTCTGTTTCCGGTTACCGCAGGTAGCAGCCAGTTTCAGGTTGGTAGCCCGTT
TTTTGATAGCACCACCATTACCTATGATGATGGTAGCGCATTTACCGTTACCGCAGATG
GTGTTAGCGAAGATGCCTTTTATGTTCAGAGCGCAACCCTGGATGGTGCAACCTTTGGT
AATACCTGGGTTGATTATGCAACCGTTGTTGGTGGTGCAGATCTGGCATTTCGTATGGG
TGAACAGCCGAGCGATTGGGGCACCGATACCGCACCGGCATTTAGCATGAGCACCGCCA

FIGURE 8A (CONTINUED)

```
CCGATGAACCGGCAGAAGGTCCTCGCGTTAGCGCAGAACCGACCACCGTGCAGACCGGT
GATGGTGGTGCACTGGATGCAACCGTTACCCTGACACTGGATGGCGCACGTCTGGCAGC
ACCGGCAGGTACAGATCTGGTTACCAGCGGTGCAGCAAGCGTTGTTGGTCTGCCGGATG
GTGTTACCGCAGCAGTTACCGTTGCAAGCCCGACCGCACTGACCGTTAGCCTGACCGGC
ACCGCATCAGCAGATGCACGTTTTTTGTGCATCTGCGTGATGCAGCACTGGCCGATGG
TGTTGCAGCCGCAAGCCTGCAGGGTCAGGGTGTTAGCGTTCGTTCTCCGCTGCGTCTGA
GCGTTGCAAGCGCAGAACGTGATGCACTGGCAGCACTGGTTGATGATGCCGTTCTGGTT
CGTCATGGTAATTATAGCAGCGTTACCTTTGATCGTTTAGCACCGCTCTGACAAAAGCA
CAGGAAGCACTGGGCGACGAAGCAGCAACCAGCATTGCACTGCGTTTTGCAGCAGATCG
TCTGGGTGCAGCAGCAGATGCACTGGATCTGACCGGTGGTGGTTATCGTACCCTGGAAG
CAGAACAGAGCGAAGCATGGTCTGGTGGTGAACTGAAAAATGAAGCCAATAGCAGCAGC
GGTAATCTGGGTGGTGTTCGTAGCGGTAGCTGGGTTCAGTATCGCGATATGACCTTTGA
AACCGCAGCCGGTGATACACCTCCGCGTTTTCTGACCGTTCGTTATGATACCAGCTTTG
CACCGACCGATACCCCGAGCACCGTTCGTGTTCATGCCGGTGATGTTTCTGGTCCGGTT
GTTGCAACCGTTGATCTGAAAGGCACCAGCGGTTGGGGTAAATATACCGAAGTTACCGC
AGAACTGGGTGATGTTCAGGCCCTGGTTGATGCCCAGGTTGTTACCTTTGAACTGCTGG
CACCGAGCGGTCGTAGCTGGGTTGGTAATTTTGATTGGTTTCGCTTTAGCGCAGAAGAT
CCGGCAGCACCGGGTCAGCCTGGTGAAAGCCCGACCGTTACCATTGAAGCCGAAGATTG
GACCGCAAGCAGCGGTCGTGGTCTGAAAAAAGAAAGCAGCACCTGGACCAGCGGTCCGG
TGACCAATGTTGGTGGTACAGCAGATGGTGATTGGATTGCCTATGGTGAAGTTGATCTG
GGTGAACTGCCGCTGGGCGAACTGAGCCGTTCATTATGTGCATAATAGCAATCGCAGCCG
TAATAATAGCGCACTGAGCCGTTTATCTGGATGCATTTCATCCGGCTAATCCGGCTGAAC
CGTTTGTTACCGTTCCGCTGCCGACCACCGGTAGCAGTTGGACCGCAGATGGCACAGCC
ACCGTTGTTCTGCCGGAAACCGTGCAGGGCACCCATGAAGTTTTTGTTCGTCTGAGCAC
CGAACCGTATGCAGATCATCCGTATGTTGCAAATCTGGATAGCCTGACCTTTGCACCGG
GTGGTCCGACCAGCGTTGTGGTTGAAAGCGAAGCCTGGACCAGCAATTCTGGTCGTGGC
CTGAAAAATGAATCTTCTACCTGGACCTCTGGTCCGGTTACAAATGTGGGTGGCACCGC
TGATGGCGATTGGCTGGCATATGGCGAAATTGATCTGGGCAGCGCAGCACTGGATCAGC
TGTCTGTGCATTATGTTCATAATTCTAATCGCTCTGGTCGTAATTCTGCACTGTCTGTG
TATCTGGATGCCTTTGATCCGGCAAATCCGGGTGAACCGTTTGTGACAGTGCCGCTGGC
AAATACCGGTAGCTCTTGGACCACCGATGGTACTGCAGTTGTGGATCTGCCGTCTACCG
TTCGTGGTAAACATCAGGTTTGGGTTCGTCTGTCTACCGAAGCATATGCCGATCATCCG
TATGTGGCCAATCTGGATTCTATGCCCTTTTTTACCGATGCATATGATGTTGAAGTTCC
TCCGACCGATACAGCAGCACTGGCAGCCGTTGTTGATCCAGCAGGTACACCGGAAGCAG
AAATTGCACGTTATGGTCGTATTGATGCCCGTGTTTTTACCCGTGAACTGGCAGCAGCA
CGTAGCGTTCTGGCCGATGCCGGTGCAACACAGGCACAGGCAGATGAACGTGCTCGTCG
TCTGGGTCTGGCAACCGATCAGCTGGTTCCGGCAGAACGTCGTCGTCTGGAAAATCTGG
TTGCCAGCGCAGAAGCACTGACCGACGAAGGTTATTCTCCGGAAAGCTGGCAGGCATTT
CGTACCGCACTGGCTGCTGCAACCGGCACCCTGGATGATGCAGCAGCATCTGATGAAGC
ACTGCATGATGCACGTCTGGCGCTGCAGGGTGCAGTTGATGCACTGGAAGAACCGGCAG
ATGTTGTTCTGGTTGAAGTTGAAGTTTCTCCGCGTTGTCTGGCAGGTAAACCGTATGTT
GCCGTTCGTGCAGTTAATGTTTCTGATGCAGCCGTTGATGTTGAACTGGCAAGCTCTCT
GGGCACCCGTAGCTTTGTTGGTGTGGCACCGGGTGCGAGCGCATATCAGAGCTTTGCAG
CCCGTAGCGCAACCGGTGATCTGGATGTTACCGTGACCGCAACCGGTGCAGATGGTACT
CAGACCGTTGAACAGGTTGTGACCGTTCCGAGCTGTAGCTAATAA
```

FIGURE 8B

ALAVVGLAPATAASAAPEPPSADYASLVDVFVGTEGDFGNDMPAAQAPNGLAKVNPRTT
PGRNNTGYDYAQSKISGFTHTNLDGVGGSGGGGDLLVVPTSGSYTARPGTGTYAHPFSH
DDEDAGPGFYSVGLGNVAGTDGAITGAPGTIEAEVAAATRSGVHRYAFPAGSTPSLVVD
LETNNTSRRSSSVQVETRADGTVELSGQVTGYFYNAAYTLYYTARTLQPATVQTWGDDD
RLVDATAQDGVDTGAILTFDPADAGEIGLQVTLSPVSVEQARIDQQVELGDLSFDAIRD
RTRAEWNATLGRVAIDASTATDPTGELQRLFYTHLYRMFAMPMNATSTSGTYRGVDGAV
HAAQGFTYYDSWATWDDFRKFSVIAYIDPALYRDMVQSLVYLFADAEATGTGGGLGGFV
HSVPTVRWERSSVVVADAIAKGFDGFDRLDEAYPALQRLVGQYSADELRRGYVAGNPGA
SVQRGYDQYGLSVIADELGLTEEAETLREQASWPIEKLTKPGAWTAADGTQVGLLTPRA
ADGSWQSADHAKFEAAGLYQGTLWQYHWYDAYDMDALVEAMGGHEAARLGMRHMFGEHA
PDDGKAMLHSNANEIDLQAPYLFNYTGEPSLTQKWARAIYTKETWNRYIATGSSSAVPS
GGGEFTPPLKTKVYRLDPRGMLPTMDNDAGTMSTMFVAAAVGLFPVTAGSSQFQVGSPF
FDSTTITYDDGSAFTVTADGVSEDAFYVQSATLDGATFGNTWVDYATVVGGADLAFRMG
EQPSDWGTDTAPAFSMSTATDEPAEGPRVSAEPTTVQTGDGGALDATVTLTLDGARLAA
PAGTDLVTSGAASVVGLPDGVTAAVTVASPTALTVSLTGTASADARFFVHLRDAALADG
VAAASLQGQGVSVRSPLRLSVASAERDALAALVDDAVLVRHGNYSSVTFDRFSTALTKA
QEALGDEAATSIALRFAADRLGAAADALDLTGGGYRTLEAEQSEAWSGGELKNEANSSS
GNLGGVRSGSWVQYRDMTFETAAGDTPPRFLTVRYDTSFAPTDTPSTVRVHAGDVSGPV
VATVDLKGTSGWGKYTEVTAELGDVQALVDAQVVTFELLAPSGRSWVGNFDWFRFSAED
PAAPGQPGESPTVTIEAEDWTASSGRGLKKESSTWTSGPVTNVGGTADGDWIAYGEVDL
GELPLGELSVHYVHNSNRSGNNSALSVYLDAFDPANPGEPFVTVPLPTTGSSWTADGTA
TVVLPETVQGTHEVFVRLSTEPYADHPYVANLDSLTFAPGGPTSVVVESEAWTSNSGRG
LKNESSTWTSGPVTNVGGTADGDWLAYGEIDLGSAALDQLSVHYVHNSNRSGRNSALSV
YLDAFDPANPGEPFVTVPLANTGSSWTTDGTAVVDLPSTVRGKHQVWVRLSTEAYADHP
YVANLDSMRFFTDAYDVEVPPTDTAALAAVVDAAGTPEAEIARYGRIDARVFTRELAAA
RSVLADAGATQAQADERARRLGLATDQLVPAERRRLENLVASAEALTDEGYSPESWQAF
RTALAAATGTLDDAAASDEALHDARLALQGAVDALEEPADVVLVEVEVSPRCLAGKPYV
AVRAVNVSDAAVDVELASSLGTRSFVGVAPGASAYQSFAARSATGDLDVTVTATGADGT
QTVEQVVTVPSCS (SEQ ID NO: 7)

FIGURE 8C

```
APEPPSADYASLVDVFVGTEGDFGNDMPAAQAPNGLAKVNPRTTPGRNNTGYDYAQSKISGF
THTNLDGVGGSGGGGDLLVVPTSGSYTARPGTGTYAHPFSHDDEDAGPGFYSVGLGNVAGTD
GAITGAPGTIEAEVAAATRSGVHRYAFPAGSTPSLVVDLETNNTSRRSSSVQVETRADGTVE
LSGQVTGYFYNAAYTLYYTARTLQPATVQTWGDDDRLVDATAQDGVDTGAILTFDPADAGEI
GLQVTLSPVSVEQARIDQQVELGDLSFDAIRDRTRAEWNATLGRVAIDASTATDPTGELQRL
FYTHLYRMFAMPMNATSTSGTYRGVDGAVHAAQGFTYYDSWATWDDFRKFSVIAYIDPALYR
DMVQSLVYLFADAEATGTGGGLGGFVHSVPTVRWERSSVVVADAIAKGFDGFDRLDEAYPAL
QRLVGQYSADELRRGYVAGNPGASVQRGYDQYGLSVIADELGLTEEAETLREQASWPIEKLT
KPGAWTAADGTQVGLLTPRAADGSWQSADHAKFEAAGLYQGTLWQYHWYDAYDMDALVEAMG
GHEAARLGMRHMFGEHAPDDGKAMLHSNANEIDLQAPYLFNYTGEPSLTQKWARAIYTKETW
NRYIATGSSSAVPSGGGEFTPPLKTKVYRLDPRGMLPTMDNDAGTMSTMFVAAAVGLFPVTA
GSSQFQVGSPFFDSTTITYDDGSAFTVTADGVSEDAFYVQSATLDGATFGNTWVDYATVVGG
ADLAFRMGEQPSDWGTDTAPAFSMSTATDEPAEGPRVSAEPTTVQTGDGGALDATVTLTLDG
ARLAAPAGTDLVTSGAASVVGLPDGVTAAVTVASPTALTVSLTGTASADARFFVHLRDAALA
DGVAAASLQGQGVSVRSPLRLSVASAERDALAALVDDAVLVRHGNYSSVTFDRFSTALTKAQ
EALGDEAATSIALRFAADRLGAAADALDLTGGGYRTLEAEQSEAWSGGELKNEANSSSGNLG
GVRSGSWVQYRDMTFETAAGDTPPRFLTVRYDTSFAPTDTPSTVRVHAGDVSGPVVATVDLK
GTSGWGKYTEVTAELGDVQALVDAQVVTFELLAPSGRSWVGNFDWFRFSAEDPAAPGQPGES
PTVTIEAEDWTASSGRGLKKESSTWTSGPVTNVGGTADGDWIAYGEVDLGELPLGELSVHYV
HNSNRSGNNSALSVYLDAFDPANPGEPFVTVPLPTTGSSWTADGTATVVLPETVQGTHEVFV
RLSTEPYADHPYVANLDSLTFAPGGPTSVVVESEAWTSNSGRGLKNESSTWTSGPVTNVGGT
ADGDWLAYGEIDLGSAALDQLSVHYVHNSNRSGRNSALSVYLDAFDPANPGEPFVTVPLANT
GSSWTTDGTAVVDLPSTVRGKHQVWVRLSTEAYADHPYVANLDSMRFFTDAYDVEVPPTDTA
ALAAVVDAAGTPEAEIARYGRIDARVFTRELAAARSVLADAGATQAQADERARRLGLATDQL
VPAERRRLENLVASAEALTDEGYSPESWQAFRTALAAATGTLDDAAASDEALHDARLALQGA
VDALEEPADVVLVEVEVSPRCLAGKPYVAVRAVNVSDAAVDVELASSLGTRSFVGVAPGASA
YQSFAARSATGDLDVTVTATGADGTQTVEQVVTVPSCS (SEQ ID NO:8)
```

FIGURE 9A

DsbA-6xHis-CcMan4(107bp - 5494bp, direct) 5388bp from
pLSAHCcMan4
ATGAAAAAGATTTGGCTGGCGCTGGCTGGTTTAGTTTTAGCGTTTAGCGCATCGGCCGG
CCATCACCATCATCACCACGTGGGGCCCGGCTCGGACGAAGTGGATGCAGAACCGGGTG
ATTTTAGCAGCAGCTTTGAATCTGGCGATCCGGCAGCACTGCCGACCACCGTTGCAGAA
CGTGATGGTGCACCGTGGCAGGCAAATGTTGGTAGCTTTACCGCAGGTCTGCCTGGTAG
CGTTCTGGGTCAGCTGAAAGGTGTTACCGCAAGCGCACAGAATCTGCCGAATGAAGGTG
CAGCAAATCTGGCAGATGGTAGCAGCGGCACCAAATGGCTGGCATTTGCAAGCACCGGT
TGGGTTCGTTATGAATTTGCAGAACCGGTTAGCTTTGTTGCATATACCATGACCAGCGG
TGATGATGCCGCAGGTCGTGATCCGAAAACCTGGACCGTTGAAGGTAGCAATGATGGTT
CTACCTGGGCAGCACTGGATCGTCGTACCGATGAAGATTTTCCGAATCGTCAGCAGACC
CGTACCTTTGAACTGGAAGCACCGACCGCAGCATATACCTATCTGCGTCTGAATGTTAC
CGCAAATAGCGGTGATAGCATTGTTCAGCTGGCAGGTTGGGATCTGAGCGCAGATCTGT
CTGCAGGTCCGAGCGCAGCACCGATGACCACCAAAGTTGGCACCGGTCCGCGTGTTAGC
TTTACCAATAAAGCCGGTGTTGGTTTTAGCGGTCTGCATAGCCTGCGTTATGATGGTAG
CCATCTGGCCGATGGTGAAACCTATGCAACCAATGTGCTGTATGATGATGTTGATGTTG
TGGTTGGTGAAGATACCCGTCTGAGCTATACCATTTTTCCGGAACTGCTGGATGATCTG
CAGTATCCGAGCACCTATGCAGCAGTTGATGTTCTGTTTACCGATGGCACCTATCTGAG
CGATCTGGGTGCACGTGATGCACATGAAACCGTTGCAACCGCACAGGCACAGGGTGAAG
GTAAAATTCTGTATGCCGATCAGTGGAATAGCGTTCGTGTTGATCTGGGTGATGTTGCA
GAAGGTAAAACCGTTGATCAGGTTCTGCTGGGTTATGATAATCCGGGTGGTCATGCAGG
CACCAAATTTGCAGGTTGGCTGGATGATGTTGAAATTACCGCAGAACCGGCAACCATTG
ATGGTAGCTCACTGGCAAATTATGTTGATACCCGTCGTGGCACCCTGGCAAGCGGTAGC
TTTAGCCGTGGTAATAATATTCCGGCAACCGCAACCCCGAATGGTTTTAATTTTTGGAC
CCCGTATACCAATGCAAGCAGCCAGAGCTGGCTGTATGAATATCATAAAGCCAATAATG
CGAATAATAAACCGGTTCTGCAGGGTTTTGGTATTAGCCATGAACCGAGCCCGTGGATG
GGTGATCGTAATCAGCTGACCTTTCTGCCGAGCACCGCAAGCGGTACACCGGATGCAAC
CCTGAGCACCCGTGGTCTGCAATTTGATCATGCAGATGAAACCGCACGTCCGGATTATT
ATGGTGTGACCTTTACCAATGGTAGCGCAATTGAAGCAACCCCGACCGATCATGGTGCA
GTTCTGCGTTTTAGCTATCCGGGTGCAAAAGGTCATGTTCTGGTGGATAAAGTTGATGG
TAGCAGTAAACTGACCTATGATCAGGCAACCGGCACCATTAGCGGTTGGGTTGAAAATG
GTAGCGGTCTGAGCGTTGGTCGTACCCGTATGTTTGTTGCAGGCACCTTTGATCGTAGC
CCGACCGCAGTTGGCACAGCAGCAGGTAATCGTGCAGATGCACGTTTTGCAACCTTTGA
AACCAGCAGCGATAAAACCGTGGAACTGCGTGTTGCAACCAGCTTTATTAGCCTGGATC
AGGCACGTAAAAATCTGGATCTGGAAGTTACCGGTAAAACCTTTACCGAAGTTAAAGCA
GCAGCAGCACAGGCATGGAATGATCGTCTGGGTGTTATTGAAGTTGAAGGTGCAAGCGA
AGATCAGCTGGTTACCCTGTATAGCAATCTGTATCGCCTGAATCTGTATCCGAATAGCC
AGTTTGAAAATACCGGCACCGCACAGGAACCGGTTTATCGTTACGCATCTCCGGTTAGC
GCAACCACCGGTAGCGCAACCGATACCCAGACCAATGCCAAAATTGTGGATGGCAAAAT
TTATGTGAATAATGGCTTTTGGGATACCTATCGTACCGCATGGCCTGCATATAGCCTGC
TGTATCCGGAACTGGCAGCAGAACTGGTTGATGGTTTTGTTCAGCAGTATCGTGATGGT
GGTTGGATTGCACGTTGGAGCAGTCCGGGTTATGCAGATCTGATGACCGGTACAAGCTC
TGATGTTGCATTTGCAGATGCCTATCTGAAAGGTAGCCTGCCGACCGGTACAGCACTGG
AAGCATATGATGCAGCACTGCGTAATGCAACCGTTGCACCTCCAGCAATGCAGTTGGT

FIGURE 9A (CONTINUED)

```
CGTAAAGGTCTGCAGACAAGCCCGTTTCTGGGTTTTACACCGGAAAGCACCCATGAAAG
CGTTAGCTGGGGTCTGGAAGGTCTGGTTAATCATTTTGGCATTGGCAATATGGCTGCAG
CACTGGCAGAAGATCCGGCAACACCGGAAGAACGTCGTGAAACCCTGCGTGAAGAAAGC
GCATATTTTCTGGAACGTGCCACCCATTATGTTGAACTGTTTGATCCGGAAGTGGATTT
TTTTGTTCCGCGTCATGAAGATGGTACATGGGCAGTTGATCCGGAAACCTATGATCCGG
AAGCATGGGGTGGTGGTTATACCGAAACCAATGGCTGGAATTTTGCATTTCATGCACCG
CAGGATGGTCAGGGTCTGGCAAATCTGTATGGTGGTAAACAGGGTCTGGAAGATAAACT
GGATGAATTTTTTAGCACACCGGAAAAAGGTGCAGGTAATGGTGGTATTCATGAACAGC
GTGAAGCACGTGATGTTCGTATGGGTCAGTGGGGTATGAGCAATCAGGTTAGCCATCAT
ATTCCGTGGCTGTATGATGCAGCCGGTGCTCCGAGCAAAGCACAGGAAAAAGTTCGCGA
AGTTACCCGTCGTCTGTTTGTTGGTAGCGAAATTGGTCAGGGTTATCCGGGTGATGAAG
ATAATGGTGAAATGTCCTCCTGGTGGATTTTTGCAAGCCTGGGTTTTTATCCGCTGCAG
GTTGGTAGCGATCAGTATGCAGTTGGTTCTCCGCTGTTTGATAAAGCAACCGTTCATCT
GCCGGATGGTGATCTGGTTGTTAATGCCGAAAATAATAGCGTGGATAATGTGTATGTTC
AGAGCCTGGCAGTTGATGGTGAAGCACGTACCAGCACCAGCCTGAGCCAGGCAGATCTG
AGCGGTGGCACCACCCTGGATTTTGTTATGGGTCCGGAACCGAGCGATTGGGGCACCGG
TGAAGATGATGCACCTCCGTCACTGACCGAAGGTGATGAACCTCCGACACCGGTTCAGG
ATGCAACCACCGCAGGCCTGGGCACCACCACCGTTGCCGATGGTGATGCCACCACCTCT
GCAGCAGCCCTGACCGATAATACCAGCGGCACCCGTACCACCTTTGCAACCACCACCCC
GAGCATTACATGGGCAGGTAATGGCATTCGTCCGACCGTTGGTAGCTATACCCTGACCT
CTGGTGCAAGCGGCACCGCAAGCCCGTCTGCATGGACCCTGGAAGGTTCTGATGATGGC
GAAACCTGGACCACACTGGATGAACGTAGCGGTGAACAGTTTCGTTGGGCACTGCAGAC
CCGTCCGTTTACCGTTGCCGAACCGACCGCATTTGCACGTTATCGTGTTACCGTTACCG
CAACCAGCGGTTCTGGTGCACTGAGCCTGGCAGAAGTTGAACTGCTGGCAGATCCGAAA
GAAAGCGGTGCAGAAGAACTGACCCTGTCTGCAGCACCGGATCGTGATGGCGTTACCGG
TCGTGAAGTTAGCGGTTCTTTTGCAACCCTGACCGGTGTTGAAGGTGATGTTGCCGCAC
TGGATGTTCAGGTTGCATTTGGTGATGGTAGCGAACCGGTTGCAGGTACACTGCGTGCC
GGTGCATTTGGTGGTTATGCAGTTGATGCAGCACATACCTGGACCGCACCGGGTGTTTA
TCCGGTTACCGTGACCGTTAGCGGTGAAGGTATTGAAACCGTTAGCGCAAGCAGCTATG
TTAGCGTTAGCCTGCTGCGTGAAGGTTCTCTGCTGGCAGCATATGATAATGTGTGCATT
GGTGATGCAGGTACAACCGTTGGTTCTTGTGATGGTCAGGGCGTTTTTTTTGATCGTGC
ACAGCTGGCAGCAAAAGGTTTTGTGCAGGGTGAACGTGCAACCGTTCCGGGTACAGATC
TGGCATTTGATGTTCCGGCAGTTCCGGCTGGTCAGCCTGATAATGCAACCGGTGATGGT
CAGACCATTGAACTGGATGTTCCGGCTGATGCAGAACAGCTGAGCGTTATTGGCACCGG
CACCGAAAAAAATCAGCAGGCAACCGGTACACTGACCTTTGATGATGGTTCTACCCAGC
CGATTGATCTGAGCTTTGGTGATTGGAGCGGTGCAGCACGTAATCCGGTGTTTGGTAAT
ATTCCGGTTGCAGTTACCGATAGCCGTCTGCGTGGTGGTTCTCCGCAGACCGGTACACC
GGCAGCATTTTTTGCCACCGCACCGATTACCCTGCCGGAAGGTAAACGTCCGGTTAGCC
TGACCCTGCCGGATCAGCCTGGTGAACTGAGCCGTGATGGTCGTATTCATGTTGTTGCA
GTTGCACATGATGGCACCTTTGCAGAACATCCTGCACTGCAAGTGACCGCAGCAGAACG
TGTTACCCTGGCAGTTGGTCAGACCTCAGATGTTGCACTGGCACAGGTTGCCGGTGGTC
GTGAAGGTGCAGATCTGCGTGCCGCAGTTACCTGGGGTGATGGTTCTGATGTGGCAGCC
GGTGCCGTTACCGATGGTAGCGTTAGCGGTAGCCATGCATATACCGCAGCAGGCACCTA
```

FIGURE 9A (CONTINUED)

```
TACCGCATATGTTGTTGTGGATGATGGTTGGACCAGCCAGGTTGTTGAAGTTCCGGTGA
CCGTTACAGAAGCCGAACCGGCACTGGCCGTTGATGTCACCGTTAGCACCCGTTGCCTG
GCAGGTAAAGCATATGTTGCAGTGCGTGCAGAAAATGGTGAAGATGTTCCGCTGGCAAT
TCGTCTGGTTACCCCGTTTGGCACCAAAGAAGTTGCAGCAGTTGCTCCGGGAGCCAATG
CATATCAGAGCTTTGCAACCCGTGTTACCGCAGTTGAAGCAGGCACCGTTACCGTTGAA
GCCACCCGTGGCACCGGTGATGAAGAAGTTACCGCCAGCATTCAGGCAGATTATGCAGC
CGTTACCTGCGGTTAATAA
```

FIGURE 9B

MTRPLPPGRAVARSGSGRARPLGLVLAAALAVPLGVPLAAPAGALAAAPAAAAEPGDFS
SSFESGDPAALPTTVAERDGAPWQANVGSFTAGLPGSVLGQLKGVTASAQNLPNEGAAN
LADGSSGTKWLAFASTGWVRYEFAEPVSFVAYTMTSGDDAAGRDPKTWTVEGSNDGSTW
AALDRRTDEDFPNRQQTRTFELEAPTAAYTYLRLNVTANSGDSIVQLAGWDLSADLSAG
PSAAPMTTKVGTGPRVSFTNKAGVGFSGLHSLRYDGSHLADGETYATNVLYDDVDVVVG
EDTRLSYTIFPELLDDLQYPSTYAAVDVLFTDGTYLSDLGARDAHETVATAQAQGEGKI
LYADQWNSVRVDLGDVAEGKTVDQVLLGYDNPGGHAGTKFAGWLDDVEITAEPATIDGS
SLANYVDTRRGTLASGSFSRGNNIPATATPNGFNFWTPYTNASSQSWLYEYHKANNANN
KPVLQGFGISHEPSPWMGDRNQLTFLPSTASGTPDATLSTRGLEFDHADETARPDYYGV
TFTNGSAIEATPTDHGAVLRFSYPGAKGHVLVDKVDGSSKLTYDQATGTISGWVENGSG
LSVGRTRMFVAGTFDRSPTAVGTAAGNRADARFATFETSSDKTVELRVATSFISLDQAR
KNLDLEVTGKTFTEVKAAAAQAWNDRLGVIEVEGASEDQLVTLYSNLYRLNLYPNSQFE
NTGTAQEPVYRYASPVSATTGSATDTQTNAKIVDGKIYVNNGFWDTYRTAWPAYSLLYP
ELAAELVDGFVQQYRDGGWIARWSSPGYADLMTGTSSDVAFADAYLKGSLPTGTALEAY
DAALRNATVAPPSNAVGRKGLQTSPFLGFTPESTHESVSWGLEGLVNDFGIGNMAAALA
EDPATPEERRETLREESAYFLERATHYVELFDPEVDFFVPRHEDGTWAVDPETYDPEAW
GGGYTETNGWNFAFHAPQDGQGLANLYGGKQGLEDKLDEFFSTPEKGAGNGGIHEQREA
RDVRMGQWGMSNQVSHHIPWLYDAAGAPSKAQEKVREVTRRLFVGSEIGQGYPGDEDNG
EMSSWWIFASLGFYPLQVGSDQYAVGSPLFDKATVHLPDGDLVVNAENNSVDNVYVQSL
AVDGEARTSTSLSQADLSGGTTLDFVMGPEPSDWGTGEDDAPPSLTEGDEPPTPVQDAT
TAGLGTTTVADGDATTSAAALTDNTSGTRTTFATTTPSITWAGNGIRPTVGSYTLTSGA
SGTASPSAWTLEGSDDGETWTTLDERSGEQFRWALQTRPFTVAEPTAFARYRVTVTATS
GSGALSLAEVELLADPKESGAEELTLSAAPDRDGVTGREVSGSFATLTGVEGDVAALDV
QVAFGDGSEPVAGTLRAGAFGGYAVDAAHTWTAPGVYPVTVTSGEGIETVSASSYVSV
SLLREGSLLAAYDNVCIGDAGTTVGSCDGQGVFFDRAQLAAKGFVQGERATVPGTDLAF
DVPAVPAGQPDNATGDGQTIELDVPADAEQLSVIGTGTEKNQQATGTLTFDDGSTQPID
LSFGDWSGAARNPVFGNIPVAVTDSRLRGGSPQTGTPAAFFATAPITLPEGKRPVSLTL
PDQPGELSRDGRIHVVAVAHDGTFAEHPALEVTAAEGVTLAVGQTSDVALAQVAGGREG
ADLRAAVTWGDGSDVAAGAVTDGSVSGSHAYTAAGTYTAYVVVDDGWTSQVVEVPVTVT
EAEPALAVDVTVSTRCLAGKAYVAVRAENGEDVPLAIRLVTPFGTKEVAAVAPGANAYQ
SFATRVTAVEAGTVTVEATRGTGDEEVTASIQADYAAVTCG

FIGURE 9B (CONTINUED)

MTRPLPPGRAVARSGSGRARPLGLVLAAALAVPLGVPLAAPAGALAAAPAAAAEPGDFS
SSFESGDPAALPTTVAERDGAPWQANVGSFTAGLPGSVLGQLKGVTASAQNLPNEGAAN
LADGSSGTKWLAFASTGWVRYEFAEPVSFVAYTMTSGDDAAGRDPKTWTVEGSNDGSTW
AALDRRTDEDFPNRQQTRTFELEAPTAAYTYLRLNVTANSGDSIVQLAGWDLSADLSAG
PSAAPMTTKVGTGPRVSFTNKAGVGFSGLHSLRYDGSHLADGETYATNVLYDDVDVVG
EDTRLSYTIFPELLDDLQYPSTYAAVDVLFTDGTYLSDLGARDAHETVATAQAQGEGKI
LYADQWNSVRVDLGDVAEGKTVDQVLLGYDNPGGHAGTKFAGWLDDVEITAEPATIDGS
SLANYVDTRRGTLASGSFSRGNNIPATATPNGFNFWTPYTNASSQSWLYEYHKANNANN
KPVLQGFGISHEPSPWMGDRNQLTFLPSTASGTPDATLSTRGLEFDHADETARPDYYGV
TFTNGSAIEATPTDHGAVLRFSYPGAKGHVLVDKVDGSSKLTYDQATGTISGWVENGSG
LSVGRTRMFVAGTFDRSPTAVGTAAGNRADARFATFETSSDKTVELRVATSFISLDQAR
KNLDLEVTGKTFTEVKAAAAQAWNDRLGVIEVEGASEDQLVTLYSNLYRLNLYPNSQFE
NTGTAQEPVYRYASPVSATTGSATDTQTNAKIVDGKIYVNNGFWDTYRTAWPAYSLLYP
ELAAELVDGFVQQYRDGGWIARWSSPGYADLMTGTSSDVAFADAYLKGSLPTGTALEAY
DAALRNATVAPPSNAVGRKGLQTSPFLGFTPESTHESVSWGLEGLVNDFGIGNMAAALA
EDPATPEERRETLREESAYFLERATHYVELFDPEVDFFVPRHEDGTWAVDPETYDPEAW
GGGYTETNGWNFAFHAPQDGQGLANLYGGKQGLEDKLDEFFSTPEKGAGNGGIHEQREA
RDVRMGQWGMSNQVSHHIPWLYDAAGAPSKAQEKVREVTRRLFVGSEIGQGYPGDEDNG
EMSSWWIFASLGFYPLQVGSDQYAVGSPLFDKATVHLPDGDLVVNAENNSVDNVYVQSL
AVDGEARTSTSLSQADLSGGTTLDFVMGPEPSDWGTGEDDAPPSLTEGDEPPTPVQDAT
TAGLGTTTVADGDATTSAAALTDNTSGTRTTFATTTPSITWAGNGIRPTVGSYTLTSGA
SGTASPSAWTLEGSDDGETWTTLDERSGEQFRWALQTRPFTVAEPTAFARYRVTVTATS
GSGALSLAEVELLADPKESGAEELTLSAAPDRDGVTGREVSGSFATLTGVEGDVAALDV
QVAFGDGSEPVAGTLRAGAFGGYAVDAAHTWTAPGVYPVTVTSGEGIETVSASSYVSV
SLLREGSLLAAYDNVCIGDAGTTVGSCDQGVFFDRAQLAAKGFVQGERATVPGTDLAF
DVPAVPAGQPDNATGDGQTIELDVPADAEQLSVIGTGTEKNQQATGTLTFDDGSTQPID
LSFGDWSGAARNPVFGNIPVAVTDSRLRGGSPQTGTPAAFFATAPITLPEGKRPVSLTL
PDQPGELSRDGRIHVVAVAHDGTFAEHPALEVTAAEGVTLAVGQTSDVALAQVAGGREG
ADLRAAVTWGDGSDVAAGAVTDGSVSGSHAYTAAGTYTAYVVVDDGWTSQVVEVPVTVT
EAEPALAVDVTVSTRCLAGKAYVAVRAENGEDVPLAIRLVTPFGTKEVAAVAPGANAYQ
SFATRVTAVEAGTVTVEATRGTGDEEVTASIQADYAAVTCG (SEQ ID NO:10)

FIGURE 10
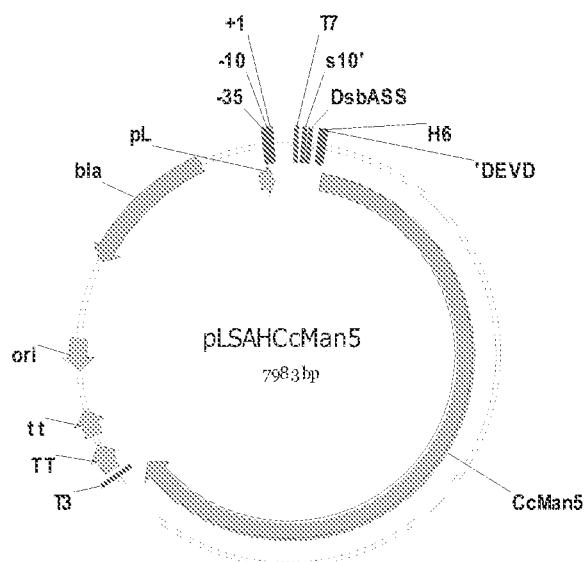
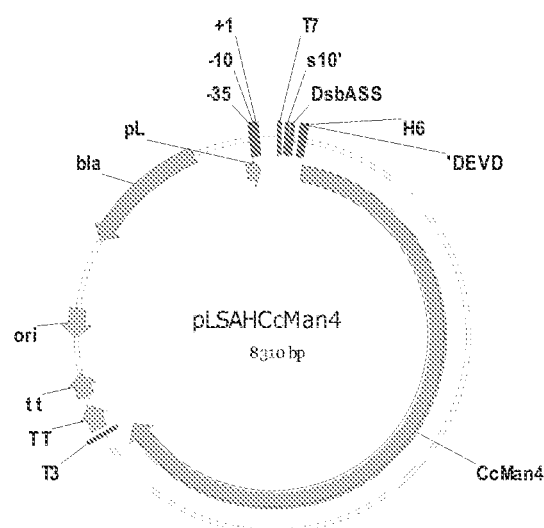

FIGURE 22

```
  1 mhlpslslsl talaiaspsa ayphfgssqp vlhsssdttq sradaikaaf shawdqylqy
 61 afphdelhpv sngygdsrng wgasavdals tavimrnati vnqildhvgk idysktnttv
121 slfettiryl ggmlsgydll kgpvsdlvqn sskidvlltq sknladvlkf afdtpsgvpy
181 nnlnitsggn dgaktnglav tgtlalewtr lsdltgdtty adlsqkaesy llnpqpksae
241 pfpglvgsni nisnqqftda qvswnggdds yyeylikmyv ydpkrfglyk drwvaaaqst
301 mqhlashpss rpdltflasy nngtlglssq hltcfdggsf llggtvlnrt dfinfgldlv
361 sgchdtynst ltgigpesfs wdtsdipssq qslyekagfy itsgayilrp eviesfyyaw
421 rvtgqetyrd wiwsafsavn dycrtssgfs gltdvnaang gsrydnqesf lfaevmkysy
481 mafaedaawq vqpgsgnqfv fnteahpvrv sst
```

```
                        SEQUENCE LISTING

<160> NUMBER OF SEQ ID NOS: 11

<210> SEQ ID NO 1
<211> LENGTH: 2743
<212> TYPE: DNA
<213> ORGANISM: Artificial Sequence
<220> FEATURE:
<223> OTHER INFORMATION: Yarrowia codon optimized sequence encoding
      alpha glucosidase

<400> SEQUENCE: 1
atgaagcttt ccaccatcct cttcacagcc tgcgctaccc tggctgccgc ccagcaggga     60
gcctctcgac ccggacoccg agatgoccag gctcacoccg gacgacctcg agctgtgocc    120 acccagtgtg acgtgccocc caactctcga ttcgactgtg ccocogacaa ggocatcacc    180 caggagcagt gcgaggccog aggctgttgt tacatococg ctaagcaggg cctgcaggge    240 gctcagatgg gocagcoctg gtgtttcttc coccoctctt accoctccta caagctggag    300 aacctgtcct cttoggagat gggctacacc gocaccctga coogaaccac cocoacctttt   360 ttocccaagg acatoctgac cotgogactg gacgtgatga tggagacoga gaacogactg    420 cacttcacca tcaaggacoc cgccaaccga cgatacgagg tgcoctgga gaccococac     480 gtgcactctc gagccocttc coccotgtac tctgtggagt tctctgagga gocottoggc    540 gtgatcgtgc gacgacagct ggacggccga gtgotgctga acaccaccgt ggocococtg    600 ttottcgocc accagttcct gcagctgtct acctctctgc cctctcagta catcaccggc    660 ctggocgagc acctgtcocc cctgatgctg tccacctctt ggactcgaat caccctgtgg    720
```

```
aaccgagacc tggcccccac ccccggtgcc aacctgtacg gctctcaccc cttctacctg    780
gccctggagg acggcggctc tgcccacggc gtgtttctgc tgaactctaa cgccatggac    840
gtggtgctgc agccctctcc cgccctgtct tggcgatcta ccggcggcat cctggacgtg    900
tacatcttcc tgggccctga gcccaagtct gtggtccagc agtacctgga cgtggtcgga    960
taccccttca tgccccccta ctggggcctg gcttccacc tgtgtcgatg gggctactct   1020
tctaccgcca tcacccgaca ggtggtggag aacatgaccc gagcccactt ccccctggac   1080
gtgcaatgga acgacctgga ctacatggac tctcgacgag acttcacctt caacaaggac   1140
ggcttccgag acttccccgc catggtccag gagctgcacc agggaggacg acgatacatg   1200
atgatcgtgg accccgccat ctcttcttcc ggacccgccg atcttaccg accctacgac   1260
gagggcctgc gacgaggcgt gttcatcacc aacgagaccg gccagcccct gatcggcaag   1320
gtgtggcccg gctctaccgc cttccccgac ttcaccaacc ccaccgccct ggcttggtgg   1380
gaggacatgg tggccgagtt ccacgaccag gtgcccttcg acggcatgtg gatcgacatg   1440
aacgagccct ctaacttcat ccgaggctct gaggacggct gtcccaacaa cgagctggag   1500
aaccccccct acgtgcccgg cgtggtgggc ggaaccctgc aggccgccac catctgtgcc   1560
tcttcgcacc agtttctgtc tacccactac aacctgcaca acctgtacgg actgaccgag   1620
gccattgcct ctcaccgagc cctggtgaag gcccgaggca cccgaccctt cgtgatctct   1680
cgatctacct tcgccggcca cggccgatac gccggacact ggaccggcga tgtgtggtcc   1740
tcttgggagc agctggcctc ttctgtgccc gagatcctgc agttcaacct gctgggcgtg   1800
cccctggtgg gcgccgacgt gtgtggcttc ctgggcaaca cctctgagga gctgtgtgtt   1860
cgatggaccc agctcggcgc cttctaccct ttcatgcgaa accacaactc cctgctgtct   1920
ctgccccagg agccctactc gttctctgag cccgctcagc aggccatgcg aaaggctctg   1980
accctgcgat acgccctgct gccccacctg tacaccctgt tccaccaggc ccacgtggct   2040
ggagagaccg tggcccgacc cctgttcctg gagttcccta aggactcttc tacctggacc   2100
gtggaccatc agctgctgtg ggcgaggcc ctcctgatca ccccgtgct gcaggccggc   2160
aaggctgagg tgaccggcta cttccctctg ggcacctggt acgacctgca gaccgtgcct   2220
gtggaggccc tgggatctct gccccctcct cccgccgctc ccgagagcc cgccatccac   2280
tctgagggcc agtgggtgac cctgcccgct ccctggaca ccatcaacgt gcacctgcga   2340
gccggctaca tcatccctct gcagggaccc ggcctgacca ccaccgagtc tcgacagcag   2400
cccatggccc tggccgtggc tctgaccaag ggcgagagg cccgaggcga gctgttctgg   2460
gacgatggcg agtctctgga ggtgctggag cgaggcgcct acacccaggt gatctttctg   2520
gccgaaaaca acaccatcgt gaacgagctg gtgcgagtga cctctgaggg cgctggtctg   2580
cagctccaga aggtgaccgt cctgggcgtg gccaccgctc ccagcaggt cctgtctaac   2640
ggcgtgcccg tgtctaactt cacctactct cccgacacca aggtgctgga catctgtgtg   2700
tctctgctga tgggcgagca gttcctggtg tcttggtgtt aac                    2743
```

<210> SEQ ID NO 2
<211> LENGTH: 913
<212> TYPE: PRT
<213> ORGANISM: Artificial Sequence
<220> FEATURE:
<223> OTHER INFORMATION: Fusion of Yarrowia LIP2 signal sequence to human alpha glucosidaseglucosidase

<400> SEQUENCE: 2

-continued

```
Met Lys Leu Ser Thr Ile Leu Phe Thr Ala Cys Ala Thr Leu Ala Ala
 1               5                   10                  15

Ala Gln Gln Gly Ala Ser Arg Pro Gly Pro Arg Asp Ala Gln Ala His
             20                  25                  30

Pro Gly Arg Pro Arg Ala Val Pro Thr Gln Cys Asp Val Pro Pro Asn
         35                  40                  45

Ser Arg Phe Asp Cys Ala Pro Asp Lys Ala Ile Thr Gln Glu Gln Cys
 50                  55                  60

Glu Ala Arg Gly Cys Cys Tyr Ile Pro Ala Lys Gln Gly Leu Gln Gly
 65                  70                  75                  80

Ala Gln Met Gly Gln Pro Trp Cys Phe Phe Pro Pro Ser Tyr Pro Ser
             85                  90                  95

Tyr Lys Leu Glu Asn Leu Ser Ser Ser Glu Met Gly Tyr Thr Ala Thr
             100                 105                 110

Leu Thr Arg Thr Thr Pro Thr Phe Phe Pro Lys Asp Ile Leu Thr Leu
         115                 120                 125

Arg Leu Asp Val Met Met Glu Thr Glu Asn Arg Leu His Phe Thr Ile
 130                 135                 140

Lys Asp Pro Ala Asn Arg Arg Tyr Glu Val Pro Leu Glu Thr Pro His
145                  150                 155                 160

Val His Ser Arg Ala Pro Ser Pro Leu Tyr Ser Val Glu Phe Ser Glu
             165                 170                 175

Glu Pro Phe Gly Val Ile Val Arg Arg Gln Leu Asp Gly Arg Val Leu
         180                 185                 190

Leu Asn Thr Thr Val Ala Pro Leu Phe Phe Ala Asp Gln Phe Leu Gln
 195                 200                 205

Leu Ser Thr Ser Leu Pro Ser Gln Tyr Ile Thr Gly Leu Ala Glu His
 210                 215                 220

Leu Ser Pro Leu Met Leu Ser Thr Ser Trp Thr Arg Ile Thr Leu Trp
225                  230                 235                 240

Asn Arg Asp Leu Ala Pro Thr Pro Gly Ala Asn Leu Tyr Gly Ser His
             245                 250                 255

Pro Phe Tyr Leu Ala Leu Glu Asp Gly Gly Ser Ala His Gly Val Phe
         260                 265                 270

Leu Leu Asn Ser Asn Ala Met Asp Val Val Leu Gln Pro Ser Pro Ala
 275                 280                 285

Leu Ser Trp Arg Ser Thr Gly Gly Ile Leu Asp Val Tyr Ile Phe Leu
 290                 295                 300

Gly Pro Glu Pro Lys Ser Val Val Gln Gln Tyr Leu Asp Val Val Gly
305                  310                 315                 320

Tyr Pro Phe Met Pro Pro Tyr Trp Gly Leu Gly Phe His Leu Cys Arg
             325                 330                 335

Trp Gly Tyr Ser Ser Thr Ala Ile Thr Arg Gln Val Val Glu Asn Met
         340                 345                 350

Thr Arg Ala His Phe Pro Leu Asp Val Gln Trp Asn Asp Leu Asp Tyr
 355                 360                 365

Met Asp Ser Arg Arg Asp Phe Thr Phe Asn Lys Asp Gly Phe Arg Asp
 370                 375                 380

Phe Pro Ala Met Val Gln Glu Leu His Gln Gly Gly Arg Arg Tyr Met
385                  390                 395                 400

Met Ile Val Asp Pro Ala Ile Ser Ser Ser Gly Pro Ala Gly Ser Tyr
             405                 410                 415
```

```
Arg Pro Tyr Asp Glu Gly Leu Arg Arg Gly Val Phe Ile Thr Asn Glu
            420                 425                 430

Thr Gly Gln Pro Leu Ile Gly Lys Val Trp Pro Gly Ser Thr Ala Phe
        435                 440                 445

Pro Asp Phe Thr Asn Pro Thr Ala Leu Ala Trp Trp Glu Asp Met Val
    450                 455                 460

Ala Glu Phe His Asp Gln Val Pro Phe Asp Gly Met Trp Ile Asp Met
465                 470                 475                 480

Asn Glu Pro Ser Asn Phe Ile Arg Gly Ser Glu Asp Gly Cys Pro Asn
                485                 490                 495

Asn Glu Leu Glu Asn Pro Pro Tyr Val Pro Gly Val Val Gly Gly Thr
            500                 505                 510

Leu Gln Ala Ala Thr Ile Cys Ala Ser Ser His Gln Phe Leu Ser Thr
        515                 520                 525

His Tyr Asn Leu His Asn Leu Tyr Gly Leu Thr Glu Ala Ile Ala Ser
    530                 535                 540

His Arg Ala Leu Val Lys Ala Arg Gly Thr Arg Pro Phe Val Ile Ser
545                 550                 555                 560

Arg Ser Thr Phe Ala Gly His Gly Arg Tyr Ala Gly His Trp Thr Gly
                565                 570                 575

Asp Val Trp Ser Ser Trp Glu Gln Leu Ala Ser Ser Val Pro Glu Ile
            580                 585                 590

Leu Gln Phe Asn Leu Leu Gly Val Pro Leu Val Gly Ala Asp Val Cys
        595                 600                 605

Gly Phe Leu Gly Asn Thr Ser Glu Glu Leu Cys Val Arg Trp Thr Gln
610                 615                 620

Leu Gly Ala Phe Tyr Pro Phe Met Arg Asn His Asn Ser Leu Leu Ser
                625                 630                 635                 640

Leu Pro Gln Glu Pro Tyr Ser Phe Ser Glu Pro Ala Gln Gln Ala Met
            645                 650                 655

Arg Lys Ala Leu Thr Leu Arg Tyr Ala Leu Leu Pro His Leu Tyr Thr
        660                 665                 670

Leu Phe His Gln Ala His Val Ala Gly Glu Thr Val Ala Arg Pro Leu
    675                 680                 685

Phe Leu Glu Phe Pro Lys Asp Ser Ser Thr Trp Thr Val Asp His Gln
690                 695                 700

Leu Leu Trp Gly Glu Ala Leu Leu Ile Thr Pro Val Leu Gln Ala Gly
705                 710                 715                 720

Lys Ala Glu Val Thr Gly Tyr Phe Pro Leu Gly Thr Trp Tyr Asp Leu
                725                 730                 735

Gln Thr Val Pro Val Glu Ala Leu Gly Ser Leu Pro Pro Pro Pro Ala
            740                 745                 750

Ala Pro Arg Glu Pro Ala Ile His Ser Glu Gly Gln Trp Val Thr Leu
        755                 760                 765

Pro Ala Pro Leu Asp Thr Ile Asn Val His Leu Arg Ala Gly Tyr Ile
    770                 775                 780

Ile Pro Leu Gln Gly Pro Gly Leu Thr Thr Thr Glu Ser Arg Gln Gln
785                 790                 795                 800

Pro Met Ala Leu Ala Val Ala Leu Thr Lys Gly Gly Glu Ala Arg Gly
                805                 810                 815

Glu Leu Phe Trp Asp Asp Gly Glu Ser Leu Glu Val Leu Glu Arg Gly
            820                 825                 830

Ala Tyr Thr Gln Val Ile Phe Leu Ala Arg Asn Asn Thr Ile Val Asn
```

|  | 835 | 840 | 845 |  |
|---|---|---|---|---|

Glu Leu Val Arg Val Thr Ser Glu Gly Ala Gly Leu Gln Leu Gln Lys
    850                           855                     860

Val Thr Val Leu Gly Val Ala Thr Ala Pro Gln Gln Val Leu Ser Asn
865                    870                    875                    880

Gly Val Pro Val Ser Asn Phe Thr Tyr Ser Pro Asp Thr Lys Val Leu
                    885                    890                    895

Asp Ile Cys Val Ser Leu Leu Met Gly Glu Gln Phe Leu Val Ser Trp
        900                      905                    910

Cys

<210> SEQ ID NO 3
<211> LENGTH: 3258
<212> TYPE: DNA
<213> ORGANISM: Artificial Sequence
<220> FEATURE:
<223> OTHER INFORMATION: Yarrowia lipolytica nucleotide sequence
     encoding AMS1 with C-terminal His-tag

<400> SEQUENCE: 3

```
atgtattcgc acttcaacaa cgagcctgtg gcgaagcggg tgaacaacct gtttaccgac        60
cgacttcgcc agttcaccag cgacggcgaa taccggtctc tcaacctgcc agctttctac       120
gagcgagaac gactggatgg caagaaccat gtggcgattg aaacgtatgc cgtttcagat       180
ctacgacggc cactgttcaa agacgccctc aagaggcag atggccactg aaaccagca        240
aagaagggct ccgagtacgg accttcctgg gccactcact ggttcaagat ccaggtctgt       300
gtgcccccag agtggaagaa gaactactac aaaaagggcg acctggtggt gttcaattgg       360
aatctcaact gtgagggtct cgtgttcagc gagtctggag aagctcttat tggtttatcc       420
ggcgaggaac gacgagaatg gcccattccc gacaactggt tcgacggaaa gtgccatacc       480
ttttacattg aggccagttg caatggcatg ttcggcaacg caacgggatc ttccatccag       540
cccccccagcg acaacagata tttcagactg gactctgcag acctcgttgt catcaactcc       600
gaggcccgac atctctttgt ggattttttgg attatcggag atgcggcccg ggagttccca       660
ggggattcgt ggcaacgtgg aaaggcacta gatgtcgcta acaagatcat ggatgccttt       720
gatcctgaaa acccagatga gagtatcgcc gagggccgaa acttgccaa ggaataccct       780
ggagatacta caaaggccta caagcaacag ctaccattcg ctgatggcct agtttacgca       840
ctcggtaact gccacatcga taccgcgtgg ctatggccct ttgctgagac tcgtcgaaag       900
gcaggtcgat cttgggcttc tcaacttgag ctcatcgaca agtaccccga gtacgtgttt       960
gtggcttccc aggcccagca gttcaagtgg ctcaaggaag actacccga cttgtttgcc      1020
aagattcaaa agcaggctaa gaagggccgc ttccttcctg tcggaggcgc ctggaccgag      1080
tgtgacacta acctgccctc tggagagtct ctcctgcgcc agttcctgct tggtcagcga      1140
ttcttcctcg aacactttgg ctcccttttct gacactttct ggctgcctga cactttcgga      1200
tactctgctc aggttcctca gctgtgtcga ttggctggca tggaccgttt cttgacccag      1260
aagttgtcct ggaataacat caactcgttc cccaattcaa catttaattg ggtggctctg      1320
gatggctcgc aggtgctctg tcacatgcca cccaacaaca cctacacttc tatgccaac       1380
tttggtgacg tctcacgaac tcagaaacag aacaagaatc ttgacaccac tcgaaactcc      1440
ctcatgctct atggccacgg agacggagga ggaggcccca ctgctgagat gctgagaag       1500
ctgcgtcgat gccgaggtgt gtccaacacc gtcggggaac ttcctcctgt aatccaggga      1560
```

-continued

```
caatctgtga ccgacttcta caatgagctt cttgatcaga ctaacaacgg caaggatctc    1620
gtaacctggg tcggggagct gtactttgag ttccaccgtg gtacctacac cagtcaagcc    1680
cagactaaaa agggtaaccg agtgtcggag aacctgctac acgatgtcga gttgttggcc    1740
actctggcca gtattcgaga ctcatcttac aagtacccct ttgcacagct tgagtctctc    1800
tgggaggatg tgtgtctttg ccagttccat gatgttcttc ctggatcatg cattgagatg    1860
gtctacaagg atgttaaaaa gatccatgga cgggttattg atactgcttc ccacctcatt    1920
gataaagccg cttctgcctt gggtctttct ggtcacccct tccaaggactc cttcgactgc    1980
actcctgttg ctctcaacac catgccttgg tcgcgaaccg aggtcgtcgc tgttccccag    2040
ccacattggg atgccaccgt ggagcttgct gagggtgtcg agatccaaga agactcgggc    2100
aatgccctcg tcatgatgtc tgaatctgga cctgttgtca ccactcaatc tgtagacttg    2160
ttcaagtctg aagacgccta catccttgag aatagccagg tcaaggtgac gatttgcaag    2220
gatgatggta ccctcaccag catttacgac aaagagaatg accgtcgggt cctgtctgga    2280
acaggtaacc gactggtatt gttcgacgac cagccgttgt cgtggcaggc ttgggacact    2340
gaggtgtttt ctcttggtaa gaagcagtac attggtgccg agaatgtgac tcgtcattcc    2400
atcgtctctt ctggccctct gcgatcaact gtcgccttca cttacgaatt caacaaatct    2460
gttgtcacaa ccgagatttc tctcgacgct aactcgcctc tggtaacttt taacacccgt    2520
gccgactggc atgaaacttg caagtttcta aaggtggaat tcctgtggaa cgtccacagt    2580
gagtctgctt cgtacgagtc tcagtttggt gttgttaagc gccccactca ttacaacacc    2640
tcttgggacg tggccaagtt tgaggtatgc tgccacaagt tgcggatct gtccgaactc    2700
gactacggcg tgtccatctt gaatgactgc aagtatggat tcgccaccca tggtaatctc    2760
atgcgactgt cgctgctgcg ggcccctaag gctcccgacg ctcatgctga tatgggtcat    2820
catgagttca agtacggagt ccttgctcac aagggacccc ttggtgctac aactgttcgg    2880
gccgcttaca acttcaacaa ccctcttcgg gtcaagtatg tgggtctctc tgaagtttcc    2940
accaagcagg cctttctctc aaaggccct gcgaatctgg tgctcagcca ggttaagagg    3000
gccgaagttg accgatctaa gaagtccacc aatgtcatct gcgagtttta cgaggctctc    3060
ggaggccgaa ctcgaggcaa actcgttatc gacttgccca acgtggtgtc tgtgaccaag    3120
acctgtgctc tggagtactc caaggagaaa caggttgttg ccaagagcga gggtgtcact    3180
tctgtagaca tttctctacg tgcttttgag gttgccacct acaaggttga gttggctcat    3240
catcaccatc accactag                                                  3258
```

<210> SEQ ID NO 4
<211> LENGTH: 3258
<212> TYPE: DNA
<213> ORGANISM: Artificial Sequence
<220> FEATURE:
<223> OTHER INFORMATION: Yarrowia lipolytica nucleotide sequence encoding AMS1 with N-terminal His-tag

<400> SEQUENCE: 4

```
atgcatcatc accatcacca ctattcgcac ttcaacaacg agcctgtggc gaagcgggtg      60
aacaacctgt ttaccgaccg acttcgccag ttcaccagcg acggcgaata ccggtctctc     120
aacctgccag cttttctacga gcgagaacga ctggatggca agaaccatgt ggcgattgaa     180
acgtatgccg tttcagatct acgacggcca ctgttcaaag acgccctcaa agaggcagat     240
ggccactgga aaccagcaaa gaagggctcc gagtacggac cttcctgggc cactcactgg     300
```

| | | | | |
|---|---|---|---|---|
| ttcaagatcc | aggtctgtgt | gcccccagag | tggaagaaga | actactacaa aaagggcgac | 360 |
| ctggtggtgt | tcaattggaa | tctcaactgt | gagggtctcg | tgttcagcga gtctggagaa | 420 |
| gctcttattg | gtttatccgg | cgaggaacga | cgagaatggc | ccattcccga caactggttc | 480 |
| gacgaaagt | gccatacctt | ttacattgag | gccagttgca | atggcatgtt cggcaacgca | 540 |
| acgggatctt | ccatccagcc | ccccagcgac | aacagatatt | tcagactgga ctctgcagac | 600 |
| ctcgttgtca | tcaactccga | ggcccgacat | ctctttgtgg | attttttggat tatcggagat | 660 |
| gcggcccggg | agttcccagg | ggattcgtgg | caacgtggaa | aggcactaga tgtcgctaac | 720 |
| aagatcatgg | atgcctttga | tcctgaaaac | ccagatgaga | gtatcgccga gggccgaaaa | 780 |
| cttgccaagg | aatacctcgg | agatactaca | aaggcctaca | agcaacagct accattcgct | 840 |
| gatggcctag | tttacgcact | cggtaactgc | cacatcgata | ccgcgtggct atggcccttt | 900 |
| gctgagactc | gtcgaaaggc | aggtcgatct | tgggcttctc | aacttgagct catcgacaag | 960 |
| taccccgagt | acgtgtttgt | ggcttcccag | gcccagcagt | tcaagtggct caaggaagac | 1020 |
| taccccgact | tgtttgccaa | gattcaaaag | caggctaaga | agggccgctt ccttcctgtc | 1080 |
| ggaggcgcct | ggaccgagtg | tgacactaac | ctgccctctg | gagagtctct cctgcgccag | 1140 |
| ttcctgcttg | gtcagcgatt | cttcctcgaa | cactttggct | ccctttctga cactttctgg | 1200 |
| ctgcctgaca | ctttcggata | tctgctcag | gttcctcagc | tgtgtcgatt ggctggcatg | 1260 |
| gaccgttttct | tgacccagaa | gttgtcctgg | aataacatca | actcgttccc caattcaaca | 1320 |
| tttaattggg | tggctctgga | tggctcgcag | gtgctctgtc | acatgccacc caacaacacc | 1380 |
| tacacttcta | tggccaactt | tggtgacgtc | tcacgaactc | agaaacagaa caagaatctt | 1440 |
| gacaccactc | gaaactccct | catgctctat | ggccacggag | acggaggagg aggccccact | 1500 |
| gctgagatgc | tggagaagct | gcgtcgatgc | cgaggtgtgt | ccaacaccgt cggggaactt | 1560 |
| cctcctgtaa | tccagggaca | atctgtgacc | gacttctaca | atgagcttct tgatcagact | 1620 |
| aacaacggca | aggatctcgt | aacctgggtc | ggggagctgt | actttgagtt ccaccgtggt | 1680 |
| acctacacca | gtcaagccca | gactaaaaag | ggtaaccgag | tgtcggagaa cctgctacac | 1740 |
| gatgtcgagt | tgttggccac | tctggccagt | attcgagact | catcttacaa gtaccccttt | 1800 |
| gcacagcttg | agtctctctg | ggaggatgtg | tgtctttgcc | agttccatga tgttcttcct | 1860 |
| ggatcatgca | ttgagatggt | ctacaaggat | gttaaaaaga | tccatggacg ggttattgat | 1920 |
| actgcttccc | acctcattga | taaagccgct | tctgccttgg | gtctttctgg tcacccttcc | 1980 |
| aaggactcct | tcgactgcac | tcctgttgct | ctcaacacca | tgccttggtc gcgaaccgag | 2040 |
| gtcgtcgctg | ttccccagcc | acattgggat | gccaccgtgg | agcttgctga gggtgtcgag | 2100 |
| atccaagaag | actcgggcaa | tgccctcgtc | atgatgtctg | aatctggacc tgttgtcacc | 2160 |
| actcaatctg | tagacttgtt | caagtctgaa | gacgcctaca | tccttgagaa tagccaggtc | 2220 |
| aaggtgacga | tttgcaagga | tgatggtacc | ctcaccagca | tttacgacaa agagaatgac | 2280 |
| cgtcgggtcc | tgtctggaac | aggtaaccga | ctggtattgt | tcgacgacca gccgttgtcg | 2340 |
| tggcaggctt | gggacactga | ggtgttttct | cttggtaaga | agcagtacat tggtgccgag | 2400 |
| aatgtgactc | gtcattccat | cgtctcttct | ggccctctgc | gatcaactgt cgccttcact | 2460 |
| tacgaattca | acaaatctgt | tgtcacaacc | gagatttctc | tcgacgctaa ctcgcctctg | 2520 |
| gtaacttttta | acacccgtgc | cgactggcat | gaaacttgca | gtttctaaa ggtggaattt | 2580 |
| cctgtggacg | tccacagtga | gtctgcttcg | tacgagtctc | agtttggtgt tgttaagcgc | 2640 |
| cccactcatt | acaacacctc | ttgggacgtg | gccaagtttg | aggtatgctg ccacaagttt | 2700 |

```
gcggatctgt ccgaactcga ctacggcgtg tccatcttga atgactgcaa gtatggattc    2760
gccacccatg gtaatctcat gcgactgtcg ctgctgcggg ccctaaggc tcccgacgct      2820 catgctgata tgggtcatca tgagttcaag tacggagtcc ttgctcacaa gggaccccct    2880
ggtgctacaa ctgttcgggc cgcttacaac ttcaacaacc ctcttcgggt caagtatgtg    2940
ggtctctctg aagtttccac caagcaggcc ttttctctca aaggccctgc gaatctggtg    3000
ctcagccagg ttaagagggc cgaagttgac cgatctaaga agtccaccaa tgtcatcttg    3060
cgagtttacg aggctctcgg aggccgaact cgaggcaaac tcgttatcga cttgcccaac    3120
gtggtgtctg tgaccaagac ctgtgctctg gagtactcca aggagaaaca ggttgttgcc    3180
aagagcgagg gtgtcacttc tgtagacatt tctctacgtg cttttgaggt tgccacctac    3240
aaggttgagt tggcttag                                                   3258
```

<210> SEQ ID NO 5
<211> LENGTH: 1079
<212> TYPE: PRT
<213> ORGANISM: Yarrowia lipolytica

<400> SEQUENCE: 5

```
Met Tyr Ser His Phe Asn Asn Glu Pro Val Ala Lys Arg Val Asn Asn
1               5                   10                  15

Leu Phe Thr Asp Arg Leu Arg Gln Phe Thr Ser Asp Gly Glu Tyr Arg
            20                  25                  30

Ser Leu Asn Leu Pro Ala Phe Tyr Glu Arg Glu Arg Leu Asp Gly Lys
        35                  40                  45

Asn His Val Ala Ile Glu Thr Tyr Ala Val Ser Asp Leu Arg Arg Pro
    50                  55                  60

Leu Phe Lys Asp Ala Leu Lys Glu Ala Asp Gly His Trp Lys Pro Ala
65                  70                  75                  80

Lys Lys Gly Ser Glu Tyr Gly Pro Ser Trp Ala Thr His Trp Phe Lys
                85                  90                  95

Ile Gln Val Cys Val Pro Pro Glu Trp Lys Lys Asn Tyr Tyr Lys Lys
            100                 105                 110

Gly Asp Leu Val Val Phe Asn Trp Asn Leu Asn Cys Glu Gly Leu Val
        115                 120                 125

Phe Ser Glu Ser Gly Glu Ala Leu Ile Gly Leu Ser Gly Glu Glu Arg
    130                 135                 140

Arg Glu Trp Pro Ile Pro Asp Asn Trp Phe Asp Gly Lys Cys His Thr
145                 150                 155                 160

Phe Tyr Ile Glu Ala Ser Cys Asn Gly Met Phe Gly Asn Ala Thr Gly
                165                 170                 175

Ser Ser Ile Gln Pro Pro Ser Asp Asn Arg Tyr Phe Arg Leu Asp Ser
            180                 185                 190

Ala Asp Leu Val Val Ile Asn Ser Glu Ala Arg His Leu Phe Val Asp
        195                 200                 205

Phe Trp Ile Ile Gly Asp Ala Ala Arg Glu Phe Pro Gly Asp Ser Trp
    210                 215                 220

Gln Arg Gly Lys Ala Leu Asp Val Ala Asn Lys Ile Met Asp Ala Phe
225                 230                 235                 240

Asp Pro Glu Asn Pro Asp Glu Ser Ile Ala Glu Gly Arg Lys Leu Ala
                245                 250                 255

Lys Glu Tyr Leu Gly Asp Thr Thr Lys Ala Tyr Lys Gln Gln Leu Pro
            260                 265                 270
```

-continued

```
Phe Ala Asp Gly Leu Val Tyr Ala Leu Gly Asn Cys His Ile Asp Thr
            275                 280                 285
Ala Trp Leu Trp Pro Phe Ala Glu Thr Arg Arg Lys Ala Gly Arg Ser
290                 295                 300
Trp Ala Ser Gln Leu Glu Leu Ile Asp Lys Tyr Pro Glu Tyr Val Phe
305                 310                 315                 320
Val Ala Ser Gln Ala Gln Gln Phe Lys Trp Leu Lys Glu Asp Tyr Pro
            325                 330                 335
Asp Leu Phe Ala Lys Ile Gln Lys Gln Ala Lys Lys Gly Arg Phe Leu
            340                 345                 350
Pro Val Gly Gly Ala Trp Thr Glu Cys Asp Thr Asn Leu Pro Ser Gly
            355                 360                 365
Glu Ser Leu Leu Arg Gln Phe Leu Leu Gly Gln Arg Phe Phe Leu Glu
            370                 375                 380
His Phe Gly Ser Leu Ser Asp Thr Phe Trp Leu Pro Asp Thr Phe Gly
385                 390                 395                 400
Tyr Ser Ala Gln Val Pro Gln Leu Cys Arg Leu Ala Gly Met Asp Arg
                405                 410                 415
Phe Leu Thr Gln Lys Leu Ser Trp Asn Ile Asn Ser Phe Pro Asn
            420                 425                 430
Ser Thr Phe Asn Trp Val Ala Leu Asp Gly Ser Gln Val Leu Cys His
            435                 440                 445
Met Pro Pro Asn Asn Thr Tyr Thr Ser Met Ala Asn Phe Gly Asp Val
450                 455                 460
Ser Arg Thr Gln Lys Gln Asn Lys Asn Leu Asp Thr Thr Arg Asn Ser
465                 470                 475                 480
Leu Met Leu Tyr Gly His Gly Asp Gly Gly Gly Pro Thr Ala Glu
                485                 490                 495
Met Leu Glu Lys Leu Arg Arg Cys Arg Gly Val Ser Asn Thr Val Gly
            500                 505                 510
Glu Leu Pro Pro Val Ile Gln Gly Gln Ser Val Thr Asp Phe Tyr Asn
            515                 520                 525
Glu Leu Leu Asp Gln Thr Asn Asn Gly Lys Asp Leu Val Thr Trp Val
            530                 535                 540
Gly Glu Leu Tyr Phe Glu Phe His Arg Gly Thr Tyr Thr Ser Gln Ala
545                 550                 555                 560
Gln Thr Lys Lys Gly Asn Arg Val Ser Glu Asn Leu Leu His Asp Val
                565                 570                 575
Glu Leu Leu Ala Thr Leu Ala Ser Ile Arg Asp Ser Ser Tyr Lys Tyr
            580                 585                 590
Pro Phe Ala Gln Leu Glu Ser Leu Trp Glu Asp Val Cys Leu Cys Gln
            595                 600                 605
Phe His Asp Val Leu Pro Gly Ser Cys Ile Glu Met Val Tyr Lys Asp
            610                 615                 620
Val Lys Lys Ile His Gly Arg Val Ile Asp Thr Ala Ser His Leu Ile
625                 630                 635                 640
Asp Lys Ala Ala Ser Ala Leu Gly Leu Ser Gly His Pro Ser Lys Asp
                645                 650                 655
Ser Phe Asp Cys Thr Pro Val Ala Leu Asn Thr Met Pro Trp Ser Arg
            660                 665                 670
Thr Glu Val Val Ala Val Pro Gln Pro His Trp Asp Ala Thr Val Glu
            675                 680                 685
```

-continued

| | | | | | | | | | | |
|---|---|---|---|---|---|---|---|---|---|---|
| Leu | Ala | Glu | Gly | Val | Glu | Ile | Gln | Glu | Asp | Ser | Gly | Asn | Ala | Leu | Val |
|  | 690 |  |  |  | 695 |  |  |  | 700 |

Met Met Ser Glu Ser Gly Pro Val Val Thr Thr Gln Ser Val Asp Leu
   705                710                  715                 720

Phe Lys Ser Glu Asp Ala Tyr Ile Leu Glu Asn Ser Gln Val Lys Val
              725                 730                 735

Thr Ile Cys Lys Asp Asp Gly Thr Leu Thr Ser Ile Tyr Asp Lys Glu
              740                 745                 750

Asn Asp Arg Arg Val Leu Ser Gly Thr Gly Asn Arg Leu Val Leu Phe
              755                 760                 765

Asp Asp Gln Pro Leu Ser Trp Gln Ala Trp Asp Thr Glu Val Phe Ser
   770                775                 780

Leu Gly Lys Lys Gln Tyr Ile Gly Ala Glu Asn Val Thr Arg His Ser
   785                790                 795                 800

Ile Val Ser Ser Gly Pro Leu Arg Ser Thr Val Ala Phe Thr Tyr Glu
              805                 810                 815

Phe Asn Lys Ser Val Val Thr Thr Glu Ile Ser Leu Asp Ala Asn Ser
              820                 825                 830

Pro Leu Val Thr Phe Asn Thr Arg Ala Asp Trp His Glu Thr Cys Lys
   835                840                 845

Phe Leu Lys Val Glu Phe Pro Val Asp Val His Ser Glu Ser Ala Ser
   850                855                 860

Tyr Glu Ser Gln Phe Gly Val Val Lys Arg Pro Thr His Tyr Asn Thr
   865                870                 875                 880

Ser Trp Asp Val Ala Lys Phe Glu Val Cys Cys His Lys Phe Ala Asp
              885                 890                 895

Leu Ser Glu Leu Asp Tyr Gly Val Ser Ile Leu Asn Asp Cys Lys Tyr
              900                 905                 910

Gly Phe Ala Thr His Gly Asn Leu Met Arg Leu Ser Leu Leu Arg Ala
              915                 920                 925

Pro Lys Ala Pro Asp Ala His Ala Asp Met Gly His His Glu Phe Lys
   930                935                 940

Tyr Gly Val Leu Ala His Lys Gly Pro Leu Gly Ala Thr Thr Val Arg
945                950                 955                 960

Ala Ala Tyr Asn Phe Asn Asn Pro Leu Arg Val Lys Tyr Val Gly Leu
              965                 970                 975

Ser Glu Val Ser Thr Lys Gln Ala Phe Ser Leu Lys Gly Pro Ala Asn
              980                 985                 990

Leu Val Leu Ser Gln Val Lys Arg Ala Glu Val Asp Arg Ser Lys Lys
   995                1000                1005

Ser Thr Asn Val Ile Leu Arg Val Tyr Glu Ala Leu Gly Gly Arg Thr
   1010               1015                1020

Arg Gly Lys Leu Val Ile Asp Leu Pro Asn Val Val Ser Val Thr Lys
1025                1030                1035                1040

Thr Cys Ala Leu Glu Tyr Ser Lys Glu Lys Gln Val Val Ala Lys Ser
              1045                1050                1055

Glu Gly Val Thr Ser Val Asp Ile Ser Leu Arg Ala Phe Glu Val Ala
              1060                1065                1070

Thr Tyr Lys Val Glu Leu Ala
              1075

<210> SEQ ID NO 6
<211> LENGTH: 5060
<212> TYPE: DNA

<213> ORGANISM: Artificial Sequence
<220> FEATURE:
<223> OTHER INFORMATION: Nucleotide sequence encoding fusion of DsbA
      signal sequence to Cellulosimicrobium cellulans mannosidase 5

<400> SEQUENCE: 6

| | | | | | |
|---|---|---|---|---|---|
| atgaaaaaga | tttggctggc | gctggctggt | ttagttttag | cgtttagcgc | atcggccggc | 60 |
| catcaccatc | atcaccacgt | ggggcccggc | tcggacgaag | tggatgcacc | ggaacctccg | 120 |
| agcgcagatt | atgcaagcct | ggttgatgtt | tttgttggca | ccgaaggtga | ttttggtaat | 180 |
| gatatgcctg | cagcacaggc | accgaatggt | ctggcaaaag | ttaatccgcg | taccacaccg | 240 |
| ggtcgtaata | taccggtta | tgattatgcc | cagagcaaaa | ttagcggttt | tacccatacc | 300 |
| aatctggatg | tgttggtgg | tagcggtggt | ggtggtgatc | tgctggttgt | tccgaccagc | 360 |
| ggtagctata | ccgcacgtcc | gggtacaggc | acctatgcac | atccgtttag | ccatgatgat | 420 |
| gaagatgcag | tccgggtttt | tatagcgtt | ggtctgggta | atgttgcagg | caccgatggt | 480 |
| gcaattaccg | tgctccggg | tacaattgaa | gcagaagttg | cagcagcaac | ccgtagcggt | 540 |
| gttcatcgtt | atgcatttcc | ggcaggtagc | accccgagcc | tggttgttga | tctggaaacc | 600 |
| aataatacca | gccgtcgtag | cagcagcgtt | caggttgaaa | cccgtgcaga | tggcaccgtt | 660 |
| gaactgagcg | gtcaggttac | cggctatttt | tataatgcag | cctatacccct | gtattatacc | 720 |
| gcacgcaccc | tgcagcctgc | aaccgttcag | acctggggtg | atgatgatcg | tctggttgat | 780 |
| gcaaccgcac | aggatggtgt | tgataccggt | gcaattctga | cctttgatcc | ggcagatgcc | 840 |
| ggtgaaattg | gtctgcaggt | taccctgtct | ccggttagcg | ttgaacaggc | acgtattgat | 900 |
| cagcaggttg | aactgggtga | tctgagcttt | gatgcaattc | gtgatcgtac | ccgtgcagaa | 960 |
| tggaatgcaa | ccctgggtcg | tgttgcaatt | gatgcaagca | ccgcaaccga | tccgaccggt | 1020 |
| gaactgcagc | gtctgtttta | tacccatctg | tatcgcatgt | ttgcaatgcc | gatgaatgca | 1080 |
| accagcacca | gcggcaccta | tcgtggtgtt | gatggtgcag | ttcatgcagc | acagggcttt | 1140 |
| acctattatg | atagctgggc | aacctgggat | gattttcgca | aatttagcgt | gattgcctat | 1200 |
| attgatccgg | cactgtatcg | tgatatggtt | cagagcctgg | tttacctgtt | tgcagatgca | 1260 |
| gaagcaaccg | tacaggcgg | tggtctgggt | ggttttgttc | atagcgttcc | gaccgttcgt | 1320 |
| tgggaacgta | gcagcgttgt | tgttgcagat | gcaattgcca | aaggctttga | tggttttgat | 1380 |
| cgtctggatg | aagcatatcc | ggcactgcag | cgcctggttg | gtcagtatag | cgcagatgaa | 1440 |
| ctgcgtcgtg | gttatgttgc | aggtaatccg | ggtgcaagcg | ttcagcgtgg | ttatgatcag | 1500 |
| tatggtctga | gcgttattgc | cgatgaactg | ggtctgaccg | aagaagcaga | aaccctgcgc | 1560 |
| gaacaggcaa | gctggccgat | tgaaaaactg | accaaaccgg | gtgcatggac | cgcagcagat | 1620 |
| ggtacacagg | ttggtctgct | gacaccgcgt | gcagccgatg | gtagctggca | gagcgcagat | 1680 |
| catgccaaat | ttgaagcagc | aggtctgtat | cagggcaccc | gtgtggcagta | tcattggtat | 1740 |
| gatgcctatg | atatggatgc | actggttgaa | gcaatgggtg | tcatgaagc | agcccgtctg | 1800 |
| ggtatgcgtc | atatgtttgg | tgaacatgca | ccggatgatg | gtaaagcaat | gctgcatagc | 1860 |
| aatgccaatg | aaattgatct | gcaggcaccg | tacctgtttta | attataccgg | tgaaccgagc | 1920 |
| ctgacccaga | atgggcacg | tgcaatttat | accaaagaaa | cctggaatcg | ctatattgca | 1980 |
| accggtagca | gctctgcagt | tccgtcaggt | ggtggtgaat | tacacctcc | gctgaaaacc | 2040 |
| aaagtttatc | gtctggaccc | tcgtggtatg | ctgccgacca | tggataatga | tgcaggtaca | 2100 |
| atgagcacca | tgtttgttgc | agcagccgtt | ggtctgtttc | cggttaccgc | aggtagcagc | 2160 |

```
cagtttcagg ttggtagccc gttttttgat agcaccacca ttacctatga tgatggtagc    2220
gcatttaccg ttaccgcaga tggtgttagc gaagatgcct tttatgttca gagcgcaacc    2280
ctggatggtg caacctttgg taatacctgg gttgattatg caaccgttgt tggtggtgca    2340
gatctggcat ttcgtatggg tgaacagccg agcgattggg gcaccgatac cgcaccggca    2400
tttagcatga gcaccgccac cgatgaaccg gcagaaggtc ctcgcgttag cgcagaaccg    2460
accaccgtgc agaccggtga tggtggtgca ctggatgcaa ccgttaccct gacactggat    2520
ggcgcacgtc tggcagcacc ggcaggtaca gatctggtta ccagcggtgc agcaagcgtt    2580
gttggtctgc cggatggtgt taccgcagca gttaccgttg caagcccgac cgcactgacc    2640
gttagcctga ccggcaccgc atcagcagat gcacgttttt ttgtgcatct gcgtgatgca    2700
gcactggccg atggtgttgc agccgcaagc ctgcagggtc aggtgttag cgttcgttct     2760
ccgctgcgtc tgagcgttgc aagcgcagaa cgtgatgcac tggcagcact ggttgatgat    2820
gccgttctgg ttcgtcatgg taattatagc agcgttacct ttgatcgttt agcaccgctc    2880
tgacaaaagc acaggaagca ctgggcgacg aagcagcaac cagcattgca ctgcgttttg    2940
cagcagatcg tctgggtgca gcagcagatg cactggatct gaccggtggt ggttatcgta    3000
ccctggaagc agaacagagc gaagcatggt ctggtggtga actgaaaaat gaagccaata    3060
gcagcagcgg taatctgggt ggtgttcgta gcggtagctg ggttcagtat cgcgatatga    3120
cctttgaaac cgcagccggt gatacacctc cgcgttttct gaccgttcgt tatgatacca    3180
gctttgcacc gaccgatacc ccgagcaccg ttcgtgttca tgccggtgat gtttctggtc    3240
cggttgttgc aaccgttgat ctgaaaggca ccagcggttg gggtaaatat accgaagtta    3300
ccgcagaact gggtgatgtt caggccctgg ttgatgccca ggttgttacc tttgaactgc    3360
tggcaccgag cggtcgtagc tgggttggta attttgattg gtttcgcttt agcgcagaag    3420
atccggcagc accgggtcag cctggtgaaa gcccgaccgt taccattgaa gccgaagatt    3480
ggaccgcaag cagcggtcgt ggtctgaaaa aagaaagcag cacctggacc agcggtccgg    3540
tgaccaatgt tggtggtaca gcagatggtg attggattgc ctatggtgaa gttgatctgg    3600
gtgaactgcc gctgggcgaa ctgagcgttc attatgtgca taatagcaat cgcagcggta    3660
ataatagcgc actgagcgtt tatctggatg catttgatcc ggctaatccg ggtgaaccgt    3720
ttgttaccgt tccgctgccg accaccggta gcagttggac cgcagatggc acagccaccg    3780
ttgttctgcc ggaaaccgtg cagggcaccc atgaagtttt tgttcgtctg agcaccgaac    3840
cgtatgcaga tcatccgtat gttgcaaatc tggatagcct gacctttgca ccgggtggtc    3900
cgaccagcgt tgtggttgaa agcgaagcct ggaccagcaa ttctggtcgt ggcctgaaaa    3960
atgaatcttc tacctggacc tctggtccgg ttacaaatgt gggtggcacc gctgatggcg    4020
attggctggc atatggcgaa attgatctgg gcagcgcagc actggatcag ctgtctgtgc    4080
attatgttca taattctaat cgctctggtc gtaattctgc actgtctgtg tatctggatg    4140
cctttgatcc ggcaaatccg ggtgaaccgt ttgtgacagt gccgctggca ataccggta    4200
gctcttggac caccgatggt actgcagttg tggatctgcc gtctaccgtt cgtggtaaac    4260
atcaggtttg ggttcgtctg tctaccgaag catatgccga tcatccgtat gtggccaatc    4320
tggattctat gcgctttttt accgatgcat atgatgttga agttcctccg accgatacag    4380
cagcactgga agccgttgtt gatgcagcag gtacaccgga agcagaaatt gcacgttatg    4440
gtcgtattga tgcccgtgtt tttacccgtg aactggcagc agcacgtagc gttctggccg    4500
atgccggtgc aacacaggca caggcagatg aacgtgctcg tcgtctgggt ctggcaaccg    4560
```

```
atcagctggt tccggcagaa cgtcgtcgtc tggaaaatct ggttgccagc gcagaagcac    4620
tgaccgacga aggttattct ccggaaagct ggcaggcatt tcgtaccgca ctggctgctg    4680
caaccggcac cctggatgat gcagcagcat ctgatgaagc actgcatgat gcacgtctgg    4740
cgctgcaggg tgcagttgat gcactggaag aaccggcaga tgttgttctg gttgaagttg    4800
aagtttctcc gcgttgtctg gcaggtaaac cgtatgttgc cgttcgtgca gttaatgttt    4860
ctgatgcagc cgttgatgtt gaactggcaa gctctctggg cacccgtagc tttgttggtg    4920
tggcaccggg tgcgagcgca tatcagagct ttgcagcccg tagcgcaacc ggtgatctgg    4980
atgttaccgt gaccgcaacc ggtgcagatg gtactcagac cgttgaacag gttgtgaccg    5040
ttccgagctg tagctaataa                                                5060
```

<210> SEQ ID NO 7
<211> LENGTH: 1665
<212> TYPE: PRT
<213> ORGANISM: Cellulosimicrobium cellulans

<400> SEQUENCE: 7

Ala Leu Ala Val Val Gly Leu Ala Pro Ala Thr Ala Ala Ser Ala Ala
1               5                   10                  15

Pro Glu Pro Pro Ser Ala Asp Tyr Ala Ser Leu Val Asp Val Phe Val
            20                  25                  30

Gly Thr Glu Gly Asp Phe Gly Asn Asp Met Pro Ala Ala Gln Ala Pro
        35                  40                  45

Asn Gly Leu Ala Lys Val Asn Pro Arg Thr Thr Pro Gly Arg Asn Asn
    50                  55                  60

Thr Gly Tyr Asp Tyr Ala Gln Ser Lys Ile Ser Gly Phe Thr His Thr
65                  70                  75                  80

Asn Leu Asp Gly Val Gly Ser Gly Gly Gly Asp Leu Leu Val
                85                  90                  95

Val Pro Thr Ser Gly Ser Tyr Thr Ala Arg Pro Gly Thr Gly Thr Tyr
            100                 105                 110

Ala His Pro Phe Ser His Asp Asp Glu Asp Ala Gly Pro Gly Phe Tyr
        115                 120                 125

Ser Val Gly Leu Gly Asn Val Ala Gly Thr Asp Gly Ala Ile Thr Gly
    130                 135                 140

Ala Pro Gly Thr Ile Glu Ala Glu Val Ala Ala Ala Thr Arg Ser Gly
145                 150                 155                 160

Val His Arg Tyr Ala Phe Pro Ala Gly Ser Thr Pro Ser Leu Val Val
                165                 170                 175

Asp Leu Glu Thr Asn Asn Thr Ser Arg Arg Ser Ser Val Gln Val
            180                 185                 190

Glu Thr Arg Ala Asp Gly Thr Val Glu Leu Ser Gly Gln Val Thr Gly
        195                 200                 205

Tyr Phe Tyr Asn Ala Ala Tyr Thr Leu Tyr Tyr Thr Ala Arg Thr Leu
    210                 215                 220

Gln Pro Ala Thr Val Gln Thr Trp Gly Asp Asp Arg Leu Val Asp
225                 230                 235                 240

Ala Thr Ala Gln Asp Gly Val Asp Thr Gly Ala Ile Leu Thr Phe Asp
                245                 250                 255

Pro Ala Asp Ala Gly Glu Ile Gly Leu Gln Val Thr Leu Ser Pro Val
            260                 265                 270

Ser Val Glu Gln Ala Arg Ile Asp Gln Gln Val Glu Leu Gly Asp Leu

```
                275                 280                 285
Ser Phe Asp Ala Ile Arg Asp Arg Thr Arg Ala Glu Trp Asn Ala Thr
290                 295                 300

Leu Gly Arg Val Ala Ile Asp Ala Ser Thr Ala Thr Asp Pro Thr Gly
305                 310                 315                 320

Glu Leu Gln Arg Leu Phe Tyr Thr His Leu Tyr Arg Met Phe Ala Met
                325                 330                 335

Pro Met Asn Ala Thr Ser Thr Ser Gly Thr Tyr Arg Gly Val Asp Gly
                340                 345                 350

Ala Val His Ala Ala Gln Gly Phe Thr Tyr Tyr Asp Ser Trp Ala Thr
                355                 360                 365

Trp Asp Asp Phe Arg Lys Phe Ser Val Ile Ala Tyr Ile Asp Pro Ala
370                 375                 380

Leu Tyr Arg Asp Met Val Gln Ser Leu Val Tyr Leu Phe Ala Asp Ala
385                 390                 395                 400

Glu Ala Thr Gly Thr Gly Gly Leu Gly Gly Phe Val His Ser Val
                405                 410                 415

Pro Thr Val Arg Trp Glu Arg Ser Val Val Ala Asp Ala Ile
                420                 425                 430

Ala Lys Gly Phe Asp Gly Phe Asp Arg Leu Asp Glu Ala Tyr Pro Ala
                435                 440                 445

Leu Gln Arg Leu Val Gly Gln Tyr Ser Ala Asp Glu Leu Arg Arg Gly
450                 455                 460

Tyr Val Ala Gly Asn Pro Gly Ala Ser Val Gln Arg Gly Tyr Asp Gln
465                 470                 475                 480

Tyr Gly Leu Ser Val Ile Ala Asp Glu Leu Gly Leu Thr Glu Glu Ala
                485                 490                 495

Glu Thr Leu Arg Glu Gln Ala Ser Trp Pro Ile Glu Lys Leu Thr Lys
                500                 505                 510

Pro Gly Ala Trp Thr Ala Ala Asp Gly Thr Gln Val Gly Leu Leu Thr
                515                 520                 525

Pro Arg Ala Ala Asp Gly Ser Trp Gln Ser Ala Asp His Ala Lys Phe
530                 535                 540

Glu Ala Ala Gly Leu Tyr Gln Gly Thr Leu Trp Gln Tyr His Trp Tyr
545                 550                 555                 560

Asp Ala Tyr Asp Met Asp Ala Leu Val Glu Ala Met Gly Gly His Glu
                565                 570                 575

Ala Ala Arg Leu Gly Met Arg His Met Phe Gly Glu His Ala Pro Asp
                580                 585                 590

Asp Gly Lys Ala Met Leu His Ser Asn Ala Asn Glu Ile Asp Leu Gln
                595                 600                 605

Ala Pro Tyr Leu Phe Asn Tyr Thr Gly Glu Pro Ser Leu Thr Gln Lys
                610                 615                 620

Trp Ala Arg Ala Ile Tyr Thr Lys Glu Thr Trp Asn Arg Tyr Ile Ala
625                 630                 635                 640

Thr Gly Ser Ser Ser Ala Val Pro Ser Gly Gly Glu Phe Thr Pro
                645                 650                 655

Pro Leu Lys Thr Lys Val Tyr Arg Leu Asp Pro Arg Gly Met Leu Pro
                660                 665                 670

Thr Met Asp Asn Asp Ala Gly Thr Met Ser Thr Met Phe Val Ala Ala
                675                 680                 685

Ala Val Gly Leu Phe Pro Val Thr Ala Gly Ser Ser Gln Phe Gln Val
                690                 695                 700
```

-continued

```
Gly Ser Pro Phe Phe Asp Ser Thr Thr Ile Thr Tyr Asp Asp Gly Ser
705                 710                 715                 720

Ala Phe Thr Val Thr Ala Asp Gly Val Ser Glu Asp Ala Phe Tyr Val
            725                 730                 735

Gln Ser Ala Thr Leu Asp Gly Thr Phe Gly Asn Thr Trp Val Asp
            740                 745                 750

Tyr Ala Thr Val Val Gly Gly Ala Asp Leu Ala Phe Arg Met Gly Glu
            755                 760                 765

Gln Pro Ser Asp Trp Gly Thr Asp Thr Ala Pro Ala Phe Ser Met Ser
            770                 775                 780

Thr Ala Thr Asp Glu Pro Ala Glu Gly Pro Arg Val Ser Ala Glu Pro
785                 790                 795                 800

Thr Thr Val Gln Thr Gly Asp Gly Gly Ala Leu Asp Ala Thr Val Thr
                805                 810                 815

Leu Thr Leu Asp Gly Ala Arg Leu Ala Ala Pro Ala Gly Thr Asp Leu
                820                 825                 830

Val Thr Ser Gly Ala Ala Ser Val Val Gly Leu Pro Asp Gly Val Thr
                835                 840                 845

Ala Ala Val Thr Val Ala Ser Pro Thr Ala Leu Thr Val Ser Leu Thr
850                 855                 860

Gly Thr Ala Ser Ala Asp Ala Arg Phe Phe Val His Leu Arg Asp Ala
865                 870                 875                 880

Ala Leu Ala Asp Gly Val Ala Ala Ser Leu Gln Gly Gln Gly Val
                885                 890                 895

Ser Val Arg Ser Pro Leu Arg Leu Ser Val Ala Ser Ala Glu Arg Asp
                900                 905                 910

Ala Leu Ala Ala Leu Val Asp Asp Ala Val Leu Val Arg His Gly Asn
                915                 920                 925

Tyr Ser Ser Val Thr Phe Asp Arg Phe Ser Thr Ala Leu Thr Lys Ala
            930                 935                 940

Gln Glu Ala Leu Gly Asp Glu Ala Ala Thr Ser Ile Ala Leu Arg Phe
945                 950                 955                 960

Ala Ala Asp Arg Leu Gly Ala Ala Ala Asp Ala Leu Asp Leu Thr Gly
                965                 970                 975

Gly Gly Tyr Arg Thr Leu Glu Ala Glu Gln Ser Glu Ala Trp Ser Gly
                980                 985                 990

Gly Glu Leu Lys Asn Glu Ala Asn Ser Ser Gly Asn Leu Gly Gly
                995             1000                1005

Val Arg Ser Gly Ser Trp Val Gln Tyr Arg Asp Met Thr Phe Glu Thr
        1010                1015                1020

Ala Ala Gly Asp Thr Pro Pro Arg Phe Leu Thr Val Arg Tyr Asp Thr
1025                1030                1035                1040

Ser Phe Ala Pro Thr Asp Thr Pro Ser Thr Val Arg Val His Ala Gly
                1045                1050                1055

Asp Val Ser Gly Pro Val Val Ala Thr Val Asp Leu Lys Gly Thr Ser
                1060                1065                1070

Gly Trp Gly Lys Tyr Thr Glu Val Thr Ala Glu Leu Gly Asp Val Gln
            1075                1080                1085

Ala Leu Val Asp Ala Gln Val Val Thr Phe Glu Leu Leu Ala Pro Ser
            1090                1095                1100

Gly Arg Ser Trp Val Gly Asn Phe Asp Trp Phe Arg Phe Ser Ala Glu
1105                1110                1115                1120
```

-continued

Asp Pro Ala Ala Pro Gly Gln Pro Gly Glu Ser Pro Thr Val Thr Ile
                1125                1130                1135

Glu Ala Glu Asp Trp Thr Ala Ser Ser Gly Arg Gly Leu Lys Lys Glu
            1140                1145                1150

Ser Ser Thr Trp Thr Ser Gly Pro Val Thr Asn Val Gly Gly Thr Ala
        1155                1160                1165

Asp Gly Asp Trp Ile Ala Tyr Gly Glu Val Asp Leu Gly Glu Leu Pro
    1170                1175                1180

Leu Gly Glu Leu Ser Val His Tyr Val His Asn Ser Asn Arg Ser Gly
1185                1190                1195                1200

Asn Asn Ser Ala Leu Ser Val Tyr Leu Asp Ala Phe Asp Pro Ala Asn
                1205                1210                1215

Pro Gly Glu Pro Phe Val Thr Val Pro Leu Pro Thr Thr Gly Ser Ser
            1220                1225                1230

Trp Thr Ala Asp Gly Thr Ala Thr Val Val Leu Pro Glu Thr Val Gln
        1235                1240                1245

Gly Thr His Glu Val Phe Val Arg Leu Ser Thr Glu Pro Tyr Ala Asp
    1250                1255                1260

His Pro Tyr Val Ala Asn Leu Asp Ser Leu Thr Phe Ala Pro Gly Gly
1265                1270                1275                1280

Pro Thr Ser Val Val Val Glu Ser Glu Ala Trp Thr Ser Asn Ser Gly
                1285                1290                1295

Arg Gly Leu Lys Asn Glu Ser Ser Thr Trp Thr Ser Gly Pro Val Thr
            1300                1305                1310

Asn Val Gly Gly Thr Ala Asp Gly Asp Trp Leu Ala Tyr Gly Glu Ile
        1315                1320                1325

Asp Leu Gly Ser Ala Ala Leu Asp Gln Leu Ser Val His Tyr Val His
    1330                1335                1340

Asn Ser Asn Arg Ser Gly Arg Asn Ser Ala Leu Ser Val Tyr Leu Asp
1345                1350                1355                1360

Ala Phe Asp Pro Ala Asn Pro Gly Glu Pro Phe Val Thr Val Pro Leu
                1365                1370                1375

Ala Asn Thr Gly Ser Ser Trp Thr Thr Asp Gly Thr Ala Val Val Asp
            1380                1385                1390

Leu Pro Ser Thr Val Arg Gly Lys His Gln Val Trp Val Arg Leu Ser
        1395                1400                1405

Thr Glu Ala Tyr Ala Asp His Pro Tyr Val Ala Asn Leu Asp Ser Met
    1410                1415                1420

Arg Phe Phe Thr Asp Ala Tyr Asp Val Glu Val Pro Pro Thr Asp Thr
1425                1430                1435                1440

Ala Ala Leu Ala Ala Val Val Asp Ala Ala Gly Thr Pro Glu Ala Glu
                1445                1450                1455

Ile Ala Arg Tyr Gly Arg Ile Asp Ala Arg Val Phe Thr Arg Glu Leu
            1460                1465                1470

Ala Ala Ala Arg Ser Val Leu Asp Ala Gly Ala Thr Gln Ala Gln
        1475                1480                1485

Ala Asp Glu Arg Ala Arg Arg Leu Gly Leu Ala Thr Asp Gln Leu Val
    1490                1495                1500

Pro Ala Glu Arg Arg Leu Glu Asn Leu Val Ala Ser Ala Glu Ala
1505                1510                1515                1520

Leu Thr Asp Glu Gly Tyr Ser Pro Glu Ser Trp Gln Ala Phe Arg Thr
                1525                1530                1535

Ala Leu Ala Ala Ala Thr Gly Thr Leu Asp Asp Ala Ala Ala Ser Asp

```
                    1540                1545                1550
Glu Ala Leu His Asp Ala Arg Leu Ala Leu Gln Gly Ala Val Asp Ala
                1555                1560                1565

Leu Glu Glu Pro Ala Asp Val Val Leu Val Glu Val Glu Val Ser Pro
            1570                1575                1580

Arg Cys Leu Ala Gly Lys Pro Tyr Val Ala Arg Ala Val Asn Val
1585                1590                1595                1600

Ser Asp Ala Ala Val Asp Val Glu Leu Ala Ser Ser Leu Gly Thr Arg
                1605                1610                1615

Ser Phe Val Gly Val Ala Pro Gly Ala Ser Ala Tyr Gln Ser Phe Ala
            1620                1625                1630

Ala Arg Ser Ala Thr Gly Asp Leu Asp Val Thr Val Thr Ala Thr Gly
            1635                1640                1645

Ala Asp Gly Thr Gln Thr Val Glu Gln Val Val Thr Val Pro Ser Cys
            1650                1655                1660

Ser
1665

<210> SEQ ID NO 8
<211> LENGTH: 1650
<212> TYPE: PRT
<213> ORGANISM: Cellulosimicrobium cellulans

<400> SEQUENCE: 8

Ala Pro Glu Pro Pro Ser Ala Asp Tyr Ala Ser Leu Val Asp Val Phe
1               5                   10                  15

Val Gly Thr Glu Gly Asp Phe Gly Asn Asp Met Pro Ala Ala Gln Ala
            20                  25                  30

Pro Asn Gly Leu Ala Lys Val Asn Pro Arg Thr Thr Pro Gly Arg Asn
        35                  40                  45

Asn Thr Gly Tyr Asp Tyr Ala Gln Ser Lys Ile Ser Gly Phe Thr His
    50                  55                  60

Thr Asn Leu Asp Gly Val Gly Gly Ser Gly Gly Gly Asp Leu Leu
65                  70                  75                  80

Val Val Pro Thr Ser Gly Ser Tyr Thr Ala Arg Pro Gly Thr Gly Thr
                85                  90                  95

Tyr Ala His Pro Phe Ser His Asp Asp Glu Asp Ala Gly Pro Gly Phe
            100                 105                 110

Tyr Ser Val Gly Leu Gly Asn Val Ala Gly Thr Asp Gly Ala Ile Thr
        115                 120                 125

Gly Ala Pro Gly Thr Ile Glu Ala Glu Val Ala Ala Thr Arg Ser
    130                 135                 140

Gly Val His Arg Tyr Ala Phe Pro Ala Gly Ser Thr Pro Ser Leu Val
145                 150                 155                 160

Val Asp Leu Glu Thr Asn Asn Thr Ser Arg Arg Ser Ser Val Gln
                165                 170                 175

Val Glu Thr Arg Ala Asp Gly Thr Val Glu Leu Ser Gly Gln Val Thr
            180                 185                 190

Gly Tyr Phe Tyr Asn Ala Ala Tyr Thr Leu Tyr Tyr Thr Ala Arg Thr
        195                 200                 205

Leu Gln Pro Ala Thr Val Gln Thr Trp Gly Asp Asp Arg Leu Val
    210                 215                 220

Asp Ala Thr Ala Gln Asp Gly Val Asp Thr Gly Ala Ile Leu Thr Phe
225                 230                 235                 240
```

```
Asp Pro Ala Asp Ala Gly Glu Ile Gly Leu Gln Val Thr Leu Ser Pro
            245                 250                 255

Val Ser Val Glu Gln Ala Arg Ile Asp Gln Gln Val Glu Leu Gly Asp
        260                 265                 270

Leu Ser Phe Asp Ala Ile Arg Asp Arg Thr Arg Ala Glu Trp Asn Ala
    275                 280                 285

Thr Leu Gly Arg Val Ala Ile Asp Ala Ser Thr Ala Thr Asp Pro Thr
290                 295                 300

Gly Glu Leu Gln Arg Leu Phe Tyr Thr His Leu Tyr Arg Met Phe Ala
305                 310                 315                 320

Met Pro Met Asn Ala Thr Ser Thr Ser Gly Thr Tyr Arg Gly Val Asp
            325                 330                 335

Gly Ala Val His Ala Ala Gln Gly Phe Thr Tyr Tyr Asp Ser Trp Ala
        340                 345                 350

Thr Trp Asp Asp Phe Arg Lys Phe Ser Val Ile Ala Tyr Ile Asp Pro
    355                 360                 365

Ala Leu Tyr Arg Asp Met Val Gln Ser Leu Val Tyr Leu Phe Ala Asp
370                 375                 380

Ala Glu Ala Thr Gly Thr Gly Gly Leu Gly Gly Phe Val His Ser
385                 390                 395                 400

Val Pro Thr Val Arg Trp Glu Arg Ser Val Val Ala Asp Ala
            405                 410                 415

Ile Ala Lys Gly Phe Asp Gly Phe Asp Arg Leu Asp Glu Ala Tyr Pro
        420                 425                 430

Ala Leu Gln Arg Leu Val Gly Gln Tyr Ser Ala Asp Glu Leu Arg Arg
    435                 440                 445

Gly Tyr Val Ala Gly Asn Pro Gly Ala Ser Val Gln Arg Gly Tyr Asp
450                 455                 460

Gln Tyr Gly Leu Ser Val Ile Ala Asp Glu Leu Gly Leu Thr Glu Glu
465                 470                 475                 480

Ala Glu Thr Leu Arg Glu Gln Ala Ser Trp Pro Ile Glu Lys Leu Thr
            485                 490                 495

Lys Pro Gly Ala Trp Thr Ala Ala Asp Gly Thr Gln Val Gly Leu Leu
        500                 505                 510

Thr Pro Arg Ala Ala Asp Gly Ser Trp Gln Ser Ala Asp His Ala Lys
    515                 520                 525

Phe Glu Ala Ala Gly Leu Tyr Gln Gly Thr Leu Trp Gln Tyr His Trp
530                 535                 540

Tyr Asp Ala Tyr Asp Met Asp Ala Leu Val Glu Ala Met Gly Gly His
545                 550                 555                 560

Glu Ala Ala Arg Leu Gly Met Arg His Met Phe Gly Glu His Ala Pro
            565                 570                 575

Asp Asp Gly Lys Ala Met Leu His Ser Asn Ala Asn Glu Ile Asp Leu
        580                 585                 590

Gln Ala Pro Tyr Leu Phe Asn Tyr Thr Gly Glu Pro Ser Leu Thr Gln
    595                 600                 605

Lys Trp Ala Arg Ala Ile Tyr Thr Lys Glu Thr Trp Asn Arg Tyr Ile
610                 615                 620

Ala Thr Gly Ser Ser Ser Ala Val Pro Ser Gly Gly Gly Glu Phe Thr
625                 630                 635                 640

Pro Pro Leu Lys Thr Lys Val Tyr Arg Leu Asp Pro Arg Gly Met Leu
            645                 650                 655

Pro Thr Met Asp Asn Asp Ala Gly Thr Met Ser Thr Met Phe Val Ala
```

```
                    660                 665                 670
Ala Ala Val Gly Leu Phe Pro Val Thr Ala Gly Ser Ser Gln Phe Gln
        675                 680                 685

Val Gly Ser Pro Phe Phe Asp Ser Thr Thr Ile Thr Tyr Asp Asp Gly
        690                 695                 700

Ser Ala Phe Thr Val Thr Ala Asp Gly Val Ser Glu Asp Ala Phe Tyr
705                 710                 715                 720

Val Gln Ser Ala Thr Leu Asp Gly Ala Thr Phe Gly Asn Thr Trp Val
                725                 730                 735

Asp Tyr Ala Thr Val Val Gly Gly Ala Asp Leu Ala Phe Arg Met Gly
                740                 745                 750

Glu Gln Pro Ser Asp Trp Gly Thr Asp Thr Ala Pro Ala Phe Ser Met
        755                 760                 765

Ser Thr Ala Thr Asp Glu Pro Ala Glu Gly Pro Arg Val Ser Ala Glu
        770                 775                 780

Pro Thr Thr Val Gln Thr Gly Asp Gly Gly Ala Leu Asp Ala Thr Val
785                 790                 795                 800

Thr Leu Thr Leu Asp Gly Ala Arg Leu Ala Ala Pro Ala Gly Thr Asp
                805                 810                 815

Leu Val Thr Ser Gly Ala Ala Ser Val Val Gly Leu Pro Asp Gly Val
                820                 825                 830

Thr Ala Ala Val Thr Val Ala Ser Pro Thr Ala Leu Thr Val Ser Leu
        835                 840                 845

Thr Gly Thr Ala Ser Ala Asp Ala Arg Phe Phe Val His Leu Arg Asp
        850                 855                 860

Ala Ala Leu Ala Asp Gly Val Ala Ala Ser Leu Gln Gly Gln Gly
865                 870                 875                 880

Val Ser Val Arg Ser Pro Leu Arg Leu Ser Val Ala Ser Ala Glu Arg
                885                 890                 895

Asp Ala Leu Ala Ala Leu Val Asp Ala Val Leu Val Arg His Gly
                900                 905                 910

Asn Tyr Ser Ser Val Thr Phe Asp Arg Phe Ser Thr Ala Leu Thr Lys
                915                 920                 925

Ala Gln Glu Ala Leu Gly Asp Glu Ala Ala Thr Ser Ile Ala Leu Arg
        930                 935                 940

Phe Ala Ala Asp Arg Leu Gly Ala Ala Asp Ala Leu Asp Leu Thr
945                 950                 955                 960

Gly Gly Gly Tyr Arg Thr Leu Glu Ala Glu Gln Ser Glu Ala Trp Ser
                965                 970                 975

Gly Gly Glu Leu Lys Asn Glu Ala Asn Ser Ser Ser Gly Asn Leu Gly
                980                 985                 990

Gly Val Arg Ser Gly Ser Trp Val Gln Tyr Arg Asp Met Thr Phe Glu
        995                 1000                1005

Thr Ala Ala Gly Asp Thr Pro Pro Arg Phe Leu Thr Val Arg Tyr Asp
        1010                1015                1020

Thr Ser Phe Ala Pro Thr Asp Thr Pro Ser Thr Val Arg Val His Ala
1025                1030                1035                1040

Gly Asp Val Ser Gly Pro Val Ala Thr Val Asp Leu Lys Gly Thr
                1045                1050                1055

Ser Gly Trp Gly Lys Tyr Thr Glu Val Thr Ala Glu Leu Gly Asp Val
                1060                1065                1070

Gln Ala Leu Val Asp Ala Gln Val Val Thr Phe Glu Leu Leu Ala Pro
        1075                1080                1085
```

-continued

```
Ser Gly Arg Ser Trp Val Gly Asn Phe Asp Trp Phe Arg Phe Ser Ala
    1090                1095                1100

Glu Asp Pro Ala Ala Pro Gly Gln Pro Gly Glu Ser Pro Thr Val Thr
1105                1110                1115                1120

Ile Glu Ala Glu Asp Trp Thr Ala Ser Ser Gly Arg Gly Leu Lys Lys
                1125                1130                1135

Glu Ser Ser Thr Trp Thr Ser Gly Pro Val Thr Asn Val Gly Gly Thr
            1140                1145                1150

Ala Asp Gly Asp Trp Ile Ala Tyr Gly Glu Val Asp Leu Gly Glu Leu
            1155                1160                1165

Pro Leu Gly Glu Leu Ser Val His Tyr Val His Asn Ser Asn Arg Ser
        1170                1175                1180

Gly Asn Asn Ser Ala Leu Ser Val Tyr Leu Asp Ala Phe Asp Pro Ala
1185                1190                1195                1200

Asn Pro Gly Glu Pro Phe Val Thr Val Pro Leu Pro Thr Thr Gly Ser
                1205                1210                1215

Ser Trp Thr Ala Asp Gly Thr Ala Thr Val Leu Pro Glu Thr Val
            1220                1225                1230

Gln Gly Thr His Glu Val Phe Val Arg Leu Ser Thr Glu Pro Tyr Ala
        1235                1240                1245

Asp His Pro Tyr Val Ala Asn Leu Asp Ser Leu Thr Phe Ala Pro Gly
        1250                1255                1260

Gly Pro Thr Ser Val Val Val Glu Ser Glu Ala Trp Thr Ser Asn Ser
1265                1270                1275                1280

Gly Arg Gly Leu Lys Asn Glu Ser Ser Thr Trp Thr Ser Gly Pro Val
                1285                1290                1295

Thr Asn Val Gly Gly Thr Ala Asp Gly Asp Trp Leu Ala Tyr Gly Glu
            1300                1305                1310

Ile Asp Leu Gly Ser Ala Ala Leu Asp Gln Leu Ser Val His Tyr Val
        1315                1320                1325

His Asn Ser Asn Arg Ser Gly Arg Asn Ser Ala Leu Ser Val Tyr Leu
    1330                1335                1340

Asp Ala Phe Asp Pro Ala Asn Pro Gly Glu Pro Phe Val Thr Val Pro
1345                1350                1355                1360

Leu Ala Asn Thr Gly Ser Ser Trp Thr Thr Asp Gly Thr Ala Val Val
                1365                1370                1375

Asp Leu Pro Ser Thr Val Arg Gly Lys His Gln Val Trp Val Arg Leu
        1380                1385                1390

Ser Thr Glu Ala Tyr Ala Asp His Pro Tyr Val Ala Asn Leu Asp Ser
        1395                1400                1405

Met Arg Phe Phe Thr Asp Ala Tyr Asp Val Glu Val Pro Pro Thr Asp
    1410                1415                1420

Thr Ala Leu Ala Ala Val Val Asp Ala Ala Gly Thr Pro Glu Ala
1425                1430                1435                1440

Glu Ile Ala Arg Tyr Gly Arg Ile Asp Ala Arg Val Phe Thr Arg Glu
                1445                1450                1455

Leu Ala Ala Ala Arg Ser Val Leu Ala Asp Ala Gly Ala Thr Gln Ala
            1460                1465                1470

Gln Ala Asp Glu Arg Ala Arg Arg Leu Gly Leu Ala Thr Asp Gln Leu
        1475                1480                1485

Val Pro Ala Glu Arg Arg Arg Leu Glu Asn Leu Val Ala Ser Ala Glu
    1490                1495                1500
```

```
Ala Leu Thr Asp Glu Gly Tyr Ser Pro Glu Ser Trp Gln Ala Phe Arg
1505                1510                1515                1520

Thr Ala Leu Ala Ala Ala Thr Gly Thr Leu Asp Asp Ala Ala Ala Ser
            1525                1530                1535

Asp Glu Ala Leu His Asp Ala Arg Leu Ala Leu Gln Gly Ala Val Asp
        1540                1545                1550

Ala Leu Glu Glu Pro Ala Asp Val Val Leu Glu Val Glu Val Ser
    1555                1560                1565

Pro Arg Cys Leu Ala Gly Lys Pro Tyr Val Ala Val Arg Ala Val Asn
    1570                1575                1580

Val Ser Asp Ala Ala Val Asp Val Glu Leu Ala Ser Ser Leu Gly Thr
1585                1590                1595                1600

Arg Ser Phe Val Gly Val Ala Pro Gly Ala Ser Ala Tyr Gln Ser Phe
            1605                1610                1615

Ala Ala Arg Ser Ala Thr Gly Asp Leu Asp Val Thr Val Thr Ala Thr
            1620                1625                1630

Gly Ala Asp Gly Thr Gln Thr Val Glu Gln Val Val Thr Val Pro Ser
        1635                1640                1645

Cys Ser
    1650

<210> SEQ ID NO 9
<211> LENGTH: 5388
<212> TYPE: DNA
<213> ORGANISM: Artificial Sequence
<220> FEATURE:
<223> OTHER INFORMATION: nucleotide sequence encoding fusion of DsbA
      signal sequence to Cellulosimicrobium cellulans mannosidase 4

<400> SEQUENCE: 9
atgaaaaaga tttggctggc gctggctggt ttagttttag cgtttagcgc atcggccggc    60
catcaccatc atcaccacgt ggggcccggc tcggacgaag tggatgcaga accgggtgat   120
tttagcagca gctttgaatc tggcgatccg gcagcactgc cgaccaccgt tgcagaacgt   180
gatggtgcac cgtggcaggc aaatgttggt agctttaccg caggtctgcc tggtagcgtt   240
ctgggtcagc tgaaaggtgt taccgcaagc gcacagaatc tgccgaatga aggtgcagca   300
aatctggcag atggtagcag cggcaccaaa tggctggcat tgcaagcac cggttgggtt   360 cgttatgaat ttgcagaacc ggttagcttt gttgcatata ccatgaccag cggtgatgat   420
gccgcaggtc gtgatccgaa aacctggacc gttgaaggta gcaatgatgg ttctacctgg   480
gcagcactgg atcgtcgtac cgatgaagat tttccgaatc gtcagcagac ccgtaccttt   540
gaactggaag caccgaccgc agcatatacc tatctgcgtc tgaatgttac cgcaaatagc   600
ggtgatagca ttgttcagct ggcaggttgg gatctgagcg cagatctgtc tgcaggtccg   660
agcgcagcac cgatgaccac caaagttggc accggtccgc gtgttagctt taccaataaa   720
gccggtgttg gttttagcgg tctgcatagc ctgcgttatg atggtagcca tctggccgat   780
ggtgaaacct atgcaaccaa tgtgctgtat gatgatgttg atgttgtggt tggtgaagat   840
acccgtctga gctataccat tttccggaa ctgctggatg atctgcagta tccgagcacc   900
tatgcagcag ttgatgttct gtttaccgat ggcacctatc tgagcgatct gggtgcacgt   960
gatgcacatg aaaccgttgc aaccgcacag gcacagggtg aaggtaaaat tctgtatgcc  1020
gatcagtgga atagcgttcg tgttgatctg ggtgatgttg cagaaggtaa accgttgat   1080 caggttctgc tgggttatga taatccgggt ggtcatgcag gcaccaaatt tgcaggttgg  1140
```

```
ctggatgatg ttgaaattac cgcagaaccg gcaaccattg atggtagctc actggcaaat    1200
tatgttgata cccgtcgtgg caccctggca agcggtagct ttagccgtgg taataatatt    1260
ccggcaaccg caaccccgaa tggttttaat ttttggaccc cgtataccaa tgcaagcagc    1320
cagagctggc tgtatgaata tcataaagcc aataatgcga ataataaacc ggttctgcag    1380
ggttttggta ttagccatga accgagcccg tggatgggtg atcgtaatca gctgaccttt    1440
ctgccgagca ccgcaagcgg tacaccggat gcaaccctga gcaccgtggt ctggaatttt    1500
gatcatgcag atgaaaccgc acgtccggat tattatggtg tgacctttac caatggtagc    1560
gcaattgaag caaccccgac cgatcatggt gcagttctgc gttttagcta tccgggtgca    1620
aaaggtcatg ttctggtgga taaagttgat ggtagcagta aactgaccta tgatcaggca    1680
accggcacca ttagcggttg ggttgaaaat ggtagcggtc tgagcgttgg tcgtacccgt    1740
atgtttgttg caggcacctt tgatcgtagc ccgaccgcag ttggcacagc agcaggtaat    1800
cgtgcagatg cacgttttgc aacctttgaa accagcagcg ataaaaccgt ggaactgcgt    1860
gttgcaacca gctttattag cctggatcag gcacgtaaaa atctggatct ggaagttacc    1920
ggtaaaacct ttaccgaagt taaagcagca gcagcacagg catggaatga tcgtctgggt    1980
gttattgaag ttgaaggtgc aagcgaagat cagctggtta ccctgtatag caatctgtat    2040
cgcctgaatc tgtatccgaa tagccagttt gaaaataccg gcaccgcaca ggaaccggtt    2100
tatcgttacg catctccggt tagcgcaacc accggtagcg caaccgatac ccagaccaat    2160
gccaaaattg tggatggcaa aatttatgtg aataatggct tttgggatac ctatcgtacc    2220
gcatggcctg catatagcct gctgtatccg gaactggcag cagaactggt tgatggtttt    2280
gttcagcagt atcgtgatgg tggttggatt gcacgttgga gcagtccggg ttatgcagat    2340
ctgatgaccg gtacaagctc tgatgttgca tttgcagatg cctatctgaa aggtagcctg    2400
ccgaccggta cagcactgga agcatatgat gcagcactgc gtaatgcaac cgttgcacct    2460
ccgagcaatg cagttggtcg taaaggtctg cagacaagcc cgtttctggg ttttacaccg    2520
gaaagcaccc atgaaagcgt tagctggggt ctggaaggtc tggttaatga ttttggcatt    2580
ggcaatatgg ctgcagcact ggcagaagat ccggcaacac cggaagaacg tcgtgaaacc    2640
ctgcgtgaag aaagcgcata ttttctggaa cgtgccaccc attatgttga actgtttgat    2700
ccggaagtgg atttttttgt tccgcgtcat gaagatggta catgggcagt tgatccggaa    2760
acctatgatc cggaagcatg gggtggtggt tataccgaaa ccaatggctg gaattttgca    2820
tttcatgcac cgcaggatgg tcagggtctg gcaaatctgt atggtggtaa acagggtctg    2880
gaagataaac tggatgaatt ttttagcaca ccggaaaaag gtgcaggtaa tggtggtatt    2940
catgaacagc gtgaagcacg tgatgttcgt atgggtcagt ggggtatgag caatcaggtt    3000
agccatcata ttccgtggct gtatgatgca gccggtgctc cgagcaaagc acaggaaaaa    3060
gttcgcgaag ttacccgtcg tctgtttgtt ggtagcgaaa ttggtcaggg ttatccgggt    3120
gatgaagata atggtgaaat gtcctcctgg tggatttttg caagcctggg tttttatccg    3180
ctgcaggttg gtagcgatca gtatgcagtt ggttctccgc tgtttgataa agcaaccgtt    3240
catctgccgg atggtgatct ggttgttaat gccgaaaata tagcgtggca taatgtgtat    3300
gttcagagcc tggcagttga tggtgaagca cgtaccagca ccagcctgag ccaggcagat    3360
ctgagcggtg caccaccct ggattttgtt atgggtccgg aaccgagcga ttggggcacc    3420
ggtgaagatg atgcacctcc gtcactgacc gaaggtgatg aacctccgac accggttcag    3480
gatgcaacca ccgcaggcct gggcaccacc accgttgccg atggtgatgc caccacctct    3540
```

```
gcagcagccc tgaccgataa taccagcggc acccgtacca cctttgcaac caccacccccg    3600 agcattacat gggcaggtaa tggcattcgt ccgaccgttg gtagctatac cctgacctct    3660
ggtgcaagcg gcaccgcaag cccgtctgca tggaccctgg aaggttctga tgatggcgaa    3720
acctggacca cactggatga acgtagcggt gaacagtttc gttgggcact gcagacccgt    3780
ccgtttaccg ttgccgaacc gaccgcattt gcacgttatc gtgttaccgt taccgcaacc    3840
agcggttctg gtgcactgag cctggcagaa gttgaactgc tggcagatcc gaaagaaagc    3900
ggtgcagaag aactgaccct gtctgcagca ccggatcgtg atggcgttac cggtcgtgaa    3960
gttagcggtt cttttgcaac cctgaccggt gttgaaggtg atgttgccgc actggatgtt    4020
caggttgcat ttggtgatgg tagcgaaccg gttgcaggta cactgcgtgc cggtgcattt    4080
ggtggttatg cagttgatgc agcacatacc tggaccgcac cgggtgttta tccggttacc    4140
gtgaccgtta gcggtgaagg tattgaaacc gttagcgcaa gcagctatgt tagcgttagc    4200
ctgctgcgtg aaggttctct gctggcagca tatgataatg tgtgcattgg tgatgcaggt    4260
acaaccgttg gttcttgtga tggtcagggc gttttttttg atcgtgcaca gctggcagca    4320 aaaggtttg tgcagggtga acgtgcaacc gttccgggta cagatctggc atttgatgtt    4380
ccggcagttc cggctggtca gcctgataat gcaaccggtg atggtcagac cattgaactg    4440
gatgttccgg ctgatgcaga acagctgagc gttattggca ccggcaccga aaaaaatcag    4500
caggcaaccg gtacactgac ctttgatgat ggttctaccc agccgattga tctgagcttt    4560
ggtgattgga gcggtgcagc acgtaatccg gtgtttggta atattccggt tgcagttacc    4620
gatagccgtc tgcgtggtgg ttctccgcag accggtacac cggcagcatt ttttgccacc    4680
gcaccgatta ccctgccgga aggtaaacgt ccggttagcc tgaccctgcc ggatcagcct    4740
ggtgaactga gccgtgatgg tcgtattcat gttgttgcag ttgcacatga tggcaccttt    4800
gcagaacatc ctgcactgga agtgaccgca gcagaaggtg ttaccctggc agttggtcag    4860
acctcagatg ttgcactggc acaggttgcc ggtggtcgtg aaggtgcaga tctgcgtgcc    4920
gcagttacct ggggtgatgg ttctgatgtg cagccggtg ccgttaccga tggtagcgtt    4980
agcggtagcc atgcatatac cgcagcaggc acctataccg catatgttgt tgtggatgat    5040
ggttggacca gccaggttgt tgaagttccg gtgaccgtta cagaagccga accggcactg    5100
gccgttgatg tcaccgttag cacccgttgc ctggcaggta agcatatgt tgcagtgcgt    5160 gcagaaaatg gtgaagatgt tccgctggca attcgtctgg ttaccccgtt tggcaccaaa    5220
gaagttgcag cagttgctcc gggagccaat gcatatcaga gctttgcaac ccgtgttacc    5280
gcagttgaag caggcaccgt taccgttgaa gccacccgtg gcaccggtga tgaagaagtt    5340
accgccagca ttcaggcaga ttatgcagcc gttacctgcg gttaataa                 5388
```

<210> SEQ ID NO 10
<211> LENGTH: 3622
<212> TYPE: PRT
<213> ORGANISM: Cellulosimicrobium cellulans

<400> SEQUENCE: 10

Met Thr Arg Pro Leu Pro Pro Gly Arg Ala Val Ala Arg Ser Gly Ser
1               5                   10                  15

Gly Arg Ala Arg Pro Leu Gly Leu Val Leu Ala Ala Leu Ala Val
            20                  25                  30

Pro Leu Gly Val Pro Leu Ala Ala Pro Ala Gly Ala Leu Ala Ala Ala
        35                  40                  45

```
Pro Ala Ala Ala Glu Pro Gly Asp Phe Ser Ser Phe Glu Ser
    50              55                  60

Gly Asp Pro Ala Ala Leu Pro Thr Thr Val Ala Glu Arg Asp Gly Ala
65              70                  75                  80

Pro Trp Gln Ala Asn Val Gly Ser Phe Thr Ala Gly Leu Pro Gly Ser
                85                  90                  95

Val Leu Gly Gln Leu Lys Gly Val Thr Ala Ser Ala Gln Asn Leu Pro
                100                 105                 110

Asn Glu Gly Ala Ala Asn Leu Ala Asp Gly Ser Ser Gly Thr Lys Trp
                115                 120                 125

Leu Ala Phe Ala Ser Thr Gly Trp Val Arg Tyr Glu Phe Ala Glu Pro
            130                 135                 140

Val Ser Phe Val Ala Tyr Thr Met Thr Ser Gly Asp Asp Ala Ala Gly
145                 150                 155                 160

Arg Asp Pro Lys Thr Trp Thr Val Glu Gly Ser Asn Asp Gly Ser Thr
                165                 170                 175

Trp Ala Ala Leu Asp Arg Arg Thr Asp Glu Asp Phe Pro Asn Arg Gln
                180                 185                 190

Gln Thr Arg Thr Phe Glu Leu Glu Ala Pro Thr Ala Ala Tyr Thr Tyr
            195                 200                 205

Leu Arg Leu Asn Val Thr Ala Asn Ser Gly Asp Ser Ile Val Gln Leu
            210                 215                 220

Ala Gly Trp Asp Leu Ser Ala Asp Leu Ser Ala Gly Pro Ser Ala Ala
225                 230                 235                 240

Pro Met Thr Thr Lys Val Gly Thr Gly Pro Arg Val Ser Phe Thr Asn
                245                 250                 255

Lys Ala Gly Val Gly Phe Ser Gly Leu His Ser Leu Arg Tyr Asp Gly
                260                 265                 270

Ser His Leu Ala Asp Gly Glu Thr Tyr Ala Thr Asn Val Leu Tyr Asp
            275                 280                 285

Asp Val Asp Val Val Gly Glu Asp Thr Arg Leu Ser Tyr Thr Ile
            290                 295                 300

Phe Pro Glu Leu Leu Asp Asp Leu Gln Tyr Pro Ser Thr Tyr Ala Ala
305                 310                 315                 320

Val Asp Val Leu Phe Thr Asp Gly Thr Tyr Leu Ser Asp Leu Gly Ala
                325                 330                 335

Arg Asp Ala His Glu Thr Val Ala Thr Ala Gln Ala Gln Gly Glu Gly
            340                 345                 350

Lys Ile Leu Tyr Ala Asp Gln Trp Asn Ser Val Arg Val Asp Leu Gly
            355                 360                 365

Asp Val Ala Glu Gly Lys Thr Val Asp Gln Val Leu Leu Gly Tyr Asp
370                 375                 380

Asn Pro Gly Gly His Ala Gly Thr Lys Phe Ala Gly Trp Leu Asp Asp
385                 390                 395                 400

Val Glu Ile Thr Ala Glu Pro Ala Thr Ile Asp Gly Ser Ser Leu Ala
                405                 410                 415

Asn Tyr Val Asp Thr Arg Arg Gly Thr Leu Ala Ser Gly Ser Phe Ser
            420                 425                 430

Arg Gly Asn Asn Ile Pro Ala Thr Ala Thr Pro Asn Gly Phe Asn Phe
            435                 440                 445

Trp Thr Pro Tyr Thr Asn Ala Ser Ser Gln Ser Trp Leu Tyr Glu Tyr
        450                 455                 460
```

-continued

His Lys Ala Asn Asn Ala Asn Asn Lys Pro Val Leu Gln Gly Phe Gly
465                 470                 475                 480

Ile Ser His Glu Pro Ser Pro Trp Met Gly Asp Arg Asn Gln Leu Thr
            485                 490                 495

Phe Leu Pro Ser Thr Ala Ser Gly Thr Pro Asp Ala Thr Leu Ser Thr
        500                 505                 510

Arg Gly Leu Glu Phe Asp His Ala Asp Glu Thr Ala Arg Pro Asp Tyr
    515                 520                 525

Tyr Gly Val Thr Phe Thr Asn Gly Ser Ala Ile Glu Ala Thr Pro Thr
530                 535                 540

Asp His Gly Ala Val Leu Arg Phe Ser Tyr Pro Gly Ala Lys Gly His
545                 550                 555                 560

Val Leu Val Asp Lys Val Asp Gly Ser Ser Lys Leu Thr Tyr Asp Gln
            565                 570                 575

Ala Thr Gly Thr Ile Ser Gly Trp Val Glu Asn Gly Ser Gly Leu Ser
        580                 585                 590

Val Gly Arg Thr Arg Met Phe Val Ala Gly Thr Phe Asp Arg Ser Pro
    595                 600                 605

Thr Ala Val Gly Thr Ala Ala Gly Asn Arg Ala Asp Ala Arg Phe Ala
610                 615                 620

Thr Phe Glu Thr Ser Ser Asp Lys Thr Val Glu Leu Arg Val Ala Thr
625                 630                 635                 640

Ser Phe Ile Ser Leu Asp Gln Ala Arg Lys Asn Leu Asp Leu Glu Val
            645                 650                 655

Thr Gly Lys Thr Phe Thr Glu Val Lys Ala Ala Ala Gln Ala Trp
        660                 665                 670

Asn Asp Arg Leu Gly Val Ile Glu Val Glu Gly Ala Ser Glu Asp Gln
    675                 680                 685

Leu Val Thr Leu Tyr Ser Asn Leu Tyr Arg Leu Asn Leu Tyr Pro Asn
690                 695                 700

Ser Gln Phe Glu Asn Thr Gly Thr Ala Gln Glu Pro Val Tyr Arg Tyr
705                 710                 715                 720

Ala Ser Pro Val Ser Ala Thr Thr Gly Ser Ala Thr Asp Thr Gln Thr
            725                 730                 735

Asn Ala Lys Ile Val Asp Gly Lys Ile Tyr Val Asn Asn Gly Phe Trp
        740                 745                 750

Asp Thr Tyr Arg Thr Ala Trp Pro Ala Tyr Ser Leu Leu Tyr Pro Glu
    755                 760                 765

Leu Ala Ala Glu Leu Val Asp Gly Phe Val Gln Gln Tyr Arg Asp Gly
770                 775                 780

Gly Trp Ile Ala Arg Trp Ser Ser Pro Gly Tyr Ala Asp Leu Met Thr
785                 790                 795                 800

Gly Thr Ser Ser Asp Val Ala Phe Ala Asp Ala Tyr Leu Lys Gly Ser
            805                 810                 815

Leu Pro Thr Gly Thr Ala Leu Glu Ala Tyr Asp Ala Ala Leu Arg Asn
        820                 825                 830

Ala Thr Val Ala Pro Pro Ser Asn Ala Val Gly Arg Lys Gly Leu Gln
    835                 840                 845

Thr Ser Pro Phe Leu Gly Phe Thr Pro Glu Ser Thr His Glu Ser Val
850                 855                 860

Ser Trp Gly Leu Glu Gly Leu Val Asn Asp Phe Gly Ile Gly Asn Met
865                 870                 875                 880

Ala Ala Ala Leu Ala Glu Asp Pro Ala Thr Pro Glu Glu Arg Arg Glu 885                 890                 895
Thr Leu Arg Glu Glu Ser Ala Tyr Phe Leu Glu Arg Ala Thr His Tyr
                900                 905                 910

Val Glu Leu Phe Asp Pro Glu Val Asp Phe Val Pro Arg His Glu
            915                 920                 925

Asp Gly Thr Trp Ala Val Asp Pro Glu Thr Tyr Asp Pro Glu Ala Trp
            930                 935                 940

Gly Gly Gly Tyr Thr Glu Thr Asn Gly Trp Asn Phe Ala Phe His Ala
945                 950                 955                 960

Pro Gln Asp Gly Gln Gly Leu Ala Asn Leu Tyr Gly Gly Lys Gln Gly
            965                 970                 975

Leu Glu Asp Lys Leu Asp Glu Phe Phe Ser Thr Pro Glu Lys Gly Ala
            980                 985                 990

Gly Asn Gly Gly Ile His Glu Gln Arg Glu Ala Arg Asp Val Arg Met
            995                1000                1005

Gly Gln Trp Gly Met Ser Asn Gln Val Ser His His Ile Pro Trp Leu
        1010                1015                1020

Tyr Asp Ala Ala Gly Ala Pro Ser Lys Ala Gln Glu Lys Val Arg Glu
1025                1030                1035                1040

Val Thr Arg Arg Leu Phe Val Gly Ser Glu Ile Gly Gln Gly Tyr Pro
            1045                1050                1055

Gly Asp Glu Asp Asn Gly Glu Met Ser Ser Trp Trp Ile Phe Ala Ser
            1060                1065                1070

Leu Gly Phe Tyr Pro Leu Gln Val Gly Ser Asp Gln Tyr Ala Val Gly
        1075                1080                1085

Ser Pro Leu Phe Asp Lys Ala Thr Val His Leu Pro Asp Gly Asp Leu
        1090                1095                1100

Val Val Asn Ala Glu Asn Asn Ser Val Asp Asn Val Tyr Val Gln Ser
1105                1110                1115                1120

Leu Ala Val Asp Gly Glu Ala Arg Thr Ser Thr Ser Leu Ser Gln Ala
            1125                1130                1135

Asp Leu Ser Gly Gly Thr Thr Leu Asp Phe Val Met Gly Pro Glu Pro
            1140                1145                1150

Ser Asp Trp Gly Thr Gly Glu Asp Asp Ala Pro Pro Ser Leu Thr Glu
        1155                1160                1165

Gly Asp Glu Pro Pro Thr Pro Val Gln Asp Ala Thr Thr Ala Gly Leu
        1170                1175                1180

Gly Thr Thr Thr Val Ala Asp Gly Asp Ala Thr Thr Ser Ala Ala Ala
1185                1190                1195                1200

Leu Thr Asp Asn Thr Ser Gly Thr Arg Thr Thr Phe Ala Thr Thr Thr
            1205                1210                1215

Pro Ser Ile Thr Trp Ala Gly Asn Gly Ile Arg Pro Thr Val Gly Ser
            1220                1225                1230

Tyr Thr Leu Thr Ser Gly Ala Ser Gly Thr Ala Ser Pro Ser Ala Trp
        1235                1240                1245

Thr Leu Glu Gly Ser Asp Asp Gly Glu Thr Trp Thr Thr Leu Asp Glu
        1250                1255                1260

Arg Ser Gly Glu Gln Phe Arg Trp Ala Leu Gln Thr Arg Pro Phe Thr
1265                1270                1275                1280

Val Ala Glu Pro Thr Ala Phe Ala Arg Tyr Arg Val Thr Val Thr Ala
            1285                1290                1295

Thr Ser Gly Ser Gly Ala Leu Ser Leu Ala Glu Val Glu Leu Leu Ala
            1300                1305                1310

```
Asp Pro Lys Glu Ser Gly Ala Glu Glu Leu Thr Leu Ser Ala Ala Pro
        1315                1320                1325

Asp Arg Asp Gly Val Thr Gly Arg Glu Val Ser Gly Ser Phe Ala Thr
        1330                1335                1340

Leu Thr Gly Val Glu Gly Asp Val Ala Ala Leu Asp Val Gln Val Ala
1345                1350                1355                1360

Phe Gly Asp Gly Ser Glu Pro Val Ala Gly Thr Leu Arg Ala Gly Ala
                1365                1370                1375

Phe Gly Gly Tyr Ala Val Asp Ala Ala His Thr Trp Thr Ala Pro Gly
            1380                1385                1390

Val Tyr Pro Val Thr Val Thr Val Ser Gly Glu Gly Ile Glu Thr Val
        1395                1400                1405

Ser Ala Ser Ser Tyr Val Ser Val Ser Leu Leu Arg Glu Gly Ser Leu
    1410                1415                1420

Leu Ala Ala Tyr Asp Asn Val Cys Ile Gly Asp Ala Gly Thr Thr Val
1425                1430                1435                1440

Gly Ser Cys Asp Gly Gln Gly Val Phe Phe Asp Arg Ala Gln Leu Ala
                1445                1450                1455

Ala Lys Gly Phe Val Gln Gly Glu Arg Ala Thr Val Pro Gly Thr Asp
            1460                1465                1470

Leu Ala Phe Asp Val Pro Ala Val Pro Ala Gly Gln Pro Asp Asn Ala
        1475                1480                1485

Thr Gly Asp Gly Gln Thr Ile Glu Leu Asp Val Pro Ala Asp Ala Glu
    1490                1495                1500

Gln Leu Ser Val Ile Gly Thr Gly Thr Glu Lys Asn Gln Gln Ala Thr
1505                1510                1515                1520

Gly Thr Leu Thr Phe Asp Asp Gly Ser Thr Gln Pro Ile Asp Leu Ser
                1525                1530                1535

Phe Gly Asp Trp Ser Gly Ala Ala Arg Asn Pro Val Phe Gly Asn Ile
            1540                1545                1550

Pro Val Ala Val Thr Asp Ser Arg Leu Arg Gly Gly Ser Pro Gln Thr
        1555                1560                1565

Gly Thr Pro Ala Ala Phe Phe Ala Thr Ala Pro Ile Thr Leu Pro Glu
    1570                1575                1580

Gly Lys Arg Pro Val Ser Leu Thr Leu Pro Asp Gln Pro Gly Glu Leu
1585                1590                1595                1600

Ser Arg Asp Gly Arg Ile His Val Val Ala Val Ala His Asp Gly Thr
                1605                1610                1615

Phe Ala Glu His Pro Ala Leu Glu Val Thr Ala Ala Glu Gly Val Thr
            1620                1625                1630

Leu Ala Val Gly Gln Thr Ser Asp Val Ala Leu Ala Gln Val Ala Gly
        1635                1640                1645

Gly Arg Glu Gly Ala Asp Leu Arg Ala Ala Val Thr Trp Gly Asp Gly
    1650                1655                1660

Ser Asp Val Ala Ala Gly Ala Val Thr Asp Gly Ser Val Ser Gly Ser
1665                1670                1675                1680

His Ala Tyr Thr Ala Ala Gly Thr Tyr Thr Ala Tyr Val Val Val Asp
                1685                1690                1695

Asp Gly Trp Thr Ser Gln Val Val Glu Val Pro Val Thr Val Thr Glu
            1700                1705                1710

Ala Glu Pro Ala Leu Ala Val Asp Val Thr Val Ser Thr Arg Cys Leu
        1715                1720                1725
```

-continued

```
Ala Gly Lys Ala Tyr Val Ala Val Arg Ala Glu Asn Gly Glu Asp Val
    1730                1735                1740
Pro Leu Ala Ile Arg Leu Val Thr Pro Phe Gly Thr Lys Glu Val Ala
1745                1750                1755                1760
Ala Val Ala Pro Gly Ala Asn Ala Tyr Gln Ser Phe Ala Thr Arg Val
                1765                1770                1775
Thr Ala Val Glu Ala Gly Thr Val Thr Val Glu Ala Thr Arg Gly Thr
            1780                1785                1790
Gly Asp Glu Glu Val Thr Ala Ser Ile Gln Ala Asp Tyr Ala Ala Val
                1795                1800                1805
Thr Cys Gly Met Thr Arg Pro Leu Pro Pro Gly Arg Ala Val Ala Arg
    1810                1815                1820
Ser Gly Ser Gly Arg Ala Arg Pro Leu Gly Leu Val Leu Ala Ala Ala
1825                1830                1835                1840
Leu Ala Val Pro Leu Gly Val Pro Leu Ala Ala Pro Ala Gly Ala Leu
                1845                1850                1855
Ala Ala Ala Pro Ala Ala Ala Ala Glu Pro Gly Asp Phe Ser Ser Ser
            1860                1865                1870
Phe Glu Ser Gly Asp Pro Ala Ala Leu Pro Thr Thr Val Ala Glu Arg
        1875                1880                1885
Asp Gly Ala Pro Trp Gln Ala Asn Val Gly Ser Phe Thr Ala Gly Leu
    1890                1895                1900
Pro Gly Ser Val Leu Gly Gln Leu Lys Gly Val Thr Ala Ser Ala Gln
1905                1910                1915                1920
Asn Leu Pro Asn Glu Gly Ala Ala Asn Leu Ala Asp Gly Ser Ser Gly
                1925                1930                1935
Thr Lys Trp Leu Ala Phe Ala Ser Thr Gly Trp Val Arg Tyr Glu Phe
            1940                1945                1950
Ala Glu Pro Val Ser Phe Val Ala Tyr Thr Met Thr Ser Gly Asp Asp
        1955                1960                1965
Ala Ala Gly Arg Asp Pro Lys Thr Trp Thr Val Glu Gly Ser Asn Asp
    1970                1975                1980
Gly Ser Thr Trp Ala Ala Leu Asp Arg Arg Thr Asp Glu Asp Phe Pro
1985                1990                1995                2000
Asn Arg Gln Gln Thr Arg Thr Phe Glu Leu Glu Ala Pro Thr Ala Ala
                2005                2010                2015
Tyr Thr Tyr Leu Arg Leu Asn Val Thr Ala Asn Ser Gly Asp Ser Ile
            2020                2025                2030
Val Gln Leu Ala Gly Trp Asp Leu Ser Ala Asp Leu Ser Ala Gly Pro
        2035                2040                2045
Ser Ala Ala Pro Met Thr Thr Lys Val Gly Thr Gly Pro Arg Val Ser
    2050                2055                2060
Phe Thr Asn Lys Ala Gly Val Gly Phe Ser Gly Leu His Ser Leu Arg
2065                2070                2075                2080
Tyr Asp Gly Ser His Leu Ala Asp Gly Glu Thr Tyr Ala Thr Asn Val
                2085                2090                2095
Leu Tyr Asp Asp Val Asp Val Val Gly Glu Asp Thr Arg Leu Ser
            2100                2105                2110
Tyr Thr Ile Phe Pro Glu Leu Leu Asp Asp Leu Gln Tyr Pro Ser Thr
        2115                2120                2125
Tyr Ala Ala Val Asp Val Leu Phe Thr Asp Gly Thr Tyr Leu Ser Asp
    2130                2135                2140
Leu Gly Ala Arg Asp Ala His Glu Thr Val Ala Thr Ala Gln Ala Gln
```

-continued

Gly Glu Gly Lys Ile Leu Tyr Ala Asp Gln Trp Asn Ser Val Arg Val
2145                2150                2155                2160

Asp Leu Gly Asp Val Ala Glu Gly Lys Thr Val Asp Gln Val Leu Leu
2165                2170                2175

Gly Tyr Asp Asn Pro Gly Gly His Ala Gly Thr Lys Phe Ala Gly Trp
2180                2185                2190

Leu Asp Asp Val Glu Ile Thr Ala Glu Pro Ala Thr Ile Asp Gly Ser
2195                2200                2205

Ser Leu Ala Asn Tyr Val Asp Thr Arg Arg Gly Thr Leu Ala Ser Gly
2210                2215                2220

Ser Phe Ser Arg Gly Asn Asn Ile Pro Ala Thr Ala Pro Asn Gly
2225                2230                2235                2240

Phe Asn Phe Trp Thr Pro Tyr Thr Asn Ala Ser Ser Gln Ser Trp Leu
2245                2250                2255

Tyr Glu Tyr His Lys Ala Asn Asn Ala Asn Asn Lys Pro Val Leu Gln
2260                2265                2270

Gly Phe Gly Ile Ser His Glu Pro Ser Pro Trp Met Gly Asp Arg Asn
2275                2280                2285

Gln Leu Thr Phe Leu Pro Ser Thr Ala Ser Gly Thr Pro Asp Ala Thr
2290                2295                2300

Leu Ser Thr Arg Gly Leu Glu Phe Asp His Ala Asp Glu Thr Ala Arg
2305                2310                2315                2320

Pro Asp Tyr Tyr Gly Val Thr Phe Thr Asn Gly Ser Ala Ile Glu Ala
2325                2330                2335

Thr Pro Thr Asp His Gly Ala Val Leu Arg Phe Ser Tyr Pro Gly Ala
2340                2345                2350

Lys Gly His Val Leu Val Asp Lys Val Asp Gly Ser Ser Lys Leu Thr
2355                2360                2365

Tyr Asp Gln Ala Thr Gly Thr Ile Ser Gly Trp Val Glu Asn Gly Ser
2370                2375                2380

Gly Leu Ser Val Gly Arg Thr Arg Met Phe Val Ala Gly Thr Phe Asp
2385                2390                2395                2400

Arg Ser Pro Thr Ala Val Gly Thr Ala Ala Gly Asn Arg Ala Asp Ala
2405                2410                2415

Arg Phe Ala Thr Phe Glu Thr Ser Ser Asp Lys Thr Val Glu Leu Arg
2420                2425                2430

Val Ala Thr Ser Phe Ile Ser Leu Asp Gln Ala Arg Lys Asn Leu Asp
2435                2440                2445

Leu Glu Val Thr Gly Lys Thr Phe Thr Glu Val Lys Ala Ala Ala Ala
2450                2455                2460

Gln Ala Trp Asn Asp Arg Leu Gly Val Ile Glu Val Glu Gly Ala Ser
2465                2470                2475                2480

Glu Asp Gln Leu Val Thr Leu Tyr Ser Asn Leu Tyr Arg Leu Asn Leu
2485                2490                2495

Tyr Pro Asn Ser Gln Phe Glu Asn Thr Gly Thr Ala Gln Glu Pro Val
2500                2505                2510

Tyr Arg Tyr Ala Ser Pro Val Ser Ala Thr Thr Gly Ser Ala Thr Asp
2515                2520                2525

Thr Gln Thr Asn Ala Lys Ile Val Asp Gly Lys Ile Tyr Val Asn Asn
2530                2535                2540

Gly Phe Trp Asp Thr Tyr Arg Thr Ala Trp Pro Ala Tyr Ser Leu Leu
2545                2550                2555                2560

2565                2570                2575

```
Tyr Pro Glu Leu Ala Ala Glu Leu Val Asp Gly Phe Val Gln Gln Tyr
            2580                2585                2590

Arg Asp Gly Gly Trp Ile Ala Arg Trp Ser Ser Pro Gly Tyr Ala Asp
2595                2600                2605

Leu Met Thr Gly Thr Ser Ser Asp Val Ala Phe Ala Asp Ala Tyr Leu
            2610                2615                2620

Lys Gly Ser Leu Pro Thr Gly Thr Ala Leu Glu Ala Tyr Asp Ala Ala
2625                2630                2635                2640

Leu Arg Asn Ala Thr Val Ala Pro Pro Ser Asn Ala Val Gly Arg Lys
            2645                2650                2655

Gly Leu Gln Thr Ser Pro Phe Leu Gly Phe Thr Pro Glu Ser Thr His
            2660                2665                2670

Glu Ser Val Ser Trp Gly Leu Glu Gly Leu Val Asn Asp Phe Gly Ile
            2675                2680                2685

Gly Asn Met Ala Ala Ala Leu Ala Glu Asp Pro Ala Thr Pro Glu Glu
            2690                2695                2700

Arg Arg Glu Thr Leu Arg Glu Glu Ser Ala Tyr Phe Leu Glu Arg Ala
2705                2710                2715                2720

Thr His Tyr Val Glu Leu Phe Asp Pro Glu Val Asp Phe Phe Val Pro
            2725                2730                2735

Arg His Glu Asp Gly Thr Trp Ala Val Asp Pro Glu Thr Tyr Asp Pro
            2740                2745                2750

Glu Ala Trp Gly Gly Gly Tyr Thr Gly Thr Asn Gly Trp Asn Phe Ala
            2755                2760                2765

Phe His Ala Pro Gln Asp Gly Gln Gly Leu Ala Asn Leu Tyr Gly Gly
            2770                2775                2780

Lys Gln Gly Leu Glu Asp Lys Leu Asp Glu Phe Phe Ser Thr Pro Glu
2785                2790                2795                2800

Lys Gly Ala Gly Asn Gly Gly Ile His Glu Gln Arg Glu Ala Arg Asp
            2805                2810                2815

Val Arg Met Gly Gln Trp Gly Met Ser Asn Gln Val Ser His His Ile
            2820                2825                2830

Pro Trp Leu Tyr Asp Ala Ala Gly Ala Pro Ser Lys Ala Gln Glu Lys
            2835                2840                2845

Val Arg Glu Val Thr Arg Arg Leu Phe Val Gly Ser Glu Ile Gly Gln
            2850                2855                2860

Gly Tyr Pro Gly Asp Glu Asp Asn Gly Glu Met Ser Ser Trp Trp Ile
2865                2870                2875                2880

Phe Ala Ser Leu Gly Phe Tyr Pro Leu Gln Val Gly Ser Asp Gln Tyr
            2885                2890                2895

Ala Val Gly Ser Pro Leu Phe Asp Lys Ala Thr Val His Leu Pro Asp
            2900                2905                2910

Gly Asp Leu Val Val Asn Ala Glu Asn Asn Ser Val Asp Asn Val Tyr
            2915                2920                2925

Val Gln Ser Leu Ala Val Asp Gly Glu Ala Arg Thr Ser Thr Ser Leu
            2930                2935                2940

Ser Gln Ala Asp Leu Ser Gly Gly Thr Thr Leu Asp Phe Val Met Gly
2945                2950                2955                2960

Pro Glu Pro Ser Asp Trp Gly Thr Gly Glu Asp Asp Ala Pro Pro Ser
            2965                2970                2975

Leu Thr Glu Gly Asp Glu Pro Pro Thr Pro Val Gln Asp Ala Thr Thr
            2980                2985                2990
```

-continued

Ala Gly Leu Gly Thr Thr Thr Val Ala Asp Gly Asp Ala Thr Thr Ser
         2995                3000                3005

Ala Ala Ala Leu Thr Asp Asn Thr Ser Gly Thr Arg Thr Thr Phe Ala
    3010                3015                3020

Thr Thr Thr Pro Ser Ile Thr Trp Ala Gly Asn Gly Ile Arg Pro Thr
3025                3030                3035                3040

Val Gly Ser Tyr Thr Leu Thr Ser Gly Ala Ser Gly Thr Ala Ser Pro
             3045                3050                3055

Ser Ala Trp Thr Leu Glu Gly Ser Asp Asp Gly Glu Thr Trp Thr Thr
         3060                3065                3070

Leu Asp Glu Arg Ser Gly Glu Gln Phe Arg Trp Ala Leu Gln Thr Arg
         3075                3080                3085

Pro Phe Thr Val Ala Glu Pro Thr Ala Phe Ala Arg Tyr Arg Val Thr
         3090                3095                3100

Val Thr Ala Thr Ser Gly Ser Gly Ala Leu Ser Leu Ala Glu Val Glu
3105                3110                3115                3120

Leu Leu Ala Asp Pro Lys Glu Ser Gly Ala Glu Glu Leu Thr Leu Ser
             3125                3130                3135

Ala Ala Pro Asp Arg Asp Gly Val Thr Gly Arg Glu Val Ser Gly Ser
         3140                3145                3150

Phe Ala Thr Leu Thr Gly Val Glu Gly Asp Val Ala Ala Leu Asp Val
         3155                3160                3165

Gln Val Ala Phe Gly Asp Gly Ser Glu Pro Val Ala Gly Thr Leu Arg
         3170                3175                3180

Ala Gly Ala Phe Gly Gly Tyr Ala Val Asp Ala Ala His Thr Trp Thr
3185                3190                3195                3200

Ala Pro Gly Val Tyr Pro Val Thr Val Thr Val Ser Gly Glu Gly Ile
             3205                3210                3215

Glu Thr Val Ser Ala Ser Ser Tyr Val Ser Val Ser Leu Leu Arg Glu
         3220                3225                3230

Gly Ser Leu Leu Ala Ala Tyr Asp Asn Val Cys Ile Gly Asp Ala Gly
         3235                3240                3245

Thr Thr Val Gly Ser Cys Asp Gly Gln Gly Val Phe Phe Asp Arg Ala
         3250                3255                3260

Gln Leu Ala Ala Lys Gly Phe Val Gln Gly Glu Arg Ala Thr Val Pro
3265                3270                3275                3280

Gly Thr Asp Leu Ala Phe Asp Val Pro Ala Val Pro Ala Gly Gln Pro
             3285                3290                3295

Asp Asn Ala Thr Gly Asp Gly Gln Thr Ile Glu Leu Ala Val Pro Ala
         3300                3305                3310

Asp Ala Glu Gln Leu Ser Val Ile Gly Thr Gly Thr Glu Lys Asn Gln
         3315                3320                3325

Gln Ala Thr Gly Thr Leu Thr Phe Asp Asp Gly Ser Thr Gln Pro Ile
         3330                3335                3340

Asp Leu Ser Phe Gly Asp Trp Ser Gly Ala Ala Arg Asn Pro Val Phe
3345                3350                3355                3360

Gly Asn Ile Pro Val Ala Val Thr Asp Ser Arg Leu Arg Gly Gly Ser
             3365                3370                3375

Pro Gln Thr Gly Thr Pro Ala Ala Phe Phe Ala Thr Ala Pro Ile Thr
         3380                3385                3390

Leu Pro Glu Gly Lys Arg Pro Val Ser Leu Thr Leu Pro Asp Gln Pro
         3395                3400                3405

Gly Glu Leu Ser Arg Asp Gly Arg Ile His Val Val Ala Val Ala His

-continued

```
                    3410                3415                3420

Asp Gly Thr Phe Ala Glu His Pro Ala Leu Glu Val Thr Ala Ala Glu
3425                3430                3435                3440

Gly Val Thr Leu Ala Val Gly Gln Thr Ser Asp Val Ala Leu Ala Gln
                    3445                3450                3455

Val Ala Gly Gly Arg Glu Gly Ala Asp Leu Arg Ala Ala Val Thr Trp
                    3460                3465                3470

Gly Asp Gly Ser Asp Val Ala Ala Gly Ala Val Thr Asp Gly Ser Val
                    3475                3480                3485

Ser Gly Ser His Ala Tyr Thr Ala Ala Gly Thr Tyr Thr Ala Tyr Val
                    3490                3495                3500

Val Val Asp Asp Gly Trp Thr Ser Gln Val Val Glu Val Pro Val Thr
3505                3510                3515                3520

Val Thr Glu Ala Glu Pro Ala Leu Ala Val Asp Val Thr Val Ser Thr
                    3525                3530                3535

Arg Cys Leu Ala Gly Lys Ala Tyr Val Ala Val Arg Ala Glu Asn Gly
                    3540                3545                3550

Glu Asp Val Pro Leu Ala Ile Arg Leu Val Thr Pro Phe Gly Thr Lys
                    3555                3560                3565

Glu Val Ala Ala Val Ala Pro Gly Ala Asn Ala Tyr Gln Ser Phe Ala
                    3570                3575                3580

Thr Arg Val Thr Ala Val Glu Ala Gly Thr Val Thr Val Glu Ala Thr
3585                3590                3595                3600

Arg Gly Thr Gly Asp Glu Glu Val Thr Ala Ser Ile Gln Ala Asp Tyr
                    3605                3610                3615

Ala Ala Val Thr Cys Gly
                    3620

<210> SEQ ID NO 11
<211> LENGTH: 513
<212> TYPE: PRT
<213> ORGANISM: Aspergillus saitoi

<400> SEQUENCE: 11

Met His Leu Pro Ser Leu Ser Leu Ser Leu Thr Ala Leu Ala Ile Ala
1               5                   10                  15

Ser Pro Ser Ala Ala Tyr Pro His Phe Gly Ser Ser Gln Pro Val Leu
            20                  25                  30

His Ser Ser Ser Asp Thr Thr Gln Ser Arg Ala Asp Ala Ile Lys Ala
        35                  40                  45

Ala Phe Ser His Ala Trp Asp Gly Tyr Leu Gln Tyr Ala Phe Pro His
    50                  55                  60

Asp Glu Leu His Pro Val Ser Asn Gly Tyr Gly Asp Ser Arg Asn Gly
65                  70                  75                  80

Trp Gly Ala Ser Ala Val Asp Ala Leu Ser Thr Ala Val Ile Met Arg
                85                  90                  95

Asn Ala Thr Ile Val Asn Gln Ile Leu Asp His Val Gly Lys Ile Asp
            100                 105                 110

Tyr Ser Lys Thr Asn Thr Thr Val Ser Leu Phe Glu Thr Thr Ile Arg
        115                 120                 125

Tyr Leu Gly Gly Met Leu Ser Gly Tyr Asp Leu Leu Lys Gly Pro Val
    130                 135                 140

Ser Asp Leu Val Gln Asn Ser Ser Lys Ile Asp Val Leu Leu Thr Gln
145                 150                 155                 160
```

-continued

```
Ser Lys Asn Leu Ala Asp Val Leu Lys Phe Ala Phe Asp Thr Pro Ser
            165                 170                 175

Gly Val Pro Tyr Asn Asn Leu Asn Ile Thr Ser Gly Gly Asn Asp Gly
            180                 185                 190

Ala Lys Thr Asn Gly Leu Ala Val Thr Gly Thr Leu Ala Leu Glu Trp
            195                 200                 205

Thr Arg Leu Ser Asp Leu Thr Gly Asp Thr Thr Tyr Ala Asp Leu Ser
    210                 215                 220

Gln Lys Ala Glu Ser Tyr Leu Leu Asn Pro Gln Pro Lys Ser Ala Glu
225                 230                 235                 240

Pro Phe Pro Gly Leu Val Gly Ser Asn Ile Asn Ile Ser Asn Gly Gln
            245                 250                 255

Phe Thr Asp Ala Gln Val Ser Trp Asn Gly Gly Asp Asp Ser Tyr Tyr
            260                 265                 270

Glu Tyr Leu Ile Lys Met Tyr Val Tyr Asp Pro Lys Arg Phe Gly Leu
            275                 280                 285

Tyr Lys Asp Arg Trp Val Ala Ala Gln Ser Thr Met Gln His Leu
            290                 295                 300

Ala Ser His Pro Ser Ser Arg Pro Asp Leu Thr Phe Leu Ala Ser Tyr
305                 310                 315                 320

Asn Asn Gly Thr Leu Gly Leu Ser Ser Gln His Leu Thr Cys Phe Asp
            325                 330                 335

Gly Gly Ser Phe Leu Leu Gly Gly Thr Val Leu Asn Arg Thr Asp Phe
            340                 345                 350

Ile Asn Phe Gly Leu Asp Leu Val Ser Gly Cys His Asp Thr Tyr Asn
            355                 360                 365

Ser Thr Leu Thr Gly Ile Gly Pro Glu Ser Phe Ser Trp Asp Thr Ser
    370                 375                 380

Asp Ile Pro Ser Ser Gln Gln Ser Leu Tyr Glu Lys Ala Gly Phe Tyr
385                 390                 395                 400

Ile Thr Ser Gly Ala Tyr Ile Leu Arg Pro Glu Val Ile Glu Ser Phe
            405                 410                 415

Tyr Tyr Ala Trp Arg Val Thr Gly Gln Glu Thr Tyr Arg Asp Trp Ile
            420                 425                 430

Trp Ser Ala Phe Ser Ala Val Asn Asp Tyr Cys Arg Thr Ser Ser Gly
            435                 440                 445

Phe Ser Gly Leu Thr Asp Val Asn Ala Ala Asn Gly Gly Ser Arg Tyr
            450                 455                 460

Asp Asn Gln Glu Ser Phe Leu Phe Ala Glu Val Met Lys Tyr Ser Tyr
465                 470                 475                 480

Met Ala Phe Ala Glu Asp Ala Ala Trp Gln Val Gln Pro Gly Ser Gly
            485                 490                 495

Asn Gln Phe Val Phe Asn Thr Glu Ala His Pro Val Arg Val Ser Ser
            500                 505                 510

Thr
```

US 9,347,050 B2

MANNOSIDASES CAPABLE OF UNCAPPING MANNOSE-1-PHOSPHO-6-MANNOSE LINKAGES AND DEMANNOSYLATING PHOSPHORYLATED N-GLYCANS AND METHODS OF FACILITATING MAMMALIAN CELLULAR UPTAKE OF GLYCOPROTEINS

CROSS-REFERENCE TO RELATED APPLICATIONS

This application is a National Stage application under 35 U.S.C. §371 of International Application No. PCT/IB2011/002770, having an International Filing Date of Sep. 29, 2011, which claims the benefit of U.S. Provisional Application Ser. No. 61/477,014, filed Apr. 19, 2011 and U.S. Provisional Application Ser. No. 61/387,940, filed Sep. 29, 2010. The disclosure of all the prior applications are considered part of (and are incorporated by reference in) the disclosure of this application.

TECHNICAL FIELD

This invention relates to mannosidases that can (i) hydrolyze a mannose-1-phospho-6-mannose linkage or moiety to phospho-6-mannose and (ii) hydrolyze a terminal alpha-1,2 mannose, alpha-1,3 mannose and/or alpha-1,6 mannose linkage or moiety of such phosphate containing glycans. The invention also relates to methods of facilitating mammalian cellular uptake of glycoproteins.

BACKGROUND

High performance expression systems are required to produce most biopharmaceuticals (e.g., recombinant proteins) currently under development. The biological activity of many of these biopharmaceuticals is dependent on their post-translational modification (e.g., phosphorylation or glycosylation). A yeast-based expression system combines the ease of genetic manipulation and fermentation of a microbial organism with the capability to secrete and to modify proteins. However, recombinant glycoproteins produced in yeast cells exhibit mainly heterogeneous high-mannose and hyper-mannose glycan structures, which can be detrimental to protein function, downstream processing, and subsequent therapeutic use, particularly where glycosylation plays a biologically significant role.

SUMMARY

This document is based on, inter alia, the discovery (i) of a mannosidase that can hydrolyze a mannose-1-phospho-6-mannose linkage or moiety to phospho-6-mannose (also referred to as "mannose-6-phosphate" herein) ("uncap") and hydrolyze a terminal alpha-1,2 mannose, alpha-1,3 mannose and/or alpha-1,6 mannose linkage or moiety of such phosphate containing glycans ("demannosylate"); and (ii) that both uncapping and demannosylation (either by separate enzymes or a single enzyme) are required to achieve mammalian cellular uptake of glycoproteins.

In one aspect, this document features a method for uncapping a mannose-1-phospho-6-mannose linkage or moiety and demannosylating a phosphorylated N-glycan on a glycoprotein. The method includes providing the glycoprotein having a phosphorylated N-glycan containing the mannose-1-phospho-6-mannose linkage or moiety; and contacting the glycoprotein with a mannosidase capable of (i) hydrolyzing a mannose-1-phospho-6-mannose linkage or moiety to mannose-6-phosphate and (ii) hydrolyzing a terminal alpha-1,2 mannose, alpha-1,3 mannose and/or alpha-1,6 mannose linkage or moiety. The mannosidase can be a family 38 glycosyl hydrolase. The mannosidase can be from *Canavalia ensiformis* or *Yarrowia lipolytica*.

This document also features a method of demannosylating phosphorylated N-glycans. The method includes providing a glyoprotein comprising a phosphorylated N-glycan; and contacting the glycoprotein with a mannosidase capable of (i) hydrolyzing a mannose-1-phospho-6-mannose linkage or moiety to mannose-6-phosphate and (ii) hydrolyzing a terminal alpha-1,2 mannose, alpha-1,3 mannose and/or alpha-1,6 mannose linkage or moiety. The mannosidase can be a family 38 glycosyl hydrolase. The mannosidase can be from *Canavalia ensiformis* or *Yarrowia lipolytica*.

The methods described herein can further include after the providing and contacting steps, contacting a mammalian cell with the glycoprotein that includes the demannosylated phosphorylated N-glycan, wherein, after the contacting, the glycoprotein is transported to the interior of the mammalian cell (e.g., a human cell).

The methods described herein further can include isolating the glycoprotein produced in the methods. The protein can be a human protein expressed in a fungal organism. For example, the fungal organism can be *Yarrowia lipolytica* or *Arxula adeninivorans*. The fungal organism also can be a methylotrophic yeast (e.g., *Pichia pastoris, Pichia methanolica, Oogataea minuta,* or *Hansenula polymorpha*) or a filamentous fungus (e.g., *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus,* or *Aspergillus versicolor*). The protein can be a pathogen protein, a lysosomal protein, a growth factor, a cytokine, a chemokine, an antibody or antigen-binding fragment thereof, or a fusion protein. For example, the lysosomal protein can be a lysosomal enzyme such as a lysosomal enzyme associated with a lysosomal storage disorder (LSD). A LSD can be Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

This document also features a method of producing a target protein having an uncapped mannose-6-phosphate linkage or moiety and demannosylated phosphorylated N-glycans in a fungal organism. The method includes providing a fungal cell genetically engineered to include a nucleic acid encoding a mannosidase that can hydrolyze a mannose-1-phospho-6-mannose linkage or moiety to a phospho-6-mannose moiety and hydrolyze a terminal alpha-1,2 mannose, alpha-1,3 mannose and/or alpha-1,6 mannose linkage or moiety of such a phosphate containing glycan; and introducing into the cell a nucleic acid encoding a target protein.

This document also features an isolated fungal cell genetically engineered to produce glycoproteins that include an uncapped mannose-6-phosphate and a demannosylated phosphorylated N-glycan. The fungal cell can be *Yarrowia lipolytica* or *Arxula adeninivorans*. The fungal cell also can be a methylotrophic yeast (e.g., *Pichia pastoris, Pichia methanolica, Oogataea minuta,* or *Hansenula polymorpha*) or a filamentous fungus (e.g., *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus,* or *Aspergillus versicolor*). The fungal cell can include a nucleic acid encoding a mannosidase, the mannosidase capable of (i) hydrolyzing a mannose-1-phospho-6-mannose linkage or moiety to mannose-6-phosphate and (ii) hydrolyzing a terminal alpha-1,2 mannose, alpha-1,3 mannose and/or alpha-1,6 mannose linkage or moiety. The fungal cell further can include a nucleic acid encoding a polypeptide capable of promoting mannosyl phosphorylation. The fungal cell can be genetically engineered to be deficient in OCH1 activity. The fungal cell further can include a nucleic acid encoding a polypeptide capable of promoting mannosyl phosphorylation, and wherein the fungal cell is genetically engineered to be deficient in OCH1 activity. The mannosidase can include a secretion signal and/or a targeting signal to target the mannosidase to an intracellular compartment.

A fungal cell further can include a nucleic acid encoding a target protein, wherein the target protein is a glycoprotein. The target protein can be a human protein. The target protein can be a pathogen protein, a lysosomal protein, a growth factor, a cytokine, a chemokine, an antibody or antigen-binding fragment thereof, or a fusion protein. The lysosomal protein can be a lysosomal enzyme. The target protein can be a protein associated with a LSD such as Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

A polypeptide capable of promoting mannosyl phosphorylation can be a MNN4 polypeptide (e.g., a *Yarrowia liplytica, S. cerevisiae, Ogataea minuta, Pichia pastoris,* or *C. albicans* polypeptide). The polypeptide capable of promoting mannosyl phosphorylation can be a *P. pastoris* PNO1 polypeptide.

In yet another aspect, this document features a substantially pure culture of *Yarrowia lipolytica, Pichia pastoris, Hansenula polymorphs, Ogataea minuta, Pichia methanolica, Arxula adeninivorans,* or *Aspergillus niger* cells, a substantial number of which are genetically engineered to produce glycoproteins that contain uncapped mannose-6-phosphate linkages or moieties and demannosylated phosphorylated N-glycans. Substantial number indicates that more than about 40% of the total number of viable cells in the culture are genetically engineered. The cells can include a nucleic acid encoding a mannosidase, the mannosidase capable of (i) hydrolyzing a mannose-1-phospho-6-mannose linkage or moiety to mannose-6-phosphate and (ii) hydrolyzing a terminal alpha-1,2 mannose, alpha-1,3 mannose and/or alpha-1,6 mannose linkage or moiety. The cells further can include a nucleic acid encoding a polypeptide capable of promoting mannosyl phosphorylation. The cells can be genetically engineered to be deficient in OCH1 activity. The cells further can include a nucleic acid encoding a polypeptide capable of promoting mannosyl phosphorylation, and can be genetically engineered to be deficient in OCH1 activity. The mannosidase can include a secretion signal and/or a targeting signal to target the mannosidase to an intracellular compartment.

This document also features a method of directing a glycoprotein to the interior of a mammalian cell. The method includes providing a glycoprotein wherein its mannose-6-phosphate linkages have been demannosylated, and contacting the cell with the demannosylated glycoprotein. The glycoprotein can be demannosylated with a family 47 or family 92 glycosyl hydrolase. The glycoprotein can be demannosylated with a mannosidase from *Aspergillus satoi* or *Cellulosimicrobium cellulans*. The glycoprotein can be demannosylated with a family 38 glycosyl hydrolase such as a mannosidase from *Canavalia ensiformis* or *Yarrowia lipolytica*.

In another aspect, this document features a method of directing a glycoprotein to the interior of a mammalian cell. The method includes providing a glycoprotein having a phosphorylated N-glycan, wherein the glycoprotein does not substantially bind to a mannose-6-phosphate receptor on the cell; contacting the glycoprotein with a mannosidase capable of hydrolyzing a terminal alpha-1,2 mannose linkage or moiety when the underlying mannose is phosphorylated to produce a demannosylated glycoprotein, wherein the glycoprotein after the demannosylation, substantially binds to the mannose-6-phosphate receptor on the cell; and contacting the cell with the demannosylated glycoprotein. The glycoprotein can be demannosylated with a family 47 or family 92 glycosyl hydrolase. The mannosidase can be from *Aspergillus satoi* or *Cellulosimicrobium cellulans*. The glycoprotein can be demannosylated with a family 38 glycosyl hydrolase such as a mannosidase from *Canavalia ensiformis* or *Yarrowia lipolytica*.

In yet another aspect, this document features a method of converting a glycoprotein from a first form that does not substantially bind to a mannose-6-phosphate receptor on a mammalian cell to a second form that does substantially bind to a mannose-6-phosphate receptor on a mammalian cell, wherein in the first form, the glycoprotein includes one or more N-glycans containing one or more terminal mannose residues that are linked at the 1 position to a mannose residue that contains a phosphate residue at the 6 position. The method includes contacting the first form of the glycoprotein with a mannosidase that demannosylates terminal mannose residues. The mannosidase can have uncapping and demannosylating activities. For example, the mannosidase can be from *Canavalia ensiformis* or *Yarrowia lipolytica*. In some embodiments, the mannosidase does not have uncapping activity (e.g., a mannosidase from *Aspergillus satoi* or *Cellulosimicrobium cellulans*).

This document also features a method of directing a glycoprotein to the interior of a mammalian cell, the glycoprotein includes one or more mannose-1-phospho-6-mannose linkages or moieties. The method includes contacting the cell with the glycoprotein after (a) uncapping the one or more mannose-1-phospho-6-mannose linkages or moieties to mannose-6-phosphate on the glycoprotein, wherein, after uncapping, the glycoprotein does not substantially bind to a mannose-6-phosphate receptor on the cell and, after step (a), (b) demannosylating phosphorylated N-glycans on the glycoprotein, wherein after both the uncapping and the demannosylation, the glycoprotein does substantially bind to a mannose-6-phosphate receptor on the cell. Steps (a) and (b) can be catalyzed by two different enzymes (e.g., a *Cellulosimicrobium cellulans* mannosidase such as CcMan5 and a *Canavalia ensiformis* mannosidase) or by a single enzyme.

In another aspect, this document features a method of directing a glycoprotein to the interior of a mammalian cell. The method includes providing a glycoprotein having uncapped and demannosylated phosphorylated N-glycans, and contacting the mammalian cell with the glycoprotein.

In the methods described herein, the glycoprotein can be a human protein.

In the methods described herein, the glycoprotein can be a pathogen protein, a lysosomal protein, a growth factor, a cytokine, a chemokine, an antibody or antigen-binding fragment thereof, or a fusion protein. The lysosomal protein can be a lysosomal enzyme (e.g., acid alpha glucosidase or alpha galactosidase). The glycoprotein can be associated with a LSD (e.g., Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia).

The document also features a glycoprotein capable of being transported to the interior of a mammalian cell, wherein the glycoprotein has been treated with any of the methods described herein, as well as a mammalian cell (e.g., human cell) that includes such a glycoprotein. In another aspect, this document features a method of treatment that includes administering such a glycoprotein to a subject in need thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DESCRIPTION OF DRAWINGS

FIG. 1A is a depiction of the codon optimized nucleotide sequence of human alpha glucosidase (GAA) with lip2 pre sequence in bold (SEQ ID NO:1). FIG. 1B is a depiction of the amino acid sequence of human GAA with the lip2 pre sequence in bold, where the * represents the stop codon (SEQ ID NO:2).

FIG. 3A is a depiction of the nucleotide sequence of the open reading frame (ORF) of *Yarrowia lipolytica* AMS1 with a C-terminal His-tag (SEQ ID NO:3). FIG. 3B is a depiction of the nucleotide sequence of the ORF of *Yarrowia lipolytica* AMS1 with N-terminal His-tag (SEQ ID NO:4). FIG. 3C is a depiction of the amino acid sequence of the *Yarrowia lipolytica* AMS1 polypeptide (SEQ ID NO:5).

FIG. 8A is a depiction of the nucleotide sequence of the open reading frame (ORF) of DsbA-*Cellulosimicrobium cellulans* mannosidase 5 (CcMan5) (SEQ ID NO:6). FIG. 8B is a depiction of the amino acid sequence of the CcMan5 polypeptide with signal sequence in bold (SEQ ID NO: 7). FIG. 8C is a depiction of the amino acid sequence of the CcMan5 polyeptpide without signal sequence (SEQ ID NO:8). The predicted molecular weight of the CcMan5 polypeptide without the signal sequence is 173 kDa.

FIG. 9A is a depiction of the nucleotide sequence of the ORF of DsbA-*C. cellulans* mannosidase 4 (CcMan4) (SEQ ID NO: 9). FIG. 9B is a depiction of the amino acid sequence of the CcMan4 polypeptide with signal sequence in bold (SEQ ID NO: 10). The predicted molecular weight of the CcMan4 polypeptide without the signal sequence is 184 kDa.

FIG. 10 is a schematic of the plasmids pLSAHCcMan5 and pLSAHCcMan4.

FIG. 22 is a depiction of the amino acid sequence of a mannosidase from *Aspergillus saitoi* (SEQ ID NO: 11).

DETAILED DESCRIPTION

Figure 2:
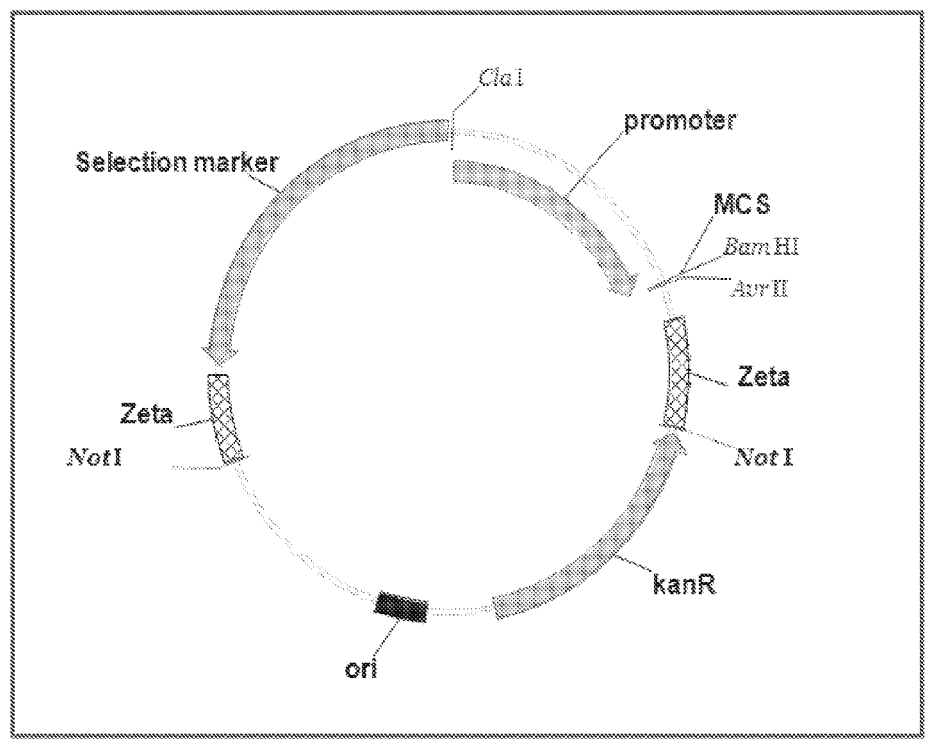
FIG. 2 is a schematic of a *Y. lipolytica* expression vector used for cloning of huGAA.

In general, this document provides methods and materials for hydrolyzing a mannose-1-phospho-6-mannose linkage or moiety to phospho-6-mannose (also referred to as "mannose-6-phosphate" herein) ("uncapping") and hydrolyzing a terminal alpha-1,2 mannose, alpha-1,3 mannose and/or alpha-1,6 mannose linkage or moiety of such a phosphate containing glycan ("demannosylating"). Also provided are methods of facilitating uptake of a glycoprotein by a mammalian cell as both uncapping and demannosylation (either by separate enzymes or a single enzyme) are required to achieve mammalian cellular uptake of glycoproteins. The methods and materials described herein are particularly useful for producing agents for treating patients with lysosomal storage disorders (LSDs), a diverse group of hereditary metabolic disorders characterized by the accumulation of storage products in the lysosomes due to impaired activity of catabolic enzymes involved in their degradation. The build-up of storage products leads to cell dysfunction and progressive clinical manifestations. Deficiencies in catabolic enzymes can be corrected by enzyme replacement therapy (ERT), provided that the administered enzyme can be targeted to the lysosomes of the diseased cells. Lysosomal enzymes typically are glycoproteins that are synthesized in the endoplasmic reticulum (ER), transported via the secretory pathway to the Golgi, and then recruited to the lysosomes. Using the methods and materials described herein, a microbial based production process can be used to obtain therapeutic proteins with demannosylated phosphorylated N-glycans. Thus, the methods and materials described herein are useful for preparing glycoproteins for the treatment of metabolic disorders such as LSDs.

Mannosidases

This document provides isolated nucleic acids encoding mannosidases that can (i) hydrolyze a mannose-1-phospho-6-mannose linkage or moiety to phospho-6-mannose and/or (ii) hydrolyze a terminal alpha-1,2 mannose, alpha-1,3 mannose and/or alpha-1,6 mannose linkage or moiety of such a phosphate containing glycan. The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

"Polypeptide" and "protein" are used interchangeably herein and mean any peptide-linked chain of amino acids, regardless of length or post-translational modification. Typically, a polypeptide described herein (e.g., a mannosidase or an uncapped and demannosylated target protein) is isolated when it constitutes at least 60%, by weight, of the total protein in a preparation, e.g., 60% of the total protein in a sample. In some embodiments, a polypeptide described herein consists of at least 75%, at least 90%, or at least 99%, by weight, of the total protein in a preparation.

An "isolated nucleic acid" refers to a nucleic acid that is separated from other nucleic acid molecules that are present in a naturally-occurring genome, including nucleic acids that normally flank one or both sides of the nucleic acid in a naturally-occurring genome (e.g., a yeast genome). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The term "exogenous" as used herein with reference to nucleic acid and a particular host cell refers to any nucleic acid that does not occur in (and cannot be obtained from) that particular cell as found in nature. Thus, a non-naturally-occurring nucleic acid is considered to be exogenous to a host cell once introduced into the host cell. It is important to note that non-naturally-occurring nucleic acids can contain nucleic acid subsequences or fragments of nucleic acid sequences that are found in nature provided that the nucleic acid as a whole does not exist in nature. For example, a nucleic acid molecule containing a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular cell. For example, an entire chromosome isolated from a cell of yeast x is an exogenous nucleic acid with respect to a cell of yeast y once that chromosome is introduced into a cell of yeast y.

A nucleic acid encoding a mannosidase can have at least 70% sequence identity (e.g., at least 80%, 85%, 90%, 95%, 97%, 98%, 99%, or 100% sequence identity) to a nucleotide sequence set forth in SEQ ID NO:3, SEQ ID NO:4, SEQ ID NO:6, or SEQ ID NO:9. In some embodiments, nucleic acids described herein can encode mannosidase polypeptides that have at least 70% (e.g., at least 75, 80, 85, 90, 95, 99, or 100 percent) identity to an amino acid sequence set forth in SEQ ID NOs: 5, 7, 8, 10, or 11. For example, a nucleic acid can encode a mannosidase having at least 90% (e.g., at least 95 or 98%) identity to the amino acid sequence set forth in SEQ ID NOs: 5, 7, 8, 10, 11 or a portion thereof. For example, a nucleic acid can encode a mannosidase having at least 90% identity to amino acid residues 1 to 774 of SEQ ID NO:8. The percent identity between a particular amino acid sequence and the amino acid sequence set forth in SEQ ID NO:5, SEQ ID NO:7, SEQ ID NO:8, SEQ ID NO:10, or SEQ ID NO:11 can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site or the U.S. government's National Center for Biotechnology Information web site. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length mannosidase polypeptide amino acid sequence followed by multiplying the resulting value by 100.

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given mannosidase polypeptide can be modified such that optimal expression in a particular species (e.g., bacteria or fungus) is obtained, using appropriate codon bias tables for that species.

Hybridization also can be used to assess homology between two nucleic acid sequences. A nucleic acid sequence described herein, or a fragment or variant thereof, can be used as a hybridization probe according to standard hybridization techniques. The hybridization of a probe of interest (e.g., a probe containing a portion of a *Yarrowia lipolytica* AMS1 nucleotide sequence) to DNA or RNA from a test source is an indication of the presence of DNA or RNA (e.g., an AMS1 nucleotide sequence) corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

Other mannosidase polypeptide candidates suitable for use herein can be identified by analysis of nucleotide and polypeptide sequence alignments. For example, performing a query on a database of nucleotide or polypeptide sequences can identify homologs and/or orthologs of mannosidase polypeptides. Sequence analysis can involve BLAST, Reciprocal BLAST, or PSI-BLAST analysis of nonredundant databases using known mannosidase amino acid sequences. Those polypeptides in the database that have greater than 40% sequence identity can be identified as candidates for further evaluation for suitability as a mannosidase polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated.

This document also provides (i) biologically active variants and (ii) biologically active fragments or biologically active variants thereof, of the mannosidases described herein. Biologically active variants of mannosidases can contain additions, deletions, or substitutions relative to the sequences set forth in SEQ ID NOs: 5, 7, 8, 10, and 11. Proteins with substitutions will generally have not more than 50 (e.g., not more than one, two, three, four, five, six, seven, eight, nine, ten, 12, 15, 20, 25, 30, 35, 40, or 50) conservative amino acid substitutions. A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Additions (addition variants) include fusion proteins containing: (a) a mannosidase set forth in SEQ ID NOs: 5, 7, 8, 10, 11 or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences also can be proteins useful as diagnostic or detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or endoplasmic reticulum or Golgi apparatus retention signals. Heterologous sequences can be of varying length and in some cases can be a longer sequences than the full-length target proteins to which the heterologous sequences are attached.

Biologically active fragments or biologically active variants of the mannosidases have at least 40% (e.g., at least: 50%; 60%; 70%; 75%; 80%; 85%; 90%; 95%; 97%; 98%; 99%; 99.5%, or 100% or even greater) of the mannosidase activity (e.g., uncapping and/or demannosylating) of the wild-type, full-length, mature protein. For example, a biologically active fragment of a mannosidase that can hydrolyze a mannose-1-phospho-6-mannose linkage or moiety to phospho-6-mannose can contain residues 1 to 774 of SEQ ID NO:8.

The mannosidases described herein can be used to produce uncapped and demannosylated target molecules. The methods can be performed in vitro or in vivo.

Methods of Demannosylating, or Uncapping and Demannosylating Glycoproteins

As described herein, glycoproteins containing a phosphorylated N-glycan can be demannosylated, and glycoproteins containing a phosphorylated N-glycan containing a mannose-1-phospho-6-mannose linkage or moiety can be uncapped and demannosylated by contacting the glycoprotein with a mannosidase capable of (i) hydrolyzing a mannose-1-phospho-6-mannose linkage or moiety to mannose-6-phosphate and (ii) hydrolyzing a terminal alpha-1,2 mannose, alpha-1,3 mannose and/or alpha-1,6 mannose linkage or moiety. Non-limiting examples of such mannosidases include a *Canavalia ensiformis* (Jack bean) mannosidase and a *Yarrowia lipolytica* mannosidase (e.g., AMS1). Both the Jack bean and AMS1 mannosidase are family 38 glycoside hydrolases.

The Jack bean mannosidase is commercially available, for example, from Sigma-Aldrich (St. Louis, Mo.) as an ammonium sulfate suspension (Catalog No. M7257) and a proteomics grade preparation (Catalog No. M5573). As described in Example 8, such commercial preparations can be further purified, for example, by gel filtration chromatography to remove contaminants such as phosphatases. The Jack bean mannosidase contains a segment with the following amino acid sequence NKIPRAGWQIDPFGHSAVQG (SEQ ID NO:12). See Howard et al., *J. Biol. Chem.*, 273(4):2067-2072, 1998.

The *Yarrowia lipolytica* AMS 1 mannosidase can be recombinantly produced. The nucleic acid sequences encoding AMS 1 with a C- or N-terminal polyhistidine tag are set forth in SEQ ID NOs. 3 and 4, respectively (see also FIGS. 3A and 3B). The amino acid sequence of the AMS1 polypeptide is set forth in SEQ ID NO:5 (see also FIG. 3C). Isolated nucleic acid molecules encoding mannosidase polypeptides can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids also can be obtained by mutagenesis of, e.g., a naturally occurring DNA.

To recombinantly produce a mannosidase polypeptide, a vector is used that contains a promoter operably linked to nucleic acid encoding the mannosidase polypeptide. As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5' end of a coding region, can also be separate from a promoter sequence and can be, e.g., within an intronic region of a gene or 3' to the coding region of the gene.

As used herein, "operably linked" means incorporated into a genetic construct (e.g., vector) so that expression control sequences effectively control expression of a coding sequence of interest.

Expression vectors can be introduced into host cells (e.g., by transformation or transfection) for expression of the encoded polypeptide, which then can be purified. Expression systems that can be used for small or large scale production of mannosidase polypeptides include, without limitation, microorganisms such as bacteria (e.g., *E. coli*) transformed with recombinant bacteriophage DNA, plasmid DNA, or cosmid DNA expression vectors containing the nucleic acid molecules, and fungal (e.g., *S. cerevisiae, Yarrowia lipolytica, Arxula adeninivorans, Pichia pastoris, Hansenula polymorpha*, or *Aspergillus*) transformed with recombinant fungal expression vectors containing the nucleic acid molecules. Useful expression systems also include insect cell systems infected with recombinant virus expression vectors (e.g., baculovirus) containing the nucleic acid molecules, and plant cell systems infected with recombinant virus expression vectors (e.g., tobacco mosaic virus) or transformed with recombinant plasmid expression vectors (e.g., Ti plasmid) containing the nucleic acid molecules. Mannosidase polypeptides also can be produced using mammalian expression systems, which include cells (e.g., immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter).

Typically, recombinant mannosidase polypeptides are tagged with a heterologous amino acid sequence such FLAG, polyhistidine (e.g., hexahistidine), hemagluttanin (HA), glutathione-S-transferase (GST), or maltose-binding protein (MBP) to aid in purifying the protein. Other methods for purifying proteins include chromatographic techniques such as ion exchange, hydrophobic and reverse phase, size exclusion, affinity, hydrophobic charge-induction chromatography, and the like (see, e.g., Scopes, Protein Purification: Principles and Practice, third edition, Springer-Verlag, New York (1993); Burton and Harding, *J. Chromatogr. A* 814:71-81 (1998)).

In some embodiments, the uncapping and demannosylating steps are catalyzed by two different enzymes. For example, uncapping of a mannose-1-phospho-6 mannose linkage or moiety can be performed using a mannosidase from *Cellulosimicrobium cellulans* (e.g., CcMan5). The amino acid sequence of the CcMan5 polypeptide containing signal sequence is set forth in SEQ ID NO: 7. The amino acid sequence of the CcMan5 polypeptide without signal sequence is set forth in SEQ ID NO:8. A nucleic acid sequence encoding a CcMan5 polypeptide is set forth in SEQ ID NO:6. In some embodiments, a biologically active fragment of the CcMan5 polypeptide is used. For example, a biologically active fragment can includes residues 1-774 of the amino acid sequence set forth in SEQ ID NO:8. See also WO 2011/039634. The CcMan5 mannosidase is a family 92 glycoside hydrolase.

Demannosylation of an uncapped glycoprotein can be catalyzed using a mannosidase from *Aspergillus satoi* (As) (also known as *Aspergillus phoenicis*) or a mannosidase from *Cellulosimicrobium cellulans* (e.g., CcMan4). The *Aspergillus satoi* mannosidase is a family 47 glycoside hydrolase and the CcMan4 mannosidase is a family 92 glycoside hydrolase. The amino acid sequence of the *Aspergillus* satoi mannosidase is set forth in SEQ ID NO:11 (see FIG. 22) and in GenBank Accession No. BAA08634. The amino acid sequence of the CcMan4 polypeptide is set forth in SEQ ID NO: 10. The nucleotide sequence set forth in SEQ ID NO:9 encodes the polypeptide of SEQ ID NO:10.

Demannosylation of an uncapped glycoprotein also can be catalyzed using a mannosidase from the family 38 glycoside hydrolases such as a *Canavalia ensiformis* (Jack bean) mannosidase or a *Yarrowia lipolytica* mannosidase (e.g., AMS1). For example, CcMan5 can be used to uncap a mannose-1-phospho-6 mannose moiety on a glycoprotein and the Jack bean mannosidase can be used to demannosylate the uncapped glycoprotein.

To produce demannosylated glycoproteins, or uncapped and demannosylated glycoproteins, a target molecule containing a mannose-1-phospho-6 mannose linkage or moiety is contacted under suitable conditions with a suitable mannosidase(s) and/or a cell lysate containing a suitable recombinantly produced mannosidase(s). Suitable mannosidases are described above. The cell lysate can be from any genetically engineered cell, including a fungal cell, a plant cell, or animal cell. Non-limiting examples of animal cells include nematode, insect, plant, bird, reptile, and mammals such as a mouse, rat, rabbit, hamster, gerbil, dog, cat, goat, pig, cow, horse, whale, monkey, or human.

Upon contacting the target molecule (e.g., a glycoprotein) with the purified mannosidases and/or cell lysate, the mannose-1-phospho-6-mannose linkage or moiety can be hydrolyzed to phospho-6-mannose and the terminal alpha-1,2 mannose, alpha-1,3 mannose and/or alpha-1,6 mannose linkage or moiety of such a phosphate containing glycan can be hydrolyzed to produces an uncapped and demannosylated target molecule. In some embodiments, one mannosidase is used that catalyzes both the uncapping and demannosylating steps. In some embodiments, one mannosidase is used to catalyze the uncapping step and a different mannosidase is used to catalyze the demannosylating step. The methods described in Example 5 can be used to determine if the target molecule has been uncapped and demannosylated. Following processing by the mannosidase, the target molecule can be isolated.

Suitable methods for obtaining cell lysates that preserve the activity or integrity of the mannosidase activity in the lysate can include the use of appropriate buffers and/or inhibitors, including nuclease, protease and phosphatase inhibitors that preserve or minimize changes in N-glycosylation activities in the cell lysate. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for obtaining lysates containing enzymatic activities are described in, e.g., Ausubel et al. Current Protocols in Molecular Biology (Supplement 47), John Wiley & Sons, New York (1999); Harlow and Lane, Antibodies: A Laboratory Manual Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999).

A cell lysate can be further processed to eliminate or minimize the presence of interfering substances, as appropriate. If desired, a cell lysate can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like.

In some embodiments, a cell lysate can be prepared in which whole cellular organelles remain intact and/or functional. For example, a lysate can contain one or more of intact rough endoplasmic reticulum, intact smooth endoplasmic reticulum, or intact Golgi apparatus. Suitable methods for preparing lysates containing intact cellular organelles and testing for the functionality of the organelles are described in, e.g., Moreau et al. (1991) *J. Biol. Chem.* 266(7):4329-4333; Moreau et al. (1991) *J. Biol. Chem.* 266(7):4322-4328; Rexach et al. (1991) *J. Cell Biol.* 114(2):219-229; and Paulik et al. (1999) *Arch. Biochem. Biophys.* 367(2):265-273.

Target molecules, as used herein, refer to (i) any molecule containing terminal mannose-1-phospho-6 mannose linkage or moiety; (ii) any molecule, when expressed in a cell of fungal origin, that contains a mannose-1-phospho-6 mannose linkage or moiety; (iii) any molecule containing a terminal alpha-1,2 mannose, alpha-1,3 mannose, and/or alpha-1,6 mannose linkage or moiety of a phosphate containing glycan; or (iv) any molecule, when expressed in a cell of fungal origin, that contains a terminal alpha-1,2 mannose, alpha-1,3 mannose, and/or alpha-1,6 mannose linkage or moiety of a phosphate containing glycan. In some embodiments, the target protein is a human glycoprotein. Suitable target proteins can include pathogen proteins such as tetanus toxoid or diptheria toxoid; viral surface proteins such as cytomegalovirus (CMV) glycoproteins B, H and gCIII, human immunodeficiency virus 1 (HIV-1) envelope glycoproteins, Rous sarcoma virus (RSV) envelope glycoproteins, herpes simplex virus (HSV) envelope glycoproteins, Epstein Barr virus (EBV) envelope glycoproteins, varicella-zoster virus (VZV) envelope glycoproteins, human papilloma virus (HPV) envelope glycoproteins, Influenza virus glycoproteins, and Hepatitis family surface antigen; lysosomal proteins (e.g., acid alpha glucosidase, alpha galatosidase, glucocerebrosidase, cerebrosidase, or galactocerebrosidase); insulin; glucagons; growth factors; cytokines; chemokines; and antibodies or fragments thereof. Growth factors include, e.g., vascular endothelial growth factor (VEGF), Insulin-like growth factor (IGF), bone morphogenic protein (BMP), Granulocyte-colony stimulating factor (G-CSF), Granulocyte-macrophage colony stimulating factor (GM-CSF), Nerve growth factor (NGF); a Neurotrophin, Platelet-derived growth factor (PDGF), Erythropoietin (EPO), Thrombopoietin (TPO), Myostatin (GDF-8), Growth Differentiation factor-9 (GDF9), basic fibroblast growth factor (bFGF or FGF2), Epidermal growth factor (EGF), Hepatocyte growth factor (HGF). Cytokines include, for example, interleukins such as IL-1 to IL-33 (e.g., IL-1, IL-2, IL-3, IL-4, IL-5, IL-6, IL-7, IL-8, IL-9, IL-10, IL-12, IL-13, or IL-15). Chemokines include, e.g., 1-309, TCA-3, MCP-1, MIP-1α, MIP-1β, RANTES, C10, MRP-2, MARC, MCP-3, MCP-2, MRP-2, CCF18, MIP-1γ, Eotaxin, MCP-5, MCP-4, NCC-1, Ckβ10, HCC-1, Leukotactin-1, LEC, NCC-4, TARC, PARC, or Eotaxin-2. Also included are tumor glycoproteins (e.g., tumor-associated antigens), for example, carcinoembryonic antigen (CEA), human mucins, HER-2/neu, and prostate-specific antigen (PSA) [Henderson and Finn, *Advances in Immunology*, 62, pp. 217-56 (1996)].

In some embodiments, the target protein can be one associated with a lysosomal storage disorder, which target proteins include, e.g., acid alpha glucosidase, alpha galactosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acetylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neuraminidase, phosphotransferase, acid lipase, acid ceramidase, sphingomyelinase, thioesterase, cathepsin K, and lipoprotein lipase.

In some embodiments, the target proteins are fusion proteins in which the target protein is fused to another polypeptide sequence, or to a polymer, a carrier, an adjuvant, an immunotoxin, or a detectable (e.g., fluorescent, luminescent, or radioactive) moiety. For example, a target protein can be joined to a polymer such as polyethyleneglycol to increase the molecular weight of small proteins and/or increase circulation residence time.

Upon contact of a mammalian cell with a target molecule containing uncapped and demannosylated phosphorylated N-glycans, the target molecule can be transported to the interior of the mammalian cell (e.g., a human cell). A glycoprotein having an uncapped, but not demannosylated, phosphorylated N-glycan does not substantially bind mannose-6-phosphate receptors on mammalian cells, and as such, is not efficiently transported to the interior of the cell. As used herein, "does not substantially bind" means that less than 15% (e.g., less than 14%, 12%, 10%, 8%, 6%, 4%, 2%, 1%, 0.5%, or less, or 0%) of the glycoprotein molecules bind to mannose-6-phosphate receptors on mammalian cells. However, if such a glycoprotein is contacted with a mannosidase capable of hydrolyzing a terminal alpha-1,2 mannose linkage or moiety when the underlying mannose is phosphorylated, a demannosylated glycoprotein is produced that substantially binds to the mannose-6-phosphate receptor on the mammalian cells and is efficiently transported to the interior of the cell. As used herein "substantially binds" means that 15% or more (e.g., greater than 16%, 18%, 20%, 25%, 30%, 35%, 40%, 45%, 50%, 55%, 60%, 65%, 70%, 75%, 80%, 85%, 90% or 95%) of the glycoprotein molecules bind to mannose-6-phosphate receptors on mammalian cells. It is understood that a preparation (e.g., a recombinant host cell or a cell-free preparation) containing an enzyme that uncaps but does not demannosylate phosphorylated N-glycans could be contaminated with an enzyme that demannosylates phosphorylated N-glycans. A target protein sample after contact with such a preparation can contain protein molecules with some phosphorylated N-glycans that are uncapped only and others that are uncapped and demannosylated. Naturally those protein molecules containing uncapped and demannosylated phosphorylated N-glycans can substantantially bind to mannose-6-phosphate receptors. The above definition of "does not substantially bind" does not apply to such a target protein sample since the phosphorylated N-glycans on the protein molecules cannot be characterized as uncapped but not demannosylated.

As set forth in Examples 9 and 12, target molecules that are uncapped and demannosylated are more efficiently taken up by mammalian cells than target molecules containing uncapped phosphorylated N-glycans. For example, an uncapped and demannosylated target molecule can be taken up at least 10 times (e.g., at least 15, 20, 25, or 30 times) more efficient than an uncapped glycoprotein.

Thus, this document provides methods of converting a glycoprotein from a first form that does not bind to a mannose-6-phosphate receptor on a mammalian cell to a second form that does bind to a mannose-6-phosphate receptor on a mammalian cell. In the first form, the glycoprotein comprises one or more N-glycans containing one or more mannose residues that are linked at the 1 position to a mannose residue that contains a phosphate residue at the 6 position. In such methods, the first form of the glycoprotein is contacted with a mannosidase that demannosylates the terminal mannose residues to result in the mannose containing the phosphate at the 6 position to become the terminal mannose. In some embodiments, the mannosidase has both uncapping and demannosylating activity (e.g., *Canavalia ensiformis* (Jack bean) or *Yarrowia lipolytica* AMS1 mannosidase). In some embodiments, the mannosidase does not have uncapping activity (e.g., a mannosidase from *Aspergillus satoi* or a mannosidase from *Cellulosimicrobium cellulans* (e.g., CcMan4)).

Transport of a glycoprotein to the interior of the cell can be assessed using a cell uptake assay such as the one set forth in Example 9. For example, mammalian cells and a target molecule containing uncapped and demannosylated phosphorylated N-glycans can be incubated, then the cells washed and lysed. Cell lysates can be assessed for the presence of the target molecule (e.g., by Western blotting) or by activity of the target molecule in the cell lysate. For example, when the target molecule is a glucosidase such as human alpha glucosidase, uptake can be assessed in fibroblasts deficient in acid alpha glucosidase activity. Intracellular activity of alpha glucosidase can be assessed using the 4-methylumbelliferyl-alpha-D-glucopyranoside (4-MUG) assay. See, Example 3. Cleavage of the substrate 4-MUG by a glucosidase leads to the generation of the fluorigenic product 4-MU, which can be visualized or detected by irradiation with UV light.

In Vivo Methods of Uncapping and Demannosylating Glycoproteins

Genetically engineered cells described herein can be used to produce uncapped and demannosylated target molecules. For example, a cell based method can include the steps of introducing into a fungal cell genetically engineered to include a nucleic acid encoding a mannosidase that is capable of hydrolyzing a mannose-1-phospho-6-mannose linkage or moiety to phospho-6-mannose, a nucleic acid encoding a target molecule, wherein the cell produces the target molecule containing uncapped phosphorylated N-glycans. Such phosphorylated N-glycans can be demannosylated as described above. Another cell based method can include the steps of introducing into a fungal cell genetically engineered to include a nucleic acid encoding a mannosidase that is capable of (i) hydrolyzing a mannose-1-phospho-6-mannose linkage or moiety to phospho-6-mannose and (ii) hydrolyzing a terminal alpha-1,2 mannose, alpha-1,3 mannose and/or alpha-1,6 mannose linkage or moiety of a phosphate containing glycan, a nucleic acid encoding a target molecule, wherein the cell produces uncapped and demannosylated target molecules. In some embodiments, the nucleic acids encoding the mannosidase and target molecule contain a secretion sequence such that the mannosidase and target molecule are co-secreted.

Genetically engineered cells described herein contain a nucleic acid encoding a mannosidase. Cells suitable for in vivo production of target molecules can be of fungal origin, including *Yarrowia lipolytica*, *Arxula adeninivorans*, methylotrophic yeast (such as a methylotrophic yeast of the genus *Candida*, *Hansenula*, *Oogataea*, *Pichia* or *Torulopsis*) or filamentous fungi of the genus *Aspergillus*, *Trichoderma*, *Neurospora*, *Fusarium*, or *Chrysosporium*. Exemplary fungal species include, without limitation, *Pichia anomala*, *Pichia bovis*, *Pichia canadensis*, *Pichia carsonii*, *Pichia farinose*, *Pichia fermentans*, *Pichia fluxuum*, *Pichia membranaefaciens*, *Pichia membranaefaciens*, *Candida valida*, *Candida albicans*, *Candida ascalaphidarum*, *Candida amphixiae*, *Candida Antarctica*, *Candida atlantica*, *Candida atmosphaerica*, *Candida blattae*, *Candida carpophila*, *Candida cerambycidarum*, *Candida chauliodes*, *Candida corydalis*, *Candida dosseyi*, *Candida dubliniensis*, *Candida ergatensis*, *Candida fructus*, *Candida glabrata*, *Candida fermentati*, *Candida guilliermondii*, *Candida haemulonii*, *Candida insectamens*, *Candida insectorum*, *Candida intermedia*, *Candida jeffresii*, *Candida kefyr*, *Candida krusei*, *Candida lusitaniae*, *Candida lyxosophila*, *Candida maltosa*, *Candida membranifaciens*, *Candida milleri*, *Candida oleophila*, *Candida oregonensis*, *Candida parapsilosis*, *Candida quercitrusa*, *Candida shehatea*, *Candida temnochilae*, *Candida tenuis*, *Candida tropicalis*, *Candida tsuchiyae*, *Candida sinolaborantium*, *Candida sojae*, *Candida viswanathii*, *Candida utilis*, *Oogataea minuta*, *Pichia membranaefaciens*, *Pichia silvestris*, *Pichia membranaefaciens*, *Pichia chodati*, *Pichia membranaefaciens*, *Pichia menbranaefaciens*, *Pichia minuscule*, *Pichia pastoris*, *Pichia pseudopolymorpha*, *Pichia quercuum*, *Pichia robertsii*, *Pichia saitoi*, *Pichia silvestrisi*, *Pichia strasburgensis*, *Pichia terricola*, *Pichia vanriji*, *Pseudozyma Antarctica*, *Rhodosporidium toruloides*, *Rhodotorula glutinis*, *Saccharomyces bayanus*, *Saccharomyces bayanus*, *Saccharomyces momdshuricus*, *Saccharomyces uvarum*, *Saccharomyces bayanus*, *Saccharomyces cerevisiae*, *Saccharomyces bisporus*, *Saccharomyces chevalieri*, *Saccharomyces delbrueckii*, *Saccharomyces exiguous*, *Saccharomyces fermentati*, *Saccharomyces fragilis*, *Saccharomyces marxianus*, *Saccharomyces mellis*, *Saccharomyces rosei*, *Saccharomyces rouxii*, *Saccharomyces uvarum*, *Saccharomyces willianus*, *Saccharomycodes ludwigii*, *Saccharomycopsis capsularis*, *Saccharomycopsis fibuligera*, *Saccharomycopsis fibuligera*, *Endomyces hordei*, *Endomycopsis fobuligera*. *Saturnispora saitoi*, *Schizosaccharomyces octosporus*, *Schizosaccharomyces pombe*, *Schwanniomyces occidentalis*, *Torulaspora delbrueckii*, *Torulaspora delbrueckii*, *Saccharomyces dairensis*, *Torulaspora delbrueckii*, *Torulaspora fermentati*, *Saccharomyces fermentati*, *Torulaspora delbrueckii*, *Torulaspora rosei*, *Saccharomyces rosei*, *Torulaspora delbrueckii*, *Saccharomyces rosei*, *Torulaspora delbrueckii*, *Saccharomyces delbrueckii*, *Torulaspora delbrueckii*, *Saccharomyces delbrueckii*, *Zygosaccharomyces mongolicus*, *Dorulaspora globosa*, *Debaryomyces globosus*, *Torulopsis globosa*, *Trichosporon cutaneum*, *Trigonopsis variabilis*, *Williopsis californica*, *Williopsis saturnus*, *Zygosaccharomyces bisporus*, *Zygosaccharomyces bisporus*, *Debaryomyces disporua*. *Saccharomyces bisporas*, *Zygosaccharomyces bisporus*, *Saccharomyces bisporus*, *Zygosaccharomyces mellis*, *Zygosaccharomyces priorianus*, *Zygosaccharomyces rouxiim*, *Zygosaccharomyces rouxii*, *Zygosaccharomyces barkeri*, *Saccharomyces rouxii*, *Zygosaccharomyces rouxii*, *Zygosaccharomyces major*, *Saccharomyces rousii*, *Pichia anomala*, *Pichia bovis*, *Pichia Canadensis*, *Pichia carsonii*, *Pichia farinose*, *Pichia fermentans*, *Pichia fluxuum*, *Pichia membranaefaciens*, *Pichia pseudopolymorpha*, *Pichia quercuum*, *Pichia robertsii*, *Pseudozyma Antarctica*, *Rhodosporidium toruloides*, *Rhodosporidium toruloides*, *Rhodotorula glutinis*, *Saccharomyces bayanus*, *Saccharomyces bayanus*, *Saccharomyces bisporus*, *Saccharomyces cerevisiae*, *Saccharomyces chevalieri*, *Saccharomyces delbrueckii*, *Saccharomyces fermentati*,

*Saccharomyces fragilis, Saccharomycodes ludwigii, Schizosaccharomyces pombe, Schwanniomyces occidentalis, Torulaspora delbrueckii, Torulaspora globosa, Trigonopsis variabilis, Williopsis californica, Williopsis saturnus, Zygosaccharomyces bisporus, Zygosaccharomyces mellis,* or *Zygosaccharomyces rouxii*. Exemplary filamentous fungi include various species of *Aspergillus* including, but not limited to, *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus,* or *Aspergillus versicolor*. Such cells, prior to the genetic engineering as specified herein, can be obtained from a variety of commercial sources and research resource facilities, such as, for example, the American Type Culture Collection (Rockville, Md.). Target molecules include proteins such as any of the target proteins described herein (see above).

Genetic engineering of a cell can include, in addition to an exogenous nucleic acid encoding a mannosidase, one or more genetic modifications such as: (i) deletion of an endogenous gene encoding an Outer CHain elongation (OCH1) protein; (ii) introduction of a recombinant nucleic acid encoding a polypeptide capable of promoting mannosyl phosphorylation (e.g, a MNN4 polypeptide from *Yarrowia lipolytica, S. cerevisiae, Ogataea minuta, Pichia pastoris*, or *C. albicans*, or PNO1 polypeptide from *P. pastoris*) to increasing phosphorylation of mannose residues; (iii) introduction or expression of an RNA molecule that interferes with the functional expression of an OCH1 protein; (iv) introduction of a recombinant nucleic acid encoding a wild-type (e.g., endogenous or exogenous) protein having a N-glycosylation activity (i.e., expressing a protein having an N-glycosylation activity); (v) introduction of a recombinant nucleic acid encoding a target molecule described above; or (v) altering the promoter or enhancer elements of one or more endogenous genes encoding proteins having N-glycosylation activity to thus alter the expression of their encoded proteins. RNA molecules include, e.g., small-interfering RNA (siRNA), short hairpin RNA (shRNA), anti-sense RNA, or micro RNA (miRNA). Genetic engineering also includes altering an endogenous gene encoding a protein having an N-glycosylation activity to produce a protein having additions (e.g., a heterologous sequence), deletions, or substitutions (e.g., mutations such as point mutations; conservative or non-conservative mutations). Mutations can be introduced specifically (e.g., by site-directed mutagenesis or homologous recombination) or can be introduced randomly (for example, cells can be chemically mutagenized as described in, e.g., Newman and Ferro-Novick (1987) *J. Cell Biol.* 105(4):1587.

Genetic modifications described herein can result in one or more of (i) an increase in one or more activities in the genetically modified cell, (ii) a decrease in one or more activities in the genetically modified cell, or (iii) a change in the localization or intracellular distribution of one or more activities in the genetically modified cell. It is understood that an increase in the amount of a particular activity (e.g., promoting mannosyl phosphorylation) can be due to overexpressing one or more proteins capable of promoting mannosyl phosphorylation, an increase in copy number of an endogenous gene (e.g., gene duplication), or an alteration in the promoter or enhancer of an endogenous gene that stimulates an increase in expression of the protein encoded by the gene. A decrease in one or more particular activities can be due to overexpression of a mutant form (e.g., a dominant negative form), introduction or expression of one or more interfering RNA molecules that reduce the expression of one or more proteins having a particular activity, or deletion of one or more endogenous genes that encode a protein having the particular activity.

To disrupt a gene by homologous recombination, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance to yeast cells, or the lacZ gene, which results in blue colonies due to the expression of β-galactosidase. Linearized DNA fragments of the gene replacement vector are then introduced into the cells using methods well known in the art (see below). Integration of the linear fragments into the genome and the disruption of the gene can be determined based on the selection marker and can be verified by, for example, Southern blot analysis. A selectable marker can be removed from the genome of the host cell by, e.g., Cre-loxP systems (see below).

Alternatively, a gene replacement vector can be constructed in such a way as to include a portion of the gene to be disrupted, which portion is devoid of any endogenous gene promoter sequence and encodes none or an inactive fragment of the coding sequence of the gene. An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene.

Expression vectors can be autonomous or integrative. A recombinant nucleic acid (e.g., one encoding a mannosidase) can be in introduced into the cell in the form of an expression vector such as a plasmid, phage, transposon, cosmid or virus particle. The recombinant nucleic acid can be maintained extrachromosomally or it can be integrated into the yeast cell chromosomal DNA. Expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids (see, e.g., U.S. Pat. No. 4,704, 362). Expression vectors can also include an autonomous replication sequence (ARS). For example, U.S. Pat. No. 4,837,148 describes autonomous replication sequences which provide a suitable means for maintaining plasmids in *Pichia pastoris*.

Integrative vectors are disclosed, e.g., in U.S. Pat. No. 4,882,279. Integrative vectors generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the species to be transformed. A nucleotide sequence containing a gene of interest (e.g., a gene encoding a protein having N-glycosylation activity) for expression is inserted in this vector between the first and second insertable DNA fragments whether before or after the marker gene. Integrative vectors can be linearized prior to yeast transformation to facilitate the integration of the nucleotide sequence of interest into the host cell genome.

An expression vector can feature a recombinant nucleic acid under the control of a yeast (e.g., *Yarrowia lipolytica, Arxula adeninivorans, P. pastoris*, or other suitable fungal species) promoter, which enables them to be expressed in fungal cells. Suitable yeast promoters include, e.g., ADC1, TPI1, ADH2, hp4d, PDX, and Gal10 (see, e.g., Guarente et al. (1982) *Proc. Natl. Acad. Sci. USA* 79(23):7410) promoters. Additional suitable promoters are described in, e.g., Zhu and Zhang (1999) *Bioinformatics* 15(7-8):608-611 and U.S. Pat. No. 6,265,185.

A promoter can be constitutive or inducible (conditional). A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

It is understood that other genetically engineered modifications can also be conditional. For example, a gene can be conditionally deleted using, e.g., a site-specific DNA recombinase such as the Cre-loxP system (see, e.g., Gossen et al. (2002) *Ann. Rev. Genetics* 36:153-173 and U.S. Application Publication No. 20060014264).

A recombinant nucleic acid can be introduced into a cell described herein using a variety of methods such as the spheroplast technique or the whole-cell lithium chloride yeast transformation method. Other methods useful for transformation of plasmids or linear nucleic acid vectors into cells are described in, for example, U.S. Pat. No. 4,929,555; Hinnen et al. (1978) *Proc. Nat. Acad. Sci. USA* 75:1929; Ito et al. (1983) *J. Bacteriol.* 153:163; U.S. Pat. No. 4,879,231; and Sreekrishna et al. (1987) *Gene* 59:115, the disclosures of each of which are incorporated herein by reference in their entirety. Electroporation and PEG1000 whole cell transformation procedures may also be used, as described by Cregg and Russel, Methods in Molecular Biology: *Pichia* Protocols, Chapter 3, Humana Press, Totowa, N.J., pp. 27-39 (1998).

Transformed fungal cells can be selected for by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or PCR analysis.

Prior to introducing the vectors into a target cell of interest, the vectors can be grown (e.g., amplified) in bacterial cells such as *Escherichia coli* (*E. coli*) as described above. The vector DNA can be isolated from bacterial cells by any of the methods known in the art which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

In some embodiments, the genetically engineered fungal cell lacks the OCH1 gene or gene products (e.g., mRNA or protein) thereof, and is deficient in OCH1 activity. In some embodiments, the genetically engineered cell expresses a polypeptide capable of promoting mannosyl phosphorylation (e.g., a MNN4 polypeptide from *Yarrowia lipolytica, S. cerevisiae, Ogataea minuta, Pichia pastoris*, or *C. albicans*, or a PNO1 polypeptide from *P. pastoris*). For example, the fungal cell can express a MNN4 polypeptide from *Y. lipolytica* (Genbank® Acccession Nos: XM_503217, Genolevures Ref: YALI0D24101g). In some embodiments, the genetically engineered cell is deficient in OCH1 activity and expresses a polypeptide capable of promoting mannosyl phosphorylation.

Following uncapping and demannosylation, the target molecule can be isolated. In some embodiments, the target molecule is maintained within the yeast cell and released upon cell lysis. In some embodiments, the target molecule is secreted into the culture medium via a mechanism provided by a coding sequence (either native to the exogenous nucleic acid or engineered into the expression vector), which directs secretion of the molecule from the cell. The presence of the uncapped and demannosylated target molecule in the cell lysate or culture medium can be verified by a variety of standard protocols for detecting the presence of the molecule. For example, where the altered target molecule is a protein, such protocols can include, but are not limited to, immunoblotting or radioimmunoprecipitation with an antibody specific for the altered target protein (or the target protein itself), binding of a ligand specific for the altered target protein (or the target protein itself), or testing for a specific enzyme activity of the altered target protein (or the target protein itself).

In some embodiments, following isolation, the uncapped and demannosylated target molecule can be attached to a heterologous moiety, e.g., using enzymatic or chemical means. A "heterologous moiety" refers to any constituent that is joined (e.g., covalently or non-covalently) to the altered target molecule, which constituent is different from a constituent originally present on the altered target molecule. Heterologous moieties include, e.g., polymers, carriers, adjuvants, immunotoxins, or detectable (e.g., fluorescent, luminescent, or radioactive) moieties. In some embodiments, an additional N-glycan can be added to the altered target molecule.

Methods for detecting glycosylation of a target molecule include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. The derivatized N-glycans can then be concentrated. Instrumentation suitable for N-glycan analysis includes, e.g., the ABI PRISM® 377 DNA sequencer (Applied Biosystems). Data analysis can be performed using, e.g., GENESCAN® 3.1 software (Applied Biosystems). Isolated mannoproteins can be further treated with one or more enzymes such as calf intestine phosphatase to confirm their N-glycan status. Additional methods of N-glycan analysis include, e.g., mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) *Glycobiology* 11(4):275-281 and Freire et al. (2006) *Bioconjug. Chem.* 17(2):559-564.

Cultures of Engineered Cells

This document also provides a substantially pure culture of any of the genetically engineered cells described herein. As used herein, a "substantially pure culture" of a genetically engineered cell is a culture of that cell in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the genetically engineered cell, e.g., bacterial, fungal (including yeast), mycoplasmal, or protozoan cells. The term "about" in this context means that the relevant percentage can be 15% percent of the specified percentage above or below the specified percentage. Thus, for example, about 20% can be 17% to 23%. Such a culture of genetically engineered cells includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

The genetically engineered cells described herein can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidized bed drying or spray drying, or any other suitable drying method.

Metabolic Disorders

Uncapped and demannosylated molecules can be used to treat a variety of metabolic disorders. A metabolic disorder is one that affects the production of energy within individual human (or animal) cells. Most metabolic disorders are genetic, though some can be "acquired" as a result of diet, toxins, infections, etc. Genetic metabolic disorders are also known as inborn errors of metabolism. In general, the genetic metabolic disorders are caused by genetic defects that result in missing or improperly constructed enzymes necessary for some step in the metabolic process of the cell. The largest classes of metabolic disorders are disorders of carbohydrate metabolism, disorders of amino acid metabolism, disorders of organic acid metabolism (organic acidurias), disorders of fatty acid oxidation and mitochondrial metabolism, disorders of porphyrin metabolism, disorders of purine or pyrimidine metabolism, disorders of steroid metabolism disorders of mitochondrial function, disorders of peroxisomal function, and lysosomal storage disorders (LSDs).

Examples of metabolic disorders that can be treated through the administration of one or more uncapped and demannosylated molecules (or pharmaceutical compositions of the same) can include hereditary hemochromatosis, oculocutaneous albinism, protein C deficiency, type I hereditary angioedema, congenital sucrase-isomaltase deficiency, Crigler-Najjar type II, Laron syndrome, hereditary Myeloperoxidase, primary hypothyroidism, congenital long QT syndrome, tyroxine binding globulin deficiency, familial hypercholesterolemia, familial chylomicronemia, abeta-lipoproteinema, low plasma lipoprotein A levels, hereditary emphysema with liver injury, congenital hypothyroidism, osteogenesis imperfecta, hereditary hypofibrinogenemia, alpha-1 antichymotrypsin deficiency, nephrogenic diabetes insipidus, neurohypophyseal diabetes insipidus, adenosine deaminase deficiency, Pelizaeus Merzbacher disease, von Willebrand disease type HA, combined factors V and VIII deficiency, spondylo-epiphyseal dysplasia tarda, choroideremia, I cell disease, Batten disease, ataxia telangiectasias, ADPKD-autosomal dominant polycystic kidney disease, microvillus inclusion disease, tuberous sclerosis, oculocerebro-renal syndrome of Lowe, amyotrophic lateral sclerosis, myelodysplastic syndrome, Bare lymphocyte syndrome, Tangier disease, familial intrahepatic cholestasis, X-linked adreno-leukodystrophy, Scott syndrome, Hermansky-Pudlak syndrome types 1 and 2, Zellweger syndrome, rhizomelic chondrodysplasia puncta, autosomal recessive primary hyperoxaluria, Mohr Tranebjaerg syndrome, spinal and bullar muscular atrophy, primary ciliary diskenesia (Kartagener's syndrome), giantism and acromegaly, galactorrhea, Addison's disease, adrenal virilism, Cushing's syndrome, ketoacidosis, primary or secondary aldosteronism, Miller Dieker syndrome, lissencephaly, motor neuron disease, Usher's syndrome, Wiskott-Aldrich syndrome, Optiz syndrome, Huntington's disease, hereditary pancreatitis, anti-phospholipid syndrome, overlap connective tissue disease, Sjögren's syndrome, stiff-man syndrome, Brugada syndrome, congenital nephritic syndrome of the Finnish type, Dubin-Johnson syndrome, X-linked hypophosphatemia, Pendred syndrome, persistent hyperinsulinemic hypoglycemia of infancy, hereditary spherocytosis, aceruloplasminemia, infantile neuronal ceroid lipofuscinosis, pseudoachondroplasia and multiple epiphyseal, Stargardt-like macular dystrophy, X-linked Charcot-Marie-Tooth disease, autosomal dominant retinitis pigmentosa, Wolcott-Rallison syndrome, Cushing's disease, limb-girdle muscular dystrophy, mucoploy-saccharidosis type IV, hereditary familial amyloidosis of Finish, Anderson disease, sarcoma, chronic myelomonocytic leukemia, cardiomyopathy, faciogenital dysplasia, Torsion disease, Huntington and spinocerebellar ataxias, hereditary hyperhomosyteinemia, polyneuropathy, lower motor neuron disease, pigmented retinitis, seronegative polyarthritis, interstitial pulmonary fibrosis, Raynaud's phenomenon, Wegner's granulomatosis, preoteinuria, CDG-Ia, CDG-Ib, CDG-Ic, CDG-Id, CDG-Ie, CDG-If, CDG-IIa, CDG-IIb, CDG-IIc, CDG-IId, Ehlers-Danlos syndrome, multiple exostoses, Griscelli syndrome (type 1 or type 2), or X-linked non-specific mental retardation. In addition, metabolic disorders can also include lysosomal storage disorders such as, but not limited to, Fabry disease, mucopolysaccharidosis I, Farber disease, Gaucher disease, $GM_1$-gangliosidosis, Tay-Sachs disease, Sandhoff disease, $GM_2$ activator disease, Krabbe disease, metachromatic leukodystrophy, Niemann-Pick disease (types A, B, and C), Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis (types II, III, and IV), cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

Symptoms of a metabolic disorder are numerous and diverse and can include one or more of, e.g., anemia, fatigue, bruising easily, low blood platelets, liver enlargement, spleen enlargement, skeletal weakening, lung impairment, infections (e.g., chest infections or pneumonias), kidney impairment, progressive brain damage, seizures, extra thick meconium, coughing, wheezing, excess saliva or mucous production, shortness of breath, abdominal pain, occluded bowel or gut, fertility problems, polyps in the nose, clubbing of the finger/toe nails and skin, pain in the hands or feet, angiokeratoma, decreased perspiration, corneal and lenticular opacities, cataracts, mitral valve prolapse and/or regurgitation, cardiomegaly, temperature intolerance, difficulty walking, difficulty swallowing, progressive vision loss, progressive hearing loss, hypotonia, macroglossia, areflexia, lower back pain, sleep apnea, orthopnea, somnolence, lordosis, or scoliosis. It is understood that due to the diverse nature of the defective or absent proteins and the resulting disease phenotypes (e.g., symptomatic presentation of a metabolic disorder), a given disorder will generally present only symptoms characteristic to that particular disorder. For example, a patient with Fabry disease can present a particular subset of the above-mentioned symptoms such as, but not limited to, temperature intolerance, corneal whirling, pain, skin rashes, nausea, or dirarrhea. A patient with Gaucher syndrome can present with splenomegaly, cirrhosis, convulsions, hypertonia, apnea, osteoporosis, or skin discoloration.

In addition to the administration of one or more uncapped and demannosylated molecules described herein, a metabolic disorder can also be treated by proper nutrition and vitamins (e.g., cofactor therapy), physical therapy, and pain medications.

Depending on the specific nature of a given metabolic disorder, a patient can present these symptoms at any age. In many cases, symptoms can present in childhood or in early adulthood. For example, symptoms of Fabry disease can present at an early age, e.g., at 10 or 11 years of age.

As used herein, a subject "at risk of developing a metabolic disorder" is a subject that has a predisposition to develop a disorder, i.e., a genetic predisposition to develop metabolic disorder as a result of a mutation in a enzyme such as acid alpha glucosidase, alpha galactosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acteylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neuromimidase, phosphotransferase, acid lipase, acid ceramidase, sphingomyelinase, thioesterase, cathepsin K, or lipoprotein lipase. Clearly, subjects "at risk of developing a metabolic disorder" are not all the subjects within a species of interest.

A subject "suspected of having a disorder" is one having one or more symptoms of a metabolic disorder such as any of those described herein.

Pharmaceutical Compositions and Methods of Treatment

An uncapped and demannosylated target molecule can be incorporated into a pharmaceutical composition containing a therapeutically effective amount of the molecule and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., Remington's Pharmaceutical Sciences (Maack Publishing Co., Easton, Pa.). Supplementary active compounds can also be incorporated into the compositions.

Administration of a pharmaceutical composition containing uncapped and demannosylated molecules can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted altered N-glycosylation molecule production cells). See, e.g., U.S. Pat. Nos. 4,407,957, 5,798,113, and 5,800,828. Administration of a pharmaceutical composition can be achieved using suitable delivery means such as: a pump (see, e.g., Annals of Pharmacotherapy, 27:912 (1993); Cancer, 41:1270 (1993); Cancer Research, 44:1698 (1984); microencapsulation (see, e.g., U.S. Pat. Nos. 4,352,883; 4,353,888; and 5,084,350); continuous release polymer implants (see, e.g., Sabel, U.S. Pat. No. 4,883,666); macroencapsulation (see, e.g., U.S. Pat. Nos. 5,284,761, 5,158,881, 4,976,859 and 4,968,733 and published PCT patent applications WO92/19195, WO 95/05452); injection, either subcutaneously, intravenously, intra-arterially, intramuscularly, or to other suitable site; or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch.

Formulations suitable for parenteral administration conveniently contain a sterile aqueous preparation of the altered N-glycosylation molecule, which preferably is isotonic with the blood of the recipient (e.g., physiological saline solution). Formulations can be presented in unit-dose or multi-dose form.

Formulations suitable for oral administration can be presented as discrete units such as capsules, cachets, tablets, or lozenges, each containing a predetermined amount of the altered N-glycosylation molecule; or a suspension in an aqueous liquor or a non-aqueous liquid, such as a syrup, an elixir, an emulsion, or a draught.

An uncapped and demannosylated molecule suitable for topical administration can be administered to a mammal (e.g., a human patient) as, e.g., a cream, a spray, a foam, a gel, an ointment, a salve, or a dry rub. A dry rub can be rehydrated at the site of administration. Such molecules can also be infused directly into (e.g., soaked into and dried) a bandage, gauze, or patch, which can then be applied topically. Such molecules can also be maintained in a semi-liquid, gelled, or fully-liquid state in a bandage, gauze, or patch for topical administration (see, e.g., U.S. Pat. No. 4,307,717).

Therapeutically effective amounts of a pharmaceutical composition can be administered to a subject in need thereof in a dosage regimen ascertainable by one of skill in the art. For example, a composition can be administered to the subject, e.g., systemically at a dosage from 0.01 µg/kg to 10,000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, an uncapped and demannosylated molecule can be first administered at different dosing regimens. The unit dose and regimen depend on factors that include, e.g., the species of mammal, its immune status, the body weight of the mammal. Typically, levels of a such a molecule in a tissue can be monitored using appropriate screening assays as part of a clinical testing procedure, e.g., to determine the efficacy of a given treatment regimen.

The frequency of dosing for an uncapped and demannosylated molecule is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status. The frequency of dosing can be varied depending on whether the treatment is prophylactic or therapeutic.

Toxicity and therapeutic efficacy of such molecules or pharmaceutical compositions thereof can be determined by known pharmaceutical procedures in, for example, cell cultures or experimental animals. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human patients). The dosage of such pharmaceutical compositions lies generally within a range of circulating concentrations that include the $ED_{50}$ with little or no toxicity. The dosage may vary within this range depending upon the dosage form employed and the route of administration utilized. For a pharmaceutical composition used as described herein (e.g., for treating a metabolic disorder in a subject), the therapeutically effective dose can be estimated initially from cell culture assays. A dose can be formulated in animal models to achieve a circulating plasma concentration range that includes the $IC_{50}$ (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

As defined herein, a "therapeutically effective amount" of an uncapped and demannosylated molecule is an amount of the molecule that is capable of producing a medically desirable result (e.g., amelioration of one or more symptoms of a metabolic disorder) in a treated subject. A therapeutically effective amount (i.e., an effective dosage) can includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a dog, a cat, or a whale.

A molecule or pharmaceutical composition thereof described herein can be administered to a subject as a combination therapy with another treatment, e.g., a treatment for a metabolic disorder (e.g., a lysosomal storage disorder). For example, the combination therapy can include administering to the subject (e.g., a human patient) one or more additional agents that provide a therapeutic benefit to the subject who has, or is at risk of developing, (or suspected of having) a metabolic disorder (e.g., a lysosomal storage disorder). Thus, the compound or pharmaceutical composition and the one or more additional agents can be administered at the same time. Alternatively, the molecule can be administered first and the one or more additional agents administered second, or vice versa.

It will be appreciated that in instances where a previous therapy is particularly toxic (e.g., a treatment for a metabolic disorder with significant side-effect profiles), administration of a molecule described herein can be used to offset and/or lessen the amount of the previously therapy to a level sufficient to give the same or improved therapeutic benefit, but without the toxicity.

Any of the pharmaceutical compositions described herein can be included in a container, pack, or dispenser together with instructions for administration.

The following are examples of the practice of the invention. They are not to be construed as limiting the scope of the invention in any way.

EXAMPLE 1

Generation of a Human Alpha Glucosidase Expression Strain

*Y. lipolytica* strain OXYY1589 was constructed as follows and contains three copies of the human alpha glucosidase gene (huGAA, also known as acid alpha glucosidase or acid maltase EC3.2.1.3) and two copies of the *Y. lipolytica* MNN4 gene. The genotype of strain OXY1589 is as follows:
MatA, leu2-958, ura3-302, xpr2-322,
gut2-744, ade2-844
POX2-Lip2pre-huGAA:URA3Ex::zeta
POX2-Lip2pre-huGAA:LEU2Ex::zeta
POX2-Lip2pre-hGM-CSF:GUTEx::zeta
YlMNN4-POX2-hp4d-YLMNN4:ADE2::PT targeted All transformations were carried out according to well established protocols with modifications for the different selective markers. Unless otherwise specified, the huGAA integration fragment was obtained by NotI restriction digestion of the expression plasmid in order to remove the kanamycin resistance gene. The fragments resulting from the restriction digest were separated by agarose gel electrophoresis followed by Qiagen column purification of the huGAA fragment. Three stable integrative transformations were performed in order to obtain the final huGAA production strain OXYY1589.

*Y. lipolytica* codon optimized huGAA expression vector: The nucleotide sequence encoding the 110 kDA huGAA precursor was chemically synthesized and codon optimized for *Y. lipolytica* expression. Table 1 shows the codon usage for *Y. lipolytica*. Data was derived from 2,945,919 codons present in 5,967 coding sequences. The contents of Table 1 were obtained from a Codon Usage Database, which can be found at world wide web at kazusa.or.jp/codon/cgi-binishowcodon.cgi?species=284591.

TABLE 1

*Yarrowia lipolytica* Codon Usage Table

| | | | |
|---|---|---|---|
| UUU 15.9(46804) | CU 21.8(64161) | AU 6.8(20043) | GU 6.1(17849) |
| UUC 23.0(67672) | CC 20.6(60695) | AC 23.1(68146) | GC 6.1(17903) |
| UUA 1.8(5280) | CA 7.8(22845) | AA 0.8(2494) | GA 0.4(1148) |
| UUG 10.4(30576) | CG 15.4(45255) | AG 0.8(2325) | GG 12.1(35555) |
| CUU 13.2(38890) | CU 17.4(51329) | AU 9.6(28191) | GU 6.0(17622) |
| CUC 22.6(66461) | CC 23.3(68633) | AC 14.4(42490) | GC 4.4(12915) |
| CUA 5.3(15548) | CA 6.9(20234) | AA 9.8(28769) | GA 21.7(63881) |
| CUG 33.5(98823) | CG 6.8(20042) | AG 32.1(94609) | GG 7.7(22606) |
| AUU 22.4(66134) | CU 16.2(47842) | AU 8.9(26184) | GU 6.7(19861) |
| AUC 24.4(71810) | CC 25.6(75551) | AC 31.3(92161) | GC 9.8(28855) |
| AUA 2.2(6342) | CA 10.5(30844) | AA 12.4(36672) | GA 8.4(24674) |
| AUG 22.6(66620) | CG 8.5(25021) | AG 46.5(136914) | GG 2.4(7208) |
| GUU 15.8(46530) | CU 25.5(75193) | AU 21.5(63259) | GU 16.6(48902) |
| GUC 21.5(63401) | CC 32.7(96219) | AC 38.3(112759) | GC 21.8(64272) |
| GUA 4.0(11840) | CA 11.2(32999) | AA 18.8(55382) | GA 20.9(61597) |
| GUG 25.7(75765) | CG 8.9(26190) | AG 46.2(136241) | GG 4.4(12883) |

Tablefields are shown as [triplet] [frequency: per thousand]([number]).

In the synthetic construct, the pre- and the pro-huGAA signal peptides were eliminated such that the protein starts at amino acid 57. The synthetic open reading frame (ORF) of huGAA (FIG. 1A) was fused in frame at the 5' end to the 3' end of the *Y. lipolytica* LIP2 signal sequence (pre), followed by the coding sequence of two Xxx-Ala cleavage sites, and flanked by BamHI and AvrII restriction sites for cloning into the expression vector. In the construct, the fused polypeptide encoding sequence was under the control of the inducible PDX2 promoter. The complete amino acid sequence of the fusion construct is shown on FIG. 1B.

A general schematic of the *Y. lipolytica* expression vector is presented in FIG. 2. The bacterial moiety is derived from the plasmid pHSS6, and contains a bacterial origin of replication (ori) and the kanamycin-resistance gene that confers resistance to kanamycin (KanR). The integration cassette comprises a) the selection marker for transformation to *Yarrowia lipolytica* (URA3; LEU2; GUT2), b) the expression cassette composed of a promoter, c) a multiple cloning site (MCS) to insert huGAA in frame with signal sequence and d) the terminator of the LIP2 gene. The integration cassette is flanked by zeta sequences for stable non-homologous integration into the *Y. lipolytica* genome. Two NotI restriction sites enable the isolation of the expression cassette before transformation. Plasmids pRAN034, pRAN036 and OXYP183 were used to generate huGAA expression vectors pRAN058, pRAN059 and pRAN060, respectively, containing URA3, LEU2 and GUT2 transformation markers, respectively.

Tandem YlMNN4 expression vector OXYP1470B: The *Y. lipolytica* MNN4 (YIMNN4) gene was cloned under control of the inducible pPDX2 promoter and under control of the (semi)constitutive hp4d promoter. These two expression cassettes of YlMNN4 were subcloned in one vector as a tandem construct carrying flanking regions (PT) of the ADE2 gene for targeted integration into the ADE2 locus of the genome and the ADE2 gene as a selection marker.

Intermediate Strain OXYY1569: The first transformation was a co-transformation of strain G014 of *Y. lipolytica* with the expression cassettes purified from the pRAN058 and pRAN059 vectors, using the URA3 and LEU2 markers to produce intermediate recombinant strain OXYY1569. Thus, OXYY1569 carries two expression constructs of huGAA under control of the pPDX2 promoter randomly integrated in the genome of strain G014.

OXYY1569 was selected as follows. Integration of the huGAA DNA into the genome of *Y. lipolytica* was confirmed by PCR screening of genomic DNA. Primers for the PCR reactions were designed to amplify a 2552bp fragment of the huGAA nucleotide sequence. Southern blot analysis of the genomic DNA also was performed in order to confirm the integration of at least 2 copies of huGAA DNA. In particular, genomic DNAs from OXYY1569 clones were digested with Hind III and probed with an huGAA DIG labeled specific probe.

In order to select a clone secreting high levels of huGAA, several randomly selected clones with confirmed integration of at least two copies of the huGAA DNA were grown in shake flasks under PDX2 inducing conditions using a medium containing 1% yeast extract, 2% peptone and 5% emulsified oleic acid. In all cases, the culture supernatant was collected 72 h post-induction and screened in a standard Western blot and enzyme activity assay analysis using the 4-MUG assay described in Example 3. N-Glycan analysis of OXYY1569 indicated the predominant structure in OXYY1569 was $Man_8GlcNAc_2$.

Intermediate Strain OXYY1584: Recombinant strain OXYY1569 was transformed with the expression cassette excised from plasmid OXYP1479B in order to integrate two copies of the *Y. lipolytica* MNN4 gene into its genome to produce OXYY1584. The expression cassette was excised from plasmid OXYP1479B with a SacII/XmaI restriction digest. The expression cassette was designed for targeted integration into the ADE2 locus of the *Y. lipolytica* genome. The recombinant strain was selected after Southern blotting and glycan analysis to evaluate the strain behavior with respect to the increased phosphorylation. Genomic DNA of several arbitrarily chosen transformants was digested with SpeI and probed with a MNN4 specific DIG labeled probe. Correct targeted integration of the MNN4 expression cassette into the ADE2 locus of *Y. lipolytica* genome produced 4207bp and 5683bp bands after SpeI digestion. Positive clones were grown in a standard shake flask procedure. N-glycan analysis of secreted proteins was performed in order to select the intermediate clone OXYY1584. Compared to the parent stain OXYY1569, the predominant structures after MNN4 overexpression were $Man_8GlcNAc_2(PMan)_1$ and $Man_8GlcNAc_2$ $(PMan)_2$.

Production strain OXYY1589: To generate the final prototrophic production strain OXYY1589, a third copy of huGAA was integrated into the genome of recombinant OXYY1584 strain. The transformation was performed with a Not I excised expression cassette from pRAN069. The genomic DNA of transformants was first screened by PCR for the presence of the additional copy of huGAA. To evaluate huGAA production, arbitrarily selected PCR positive clones were further analyzed for expression after a standard shake flask cultivation. The clone expressing the highest level of huGAA (OXYY1589) was chosen after Western blot analysis and enzymatic activity assay (4-MUG assay described in Example 3). It also was reconfirmed that the conversion levels of M8 to MP2-M8 and MP-M8 N-glycans was not influenced by the presence of the additional huGAA expression cassette.

EXAMPLE 2

Fed Batch Cultivation of Strain OXYY1589

To produce huGAA from strain OXYY1589 (Example 1), a fed batch process was established using a 10 L stirred tank, with a working volume of 6-8 liters. The process was divided in two phases:
1) Batch growth on glucose for biomass formation
2) Product formation by induction with help of a limited oleic acid feed.

Typically the batch phase was about 20 hours (h) and the production phase approximately 72 hours. At the end of the process, the culture broth was centrifuged and the supernatant was collected. The supernatant was used as starting material for the purification of huGAA (see Example 3).

The following parameters were controlled during the fermentation. Aeration was maintained at a constant value of 1.5 vvm air (volume per volume per minute). Dissolved oxygen (DO) was initially kept at 30%. The stirring was increased from 600 to 1200 rpm depending on the DO levels. Once it reached the maximum of 1200 rpm, the speed was kept constant and the DO-setpoint was set to 10%. To maintain 10% DO, oxygen was spiked into the reactor with a maximal percentage of 50%. Foam evolution was controlled by a foam probe. If foam was detected, antifoam was added to the bioreactor. The pH was controlled by adding 14% (v/v) ammonia (base) or 10% phosphoric acid to maintain a constant value of pH 6.8. The temperature was kept constant at 28° C. throughout the whole process.

Biomass was monitored by measurement of optical density at 600 nm (OD600). The samples were diluted 2-1000 times in distilled water to obtain values in the linear range of the spectrophotometer. Product formation was detected by Western blot analysis and specific enzymatic activity tests.

EXAMPLE 3

Purification of Recombinant huGAA (rhGAA)

The supernatant after cultivation (see Example 2) was clarified via depth filtration. The resulting material then was concentrated 20 times via tangential flow filtration (TFF) and diafiltered against 20 mM sodium phosphate pH 6 and 100 mM NaCl using a 10 kDa MWCO membrane (Millipore).

Purification of rhGAA was started by adding ammonium sulphate up to a concentration of 1 M. After centrifugation, the supernatant was loaded on a Toyopearl-Phenyl 650M (Tosoh Biosciences) packed XK16/40 column. A linear gradient from 1 to 0 M ammonium sulphate was applied for elution. Those fractions that contained rhGAA were then pooled and subjected to a buffer exchange into 10 mM BIS-TRIS pH 6. Further purification was achieved via anion exchange chromatography on a source 30Q packed Tricorn 10/50 or XK25/20 column (GE Healthcare) using a linear salt gradient from 0 to 1 M NaCl. The resulting GAA-containing fractions were then concentrated before loading onto a final Hiload 16/60 superdex 200 gel filtration column (GE Healthcare) that was pre-equilibrated with 50 mM sodium phosphate pH 6 and 200 mM NaCl. Fractions were selected on the basis of specific activity and purity on Coomassie-stained SDS-PAGE gels and then combined and concentrated to a final concentration of 5-10 mg/ml. Proteins were concentrated using 15 ml Amicon Ultra centrifugal devices (Millipore) with a MWCO of 10 kDa.

The 4-methylumbelliferyl-alpha-D-glucopyranoside (4-MUG) assay was used to screen rhGAA. Cleavage of the substrate 4-MUG by a glucosidase leads to the generation of the fluorigenic product 4-MU, which can be visualized or detected by irradiation with UV light. The reactions for the qualitative screening for rhGAA were started by adding the reaction buffer consisting of 0.35 mM 4-MUG, 0.1% BSA and 100 mM sodium acetate pH 4 in a 10:1 or 20:1 volume proportion to 10 or 5 µl of the elution fraction. All reactions were done in 96-well flat-bottom microtiter plates. After an incubation period of 30 minutes to 1 hour at 37° C., an equal volume of 100 mM glycine pH 11 was added to stop the reaction and the release of the fluorigenic reaction product 4-methylumbelliferone (4MU) was observed under UV-light. Specific activities (units/mg protein) were determined using a colorimetric assay with the synthetic substrate p-nitrophenyl-α-D-glucopyranoside (PNPG) that measures the enzymatic release of the yellow coloured p-nitrophenolate reaction product. The reactions were started by mixing 10 µl of enzyme solution and 90 µl of substrate reaction buffer (2 mM PNPG in 150 mM citrate-phosphate buffer pH 4, 1% BSA) in reaction wells of a microtiter plate and were subsequently incubated at 37° C. After incubating for 1 to 2 hours, an equal volume of stop buffer, 10% sodium carbonate pH 12, was added to quench the reaction and bring the released p-nitrophenol (PNP) in its ionized state. Background-corrected absorbances and p-nitrophenolate standards were measured at a wavelength of 405 nm and specific activities were calculated. Protein concentrations were determined by the bicinchoninic acid (BCA) method. One unit was defined as the amount of enzyme that catalyzes the conversion of 1 nmol of PNPG to 1 nmol PNP and D-glucose per min at 37° C. at a final substrate concentration of 2 mM in a citrate-phosphate buffer, pH 4.0.

EXAMPLE 4

Cloning and Expression of YlAMS1

The Ams1 gene from *Yarrowia lipolytica* (YlAms1) was PCR amplified from *Yarrowia* genomic DNA using gene specific primers. A HIS6-tag coding sequence was fused to the 3' end of the YlAms1 ORF such that YlAMS1 protein with a C-terminal His-tag could be produced, and was also fused to the 5' end of the YlAms1 ORF such that YLAMS 1 protein with an N-terminal His tag could be produced. Both ORFs were cloned under control of the semi constitutive hp4d promoter (FIG. 3A and FIG. 3B) and the expression cassettes were transformed into *Yarrowia lipolytica*. Cells were grown in complex medium (YPD) and harvested after 72 h growth. After disrupting the cells by sonication, the AMS 1 protein was purified using a NTA column. Purified material was analyzed for activity using PNP-mannose as a substrate. Active fractions were pooled and kept for glycan analysis.

EXAMPLE 5

Figure 4:
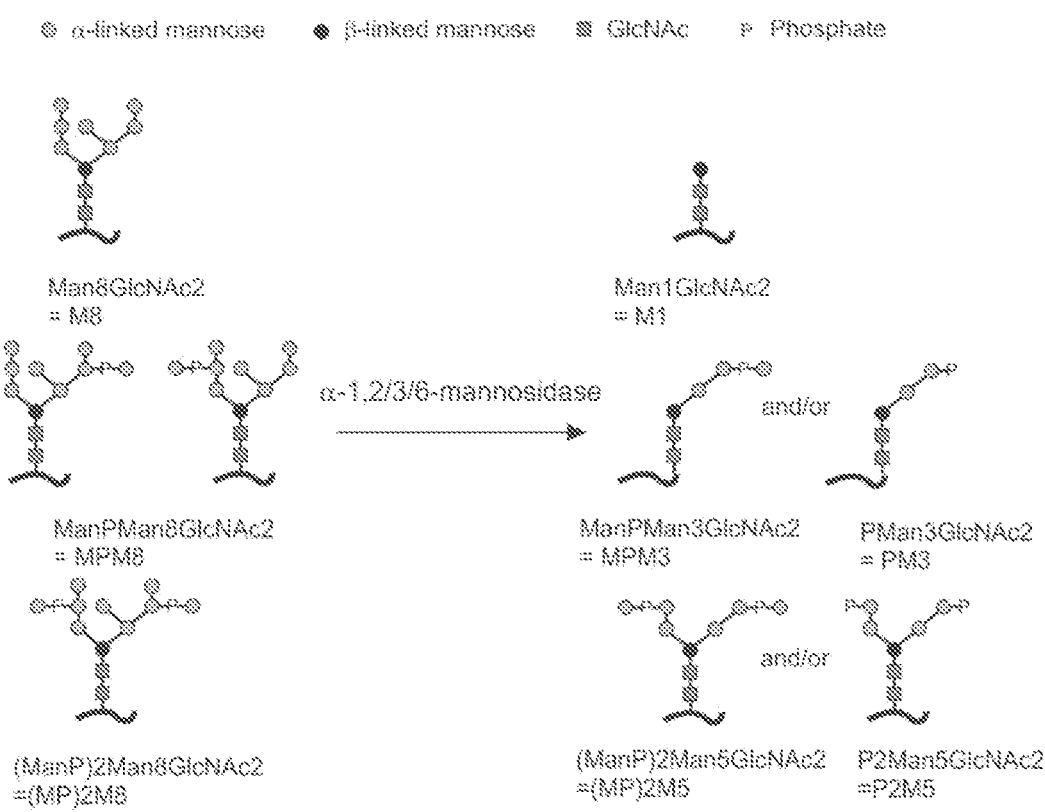
FIG. 4 is a schematic of the potential final hydrolysis products from 8-amino-1,3,6,-pyrenetrisulfonic acid (APTS)-labeled sugars derived from an MNN4 overexpressing *Yarrowia lipolytica* strain, which contains $Man_8GlcNAc_2$ (M8), the monophosphorylated $ManP-Man_8GlcNAc_2$ (MP-M8) and/or the diphosphorylated $(ManP)_2-Man_8GlcNAc_2$ (($MP)_2$-M8) sugars (referred to as MNN4 sugars or MNN4 N-glycans) assuming that the alpha-mannosidases can also fully remove mannose residues from the MNN4 N-glycans.

De-mannosylation and Phosphate Uncapping of APTS-labeled Phosphorylated N-glycans with GH38 α-mannosidases Jack bean α-mannosidase (*Canavalia ensiformis*) was obtained from Sigma-Aldrich. Both a 3.0 M ammonium sulphate suspension (Sigma-M7257) and a proteomics grade Jack bean α-mannosidase (Sigma-M5573) were used in the N-glycan analyses. Both batches gave identical results and are named JbMan in the further description. YlAms1 was expressed and purified as described in Example 4. JbMan and YlAMS1 were tested on a mixture of 8-amino-1,3,6,-pyrenetrisulfonic acid (APTS)-labeled sugars derived from an MNN4 overexpressing *Yarrowia lipolytica* strain, which contains $Man_8GlcNAc_2$ (M8), the monophosphorylated ManP-$Man_8GlcNAc_2$ (MP-M8) and/or the diphosphorylated $(ManP)_2$-$Man_8GlcNAc_2$ $((MP)_2$-M8) sugars (referred to as MNN4 sugars or MNN4 N-glycans). In FIG. 4, the potential final hydrolysis products are schematically presented, assuming that the α-mannosidases also can fully trim the MNN4 N-glycans, including hydrolysis of the non-phosphorylated arm, hydrolysis of the terminal α-1,2-mannose if the underlying mannose is phosphorylated, and/or uncapping of the phosphate in the mannose-1-phospho-6-mannose linkage.

Unless otherwise stated all reactions with JbMan and YlAMS1 on APTS-labeled N-glycans were performed overnight at 37° C. in an ammonium acetate buffer, 10 mM, pH 5.0 with 2 mM $CaCl_2$.

Figure 5:
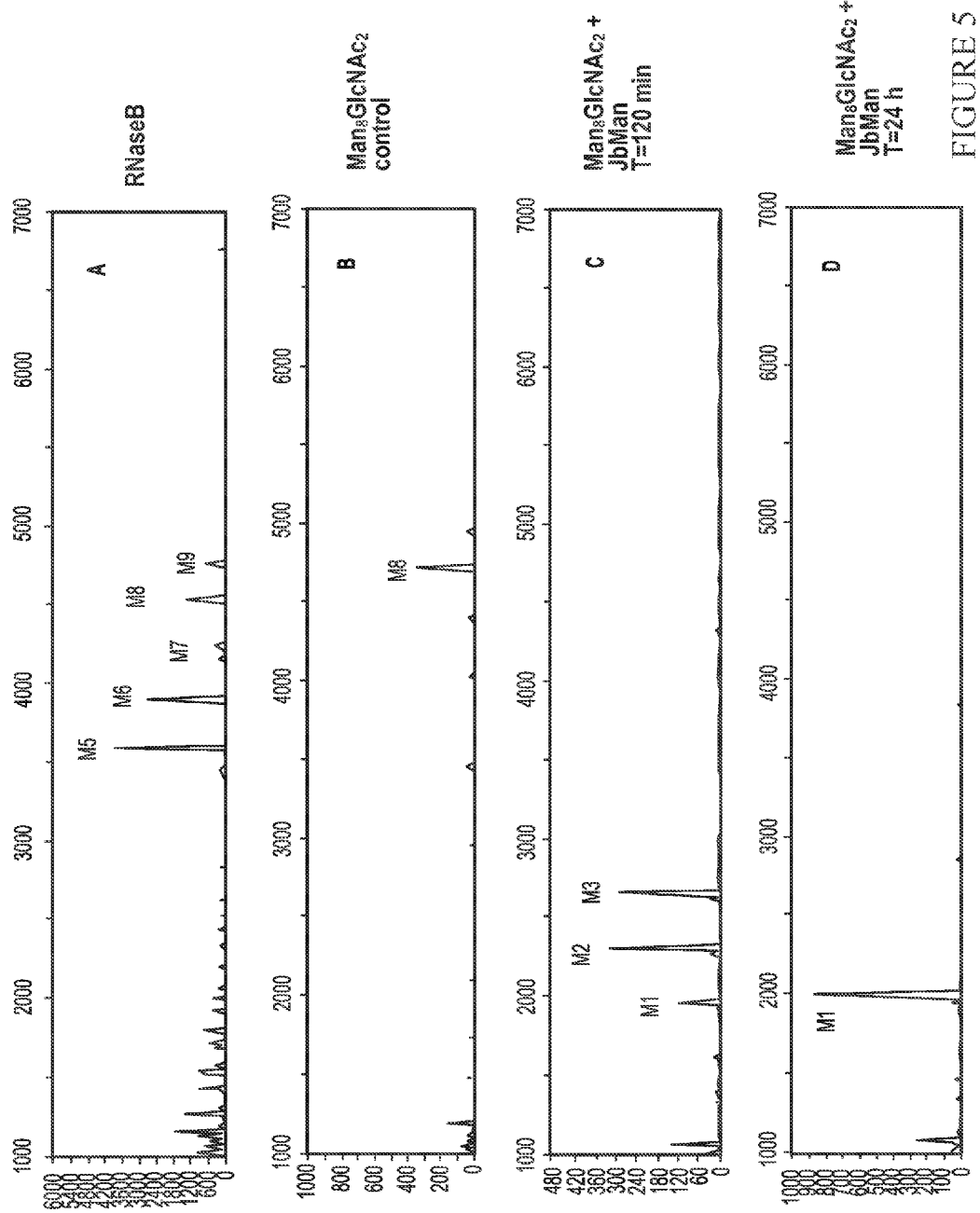
FIG. 5 is a series of electropherograms depicting the N-glycan analysis of MNN4 N-glycans treated with Jack bean (Jb) alpha-mannosidase. Analysis was performed using DNA sequencer-assisted, fluorophore-assisted carbohydrate electrophoresis (DSA-FACE). "M1," "M2," "M3," "M4," "M5," "M6," "M8," and "M9" refer to the number of mannose residues conjugated to the base N-acetylglucosamine structure. The Y-axis represents the relative fluorescence units as an indication of the amount of each N-glycan structure. The X-axis represents the relative mobility of each N-glycan structure through a capillary.
Figure 5:
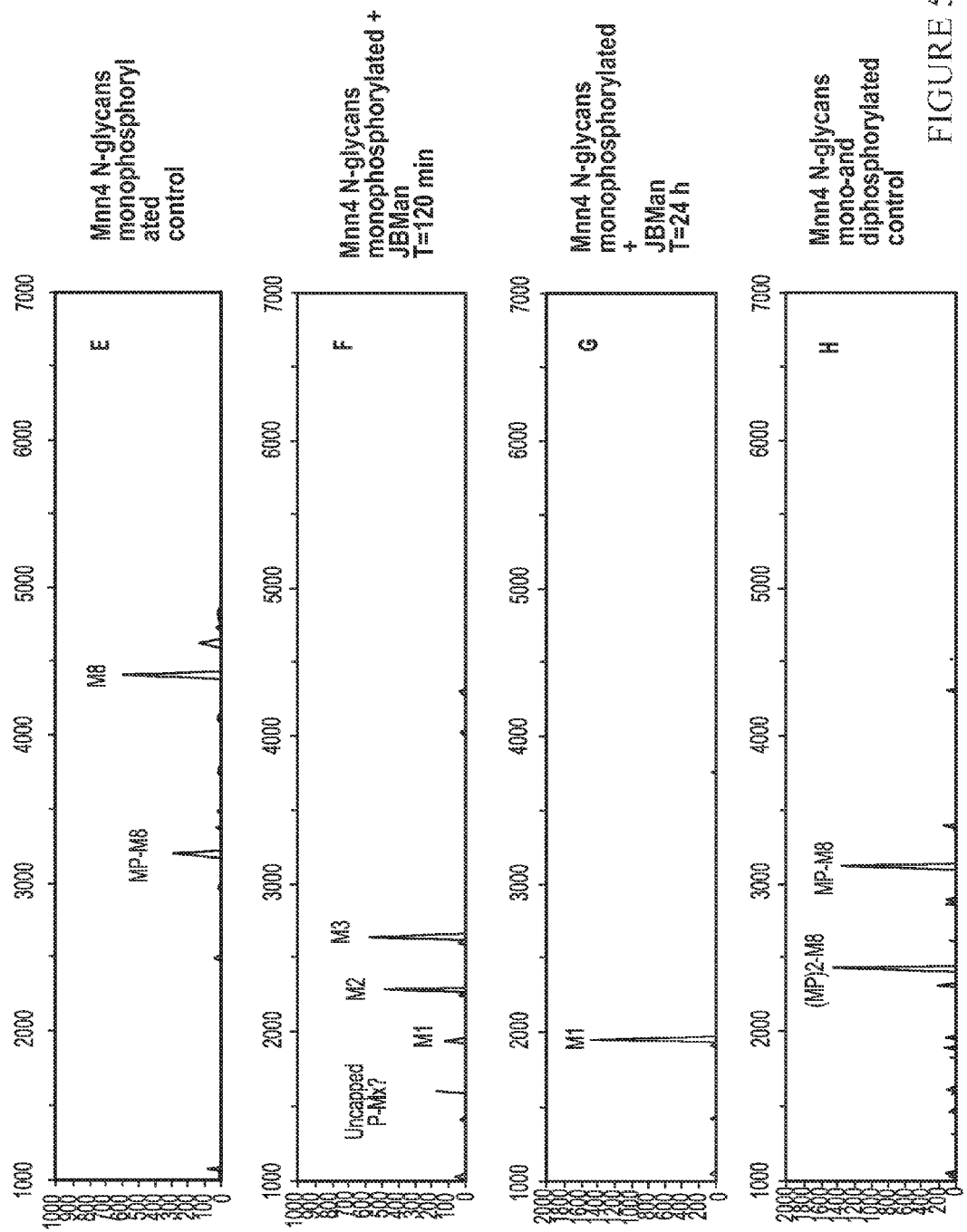

In FIG. 5, the DSA-FACE electroferograms are presented depicting the hydrolysis of the MNN4 N-glycans with JbMan. A sample was included with $Man_8GlcNAc_2$ as the substrate (Panel B) to be able to identify newly appearing peaks. JbMan sequentially hydrolyzed $Man_8GlcNAc_2$ (Panel C) till only $Man_1GlcNAc_2$ was obtained after overnight incubation (Panel D). The hydrolysis of a substrate solution containing $Man_8GlcNAc_2$ and ManP-$Man_8GlcNAc_2$ (Panel E) was more complex. Both the de-mannosylation and phosphate uncapping activities were responsible for the appearance of the fast-running peak at the left hand side of the electropherogram when the substrate was incubated with JbMan during 2 hours (Panel F). The extra charge of a terminal phosphate together with the de-mannosylation reaction was responsible for the appearance of peaks displaying fast electrophoretic mobility. Nevertheless, after overnight incubation, only a peak identified as $Man_1GlcNAc_2$ was observed (Panel G). Phosphatase activity present in the commercial JbMan preparation is responsible for this result.

The digestion of MNN4 sugars with JbMan was repeated with a substrate solution containing ManP-$Man_8GlcNAc_2$ and $(ManP)_2$-$Man_8GlcNAc_2$ (Panel H). After incubating for 2 hours, a potential uncapped peak appeared and is indicated with "P-Mx" and "P2Mx" in panel I. In the fast electrophoretic mobility region, the peak resolution is smaller and it is possible that mono- and diphosphorylated uncapped structures, e.g., P-$Man_4GlcNAc_2$ and P2-$Man_6GlcNac_2$, ran together. The result after overnight digestion suggests a further de-mannosylation. The peaks indicated with P-My and P2-My in panel J could be P-$Man_3GlcNAc_2$ and P2-$Man_5GlcNAc_2$, but neutral $Man_1GlcNAc_2$, $Man_2GlcNAc_2$ and $Man_3GlcNAc_2$ also can be observed in panel J. As no $Man_8GlcNAc_2$ was present in the substrate solutions, these peaks are the result of a potential contaminating phosphatase activity and further mannose trimming.

To identify the uncapped peaks in panel J, the reaction mixture was treated with calf intestine phosphatase (CIP). Treatment of the uncapped glycans (thus containing a terminal phosphate) resulted in neutral oligosaccharides that ran much slower and appeared more to the right in the electropherogram. Indeed, $Man_3GlcNAc_2$ through $Man_6GlcNac_2$ appear in panel K. Although the activity was hampered by the presence of phosphatase activity in the commercial JbMan preparation, the presented data reveal that fully de-mannosylated and phosphate uncapped structures (i.e., P-$Man_3GlcNAc_2$ and P2-$Man_5GlcNAc_2$) can be obtained when treating APTS-labeled MNN4 sugars with JbMan.

Figure 6:
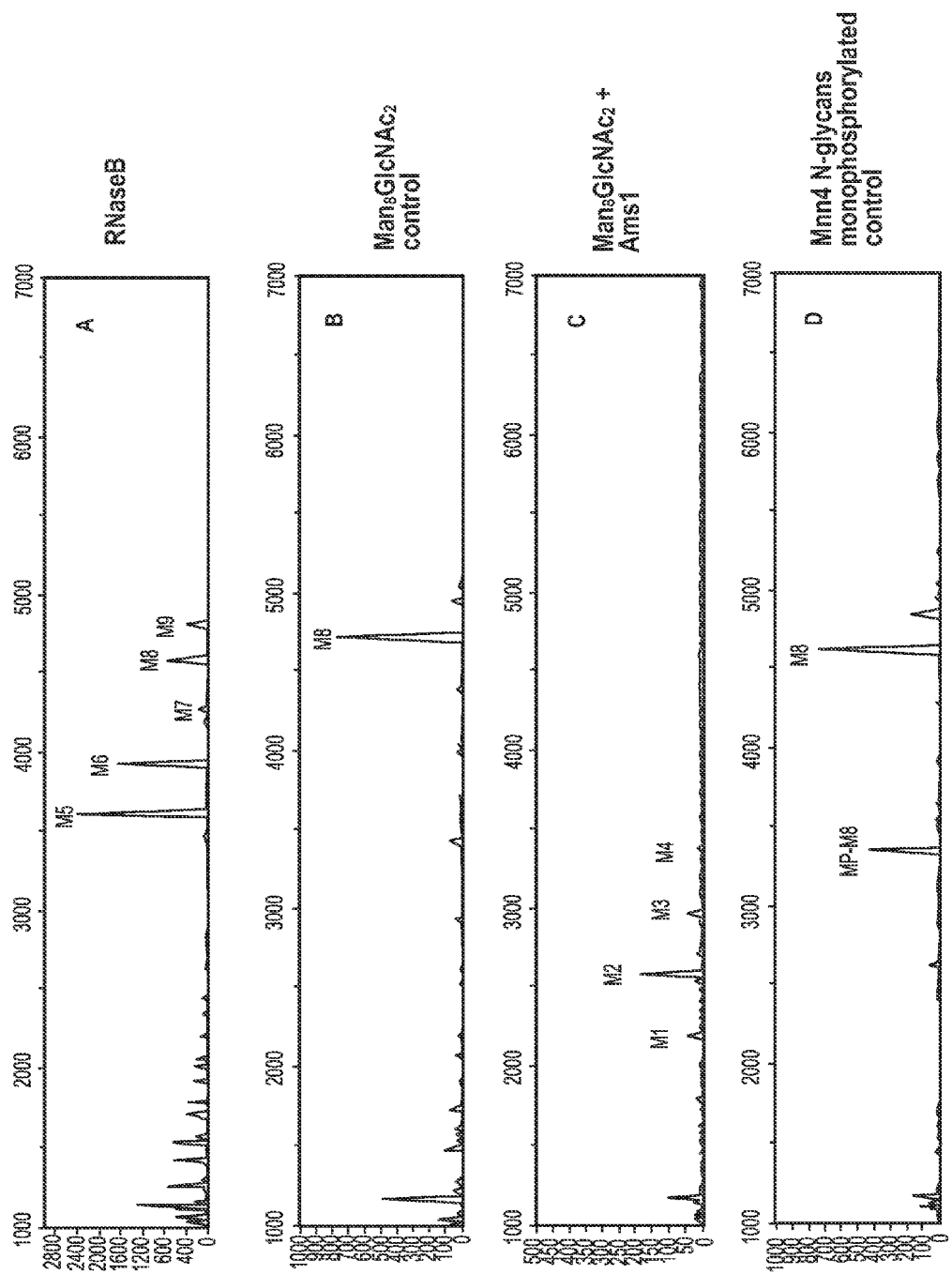
FIG. 6 is a series of electropherograms showing de-mannosylation and phosphate uncapping activity using AMS1 from *Yarrowia lipolytica* (YlAms1).
Figure 6:
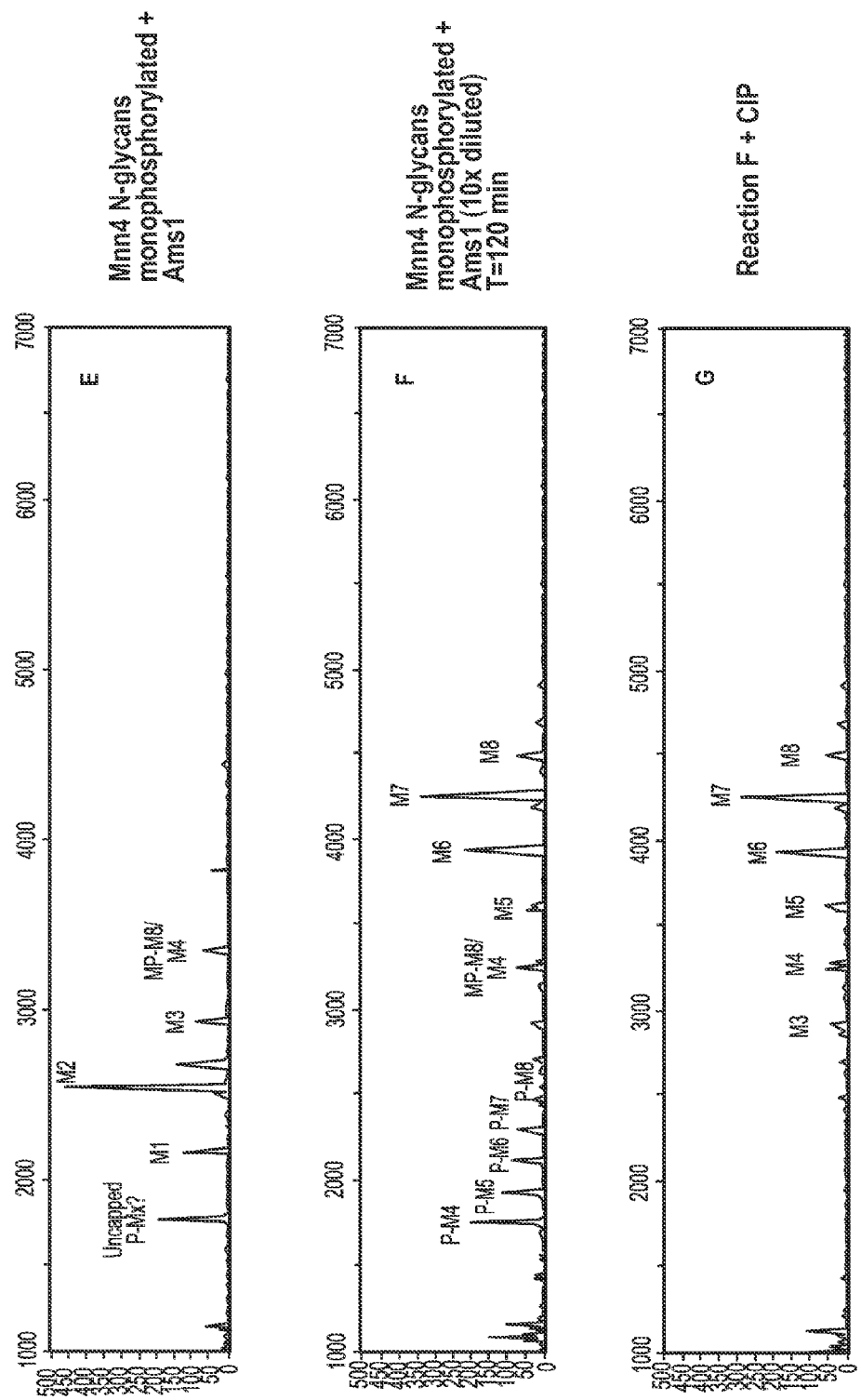
Figure 6:
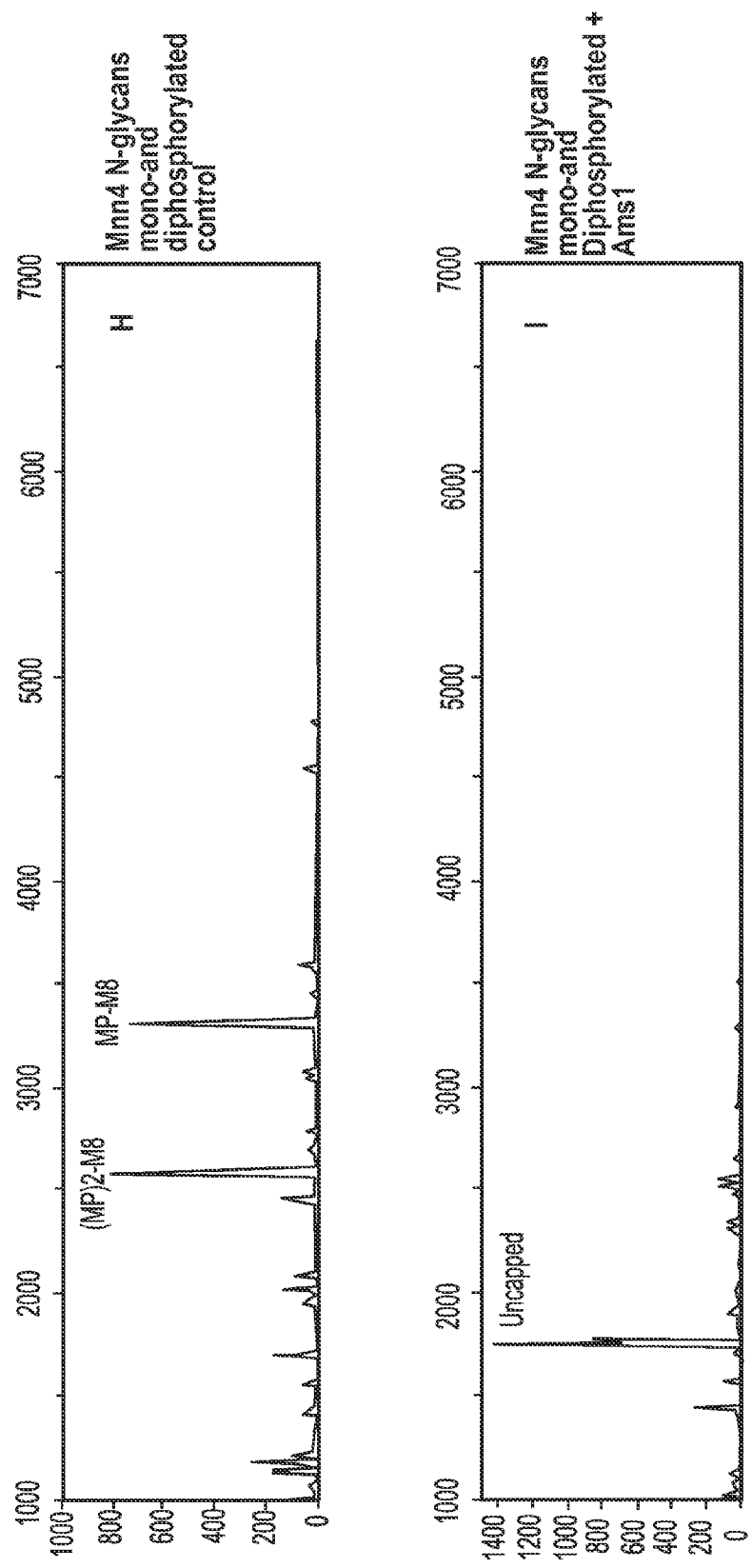

De-mannosylation and phosphate uncapping activity also is observed with YlAMS1, as shown in FIG. 6. YlAMS1 can fully hydrolyze $Man_8GlcNAc_2$ through $Man_1GlcNAc_2$ (panel C). Incubation of YlAMS1 with a substrate solution containing $Man_8GlcNAc_2$ and ManP-$Man_8GlcNAc_2$ (Panel D) yields a product with a fast electrophoretic mobility, likely a phosphate uncapped glycan (Panel E). A series of uncapped N-glycans were observed when the reaction was repeated with a diluted YlAMS1 sample during a 2 hour incubation (Panel F). The presence of phosphate uncapped glycans was confirmed by treating the reaction mixture with CIP, yielding a series of neutral N-glycans (Panel G). Thus, YlAMS1 can uncap $(ManP)_2$-$Man_8GlcNAc_2$ as observed in panel I, but it is still unclear which product is formed, P2-$Man_8GlcNAc_2$ or a further mannose trimmed glycan.

EXAMPLE 6

De-mannosylation and Phosphate Uncapping of Glycoproteins Expressed in a *Yarrowia lypolytica* Strain with a Higher Degree of Phosphorylated N-glycans with GH38 α-mannosidases The human lysosomal α-glucosidase huGAA was expressed in *Y. lipolytica* strain OXYY1589 to yield a glycoprotein with a high degree of phosphorylated N-glycan structures. The huGAA was purified as described in Example 3.

Figure 7:
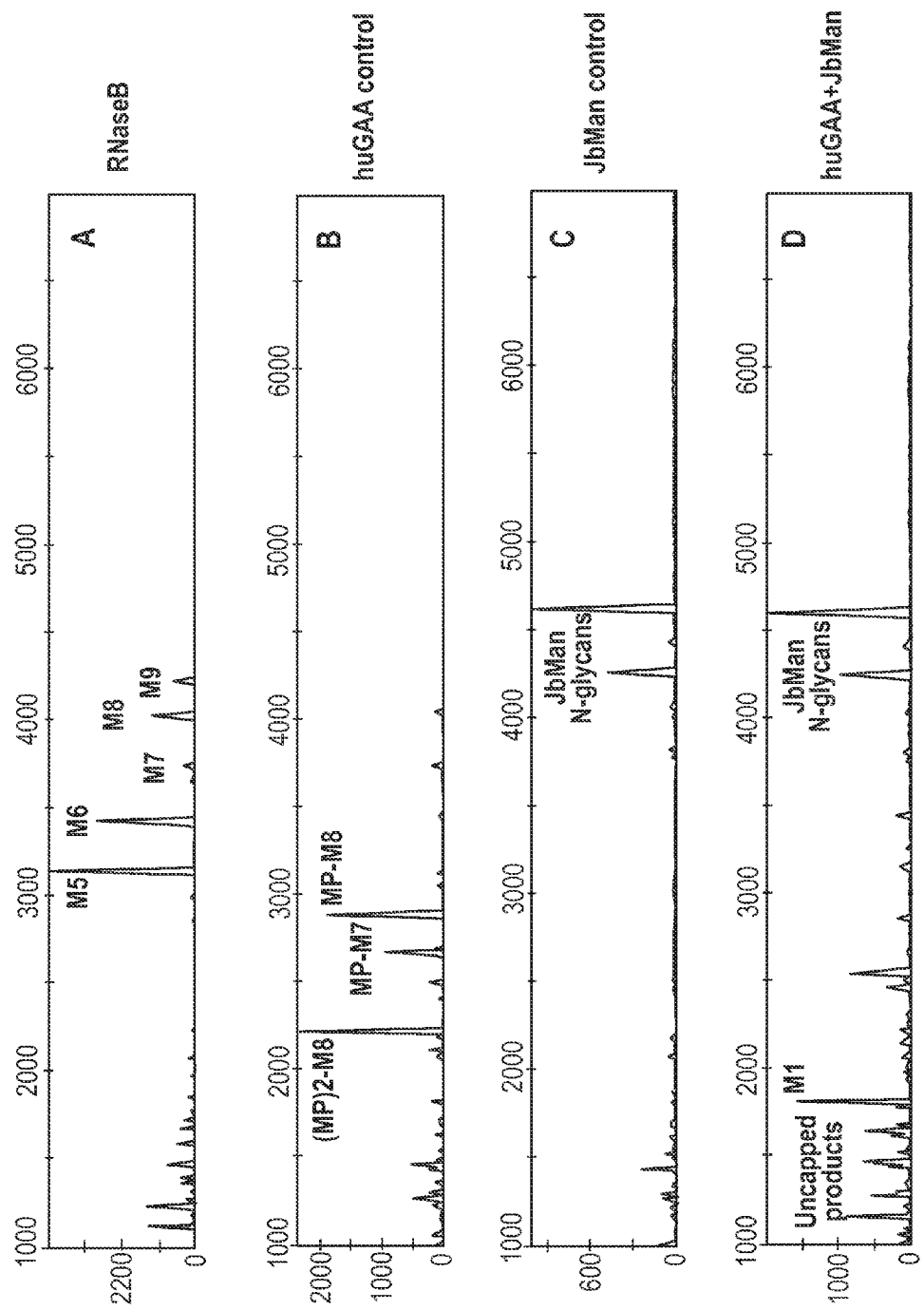
FIG. 7 is a series of electropherograms depicting the N-glycan profiles of huGAA before and after the Jack bean alpha-1,2-mannosidase treatment.

Jack bean α-mannosidase (JbMan) was added to a solution of huGAA in 100 mM ammonium acetate, pH 5.0 with 2 mM $CaCl_2$. The reaction mixture was incubated overnight at room temperature. The N-glycans were released with PNGaseF, labelled with APTS and subsequently analyzed on DSA-FACE, essentially as described in Laroy, et al., Nature Protocols, 1:397-405 (2006). The N-glycan profiles before and after the α-1,2-mannosidase treatment are shown in FIG. 7. The N-glycan mixture released from purified huGAA was mainly composed of ManP-$Man_8GlcNAc_2$ and $(ManP)_2$-$Man_8GlcNAc_2$ (panel B). A peak running slightly faster than ManP-$Man_8GlcNAc_2$ was assigned to ManP-$Man_7GlcNAc_2$. Only very minor amounts of $Man_8GlcNAc_2$ and $Man_7GlcNAc_2$ were present. Since JbMan is a glycoprotein, a control sample is presented in panel C in order to be able to correct for the Jack bean specific N-glycans. In panel D, the N-glycans obtained after incubating huGAA with JbMan are presented. The peaks corresponding to ManP-$Man_8GlcNAc_2$ and $(ManP)_2$-$Man_8GlcNAc_2$ were no longer present. Instead, a number of peaks appeared on the left hand side of the electropherogram (potentially phosphate uncapped N-glycans) together with $Man_1GlcNAc_2$. The latter mainly resulted from phosphatase activity present in the commercial JbMan preparation and further de-mannosylation of the obtained neutral N-glycans.

EXAMPLE 7

Uncapping and De-mannosylation of Recombinant Human α-glucosidase (huGAA) with CcMan5 and CcMan4

Nucleic acids encoding *Cellulosimicrobium cellulans* mannosidase 4 (CcMan4) and *Cellulosimicrobium cellulans* mannosidase 5 (CcMan5) were cloned into vector pLSAH36, which contains a DsbA signal sequence and results in the expression of a protein with an N-terminal HIS tag. The nucleotide sequences of the open reading frame of DsbA-CcMan5 and DsbA-CcMan4 are provided in FIGS. 8 and 9, respectively. The proteins were expressed in *E. coli* B21 cells and proteins residing in the periplasm were isolated and purified using a Talon column. A graphical representation of the plasmids pLSAHCcMan5 and pLSAHCcMan4 is given in FIG. 10.

A series of CcMan5 uncapping and CcMan4 de-mannosylation experiments were performed with 100 μg batches of huGAA purified as described in Example 3. Thirty (30) μL of huGAA (3.7 mg/mL in 25 mM phosphate buffer, pH 6.0, with 100 mM mannitol) were added to 46 μL of 100 mM HEPES buffer, pH 7.0 with 3 mM $CaCl_2$. In one experiment (referred to as huGAA_CcMan4), a weight:weight (w:w) ratio of 100:1 of huGAA:CcMan4 was used in which 14 μL of CcMan4 (80 μg/ml formulated in PBS) was added to the huGAA solution. In another experiment (referred to as huGAA_CcMan5), a w:w ratio of 100:2 of huGAA:CcMan5 was used in which 14 μL CcMan5 (154 μg/mL formulated in PBS) was added to the huGAA solution. In a combined experiment (referred to as huGAA_CcMan4/5), a w:w ratio of 100:2:1 of huGAA:CcMan5:CcMan4 was used in which 14 μL of CcMan5 and 14 μL of CcMan4 were added to 30 μL of huGAA and 32 μL of 100 mM HEPES buffer, pH 7.0 with 3 mM $CaCl_2$. In a control experiment (huGAA_control), 10 μL huGAA was diluted with 20 μL of 100 mM HEPES buffer, pH 7.0 with 3 mM $CaCl_2$. After incubating all of the samples for 16 hours at 30° C., the samples were kept at 4° C. until used.

Figure 11:
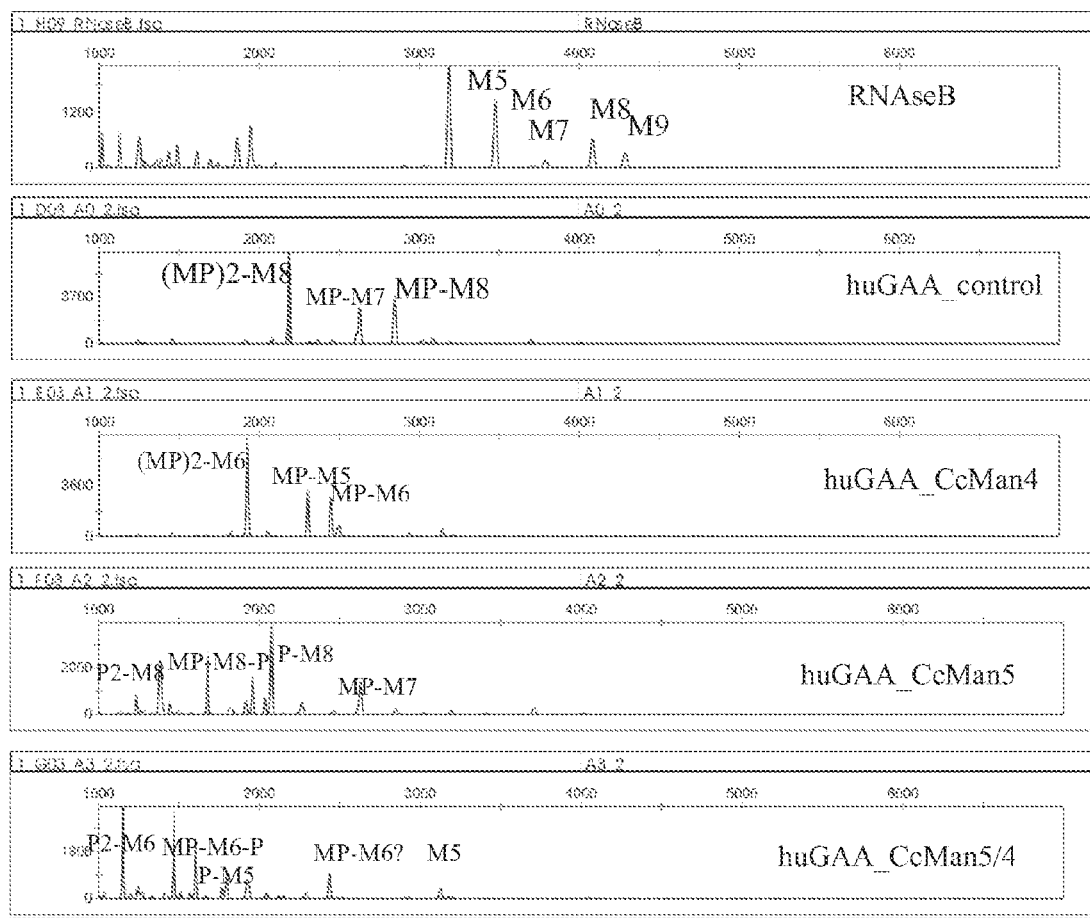
FIG. 11 is a series of electropherograms depicting the N-glycan analysis of human alpha glucosidase (GAA) treated with CcMan4 and/or CcMan5.
Figure 12:
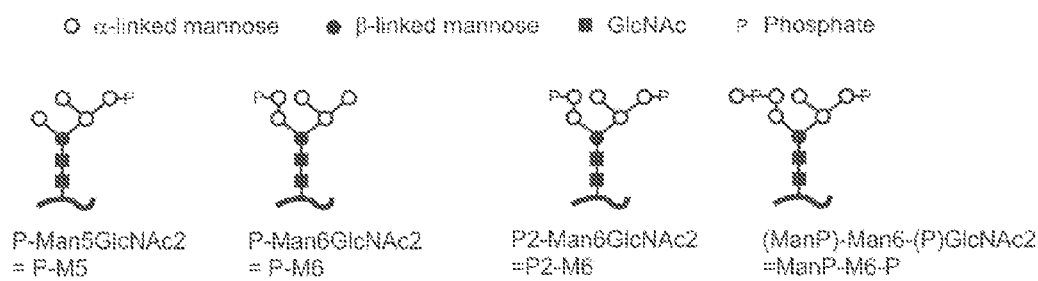
FIG. 12 is a schematic representation of the capped N-glycans, where P refers to phosphate, a filled square refers to a GlcNac moiety, an open circle refers to a beta-linked mannose, and a filled circle refers to an alpha-linked mannose.

Two (2) μL of each sample were used for N-glycan analysis as described in Example 6. The DSA-FACE electropherograms of the huGAA treated samples are presented in FIG. 11. CcMan4 treatment resulted in the complete de-mannosylation of ManP-$Man_8GlcNAc_2$ and $(ManP)_2$-$Man_8GlcNAc_2$ with the formation of the products ManP-$Man_5GlcNAc_2$, ManP-$Man_6GlcNAc_2$ and $(ManP)_2$-$Man_6GlcNAc_2$ (FIG. 11, third panel). Under the above reaction conditions, the phosphate uncapping with CcMan5 was complete for the ManP-$Man_8GlcNAc_2$ N-glycan with the formation of P-$Man_8GlcNAc_2$. The diphosphorylated N-glycan $(ManP)_2$-$Man_8GlcNAc_2$ was hydrolyzed to the fully uncapped P2-$Man_8GlcNAc_2$, but also a slower running peak with comparable peak height was observed and corresponded to partially uncapped (ManP)-$Man_8$-(P)$GlcNAc_2$ (potentially with an uncapped phosphate on the α-1,6 arm and a capped phosphate on the α-1,3 arm of the N-glycan) (FIG. 11, fourth panel). Uncapped and de-mannosylated huGAA was obtained after treatment with CcMan5 and CcMan4, and resulted in an N-glycan profile with $P_2$-$Man_6GlcNAc_2$, (ManP)-$Man_6$-(P)$GlcNAc_2$, and P-$Man_5GlcNAc_2$. Minor peaks corresponding to $Man_x$ and P-$Man_6GlcNAc_2$, P-$Man_7GlcNAc_2$, ManP-$Man_7GlcNAc_2$ (the latter phosphorylated N-glycans potentially with the α-1,3 arm phosphorylated) were observed (FIG. 11, fifth panel. A schematic presentation of the uncapped N-glycans is shown in FIG. 12 (B).

Figure 13:
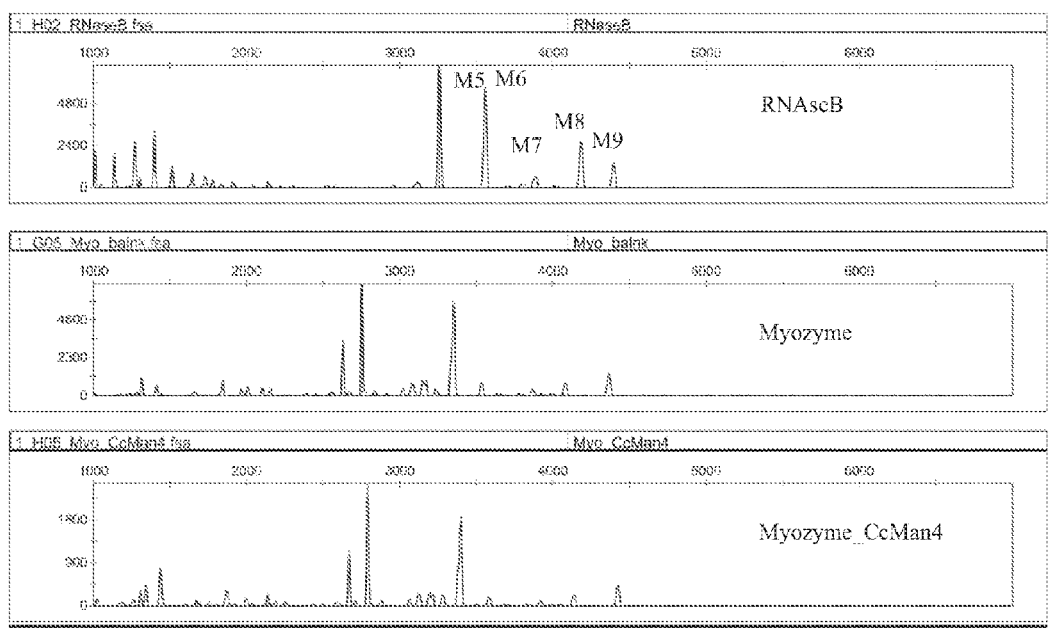
FIG. 13 is a series of electropherograms depicting the N-glycan analysis of Myozyme® treated with CcMan4.

Another CcMan5/CcMan4 uncapping and de-mannosylation experiment was performed with huGAA from the same purification batch. The experiment was performed essentially as described above, except that the formulation buffer for huGAA was 100 mM HEPES, pH 7.0 with 2 mM $CaCl_2$ and 100 mM mannitol (rather than 25 mM phosphate buffer, pH 6.0 with 100 mM mannitol). A w:w ratio of 100:3:0.5 for huGAA:CcMan5:CcMan4 was used. The reaction was incubated at 37° C. for 24 hours. A sample of the commercial available human α-glucosidase, Myozyme® (alglucosidase alpha, Genzyme) was treated under identical conditions with CcMan4 at a w:w ratio of 100:0.5 for Myozyme:CcMan4. The N-glycan analysis of these samples was performed as discussed above. The N-glycan profile for huGAA purified in this manner and treated with CcMan5 and CcMan4 was similar to that presented in FIG. 11. The DSA-FACE electropherograms for Myozyme® treated with CcMan4 are presented in FIG. 13.

Figure 14:
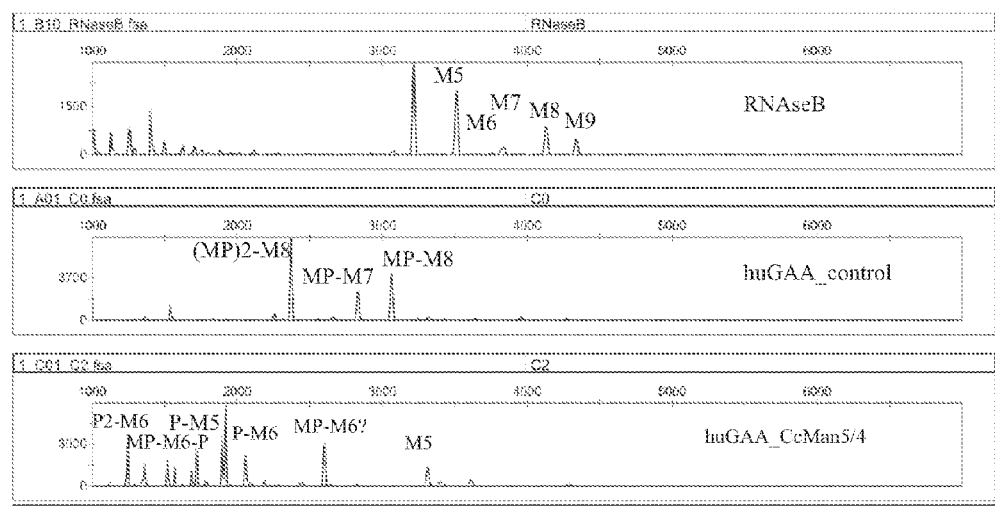
FIG. 14 is a series of electropherograms depicting the N-glycan analysis of human alpha glucosidase (GAA) treated with CcMan4 and/or CcMan5.

To follow intracellular huGAA processing (see example 10), a CcMan5/CcMan4 uncapping and de-mannosylation experiment was performed with huGAA from a different purification batch. The purification was performed under conditions similar to those described above, again using 100 mM HEPES, pH 7.0 with 2 mM $CaCl_2$ and 100 mM mannitol as the huGAA formulation buffer. The uncapping and de-mannosylation was performed at a w:w ratio of 100:3:0.5 for huGAA:CcMan5:CcMan4 and the reaction mixture was incubated for 24 hours at 30 C. The N-glycan profiles are shown in FIG. 14. In this experiment, the diphosphorylated N-glycans $P_2$-$Man_6GlcNAc_2$ and (ManP)-$Man_6$-(P)$GlcNAc_2$ were partially dephosphorylated to P-$Man_6GlcNAc_2$, (ManP)-$Man_6GlcNAc_2$ respectively. Phosphatase activity was detected in the huGAA sample using the general phosphatase substrate paranitrophenylphosphate (PNPP) in 100 mM HEPES buffer, pH 7.5 with 1 mM $MgCl_2$.

EXAMPLE 8

Uncapping and De-mannosylation of Recombinant huGAA with Jack Bean α-mannosidase The uncapping and de-mannosylation experiments of Example 6 were repeated after the ammonium sulphate suspension of JbMan was further purified by gel filtration through a Superdex 200 column to remove contaminating phosphatase activities.

Figure 15:
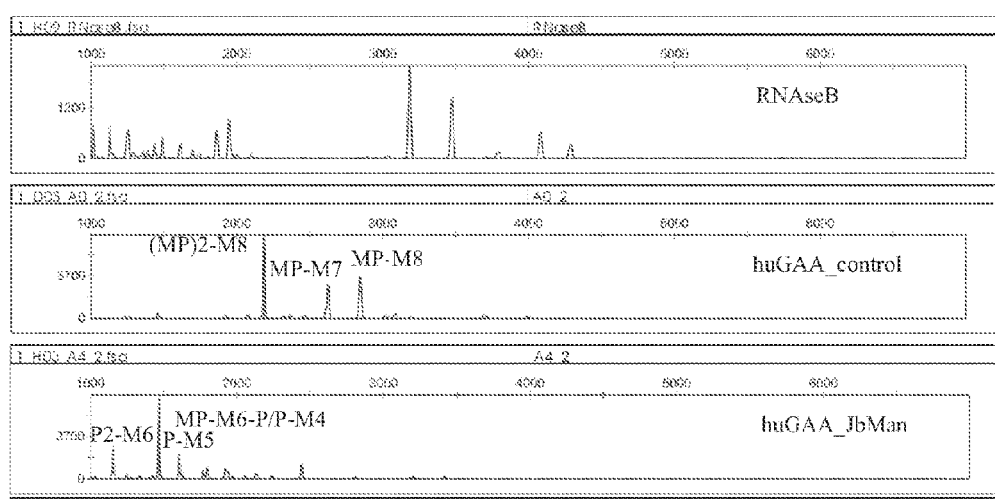
FIG. 15 is a series of electropherograms depicting the N-glycan analysis of human GAA treated with JbMan.

In one experiment referred to as huGAA_JbMan, a w:w ratio of 100:15 of huGAA:JbMan was used. Ten (10) μl of JbMan (1.5 mg/ml in PBS) was added to a solution containing thirty (30) μl of huGAA (3.7 mg/ml in 25 mM phosphate buffer, pH 6.0 with 100 mM mannitol) and 50 μl 100 mM sodium acetate buffer, pH 5.0. The control sample (huGAA_control) contained huGAA but no JbMan. After 16 hours incubation at 30° C., the samples were maintained at 4° C. until further use. For N-glycan analysis, 2 μL of each sample was used to release and label the N-glycans as described in Example 6. The DSA-FACE electropherograms of the N-glycans from the huGAA treated with JbMan are presented in FIG. 15. Treatment with JbMan resulted in the partial uncapping and de-mannosylation of ManP-$Man_8GlcNAc_2$ and $(ManP)_2$-$Man_8GlcNAc_2$ on huGAA, with the formation of mainly P-$Man_5GlcNAc_2$ and (ManP)-$Man_6$-(P)$GlcNAc_2$. The latter N-glycan runs together with P-$Man_5GlcNAc_2$ on the electropherogram. A minor amount of fully uncapped P2-Man$_6$GlcNAc$_2$ is also present. A peak running slower than P-Man$_5$GlcNAc$_2$ may be the neutral Man$_3$GlcNAc$_2$. P2-Man$_6$GlcNAc$_2$ and P-Man$_4$GlcNAc$_2$ are not further de-mannosylated by JbMan (FIG. 15, third panel).

A second JbMan uncapping and de-mannosylation experiment was performed with huGAA from the same purification batch. The experiment was performed, essentially as described above, 100 mM sodium acetate, pH 5.0 with 1 mM ZnCl$_2$ and 100 mM mannitol as the huGAA formulation buffer. A w:w ratio of 100:10 for huGAA:JbMan was used. The reaction was incubated at 37° C. for 24 hours. The N-glycan profile of these samples after JbMan treatment was similar to the N-glycan profile shown in FIG. 15.

Figure 16:
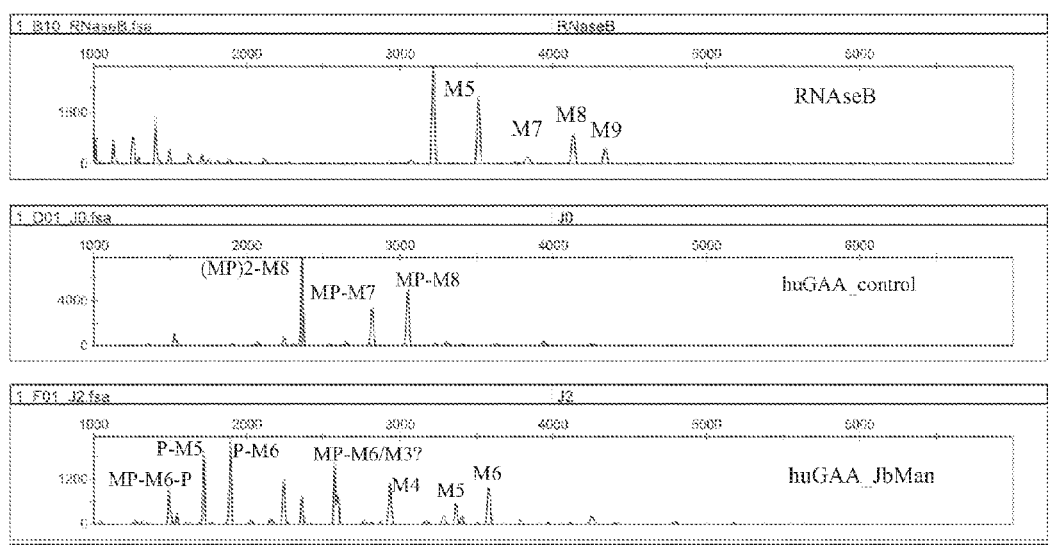
FIG. 16 is a series of electropherograms depicting the N-glycan analysis of human GAA treated with JbMan.

To follow intracellular huGAA processing (see Example 10), an uncapping and de-mannosylation experiment with JbMan was performed with huGAA from a different purification batch. Similar reaction conditions as described above were used. The huGAA formulation buffer used was 100 mM sodium acetate, pH 5.0 with 1 mM ZnCl$_2$ and 100 mM mannitol, a w:w ratio of 100:10 for huGAA:JbMan was used, and the reaction mixture was incubated for 24 hours at 30° C. The N-glycan profiles are shown in FIG. 16. The diphosphorylated N-glycan P$_2$-Man$_6$GlcNAc$_2$ is not observed in the electropherogram. Due to the presence of phosphatase activity in the huGAA sample, partial dephosphorylation occurred, resulting in the presence of the relatively high amounts of monophosphorylated P-Man$_6$GlcNAc$_2$ and ManP-Man$_6$GlcNAc$_2$, together with the neutral N-glycans Man$_3$GlcNAc$_2$ to Man$_6$GlcNAc$_2$.

EXAMPLE 9

Uptake of Recombinant huGAA into Pompe Fibroblasts

The uncapped and demannosylated huGAA and Myozyme® (non-treated and treated with CcMan4) from Example 7 and 8 were used in the cell uptake experiments. The specific enzyme activities of capped huGAA or huGAA treated with either CcMan5 (huGAA_CcMan5), Ccman4 (huGAA_CcMan4), a combination of CcMan4 and CcMan5 (huGAA_CcMan4/5), or Jack Bean mannosidase (huGAA_JBMan) (see Examples 7 and 8) were tested using the 4-MUG assay. Cleavage of the substrate 4-MUG by a glucosidase leads to the generation of the fluorogenic product 4-MU, which can be visualized or detected by irradiation with UV light. See Example 3. The activity of huGAA was compared with that of Myozyme®. The enzymes were diluted to three different concentrations (125 ng/ml, 62.5 ng/ml, and 31.25 ng/ml) in 100 mM sodium acetate buffer pH 4.0 containing 0.1% BSA (reaction buffer), and 50 µl of each dilution was added to a 96-well plate in triplicate. The 4-MUG substrate (Sigma) was diluted to 4 mM in reaction buffer and 50 µl of the diluted substrate was added to each well. The enzymatic reaction was incubated for 60 min at 37° C. followed by the addition of 100 µl 150 mM EDTA-Na$_2$ salt, pH 11.5 to quench the reaction. The fluorescence was measured at excitation 360/40 nm and emission 460/40 nm. A standard curve with 4-methylumbelliferone (4-MU) was measured to calculate the specific activity. The activity of the various enzymes was reported as U/mg where 1 unit is defined as the amount of enzyme that catalyzes the hydrolysis of 1 nmol substrate per hour at 2 mM substrate concentration in 100 mM sodium acetate buffer, pH 4.0+0.1% BSA. The specific activity of each of the enzymes was around $200 \times 10^3$ U/mg.

The uptake of huGAA treated with CcMan5 (huGAA_CcMan5), Ccman4 (huGAA_CcMan4), a combination of CcMan4 and CcMan5 (huGAA_CcMan4/5), or Jack Bean mannosidase was assessed in GM00248 fibroblasts, a human Pompe fibroblast cell line (Coriell Cell Repository, Camden, N.J.). The GM00248 fibroblasts are deficient in acid alpha glucosidase activity (0.27% of normal) and have no detectable levels of GAA mRNA or protein. The GM00248 fibroblasts were seeded and grown to confluence in Minimum Essential Medium (MEM, Invitrogen) containing Earle's salts and nonessential amino acids supplemented with 15% FCS and 2 mM glutamine. One day before administration of enzymes, cells were seeded in 24-well plates in Ham's F10 medium supplemented with 5% heat inactivated FCS (30 min at 56° C.).

On the day of the experiment, capped huGAA and uncapped huGAA were diluted in uptake medium to various enzyme activities followed by filtration through a 0.22 µm filter. The activity of each enzyme dilution in uptake medium was measured again using the 4-MUG assay to determine the actual enzyme activity that was added to the cells.

The GM00248 fibroblasts were incubated with the enzymes for 16 hours, washed twice with ice-cold PBS, and then lysed with 0.5 ml PBS+0.5% Triton X 100 (30 min, 4° C.) supplemented with protease inhibitors. Cell lysates were spun at 10000×g to remove cell debris. The intracellular activity of huGAA was measured using the 4-MUG activity assay as described above. Protein concentrations were determined by the bicinchoninic acid method (microBCA kit, Pierce) following the manufacturer's protocol. The intracellular activity of huGAA is expressed as units per mg total protein (U/mg).

Figure 17:
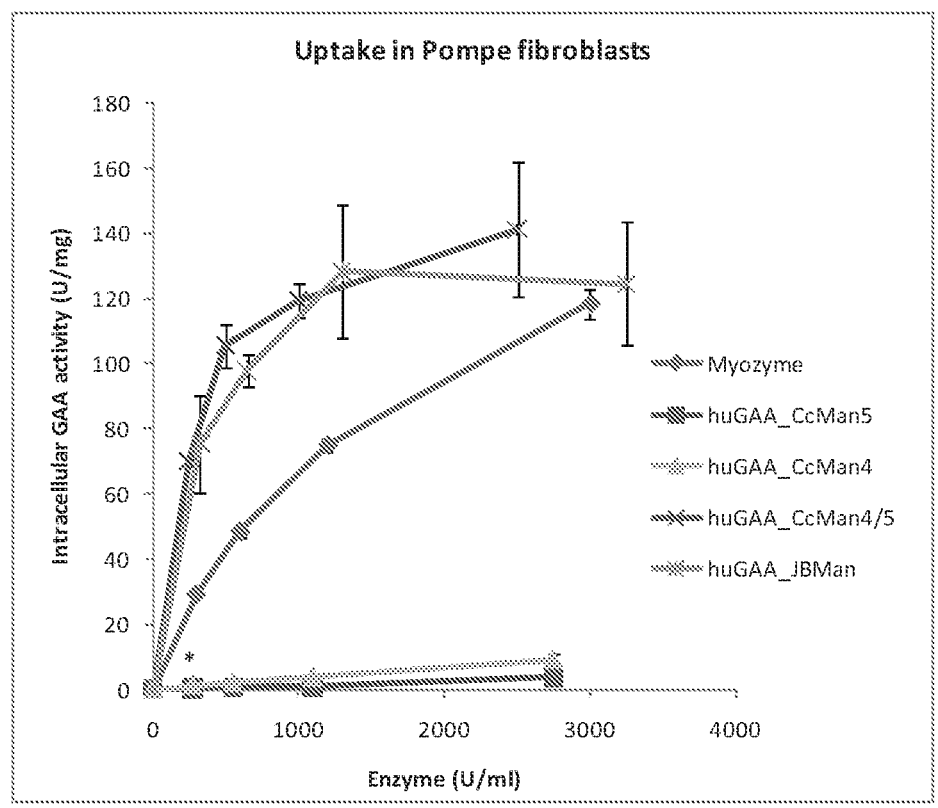
FIG. 17 is a line graph of the intracellular GAA activity (U/mg) of Myozyme® (diamonds) or human GAA treated with CcMan5 (squares), CcMan4 (triangles), CcMan4 and CcMan5 (×), or JbMan (✱) at the indicated concentration of enzyme (U/mL). Each data point represents the average of duplicates per dose±the standard deviation. Data points marked with an asterisk are results from a single stimulation condition per dose.

FIG. 17 shows the intracellular activity of huGAA in the GM00248 human Pompe fibroblasts. Capped huGAA that contains a mixture of ManP-Man$_8$GlcNAc$_2$ and (ManP)$_2$-Man$_8$GlcNAc$_2$ N-glycans (see FIG. 11, second panel) did not enter the cells. The intracellular activity of cells treated with capped huGAA was similar to non-treated cells (data not shown). HuGAA_CcMan4, which is completely de-mannosylated (see FIG. 11, third panel), also showed no uptake in Pompe fibroblasts. Although CcMan5 treatment resulted in the formation of uncapped monophosphorylated P-Man$_8$GlcNAc$_2$ and fully uncapped diphosphorylated P$_2$-Man$_8$GlcNAc$_2$, no cellular uptake was observed over the tested dose range (FIG. 17). Dose-dependent cellular uptake was observed for HuGAA that was uncapped and de-mannosylated huGAA with either the combination of CcMan4 and CcMan5 (huGAA_CcMan4/5) or with Jack Bean mannosidase (huGAA_JBMan). The intracellular activity of huGAA treated with either CcMan4/5 or JbMan reached a plateau level at around 500-1000 U/ml while the intracellular activity of Myozyme® did not reach a plateau at 2500 U/ml. Phosphate-uncapped and de-mannosylated huGAA was taken up approximately 2.5 times more efficiently than Myozyme®.

A second set of experiments was performed to investigate whether the uptake was due to binding to the mannose-6-phosphate (M6P) receptor. For these experiments, huGAA from the same purification batch used in the above experiments was treated with CcMan4 and CcMan5 mannosidases for uncapping the mannose-1-phosphate-6-mannose linked glycans as described in Example 7 or with Jack Bean mannosidase as described in Example 8. Myozyme® was used as a reference. To investigate the effect of terminal α-1,2 mannoses on the uptake efficiency of huGAA, Myozyme® was treated with CcMan4 mannosidase. The specific activity of the enzymes was determined using the 4-MUG assay as described above. The uptake assay was performed as described above. The enzymes were diluted to equal enzyme activities in uptake medium, filtered, and various doses were added to the GM00248 fibroblasts with or without the presence of 5 mM M6P (Sigma) and incubated for 16 hours. Each cell uptake experiment was performed in duplicate. After incubation, cells were washed with ice-cold PBS, lysed with 0.5 ml PBS+0.5% Triton X 100 supplemented with protease inhibitors and assayed for intracellular huGAA activity using the 4-MUG assay.

Figure 18:
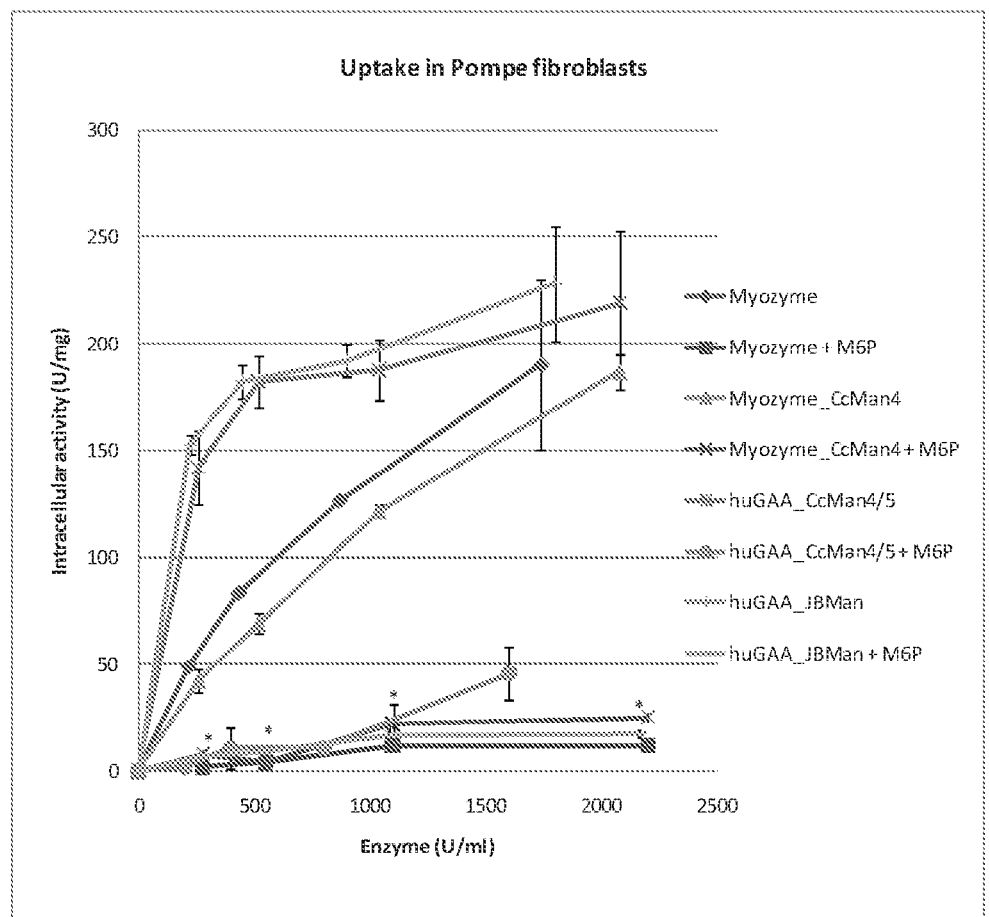
FIG. 18 is a line graph of the intracellular GAA activity (U/mg) of Myozyme® (diamonds), Myozyme® plus M6P (squares), Myozyme® treated with CcMan4 (triangles), Myozyme® treated with CcMan4, plus M6P (×), human GAA treated with CcMan4 and CcMan5 (✱), human GAA treated with CcMan4 and CcMan5, plus M6P (circles), human GAA treated with JbMan (1), or human GAA treated with JbMan, plus M6P ( ) at the indicated concentration of enzyme (U/mL). Each data point represents the average of duplicates per dose±the standard deviation. Data points marked with an asterisk are results from a single stimulation condition per dose.

FIG. 18 shows the uptake of huGAA enzymes in GM00248 fibroblasts. Treatment of Myozyme® with CcMan4 did not change the N-glycan profile of Myozyme® (see FIG. 13, third panel), nor did it change its uptake efficiency. The uptake of Myozyme® was inhibited by the addition of free M6P. The results in FIG. 18 show a dose-dependent uptake of uncapped and de-mannosylated huGAA (huGAA_CcMan4/5, huGAA_JBMan), which is inhibited by the addition of M6P. These results indicate that the uptake of uncapped and de-mannosylated huGAA is mediated via the M6P receptor.

EXAMPLE 10

Processing of huGAA in the Lysosomes of Pompe Fibroblasts

HuGAA is produced in the endoplasmic reticulum as a 110 kDa precursor. It undergoes N-glycan processing in the Golgi apparatus and is further proteolytically processed in the lysosomes into active proteins of 76 kDa and 70 kDa, through an intermediate molecular form of 95 kDa. The active proteins are responsible for degrading its natural substrate glycogen. In the following experiments, the intracellular processing of purified recombinant huGAA, produced as a 110 kDa protein in *Y. lipolytica*, was investigated. For these experiments, huGAA from a different purification batch than that used in Example 9, and in which the formulation buffer was exchanged to 100 mM HEPES, pH 7 with 2 mM $CaCl_2$ and 100 mM mannitol (see Example 7) was treated with the combination CcMan4 and CcMan5 or with Jack Bean mannosidase as described in Example 7. The specific activity of the uncapped enzymes was determined using the 4-MUG assay. One day before the experiment, GM00248 fibroblasts were seeded in 6-well plates at a density of $5 \times 10^5$ cells/well in uptake medium as described above. The next day, the fibroblasts were incubated with 1000 U/ml huGAA_CcMan4/5 or huGAA_JBMan in 2 ml uptake medium for 14 hours or for 46 hours. As a reference, cells were incubated with Myozyme®; and cells that were not incubated with an enzyme were used as a negative control. Each cell uptake experiment was performed in duplicate. After incubation, the GM00248 fibroblasts were washed with ice-cold PBS and harvested by trypsinization (0.05% trypsin with 0.53 mM EDTA). Cells were centrifuged and lysed in 0.5 ml PBS+0.5% TritonX100, supplemented with protease inhibitors. Cell lysates were centrifuged to remove cell debris and assayed for intracellular GAA activity with the 4-MUG assay as described above. Protein concentration was determined with the BCA method.

Figure 19:
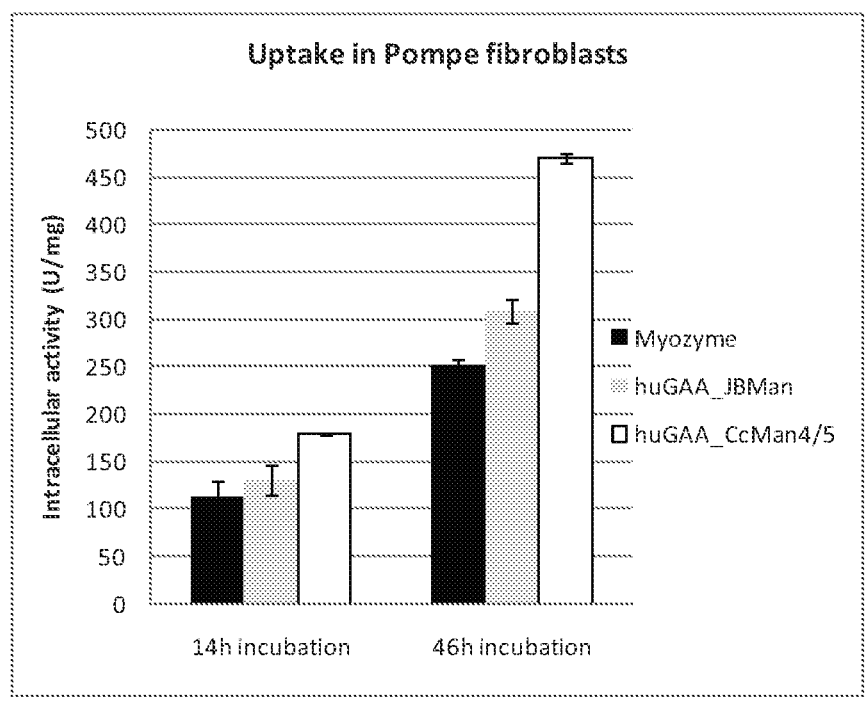
FIG. 19 is a bar graph of the intracellular GAA activity (U/mg) in Pompe fibroblasts incubated with Myozyme, JbMan, or the combination of CcMan4 and CcMan5 for either 14 hours or 46 hours. The average of duplicates±the standard deviation is presented.

FIG. 19 shows the intracellular huGAA activity. Although huGAA_Ccman4/5 was partially dephosphorylated to P-$Man_6GlcNA_2$ and (ManP)-$Man_6GlcNac_2$ (FIG. 14, third panel), the enzyme was taken up 1.8 times better than Myozyme® at both tested incubation times. HuGAA_JBMan also was taken up better than Myozyme® but was less efficient compared to huGAA_CcMan4/5, probably due to the absence of the diphosphorylated N-glycan P2-$Man_6GlcNAc_2$ (FIG. 16, third panel).

The purpose of this experiment was to test whether huGAA taken up by the fibroblasts was processed to the active forms of 76 kDa and 70 kDa. Therefore, cell samples were precipitated by the trichloroacetic acid (TCA)/deoxycholate (DOC) method. Samples (500 µl, containing 160 µg protein) were mixed with 50 µl of 0.5% DOC and incubated on ice for 30 minutes. After adding TCA 100% (100 µl) to obtain a final TCA concentration of 15%, samples were mixed and precipitated overnight at −20° C. The precipitate was centrifuged at 13000 rpm in a microcentrifuge for 30 min, followed by aspiration of TCA from the pellet. The pellet was washed with 500-700 µl of ice-cold acetone, mixed and centrifuged at 13000 rpm. The pellet was dried for 10 min at 50° C. followed by re-solubilization in 1× NuPAGE® LDS sample buffer containing NuPAGE® sample reducing agent. After boiling the sample for 3 min at 100° C., 20 µg protein (10 µl) was loaded on a 4-12% NuPAGE® Bis-Tris gel (Invitrogen) with 1× MOPS SDS running buffer containing 500 µl of NuPAGE® antioxidant. Myozyme® (50 ng) were loaded on the gel as a reference. The samples were blotted overnight on a nitrocellulose membrane and the intracellular huGAA was detected using polyclonal rabbit anti-huGAA sera (1/2000 dilution) as primary antibody and a goat anti-rabbit IgG peroxidase conjugated antibody (1/5000 dilution, Sigma) as a secondary antibody. After washing the membrane with PBS/Tween, the membrane was developed using the ECL western blotting detection reagent (GeHealthcare). A 14 h incubation period with the uncapped enzymes and with Myozyme® resulted in the presence of mainly the precursor protein. In the huGAA_Ccman4/5 treated cells, a minor amount of the 76 kDa protein was observed. After the 46 h incubation, the uncapped enzymes were processed to the 76 kDa active polypeptide. Myozyme® also is processed to the active polypeptide but the bands were less intense.

EXAMPLE 11

Uncapping and De-mannosylation of Recombinant huGAA with CcMan5 and Jack Bean α-mannosidase Recombinant huGAA was uncapped and demannosylated with CcMan5 and JBMan at a w:w ratio of 100:5:10 for huGAA:CcMan5:JbMan. To a solution of 1.08 ml huGAA (4.8 mg/ml in 10 mM sodium phosphate buffer, pH 6.0 with 40 mM NaCl), 1.69 ml of CcMan5 (0.154 mg/ml in PBS buffer) and 1.04 ml of JbMan (0.5 mg/ml in PBS buffer) were added. The total reaction volume was adjusted to 5.2 ml with 100 mM sodium acetate buffer, pH 5.0, containing 2 mM $CaCl_2$. The reaction mixture was incubated at 30° C. for 15 hours. The uncapped and demannosylated huGAA was purified using a Hiload 16/60 superdex 200 gel filtration column (GE Healthcare) as described in Example 3.

Figure 20:
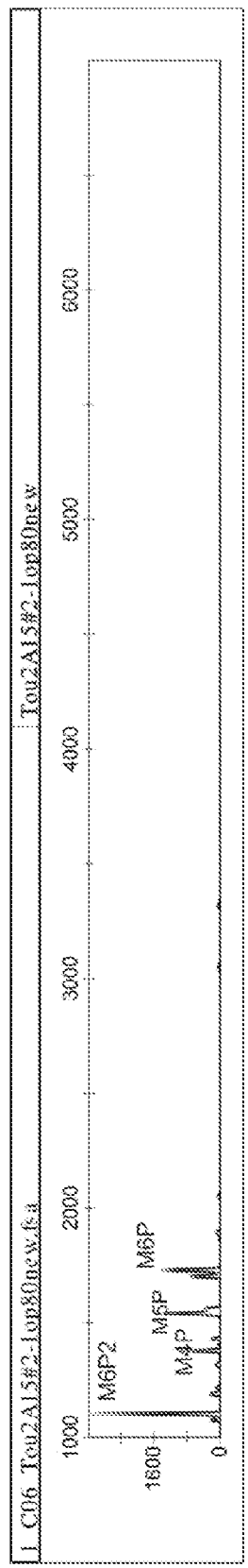
FIG. 20 is a series of electropherograms depicting the N-glycan analysis of human GAA treated with CcMan5 and JbMan.

The N-glycans were released from 10 µg of the final purified huGAA and labeled as described in Example 6. The DSA-FACE electropherogram of the N-glycans from the huGAA treated with both CcMan5 and JbMan is presented in FIG. 20. The main peaks observed after uncapping and demannosylation were the double phosphorylated P2-$Man_6GlcNAc_2$ and the monophosphorylated P-$Man_4GlcNAc_2$, P-$Man_5GlcNAc_2$ and P-$ManGlcNAc_2$.

EXAMPLE 12

Uptake of Uncapped and Demannosylated Recombinant huGAA with CcMan 5 and JbMan into Pompe Fibroblasts The cellular uptake of uncapped, demannosylated, and purified huGAA (treated with JbMan and CcMan5 as described in Example 11) was compared to the cellular uptake of Myozyme® using the GM00248 fibroblast cell line as described in Example 9.

Figure 21:
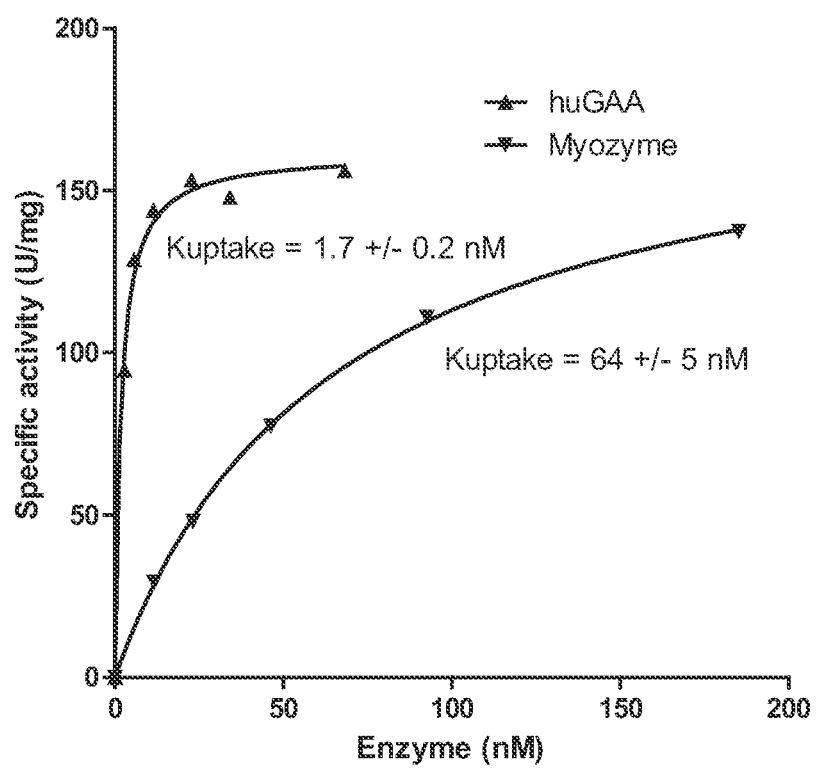
FIG. 21 is a line graph of the intracellular activity of purified, uncapped and demannosylated huGAA versus the intracellular activity of Myozyme® after extracellular stimulation of the cells with the huGAA and Myozyme respectively. The amount of enzyme (expressed as enzyme activity units) added to the cells was converted to enzyme concentration (expressed as nM) and plotted versus the specific activity (expressed in U/mg) for the calculations of the $K_{uptake}$. $K_{uptake}$ and the standard deviation were calculated in GraphPrism using non-linear regression through 14 data points (2 data points per concentration) for huGAA and through 12 data points for Myozyme®.

FIG. 21 shows the intracellular activity of purified uncapped and demannosylated huGAA versus the intracellular activity of Myozyme®. The amount of enzyme (expressed as enzyme activity units) added to the cells was converted to enzyme concentration (expressed as nM) and plotted versus the specific activity (expressed in U/mg) for the calculations of the $K_{uptake}$. $K_{uptake}$ and the standard deviation were calculated in GraphPrism using non-linear regression through 14 data points (2 data points per concentration) for huGAA and through 12 data points for Myozyme®. Dose-dependent cellular uptake was observed for huGAA, reaching a plateau level at around 25 nM and a $K_{uptake}$ of 1.7±0.2 nM, while the intracellular activity of Myozyme did not reach a plateau at 200 nM and has a $K_{uptake}$ of 64±5 nM. Uncapped, demannosylated huGAA produced in *Yarrowia lipolytica* was taken up 30 times more efficiently than Myozyme® in Pompe fibroblasts.

EXAMPLE 13

Processing of Uncapped and Demannosylated Recombinant huGAA with CcMan 5 and JbMan in the Lysosomes of Pompe Fibroblasts A cell uptake assay was performed to determine if the *Yarrowia* produced huGAA that was treated with CcMan5 and JbMan as described in Example 11 was processed to its mature forms in the lysosomes. One day before the experiment, GM00248 fibroblasts were seeded in a 6-well plate at a density of 3×10$^5$ cells/well in uptake medium. The next day, fibroblasts were stimulated with 2000 U/ml huGAA in 2 ml uptake medium for 8 hours or 24 hours, or stimulated for 24 hours ("pulse" period) then the cells were washed and 2 ml growth medium were added to the cells for a chase period of up to 100 hours. Cells not treated with enzyme were used as a negative control.

After incubation, cells were washed and cell lysates were precipitated using the DOC/TCA method as described in Example 10 and subjected to Western blotting. As a reference, purified huGAA (30 ng) was loaded on the gel. The samples were blotted overnight and the intracellular huGAA was detected using polyclonal rabbit anti-huGAA sera (1/2000 dilution) as primary antibody and a goat anti-rabbit IgG peroxidase conjugated antibody (1/8000 dilution, Abcam) as a secondary antibody. The membrane was developed using the ECL western blotting detection reagent (GeHealthcare).

An 8 hour incubation period with the uncapped and demannosylated enzyme resulted in the presence of the precursor protein (110 kDa). A 24 hour incubation period resulted in the presence of both the precursor protein and the processed protein (76 kD), while after a 24 hour pulse and up to 100 hour chase period, almost all protein was processed towards the 76 kD active polypeptide. These results demonstrate that the uncapped and demannosylated huGAA was taken up by the fibroblasts and processed to its active polypeptides in the lysosomes.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of directing a glycoprotein to the interior of a mammalian cell, the glycoprotein comprising a mannose-1-phospho-6-mannose moiety, wherein the mannose residue that has a phosphate residue bound at the 6 position is linked to a terminal mannose residue at the 1 position of the terminal mannose residue, the method comprising contacting the cell with the glycoprotein after it has undergone:

(a) uncapping of the mannose-1-phospho-6-mannose moiety to mannose-6-phosphate on the glycoprotein; and (b) removal of the terminal mannose residue, wherein the glycoprotein that has undergone (a) and not (b) or (b) but not (a) does not substantially bind to a mannose-6-phosphate receptor on the cell, wherein the glycoprotein that has undergone (a) and (b) does substantially bind to a mannose-6-phosphate receptor on the cell, and wherein steps (a) and (b) are catalyzed by a single mannosidase enzyme that is a family 38 glycosyl hydrolase (GH38 family) mannosidase.

2. The method of claim 1, wherein said glycoprotein is a human protein.

3. The method of claim 1, wherein said glycoprotein is a pathogen protein, a lysosomal protein, a growth factor, a cytokine, a chemokine, an antibody or antigen-binding fragment thereof, or a fusion protein.

4. The method of claim 3, wherein said lysosomal protein is a lysosomal enzyme.

5. The method of claim 4, wherein said lysosomal enzyme is acid alpha glucosidase or alpha galactosidase.

6. The method of claim 1, wherein said glycoprotein is associated with a lysosomal storage disease (LSD).

7. The method of claim 6, wherein said LSD is Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

\* \* \* \* \*